US010899823B2

(12) United States Patent
Gao et al.

(10) Patent No.: US 10,899,823 B2
(45) Date of Patent: Jan. 26, 2021

(54) PROGRAMMABLE PROTEIN CIRCUITS IN LIVING CELLS

(71) Applicant: California Institute of Technology, Pasadena, CA (US)

(72) Inventors: Xiaojing Gao, Los Angeles, CA (US); Lucy S. Chong, Pasadena, CA (US); Michael Elowitz, Los Angeles, CA (US); Mark William Budde, Arcadia, CA (US); Matthew Sun-min Kim, Northridge, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/250,314

(22) Filed: Jan. 17, 2019

(65) Prior Publication Data

US 2019/0248873 A1  Aug. 15, 2019

Related U.S. Application Data

(60) Provisional application No. 62/619,001, filed on Jan. 18, 2018, provisional application No. 62/688,859, filed on Jun. 22, 2018.

(51) Int. Cl.
*C07K 14/81* (2006.01)
*C12N 15/52* (2006.01)

(52) U.S. Cl.
CPC .............. *C07K 14/81* (2013.01); *C12N 15/52* (2013.01); *C07K 2319/20* (2013.01); *C07K 2319/33* (2013.01); *C07K 2319/50* (2013.01)

(58) Field of Classification Search
CPC ...................... C07K 2319/00; C06K 2319/50
USPC ...................................................... 435/69.7
See application file for complete search history.

(56) References Cited

U.S. PATENT DOCUMENTS

| 5,739,002 | A  | 4/1998  | De Francesco et al. |
| 6,005,079 | A  | 12/1999 | Casterman et al. |
| 6,348,584 | B1 | 2/2002  | Hodgson et al. |
| 6,673,901 | B2 | 1/2004  | Koide |
| 6,884,870 | B2 | 4/2005  | Hay et al. |
| 8,394,604 | B2 | 3/2013  | Liu et al. |
| 2002/0132327 | A1 | 9/2002  | Hay et al. |
| 2005/0271647 | A1 | 12/2005 | Baltimore et al. |
| 2009/0162341 | A1 | 6/2009  | Foster et al. |
| 2013/0230863 | A1 | 9/2013  | Tang et al. |
| 2017/0315114 | A1 | 11/2017 | Stein et al. |
| 2018/0118818 | A1 | 5/2018  | Tang et al. |
| 2019/0248873 | A1 | 8/2019  | Gao et al. |

FOREIGN PATENT DOCUMENTS

| WO | WO1994004678 | 3/1994 |
| WO | WO1994025591 | 11/1994 |
| WO | WO2014040129 | 3/2014 |
| WO | WO2018069782 | 4/2018 |
| WO | WO2019147478 | 8/2019 |

OTHER PUBLICATIONS

Gao et al., Programmable protein circuits in living cells. Science 361, 1252-1258 (2018).*
Griesbeck et al., "Reducing the Environmental Sensitivity of Yellow Fluorescent Protein," The Journal of Biological Chemistry 2001, 276(31), 29188-29194. doi:10.1074/jbc.M102815200.
Adams et al., "Overview and analysis of the polyprotein cleavage sites in the family Potyviridae," Molecular Plant Pathology 2005, 6(4), 471-487.
Angelici et al., "Synthetic Biology Platform for Sensing and Integrating Endogenous Transcriptional Inputs in Mammalian Cells," Cell Reports 2016, 16, 2525-2537.
Aronheim et al., "Membrane Targeting of the Nucleotide Exchange Factor Sos Is Sufficient for Activating the Ras Signaling Pathway," Cell 1994, 78 ,949-961.
Auslander et al., "Programmable single-cell mammalian biocomputers," Nature 2012, 487, 123-127.
Banaszynski et al., "A Rapid, Reversible, and Tunable Method to Regulate Protein Function in Living Cells Using Synthetic Small Molecules," Cell 2006, 126, 995-1004.
Barnea et al., "The genetic design of signaling cascades to record receptor activation," PNAS 2008, 105(1), 64-69.
Barrett et al., "Chimeric Antigen Receptor Therapy for Cancer," Annual Review of Medicine 2014, 65, 333-347.
Bartenschlager et al., "The NS3/4A proteinase of the hepatitis C virus: unravelling structure and function of an unusual enzyme and a prime target for antiviral therapy," Journal of Viral Hepatitis 1999, 6, 165-181.
Basu et al., "A synthetic multicellular system for programmed pattern formation," Nature 2005, 434, 1130-1134.
Basu et al., "Spatiotemporal control of gene expression with pulse-generating networks," PNAS 2004, 101(17), 6355-6360.
Bintu et al., "Dynamics of epigenetic regulation at the single-cell level," Science 2016, 351(6274), 720-724.
Boerger et al., "Retroviral vectors preloaded with a viral receptor-ligand bridge protein are targeted to specific cell types," PNAS 1999, 96, 9867-9872.
Bonnet et al., "Amplifying Genetic Logic Gates," Science 2013, 340, 599-602.
Budihardjo et al., "Biochemical Pathways of Caspase Activation During Apoptosis," Annual Review of Cellular Development and Biology 1999, 15, 269-290.
Butko et al., "Fluorescent and photo-oxidizing TimeSTAMP tags track protein fates in light and electron microscopy," Nature Neuroscience 2012, 15(12), 1742-1751.
Camacho-Soto et al., "Small Molecule Gated Split-Tyrosine Phosphatases and Orthogonal Split-Tyrosine Kinases," Journal of the American Chemical Society 2014, 136, 17078-17086.

(Continued)

*Primary Examiner* — Sheridan Swope
(74) *Attorney, Agent, or Firm* — Sheppard, Mullin, Richter & Hampton LLP

(57) ABSTRACT

Some embodiments of the systems, methods and compositions provided herein relate to a compound protease. In some embodiments, the compound protease includes a protease domain and a cut site for another enzyme. In some embodiments, the compound protease includes an association domain. In some embodiments, the compound protease is part of a protein circuit.

16 Claims, 84 Drawing Sheets

(56) References Cited

OTHER PUBLICATIONS

Camacho-Soto et al., "Ligand-Gated Split-Kinases," Journal of the American Chemical Society 2014, 136, 3995-4002.
Carrington et al., "A viral cleavage site cassette: Identification of amino acid sequences required for tobacco etch virus polyprotein processing," PNAS 1988, 85, 3391-3395.
Chen et al., "Predicting PDZ domain-peptide interactions from primary sequences," Nature Biotechnology 2008, 26(9), 1041-1045.
Choi et al., "Selective viral vector transduction of ErbB4 expressing cortical interneurons in vivo with a viral receptor-ligand bridge protein," PNAS 2010, 107(38),16703-16708.
Chung et al., "Tunable and reversible drug control of protein production via a self-excising degron," Nature Chemical Biology 2015, 11, 713-720.
Cox et al., "Drugging the undruggable Ras: mission possible," Nature Reviews Drug Discovery 2014, 13(11), 828-851.
Dagliyan et al., "Computational design of chemogenetic and optogenetic split proteins," Nature Communications, 9(4042), 1-8.
Daringer et al., "Modular Extracellular Sensor Architecture for Engineering Mammalian Cell-based Devices," ACS Synthetic Biology 2014, 3, 892-902.
De Felipe, "Skipping the co-expression problem: the new 2A "CHYSEL" technology," Genetic Vaccines and Therapy 2004, 2(13).
De Felipe et al., "Targeting of Proteins Derived from Self-Processing Polyproteins Containing Multiple Signal Sequences," Traffic 2004, 5, 616-626.
Downward, "Targeting RAS Signaling Pathways in Cancer Therapy," Nature Publishing Group 2003, 3, 11-22.
Dueber et al., "Reprogramming Control of an Allosteric Signaling Switch Through Modular Recombination," Science 2003, 301, 1904-1908.
Elowitz et al., "A synthetic oscillatory network of transcriptional regulators," Nature 2000, 403, 335-338.
Fernandez-Rodriguez et al., "Post-translational control of genetic circuits using Potyvirus proteases," Nucleic Acids Research 2016, 44(13), 6493-6502.
Ferrell et al., "Ultrasensitivity Part II: Multisite phosphorylation, stoichiometric inhibitors, and positive feedback," Trends in Biochemical Sciences 2014, 39(11), 556-569.
Fink et al., "Design of fast proteolysis-based signaling and logic circuits in mammalian cells," Nature Chemical Biology 2018, 15, 115-122.
Gao et al., "Programmable protein circuits in living cells," Science 2018, 361, 1252-1258.
Gardner et al., "Construction of a genetic toggle switch in *Escherichia coli*," Nature, 403, 339-342.
Ghabrial et al., "Molecular genetic analyses of the soybean mosaic virus Nla proteinase," Journal of General Virology 1990, 71, 1921-1927.
Ghosh et al., "Antiparallel Leucine Zipper-Directed Protein Reassembly: Application to the Green Fluorescent Protein," Journal of the American Chemical Society 2000, 122, 5658-5659.
Gramespacher et al., "Intein Zymogens: Conditional Assembly and Splicing of Split Inteins via Targeted Proteolysis," Journal of the American Chemical Society 2017, 139, 8074-8077.
Gray et al., "Activation of Specific Apoptotic Caspases with an Engineered Small Molecule-Activated Protease," Cell 2010, 142(4), 637-646.
Greber et al., "An engineered mammalian band-pass network," Nucleic Acids Research 2010, 38(18), e174.
Hancock et al., "A CAAX or a CAAL motif and a second signal are sufficient for plasma membrane targeting of ras proteins," The EMBO Journal 1991, 10(13), 4033-4039.
Hart et al., "The Utility of Paradoxical Components in Biological Circuits," Molecular Cell 2013, 49, 213-221.
Herrmann et al., "Quantitative Analysis of the Complex between p21ras and the Ras-binding Domain of the Human Raf-1 Protein Kinase," Journal of Biological Chemistry 1995, 270(7), 2901-2905.

Howard et al., "Redirecting tyrosine kinase signaling to an apoptotic caspase pathway through chimeric adaptor proteins," PNAS 2003, 100(20), 11267-11272.
International Search Report and Written Opinion dated Aug. 12, 2019 in PCT Patent Application PCT/US2019/014078.
International Search Report and Written Opinion dated Dec. 19, 2019 in PCT Patent Application PCT/US2019/048914.
Iwamoto et al., "A General Chemical Method to Regulate Protein Stability in the Mammalian Central Nervous System," Chemistry & Biology 2010, 17, 981-988.
Jacobs et al., "StaPLs: versatile genetically encoded modules for engineering drug-inducible proteins," Nature Methods 2018, 15(7), 523-526.
Khalil et al., "A Synthetic Biology Framework for Programming Eukaryotic Transcription Functions," Cell 2012, 150, 647-658.
Kim et al., "Time-gated detection of protein-protein interactions with transcriptional readout," eLife 2017, 6, e30233.
Kipniss et al., "Engineering cell sensing and responses using a GPCR-coupled CRISPR-Cas system," Nature Communications 2017, 8, 2212.
Koch-Nolte et al., "Single domain antibodies from llama effectively and specifically block T cell ecto-ADP-ribosyltransferase ART2.2 in vivo," The FASEB Journal 2007, 21, 3490-3498.
Koh et al., "An Internal Ribosome Entry Site (IRES) Mutant Library for Tuning Expression Level of Multiple Genes in Mammalian Cells," PLOS One 2013, 8(12), e82100.
Kojima et al., "Toward a world of theranostic medication: Programming biological sentinel systems for therapeutic intervention," Advanced Drug Delivery Reviews 2016, 105, 66-76.
Lichty et al., "Vesicular stomatitis virus: re-inventing the bullet," TRENDS in Molecular Medicine 2004, 10(5), 210-216.
Lienert et al., "Synthetic biology in mammalian cells: Next generation research tools and therapeutics," Nature Reviews of Molecular Cell Biology 2014, 15(2), 95-107.
Lohmueller et al., "A tunable zinc finger-based framework for Boolean logic computation in mammalian cells," Nucleic Acids Research 2012, 40(11), 5180-5187.
Ma et al., "Defining Network Topologies that Can Achieve Biochemical Adaptation," Cell 2009, 138, 760-773.
Marchisio et al., "Computational design of synthetic gene circuits with composable parts," Bioinformatics 2008, 24(17), 1903-1910.
Morsut et al., "Engineering Customized Cell Sensing and Response Behaviors Using Synthetic Notch Receptors," Cell 2016, 164(4), 780-791.
Nakanishi et al., Development of Sendai Virus Vectors and their Potential Applications in Gene Therapy and Regenerative Medicine, Current Gene Therapy 2012, 12, 410-416.
Nallamsetty et al., "Efficient site-specific processing of fusion proteins by tobacco vein mottling virus protease in vivo and in vitro," Protein Expression and Purification 2004, 38, 108-115.
Nelson, "Antibody fragments," mAbs 2010, 2(1), 77-83.
Nielsen et al., "Genetic circuit design automation," Science 2016, 352(6281), aac7341.
Nissim et al., "A tunable dual-promoter integrator for targeting of cancer cells," Molecular Systems Biology 2010, 6(444), 1-9.
Oliveira et al., "An Improved Ras Sensor for Highly Sensitive and Quantitative FRET-FLIM Imaging," PLOS One 2013, 8(1), e52874.
Park et al., "Rewiring MAP Kinase Pathways Using Alternative Scaffold Assembly Mechanisms," Science 2003, 299, 1061-1064.
Porcher et al., "The Bicoid Morphogen System," Current Biology 2010, 20(5), R249-R254.
Pu et al., "Evolution of a split RNA polymerase as a versatile biosensor platform," Nature Chemical Biology 2017, 13(4), 432-438.
Reinke et al., "A synthetic coiled-coil interactome provides heterospecific modules for molecular engineering," Journal of the American Chemical Society 2010, 132(17), 6025-6031.
Riechmann et al., "Single domain antibodies: comparison of camel VH and camelised human VH domains," Journal of Immunological Methods 1999, 231, 25-38.
Rinaudo et al., "A universal RNAi-based logic evaluator that operates in mammalian cells," Nature Biotechnology 2007, 1-6.

(56) References Cited

OTHER PUBLICATIONS

Roquet et al., "Synthetic recombinase-based state machines in living cells," Science 2016, 353(6297), aad8559.
Rossi et al., "Monitoring protein-protein interactions in intact eukaryotic cells by b-galactosidase complementation," PNAS 1997, 94, 8405-8410.
Roybal et al., "Precision Tumor Recognition by T Cells With Combinatorial Antigen-Sensing Circuits," Cell 2016, 164, 770-779.
Russell et al., "Oncolytic Virotherapy," Nature Biotechnology 2012, 30(7).
Schnell et al., "Infectious rabies viruses from cloned cDNA," The EMBO Journal 1994, 13(18), 4195-4203.
Schwanhausser et al. "Global quantification of mammalian gene expression control" Nature 2011, 473, 337-342.
Snitkovsky et al., "A TVA-Single-Chain Antibody Fusion Protein Mediates Specific Targeting of a Subgroup A Avian Leukosis Virus Vector to Cells Expressing a Tumor-Specific Form of Epidermal Growth Factor Receptor," Journal of Virology 2000, 74(20), 9540-9545.
Stein et al., "Ultrasensitive Scaffold-Dependent Protease Sensors with Large Dynamic Range," ACS Synthetic Biology 2017, 6, 1337-1342.
Stein et al., "Protease-based synthetic sensing and signal amplification," PNAS 2014, 1-6.
Stevens et al., "Design of a Split Intein with Exceptional Protein Splicing Activity," Journal of the American Chemical Society 2016, 138, 2162-2165.
Stricker et al. "A fast, robust and tunable synthetic gene oscillator," Nature 2008, 456, 516-520.
Szymczak et al., "Correction of multi-gene deficiency in vivo using a single 'self-cleaving' 2A peptide-based retroviral vector," Nature Biotechnology 2004, 22, 589-594.
Tang et al., "Detection and manipulation of live antigen-expressing cells using conditionally stable nanobodies," eLIFE 2016, 5, e15312.
Taremi et al., "Construction, expression, and characterization of a novel fully activated recombinant single-chain hepatitis C virus protease," Protein Science 1998, 7, 2143-2149.
Taxis et al., "Efficient protein depletion by genetically controlled deprotection of a dormant N-degron," Molecular Systems Biology 2009, 5(267), 1-7.

To et al., "Rationally designed fluorogenic protease reporter visualizes spatiotemporal dynamics of apoptosis in vivo," PNAS 2015, 112(11), 3338-3343.
Tozser et al., "Comparison of the substrate specificity of two potyvirus proteases," The FEBS Journal 2005, 272, 514-523.
Truong et al., "Development of an intein-mediated split-Cas9 system for gene therapy," Nucleic Acids Research 2015, 43(13), 6450-6458.
Varshavsky, "The N-end rule: Functions, mysteries, uses," PNAS 1996, 93, 12142-12149.
Waugh, "An overview of enzymatic reagents for the removal of affinity tags," Protein Expression and Purification 2011.
Wehr et al., "Monitoring regulated protein-protein interactions using split TEV," Nature Methods 2006, 3(12), 985-993.
Weinberg et al., "Large-scale design of robust genetic circuits with multiple inputs and outputs for mammalian cells," Nature Biotechnology 2017, 35(5), 453-462.
Weinheimer et al., "Autoproteolysis of Herpes Simplex Virus Type 1 Protease Releases an Active Catalytic Domain Found in Intermediate Capsid Particles," Journal of Virology 1993, 67(10), 5813-5822.
Wikstrand et al., "The class III variant of the epidermal growth factor receptor (EGFRvIII): characterization and utilization as an immunotherapeutic target," Journal of NeuroVirology 1998, 4, 148-158.
Wroblewska et al., "Mammalian synthetic circuits with RNA binding proteins delivered by RNA," Nature Biotechnology 2015, 33(8), 839-841.
Xie et al., "Multi-Input RNAi-Based Logic Circuit for Identification of Specific Cancer Cells," Science 2011, 333, 1307-1311.
Yasuda et al., "Supersensitive Ras activation in dendrites and spines revealed by two-photon fluorescence lifetime imaging," Nature Neuroscience 2006, 9(2), 283-291.
Yeh et al., "Rewiring cellular morphology pathways with synthetic guanine nucleotide exchange factors," Nature 2007, 447, 596-600.
Zetche et al., "A Split Cas9 Architecture for Inducible Genome Editing and Transcription Modulation," Nature Biotechnology 2015, 33(2), 139-142.

* cited by examiner

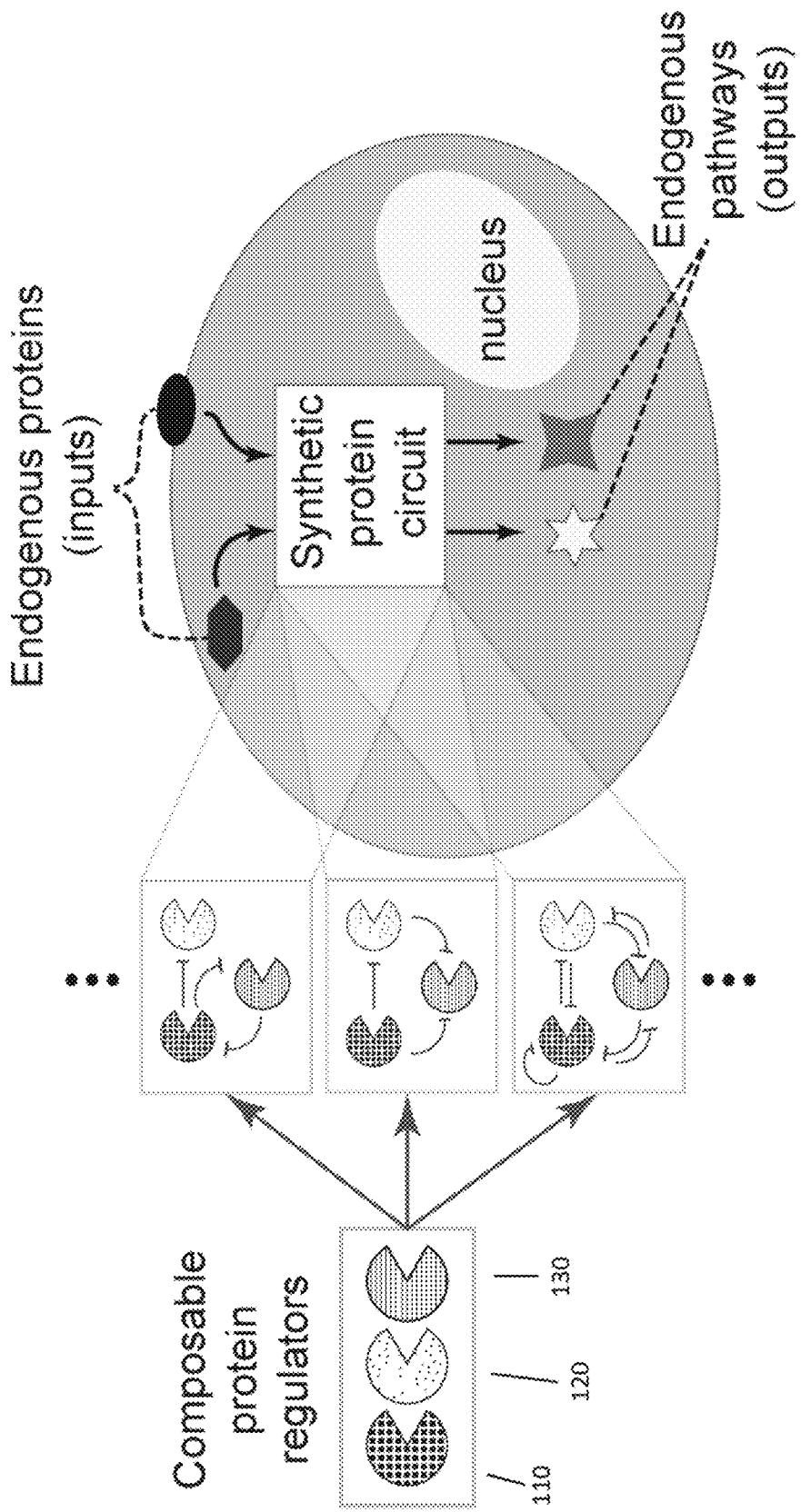

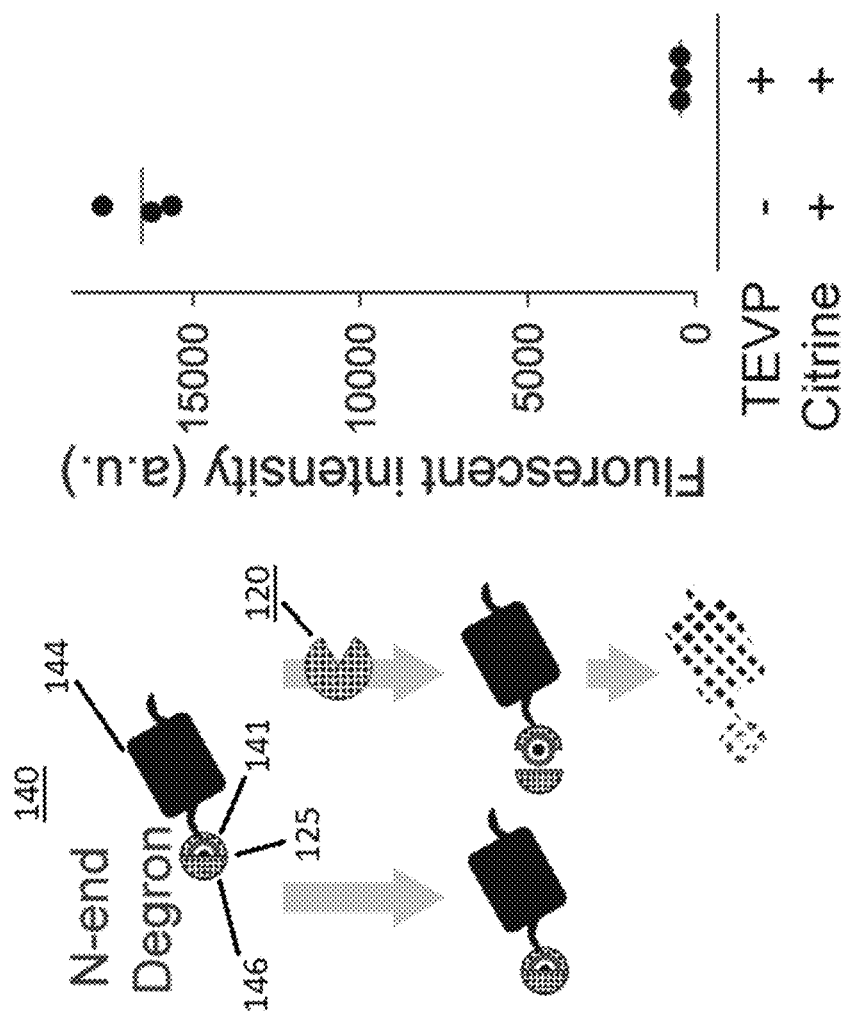

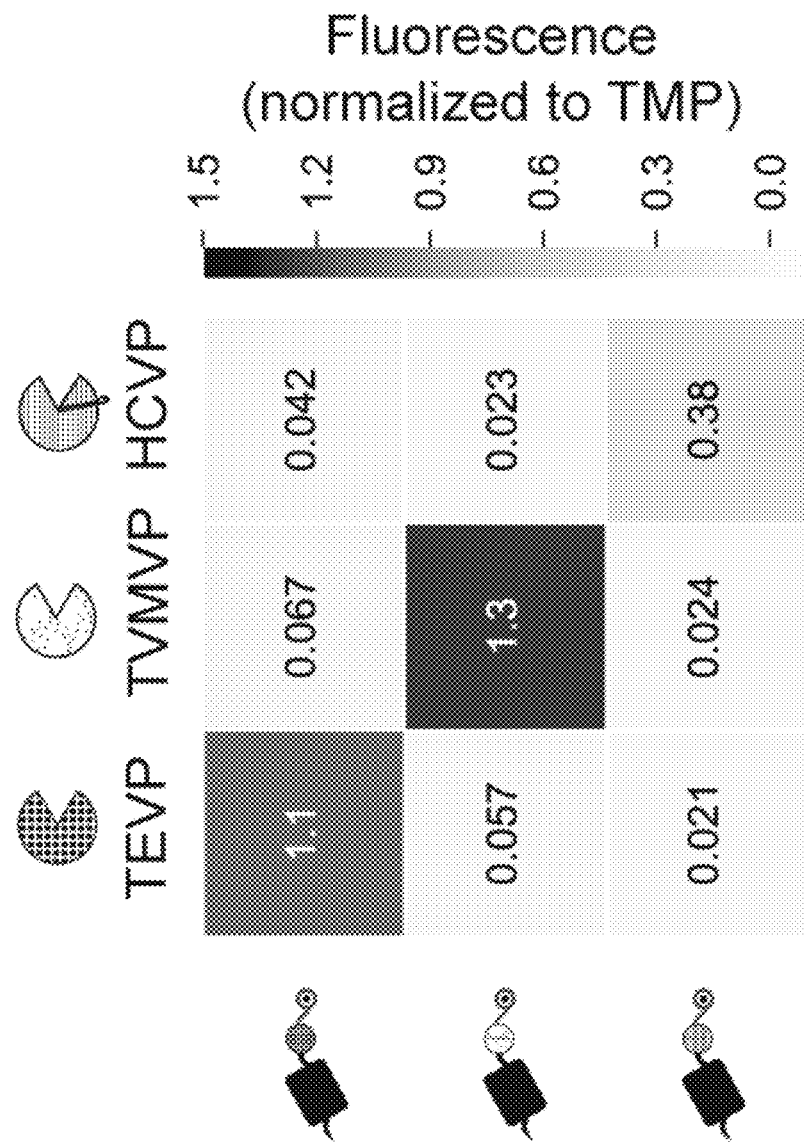

Single-chain variant

Three-protease cascade

Fig. 1K protease
○ protease cleavage site
◉ degron degradation signal
〰 anti-parallel leucine zippers
▰ fluorescent reporter
▱ TMP stabilizing drug

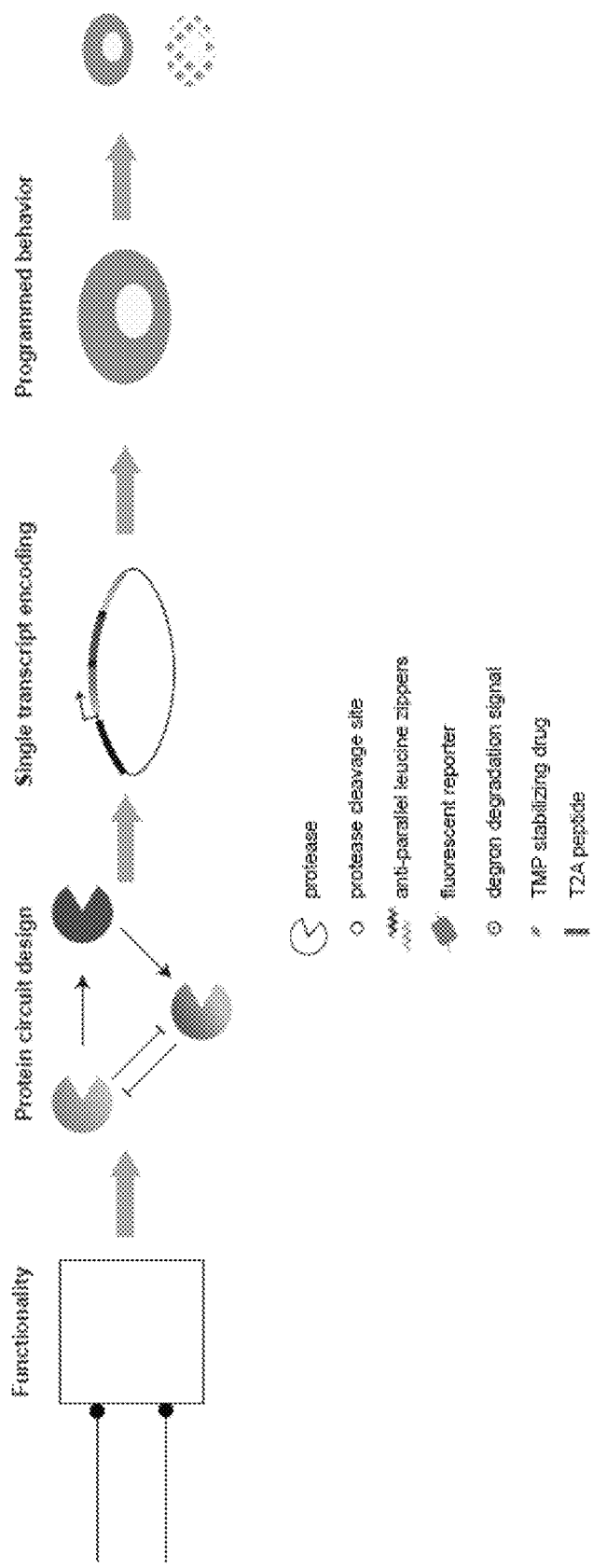

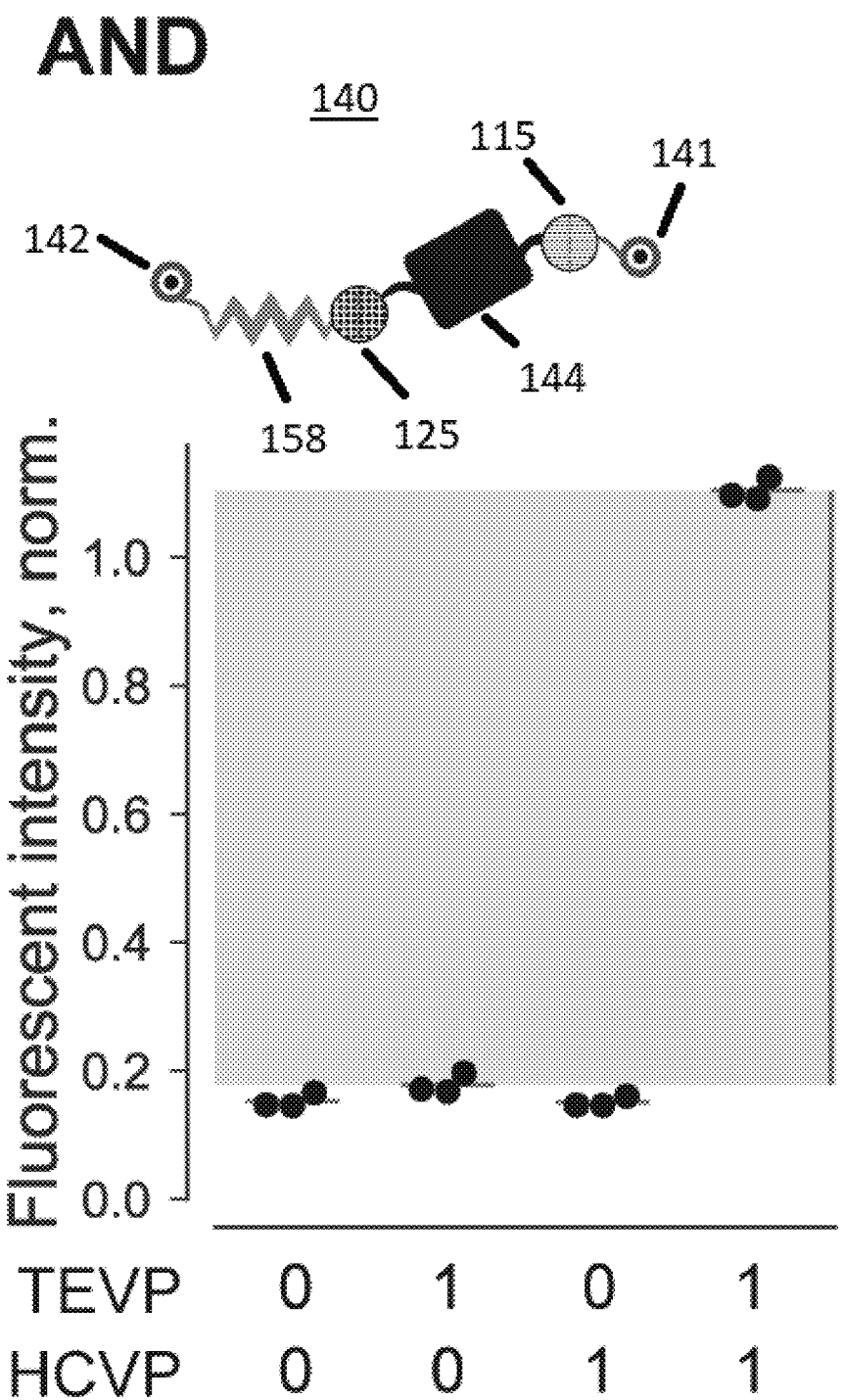

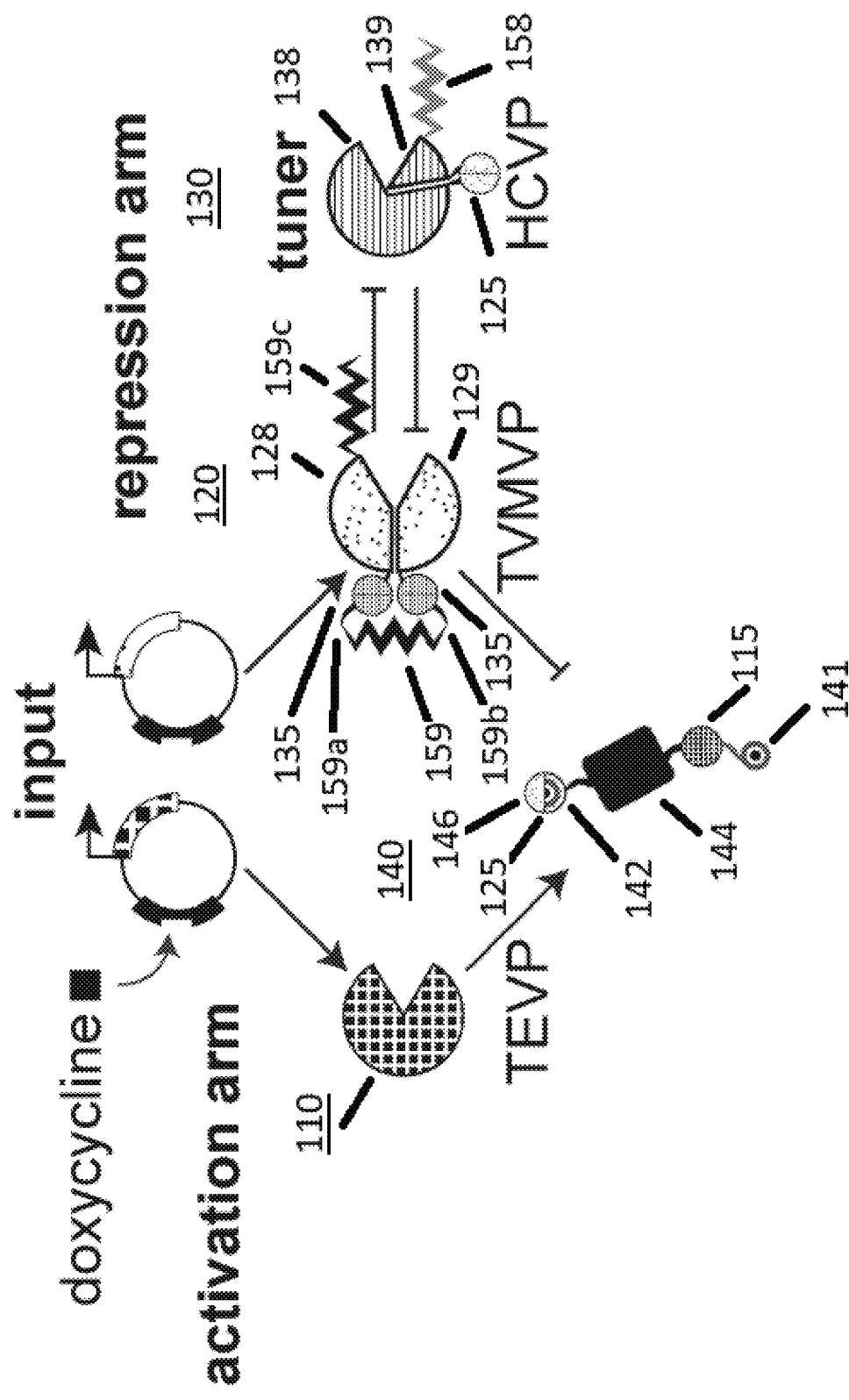

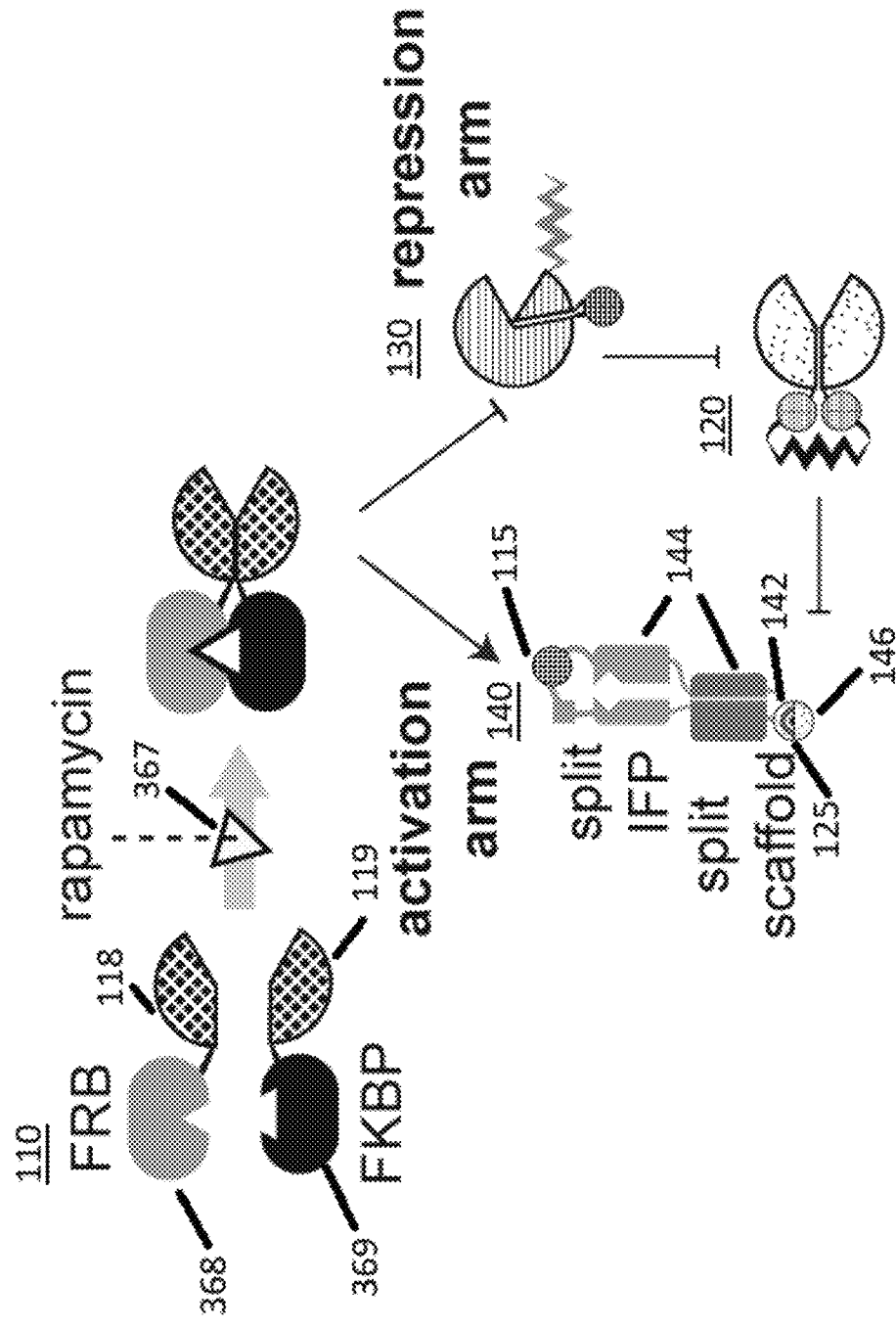

Single transcript adaptive pulse circuit

Time-lapse images of adaptive pulse circuit

Protease regulation of Caspase-3

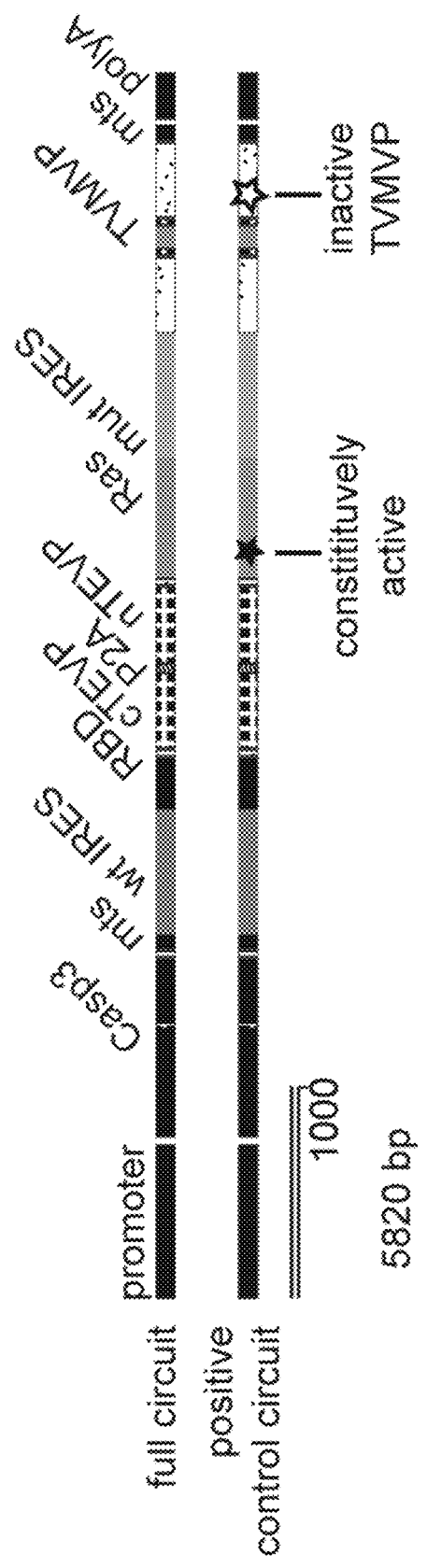

Engineering input and ouput modules of CHOMPKill circuit

Output: membrane-tethered Caspase-3

Input: Ras/Raf pathway

Effect of leucine zipper on repressing split TEVP

Sequence alignment

Three protease cascade

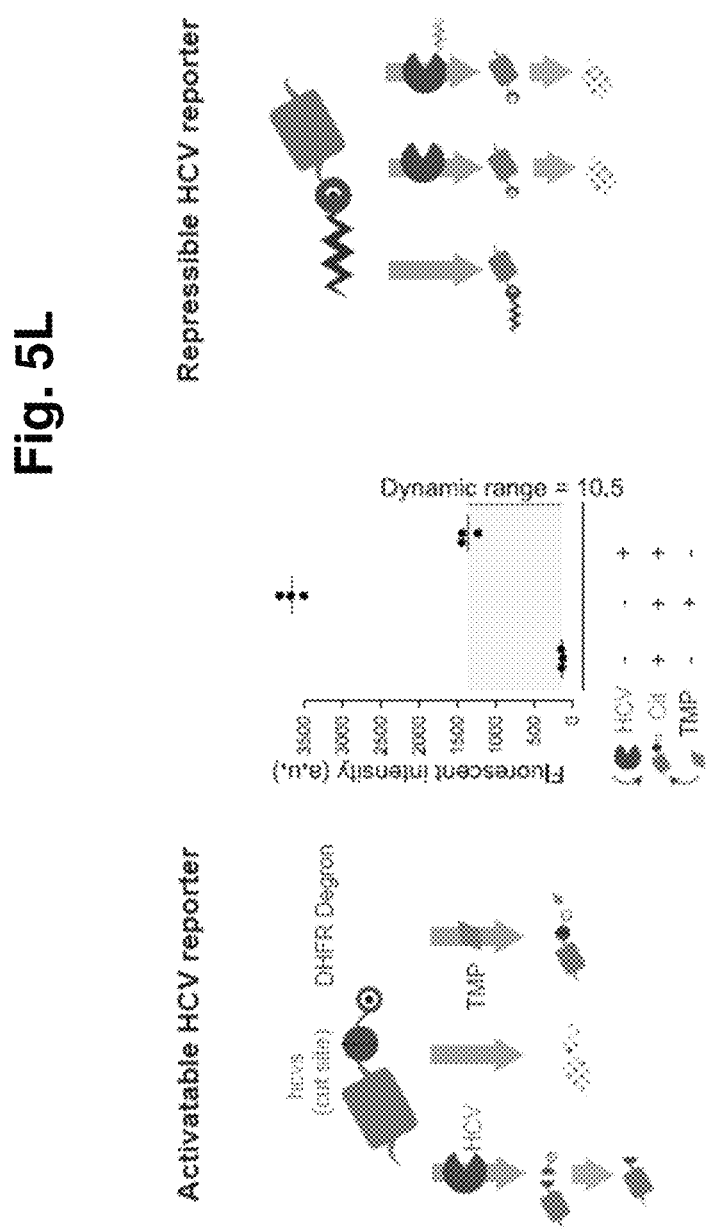

Split TVMV repressed by TEV

One-piece TEV repressed by TVMV

Fig. 5P

One-piece TVMV repressed by HCV

Fig. 5Q

One-piece TVMV repressed by TEV

Expanded schematics for logic gates and each input state

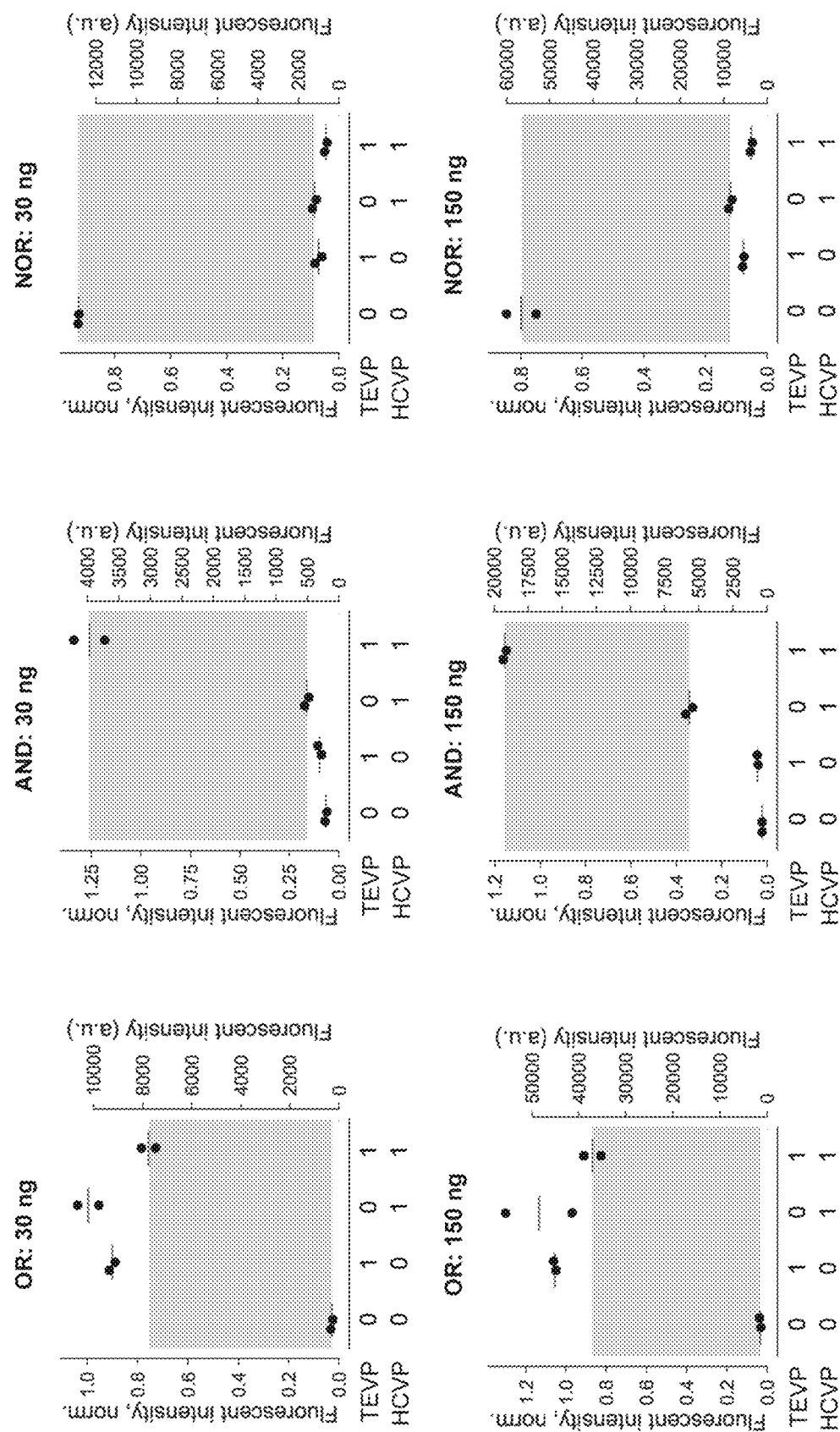

Rapamycin-induced dimerization of TEVP

Flow cytometry analysis of pulse-generation circuit

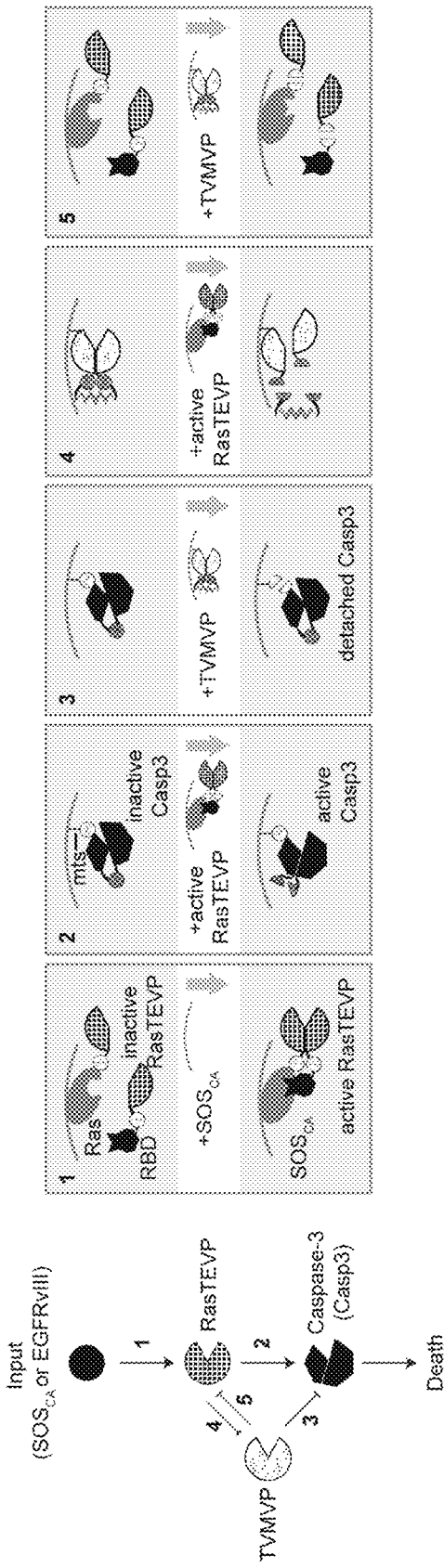

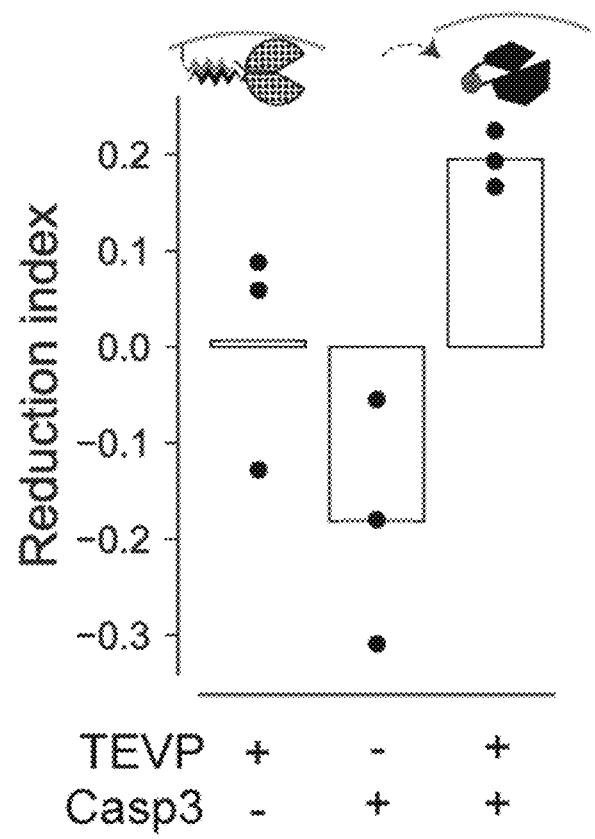

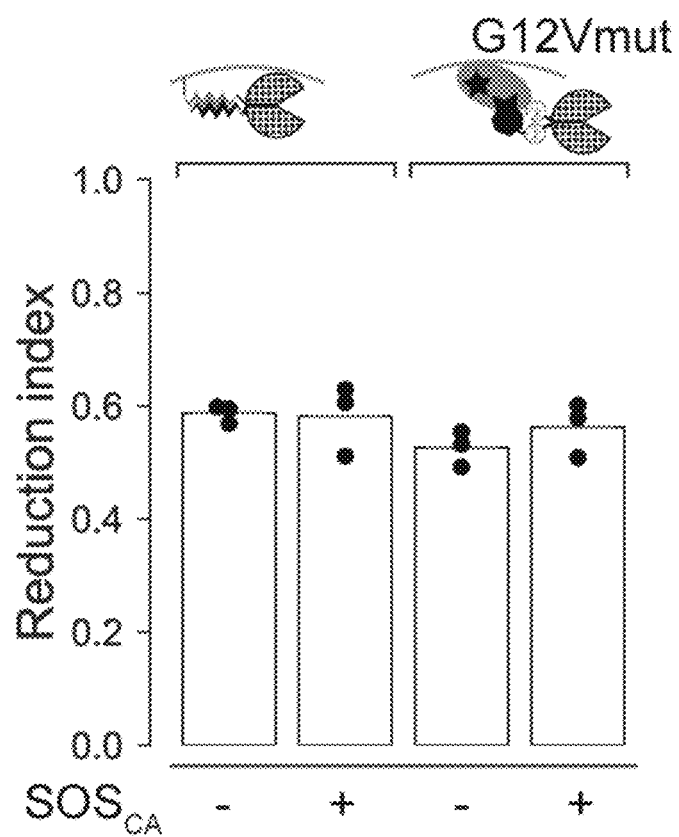

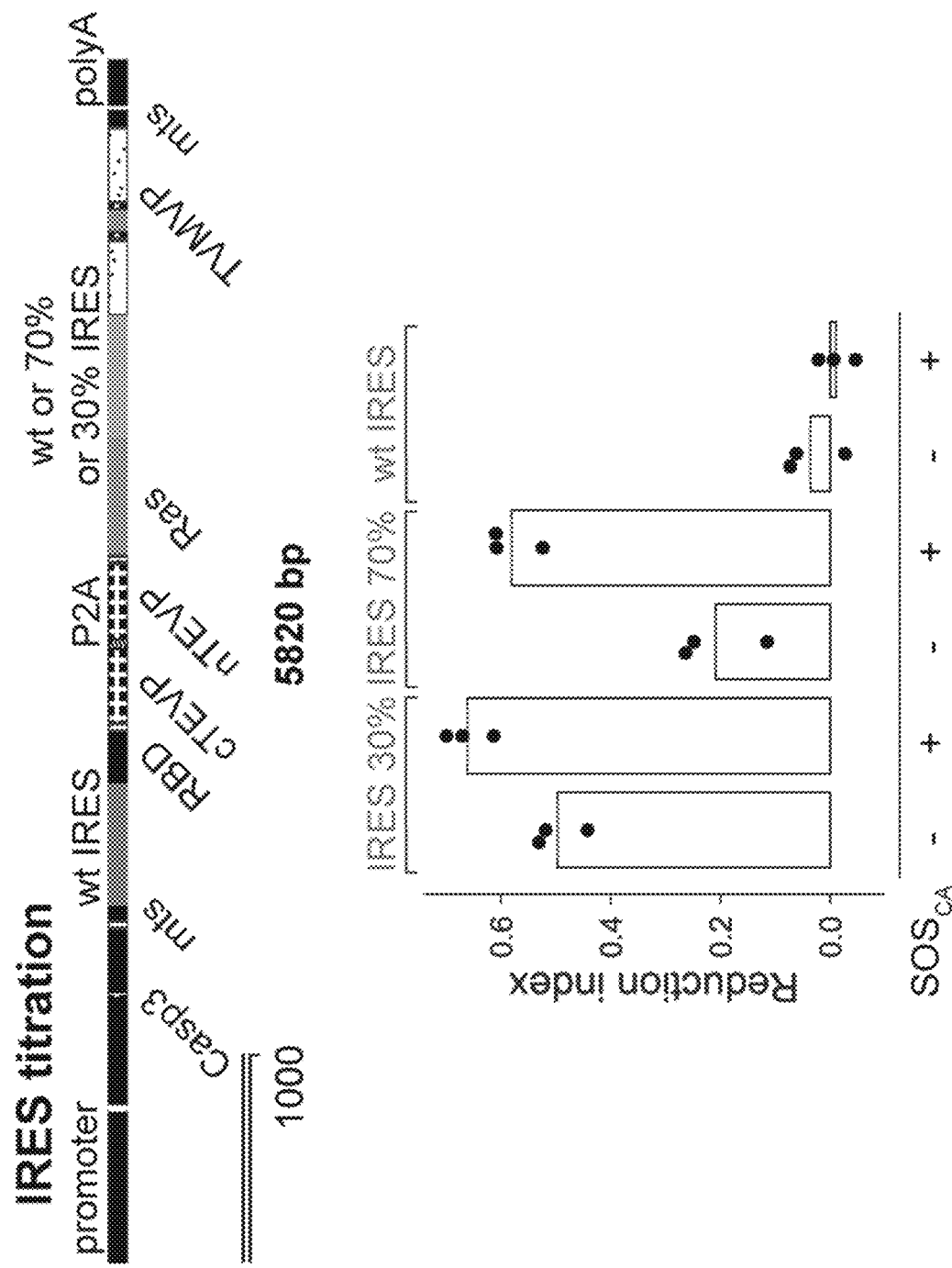

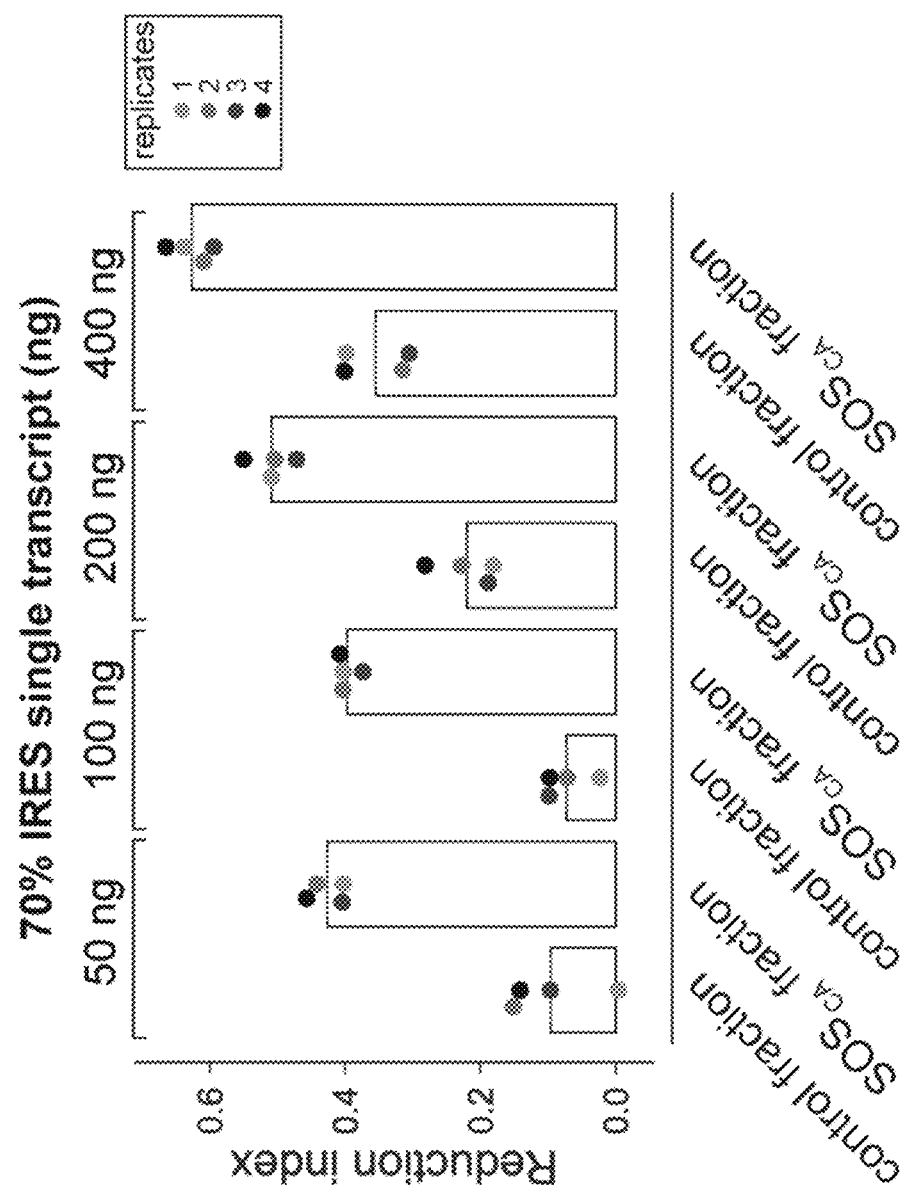

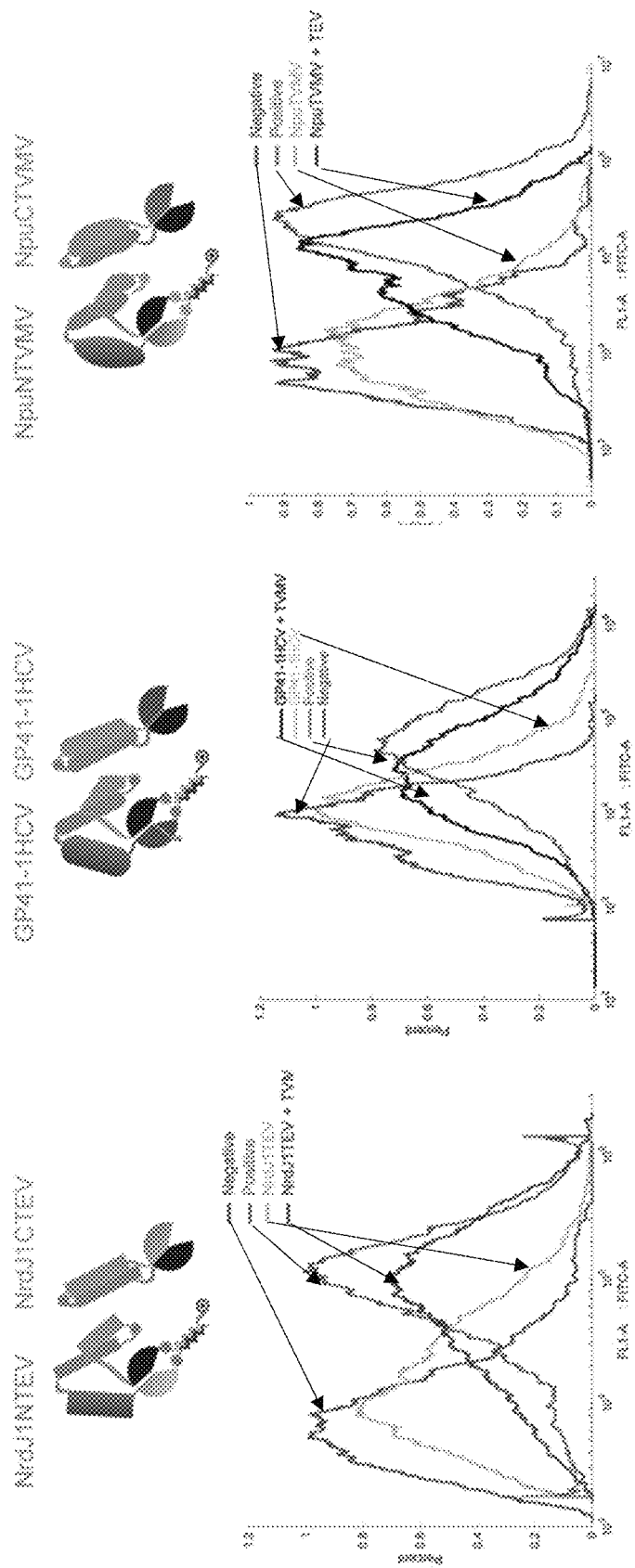

PROGRAMMABLE PROTEIN CIRCUITS IN LIVING CELLS

CROSS-REFERENCE TO RELATED APPLICATIONS

The present application claims priority to U.S. Provisional Application No. 62/619,001, filed Jan. 18, 2018; and U.S. Provisional Application No. 62/688,859, filed Jun. 22, 2018. The entire contents of these applications are hereby expressly incorporated by reference in their entireties.

STATEMENT REGARDING FEDERALLY SPONSORED R&D

This invention was made with government support under Grant No, HR0011-17-2-0008 awarded by DARPA. The government has certain rights in the invention.

FIELD

Some embodiments of the systems, methods and compositions provided herein relate to a compound protease. In some embodiments, the compound protease includes a protease domain and a cut site for another enzyme. In some embodiments, the compound protease includes an association domain. In some embodiments, the compound protease is part of a protein circuit.

BACKGROUND

Synthetic biology may enable design of new functions in living cells. Many natural cellular functions are implemented by protein-level circuits, in which proteins specifically modify each other's activity, localization, or stability. Synthetic protein circuits could provide advantages over gene regulation circuits in enabling the design of new functions in living cells.

SUMMARY

Some embodiments relate to a compound protease, the compound protease comprising: a) a protease domain comprising: a first part of the protease domain, and a second part of the protease domain, wherein when the first part and the second part of the protease domain are associated together, they form an active protease domain, and wherein the first part and the second part of the protease domain do not self-associate on their own to form the active protease domain; b) a cut site, wherein the cut site comprises: a first part of the cut site, wherein the first part of the cut site is linked to the first part of the protease domain; and a second part of the cut site, wherein the second part of the cut site is linked to the second part of the protease domain, wherein when the first and second parts of the cut site are associated together they form an active cut site for an enzyme, and wherein when the active cut site is cut by the enzyme, the first and second parts of the cut site dissociate from one another; and c) an association domain, the association domain comprising: a first part of the association domain that is conjugated to the second part of the cut site; a second part of the association domain that is linked to the second part of the protease domain, wherein the association domain is configured to stabilize the active protease domain. In some embodiments, the first and second parts of the association domain of the compound protease comprise separate peptide strands that hybridize together. In some embodiments, the first and second parts of the association domain of the compound protease are a single peptide strand.

Some embodiments relate to a compound protease, the compound protease comprising: a) a protease domain comprising: a first part of the protease domain, and a second part of the protease domain, wherein when the first part and the second part of the protease domain are associated together, they form an active protease domain, and wherein the first part and the second part of the protease domain do not self-associate on their own to form the active protease domain; b) a cut site, wherein the cut site comprises: a first part of the cut site, wherein the first part of the cut site is linked to the first part of the protease domain; and a second part of the cut site, wherein the second part of the cut site is linked to the second part of the protease domain, wherein when the first and second parts of the cut site are associated together they form an active cut site for an enzyme, and wherein when the active cut site is cut by the enzyme, the first and second parts of the cut site dissociate from one another; c) a first peptide connecting the first part of the protease domain to the first part of the cut site; and d) a second peptide connecting the second part of the protease domain to the second part of the cut site, wherein the first and second linkers are configured to stabilize the active protease domain. In some embodiments, the first peptide connecting the first part of the protease domain to the first part of the cut site comprises a linker. In some embodiments, the second peptide connecting the second part of the protease domain to the second part of the cut site comprises a linker.

Some embodiments relate to a method, comprising: providing a reaction solution with the compound protease and the enzyme; and subjecting the reaction solution to a condition that allows the enzyme to cleave the cut site of the compound protease.

Some embodiments relate to a synthetic protein circuit, comprising: a first protease; and a second protease comprising a cut site specific for the first protease, wherein the second protease is inactivated by cleavage of the cut site specific for the first protease. Some embodiments comprise a target protein comprising: a degron of the target protein that destabilizes the target protein when present on the target protein by enhancing degradation of the target protein, and a cut site specific for the second protease, wherein the target protein is configured to be stabilized or destabilized by cleavage of the cut site specific for the second protease.

In some embodiments of the synthetic protein circuit, the first protease and the second protease each comprise an HCV protease, a TEV protease, or a TVMV protease.

In some embodiments of the synthetic protein circuit, the second protease comprises a first cleavage domain and a second part of the cleavage domain, the first part connecting to the cut site specific for the first protease, and the second part connecting to another cut site specific for the first protease, the second protease's two cut sites specific for the first protease each connecting to an association domain of the second protease such as a leucine zipper. In some embodiments, the second protease's two cut sites specific for the first protease each connect to a separate association domain of the second protease, wherein the second protease is active when the separate association domains bind together, and wherein the second protease is configured to be deactivated by cleavage of either of its two cut sites specific for the first protease. In some embodiments, one of the second protease's association domains comprises a complementary association domain such as leucine zipper that is complementary to the other association domain of the second protease. In some embodiments, the second protease's two cut sites specific for the first protease each connect to a single association domain of the second protease, and wherein the second protease is configured to be deactivated by cleavage of either of its two cut sites specific for the first protease.

In some embodiments of the synthetic protein circuit, the first protease comprises an association domain of the first protease that binds to a complementary association domain of the second protease, thereby enhancing the first protease's ability to cleave a cut site specific to the first protease on the second protease.

Some embodiments of the synthetic protein circuit comprise a third, fourth, fifth, sixth, seventh, eighth, ninth and/or tenth protease, each protease comprising a cut site specific to at least one of the proteases, and wherein each protease is configured to be destabilized or deactivated by cleavage of its cut site.

In some embodiments of the synthetic protein circuit, the target protein's cut site specific to the second protease comprises a first part of the cut site of the target protein and a second part of the cut site of the target protein, the first part of the cut site of the target protein connecting to a domain or motif of the target protein, and the second part of the cut site of the target protein connecting to the degron of the target protein, and wherein the target protein is stabilized by cleavage of its cut site specific for the second protease.

In some embodiments of the synthetic protein circuit, the degron of the target protein comprises a masking peptide that connects to the degron of the target protein and blocks cleavage of the target protein's cut site specific for the second protease, wherein the masking peptide of the degron of the target protein comprises the target protein's cut site specific for the second protease, and wherein the target protein is configured to be destabilized by cleavage of its cut site specific for the second protease, wherein cleavage of the target protein's cut site specific for the second protease uncovers the target protein's degron.

In some embodiments of the synthetic protein circuit, the target protein comprises a protease, a reporter protein, a fluorescent protein, a scaffold, an actuator protein, a transcriptional regulator, or a signaling protein.

Some embodiments relate to a synthetic protein circuit, comprising: a first protease, optionally comprising an association domain of the first protease; a second protease, optionally comprising a complementary association domain of the second protease; and a target protein comprising a degron of the target protein that destabilizes the target protein when present on the target protein by enhancing degradation of the target protein; wherein the target protein is configured to interact with the first protease, the second protease, a third protease and/or a fourth protease to form an OR, AND, NOR, NAND, IMPLY, NIMPLY, XOR or XNOR logic gate.

In some embodiments of the synthetic protein circuit, the target protein comprises a cut site specific for the first protease and a cut site specific for the second protease between the degron of the target protein and a part of the target protein, and wherein the target protein is stabilized by cleavage of either of its cut sites.

In some embodiments of the synthetic protein circuit, the target protein comprises a cut site of the target protein specific for the first protease between the degron of the target protein and a part of the target protein, and a cut site specific for the second protease connected to another degron of the target protein and an optional association domain of the target protein, and wherein the target protein is stabilized by cleavage of both of its cut sites.

Some embodiments of the synthetic protein circuit comprise: a third protease comprising: a cut site specific for the first protease, a cut site specific for the second protease, and an optional association domain of the third protease, wherein the third protease is configured to be deactivated by cleavage of either of its cut sites; and wherein the target protein comprises a cut site specific for the third protease between the degron of the target protein and a part of the target protein, wherein the target protein is stabilized by cleavage of its cut site specific for the third protease. In some embodiments, the third protease comprises a first domain of the third protease and a second domain of the third protease; wherein the first domain of the third protease comprises the third protease's cut sites specific for the first and second proteases and the optional association domain of the third protease; wherein the second domain the third protease comprises another cut site specific for the first protease, another cut site specific for the second protease, and an optional complementary association domain the third protease; and wherein the third protease is configured to be deactivated by cleavage of any of its cut sites.

Some embodiments of the synthetic protein circuit comprise: a third protease comprising a cut site specific for the first protease, and configured to be deactivated by cleavage of its cut site; and a fourth protease comprising a cut site specific for the second protease, and configured to be deactivated by cleavage of its cut site; wherein the target protein comprises a cut site specific for the third and fourth proteases between the degron of the target protein and a part of the target protein, wherein the target protein is stabilized by cleavage of its cut site. In some embodiments, the third protease comprises a first domain of the third protease, a second domain of the third protease, and an optional complementary association domain of the third protease; wherein the first domain of the third protease comprises the cut site specific for the first protease; wherein the second domain of the third protease comprises another cut site specific for the first protease; wherein the complementary association domain the third protease optionally comprises two parts of the third protease, each part, the third protease connected to one of the third protease's cut sites; and wherein the third protease is configured to be deactivated by cleavage of either of its cut sites.

In some embodiments of the synthetic protein circuit, the fourth protease comprises a first domain of the fourth protease, a second domain of the fourth protease, and an optional association domain of the fourth protease; wherein the first domain of the fourth protease comprises the cut site specific for the second protease; wherein the second domain of the fourth protease comprises another cut site specific for the second protease; wherein the association domain of the fourth protease optionally comprises two parts, each part connected to one of the fourth protease's cut sites; and wherein the fourth protease is configured to be deactivated by cleavage of either of its cut sites.

Some embodiments of the synthetic protein circuit comprise: a third protease comprising a cut site specific for the second protease, and configured to be deactivated by cleavage of its cut site; wherein the target protein comprises a cut site specific for the first protease and a cut site specific for the third protease between the degron of the target protein and a part of the target protein, and wherein the target protein is stabilized by cleavage of either cut sites. In some embodiments, wherein the third protease comprises a first domain, a second domain, and an optional association domain; wherein the first domain of the third protease comprises the third protease's cut site specific for the second protease; wherein the second domain of the third protease comprises another cut site specific for the second protease; wherein the association domain of the third protease optionally comprises two parts of the third protease, each part of the third protease connected to one of the third protease's cut sites; and wherein the third protease is configured to be deactivated by cleavage of either of its cut sites.

Some embodiments of the synthetic protein circuit comprise: a third protease comprising a cut site specific for the first protease, and configured to be deactivated by cleavage of its cut site; wherein the target protein comprises a cut site specific for the third protease between the degron and a part of the target protein, and a cut site specific for the second protease connected to another degron of the target protein and an optional association domain of the target protein, and wherein the target protein is stabilized by cleavage of both of its cut sites. In some embodiments, the third protease comprises a first domain of the third protease, a second domain of the third protease, and an optional complementary association domain of the third protease; wherein the first domain of the third protease comprises the cut site specific for the first protease; wherein the second domain of the third protease comprises another cut site specific for the first protease; wherein the complementary association domain of the third protease optionally comprises two parts of the third protease, each part of the third protease connected to one of the third protease's cut sites; and wherein the third protease is configured to be deactivated by cleavage of either of its cut sites.

Some embodiments of the synthetic protein circuit comprise: a second target protein comprising a degron of the second target protein that destabilizes the second target protein when present on the second target protein; wherein the target protein comprises a cut site specific for the first protease between its degron and a part of the target protein, an other degron of the target protein, and a cut site specific for the second protease connected to the other degron of the target protein, wherein the target protein is destabilized by its first degron unless its cut site specific for the first protease is cleaved by the first protease, and wherein the target protein is destabilized by cleavage of its cut site specific for the second protease; and wherein the second target protein comprises a cut site specific for the second protease between its degron and the part of the second target protein, an other degron of the second target protein, and a cut site specific for the first protease connected to the other degron of the second target protein, wherein the second target protein is destabilized by its first degron unless its cut site specific for the second protease is cleaved by the second protease, and wherein the second target protein is destabilized by cleavage of its cut site specific for the first protease. In some embodiments, the second target protein comprises a complementary association domain of the second target protein connected at or near the other degron of the second target protein or the second target protein's cut site specific for the first protease. In some embodiments, the target protein's other degron comprises a masking peptide of the other degron of the target protein connected to the target protein's other degron, wherein the masking peptide of the other degron of the target protein prevents the target protein's other degron from destabilizing the target protein when the masking peptide of the other degron of the target protein is present on the target protein, wherein the masking peptide of the other degron of the target protein is configured to be cleaved from the target protein when the target protein's cut site specific for the second protease is cleaved by the second protease, wherein the target protein is configured to be destabilized by cleavage of its cut site specific for the second protease, wherein cleavage of the target protein's cut site specific for the second protease uncovers the target protein's other degron thereby destabilizing the target protein. In some embodiments, the second target protein's other degron comprises a masking peptide of the other degron of the second target protein connected to the second target protein's other degron, wherein the masking peptide of the other degron of the second target protein prevents the second target protein's other degron from destabilizing the second target protein when the masking peptide of the other degron of the second target protein is present on the second target protein, wherein the masking peptide of the other degron of the second target protein is configured to be cleaved from the second target protein when the second target protein's cut site specific for the first protease is cleaved by the first protease, wherein the second target protein is configured to be destabilized by cleavage of its cut site specific for the first protease, wherein cleavage of the second target protein's cut site specific for the first protease uncovers the second target protein's other degron thereby destabilizing the second target protein.

Some embodiments of the synthetic protein circuit comprise: a third protease comprising a cut site specific for the first protease, a cut site specific for the second protease, and one or more optional association domains of the third protease, wherein the third protease is configured to be deactivated by cleavage of either of its cut sites; wherein the target protein comprises a second degron of the target protein, a cut site specific for the first protease, a cut site specific for the second protease, and two cut sites specific for the third protease, and wherein the target protein is stabilized by cleavage of: its cut site specific for the first protease and its cut site specific for the second protease, or both of its cut sites specific for the third protease.

In some embodiments of the synthetic protein circuit, the third protease comprises a first domain of the third protease and a second domain of the third protease; wherein the first domain of the third protease comprises the cut sites specific for the first and second proteases and the optional association domain of the third protease; wherein the second domain of the third protease comprises another cut site specific for the first protease, another cut site specific for the second protease, and an optional complementary association domain of the third protease; and wherein the third protease is configured to be deactivated by cleavage of any of its cut sites. In some embodiments, the target protein's cut site specific for the first protease and one of the target protein's two cut sites specific for the third protease separate the target protein's first degron from a part of the target protein; and wherein the target protein's cut site specific for the second protease the other of the two cut sites specific for the third protease, and the association domain of the target protein separate the target protein's second degron from the part of the target protein.

Some embodiments relate to a system such as a synthetic protein circuit, comprising: a first protease; a second protease; and target proteins each comprising: a first degron of the target protein that destabilizes the target protein when present on the target protein by enhancing degradation of the target protein, a cut site specific for the first protease between the degron of the target protein and a part of the target protein, wherein the target protein is configured to be stabilized by cleavage of its cut site specific for the first protease, and a cut site specific for the second protease connected to another degron of the target protein, wherein the target protein is configured to be destabilized by cleavage of the cut site specific for the second protease regardless of whether the first degron of the target protein is present on the target protein. In some embodiments, the other degron of each target protein comprises a conditional N-end degron such as an N-end degron that is conditional on cleavage of the cut site specific for the second protease. Some embodiments comprise a third protease comprising a cut site specific for the second protease, wherein the third protease is configured to be deactivated by cleavage of its cut site specific for the second protease; and wherein the second protease comprises a cut site specific for the third protease, wherein the second protease is configured to be deactivated by cleavage of its cut site specific for the third protease. In some embodiments, the second protease comprises a first domain of the second protease, a second domain of the second protease, a first complementary association domain, and an optional second complementary association domain of the second protease connected to the first or second domain of the second protease; wherein the first domain of the second protease comprises the cut site specific for the third protease; wherein the second domain of the second protease comprises another cut site specific for the third protease; wherein the first complementary association domain of the second protease optionally comprises two parts of the complementary association domain of the second protease, each part of the complementary association domain of the second protease connecting to one of the second protease's cut sites specific for the third protease; and wherein the second protease is configured to be deactivated by cleavage of either of its cut sites. In some embodiments, the third protease comprises an optional association domain of the third protease, and wherein cleavage of the third protease's cut site by the second protease removes at least part of a cleavage domain of the third protease, thereby deactivating the third protease. In some embodiments, the stability of the target proteins comprises an analog behavior that is dependent on a concentration of the first protease, wherein a higher concentration of the first protease has a greater stabilizing effect on the target proteins than a lower concentration of the first protease. In some embodiments, the stability of the target proteins comprises an analog behavior that is dependent on a concentration of the second protease, wherein a higher concentration of the second protease has a greater destabilizing effect on the target proteins than a lower concentration of the second protease. In some embodiments, the concentration of the second protease is decreased by a higher concentration of the third protease as compared to a lower concentration of the third protease or by a higher amount of a nucleic acid encoding the third protease as compared to a lower amount of a nucleic acid encoding the third protease. In some embodiments, the analog behavior of the target protein that is dependent on a concentration of the second protease is more sharp and/or comprises a greater threshold for destability of the target protein at a higher concentration of the third protease as compared to a lower concentration of the third protease, or at a higher amount of a nucleic acid encoding the third protease as compared to a lower amount of a nucleic acid encoding the third protease. In some embodiments, the analog behavior of the target protein comprises a bandpass behavior. In some embodiments, the first protease comprises a first domain of the first protease and a second domain of the first protease; wherein the first domain of the first protease connects to a first conditional dimerization domain of the first protease; wherein the second domain of the first protease connects to a second conditional dimerization domain of the first protease; wherein the first and second conditional dimerization domains of the first protease are configured to dimerize with each other upon binding a dimerizing agent. In some embodiments, the conditional dimerization domains of the first protease each comprise one of an FK506 binding protein (FKBP), GyrB, GAI, Snap-tag, eDHFR, BCL-xL, CalcineurinA (CNA), CyP-Fas, FRB domain of mTOR, GID1, HaloTag, and/or Fab (AZ1). In some embodiments, the dimerizing agent comprises FK1012, FK506, FKCsA, Rapamycin, Coumermycin, Gibberellin, HaXS, TMP-HTag, or ABT-737.

Some embodiments relate to a method of activating a signaling pathway in a cell, comprising providing to the cell a synthetic protein circuit or a nucleic acid encoding the synthetic protein circuit, the synthetic protein circuit comprising: a protease comprising a first part of the protease and a second part of the protease, the first part of the protease connecting to a signaling protein, and the second part of the protease connecting to a binding protein that binds to an activated form of the signaling protein, wherein the first part and the second part are configured to form an active protease when the binding protein binds to the activated form of the signaling protein; and an effector protein comprising a cut site specific for the protease, wherein the effector protein configured to be activated by cleavage of its cut site specific for the protease.

In some embodiments of the method, the synthetic protein circuit comprises a second protease that inactivates the first protease and/or the effector protein. In some embodiments, the signaling pathway comprises a cell death pathway. In some embodiments, the signaling protein comprises a signal transduction protein such as Ras or a fragment thereof. In some embodiments, the binding protein comprises Raf or a fragment thereof such as a Ras-binding domain (RBD). In some embodiments, the effector protein comprises a protease or cell death protein such as a caspase.

Some embodiments relate to a nucleic acid encoding all or a portion of a synthetic protein circuit as described herein. In some embodiments, the nucleic acid comprises DNA. In some embodiments, the DNA comprises a vector configured for transient expression in a cell. In some embodiments, the DNA comprises an expression construct configured to integrate into a host cell's DNA. In some embodiments, the nucleic acid comprises RNA such as an mRNA.

Some embodiments relate to a compound protease, the compound protease comprising: a) a protease domain comprising: a first part of the protease domain, and a second part of the protease domain, wherein when the first part and the second part of the protease domain are associated together, they form an active protease, and wherein the first part and the second part of the protease domain do not self-associate on their own to form the active protease; and b) a cut site, wherein the cut site comprises: a first part of the cut site, wherein the first part of the cut site is linked to the first part of the protease domain; and a second part of the cut site, wherein the second part of the cut site is linked or indirectly connected to the second part of the protease domain, wherein when the first and second parts of the cut site are associated together they form an active cut site for an enzyme, and wherein when the active cut site is cut by the enzyme, the first and second parts of the cut site dissociate from one another.

In some embodiments of the compound protease, the first part of the cut site is covalently linked to the first part of the protease domain by a first peptide linkage, and/or wherein the second part of the cut site is covalently linked to the second part of the protease domain by a second peptide linkage. In some embodiments, the first peptide linkage comprises a linker peptide comprising 1-10, 10-25, 25-50, 50-100, or 100-1000 amino acids. In some embodiments, the second peptide linkage comprises a linker peptide comprising 1-10, 10-25, 25-50, 50-100, or 100-1000 amino acids.

In some embodiments of the compound protease, the second part of the protease domain comprises a part of an association domain connected to the second part of the protease domain, wherein the part of the association domain connected to the second part of the protease domain is configured to recruit the enzyme to the active cut site by binding a second part of the association domain on the enzyme.

Some embodiments of the compound comprise a second cut site, wherein the second cut site comprises: a first part of the second cut site, wherein the first part of the second cut site is linked to the second part of the protease domain; and a second part of the second cut site, wherein the second part of the second cut site is linked or indirectly connected to the first part of the protease domain; wherein when the first and second parts of the second cut site are associated together they form an active second cut site for the enzyme, and wherein when the active second cut site is cut by the enzyme, the first and second parts of the second cut site dissociate from one another. Some embodiments comprise an association domain the association domain comprising: a first part of the association domain, conjugated to the second part of the first cut site; a second part of the association domain, conjugated to the second part of the second cut site, wherein the association domain is configure to stabilize the active protease domain. In some embodiments, the first part of the cut site is covalently linked to the first part of the protease domain by a first peptide linkage, and/or wherein the first part of the second cut site is covalently linked to the second part of the protease domain by a second peptide linkage. In some embodiments, the first peptide linkage comprises a linker peptide comprising 1-10, 10-25, 25-50, 50-100, or 100-1000 amino acids. In some embodiments, the second peptide linkage comprises a linker peptide comprising 1-10, 10-25, 25-50, 50-100, or 100-1000 amino acids. In some embodiments, the second part of the cut site is indirectly connected to the second part of the protease domain through the association domain, wherein the first and second parts of the association domain are covalently or non-covalently linked together.

Some embodiments of the compound protease comprise an association domain of the compound protease comprising a first part and a second part, wherein the first part of the association domain links to the second part of the first cut site, and wherein the second part of the association domain links to the second part of the second cut site. In some embodiments, the first part of the cut site is covalently linked to the first part of the protease domain by a first peptide linkage, and/or wherein the first part of the second cut site is covalently linked to the second part of the protease domain by a second peptide linkage. In some embodiments, the first peptide linkage comprises a linker peptide comprising 1-10, 10-25, 25-50, 50-100, or 100-1000 amino acids. In some embodiments, the second peptide linkage comprises a linker peptide comprising 1-10, 10-25, 25-50, 50-100, or 100-1000 amino acids. In some embodiments, the second part of the cut site is indirectly connected to the second part of the protease domain through the association domain (for example, as in FIGS. 1A and 1B). In some embodiments, the association domain connecting to the second part of the cut site and to the to the second part of the second cut site is configured to recruit the enzyme to the active cut site and/or to the active second cut site by binding a second part of the association domain on the enzyme.

Some embodiments relate to system such as a synthetic protein circuit, comprising: a first protease; a second protease; and a target protein comprising: one or more cut sites specific for a first, second, and/or third protease, and a degron of the target protein configured to stabilize or destabilize the target protein based on its configuration with one or more of the target protein's cut sites specific for the first, second, and/or third proteases. In some embodiments, the first protease comprises a first domain of the first protease and a second domain of the first protease; wherein the first domain of the first protease connects to a first conditional dimerization domain of the first protease; wherein the second domain of the first protease connects to a second conditional dimerization domain of the first protease; wherein the first and second conditional dimerization domains of the first protease are configured to dimerize with each other upon binding a dimerizing agent.

In some embodiments of the synthetic protein circuit or method, the/a first protease, second protease, third protease, and/or fourth protease comprises a compound protease as described herein.

BRIEF DESCRIPTION OF THE DRAWINGS

FIGS. 1D-1J depict information relating to design of composable protein circuit components of some embodiments. FIG. 1D, Composable protein units can regulate one another in arbitrary configurations with diverse functions (middle). Protein-level circuits can interface directly with endogenous protein pathways and operate without modifying the genome or entering the nucleus. (right). FIG. 1E, The protease-activatable reporter can be stabilized by removal of a DHFR degron through protease cleavage of a corresponding target site. TMP inhibits the degron, and thus stabilizes the reporter. Middle, flow cytometry distributions of reporter fluorescence with or without TEVP. Distributions are limited to the gated area in FIG. 5A. Solid curves indicate skew Gaussian fits. Vertical dashed lines and stars indicate distribution modes, which are plotted in subsequent figure panels. Right, analysis of reporter response to TMP and/or TEVP. Each dot represents one replicate. Stars indicate data from middle panel. FIG. 1F, In the protease-repressible reporter, protease cleavage exposes an N-end degron (covered target) to destabilize reporter. FIG. 1G, Three proteases (columns) exhibit orthogonal regulation of three reporters (rows). Mean fluorescent intensity of 3 independent measurements were normalized to the TMP-stabilized value of its corresponding reporter. FIG. 1H, Design for some protease-repressible proteases. TEVP was split as indicated and then reconstituted through dimerizing leucine zippers. A leucine-zipper-tagged HCVP can dock with the target TEVP and cleave it to remove leucine zippers, effectively repressing TEVP. TVMVP can be regulated using the same design. FIG. 1I, A single-chain variant of the HCV-repressible TEVP allows docking of, and repressive cleavage by, HCVP. FIG. 1J, Protease regulation can propagate through a three-stage cascade. Repressible HCVP uses a variant design, in which TEVP cleavage separates core HCVP from its docking leucine zipper and activity-enhancing co-peptide.

FIG. 1K depicts a legend for the symbols shown in FIGS. 1A-1J and in other Figures.

FIG. 1L depicts some examples of protein circuits and their use.

FIGS. 2A-2I depict example CHOMP circuits implementing binary logic gates in accordance with some embodiments. For each indicated gate, TEVP and HCVP served as binary inputs, which were either included or excluded in transfections. Citrine fluorescence serves as gate output. The design and performance of each non-trivial two-input logic gate is shown for triplicate experiments (black dots). Fluorescent intensity in each panel was normalized to the corresponding reporter stabilized with TMP (for gates containing only C-terminal degrons) or Shield-1+TMP (for gates containing degrons at both termini). Grey regions indicate range from maximum "OFF" value to minimum "ON" value for that gate.

FIGS. 3A-3H depict information relating to bandpass filtering and pulse generation circuits according to some embodiments. FIG. 3A, For bandpass filtering, the expression of co-regulated inputs TEVP and TVMVP were controlled by the amount of transfected DNA, or by doxycycline (square) induction. The amount of HCVP plasmid can be varied to tune the repression arm. FIG. 3B, Input-output curve of the activation arm in the absence of TVMVP. Here and in subsequent panels, dots indicate duplicate measurements, and curve is a model fit. FIG. 3C, Input-output curve of the repression arm, in the presence of constant TEVP and increasing levels of HCVP, which increased the repression threshold and sharpens the response. FIG. 3D, Bandpass behavior of a complete circuit. Increasing HCVP expression shifted the position and increases the amplitude of the peak response. Data in FIGS. 3B-3D were normalized to the TMP-stabilized reporter. FIG. 3E, Delayed repression can enable pulse generation. In this design, rapamycin-induced dimerization of FKBP and FRB domains reconstituted TEVP. Cleavage of the reporter by TEVP allowed maturation of far-red fluorescent protein (IFP, FIG. 8D). FIG. 3F, The pulse circuit was completely encoded on a single transcript, with protein components (indicated) separated by "self-cleaving" sequences (T2A, P2A). FIG. 3G, Filmstrips of a single cell stably incorporating both the pulse generation circuit, as well as a constitutive Cerulean segmentation marker. After rapamycin induction (t=0), the output IFP signal increased and then decayed, while Cerulean signal remained constant. FIG. 3H, Traces of IFP fluorescence in 24 individual cells. This analysis omitted cells that exhibited phototoxicity or moved out of the field of view. Black line indicates median fluorescence over all cells at each time point.

FIGS. 4A to 4E depict information relating to example CHOMP circuits that enable conditional activation of Casp3 in Ras-activating cells. FIG. 4A, The core circuit (left) links Ras activation by $SOS_{CA}$ or EGFRvIII to Casp3 activation. The full circuit (right) incorporates an additional TVMVP component to enhance selectivity. New regulatory features introduced in this circuit are explained schematically in corresponding numbered boxes. Box 1, input from upstream activators of Ras such as $SOS_{CA}$ and EGFRvIII activates Ras, causing it to bind RBD, reconstituting RasTEVP. Box 2, Engineered Casp3 tagged with a membrane localization sequence ("mts") can be converted from an inactive to an active state by TEVP cleavage. Box 3, TVMVP cleavage detaches Casp3 from the membrane, reducing its ability to be activated by membrane-localized TEVP. FIG. 4B, TEVP activates the engineered Casp3, while TVMVP inhibits this activation. Cells transfected with indicated components were analyzed to determine the reduction index (percentage of cell number reduction compared to cells transfected with only a fluorescent marker, see FIG. 9B). FIG. 4C, The core circuit preferentially reduced cell number in the presence of ectopic $SOS_{CA}$. The full circuit exhibited improved selectivity. FIG. 4D, The full circuit (top diagram) and a positive control circuit incorporating a G12V mutation that makes Ras constitutively active and a C152A mutation that abolishes TVMVP activity (bottom diagram) were each encoded as a single transcript. FIG. 4E, In a mixed population, the single-transcript circuit (FIG. 4D, top) conditionally reduced the number of EGFRvIII cells (left) and $SOS_{CA}$ cells (right) compared to that of co-cultured control cells. The positive control circuit (FIG. 4D, bottom) reduced the number of both fractions. Dashed line indicates the upper limit of reduction index measured with the positive control circuit.

FIG. 5A, Three representative log-log flow cytometry scatter plots showing autofluorescence as well as reporter co-transfected with and without TEVP. Citrine signal is represented on the y-axis and the co-transfection marker mCherry on the x-axis. Dashed lines indicate the gate on mCherry expression analyzed in FIG. 1E. The histograms and data points are the same as in FIG. 1E, except for the additionally displayed autofluorescence distribution. FIG. 5B, Dose-response curves for activatable (left) and repressible (right) TEVP reporters (indicated schematically above each plot). The solid lines are fits based on the same equations as those used in bandpass analysis. FIG. 5C, FIG. 5D, Reporters activatable (left) and repressible (right) by TVMVP (FIG. 5C) and HCVP (FIG. 5D). The designs are identical to those of the TEVP reporters with two exceptions: First, the specific cleavage site sequences have been replaced with those of the regulatory protease. Second, the repressible HCVP reporter contains an additional leucine zipper compared to the other constructs, and it exhibits stronger repression when HCVP is tagged with the complementary leucine zipper (both shown in schematic, right-hand side of (FIG. 5D). FIG. 5E, Incorporating a leucine zipper (zig-zag) on HCVP (left) enhances repression of TEVP but has minimal effects when used on TVMVP (right). FIG. 5F, Alignment of TEVP and TVMVP sequences enables identification of TVMVP split site (vertical bars). FIG. 5G, A similar design enables repression of split TVMVP by TEVP. FIG. 5H, TVMVP can repress a single-chain TEVP. FIG. 5I, The single-chain TVMVP is repressed by HCVP (left) and TEVP (right). FIG. 5J, An alternative three protease cascade, distinct from that in FIG. 1J, can also propagate signals.

FIGS. 5K-5R depict non-limiting examples of target proteins and synthetic protein circuits in accordance with some embodiments.

FIGS. 6A-6C depict expanded schematics for examples of logic gates and characterization of examples of OR, AND, and NOR logic gates. FIG. 6A, Expanded schematic diagrams of logic gates for each input state. For each gate, the corresponding diagram is shown on top, followed by the expected behavior in each of the four input states, with or without TEVP and HCVP. The presence of Citrine indicates the "ON" output state, while degraded Citrine (shown as chopped up reporter) represents the "OFF" state. FIG. 6B, Responses of logic gates across 16 input concentration combinations for OR, AND, and NOR gates. Fluorescent intensities were normalized to the corresponding reporter stabilized with TMP (OR and NOR) or TMP and SHIELD1

(AND). In each case, reporter was used at a concentration of 150 ng. FIG. 6C, Varying reporter expression levels by transfecting OR, AND, and NOR reporter plasmids at 30 ng and 150 ng. Left axis displays fluorescent intensity values normalized to reporter stabilized with TMP or TMP and SHIELD1 Inputs TEVP and HCVP at 150 ng each. Right axis shows raw fluorescent intensity values.

FIG. 7A, Characterization of OR, AND, and NOR gates using small molecule inputs. Asunaprevir (ASV), an inhibitor of HCVP and rapamycin, a chemical inducer of dimerization of a FRB/FKBP and thereby an inducer of split TEVP, were used as inputs. Each plot shows the output behavior in the presence or absence of each of the two small molecule inputs. The expected presence or absence of input protease activities is shown below the inducer rows. FIG. 7B, NOR gates can be composed. Left, diagram of nested NOR gate. In this example, soybean mosaic virus protease (SMVP) and herpes simplex virus Protease (HSVP) are inputs to HCVP activity. HCVP and TEVP are, in turn, inputs to TVMVP. Finally, TVMVP stabilizes the Citrine reporter. Right, performance of the nested NOR gate with protease inputs SMBVP, HSVP, and TEVP indicated in graph. SMVP at 80 ng, HSVP at 150 ng, TEVP at 30 ng, HCVP at 100 ng, and TVMVP at 100 ng.

FIG. 8A, Linear correlation between the amount of transfected DNA and Citrine expression from CMV promoter. FIG. 8B, Bandpass behavior in response to TEVP and TVMVP expressed at constant DNA concentration but with different levels of induction by tetracycline analog 4-epi-Tc, x-axis). FIG. 8C, A TEVP variant activated by rapamycin-mediated dimerization of FKBP and FRB domains exhibits rapamycin-dependent activation. FIG. 8D, Left, diagram for activation of the IFP reporter by TEVP cleavage. Right, flow cytometry analysis of the dynamics of the pulse generation circuit (also see FIGS. 3E and 3F for diagrams). Each dot represents the mode of the reporter fluorescence distribution at each time point. These data were obtained with the same stable cell line as in FIG. 3H.

FIGS. 9A-9G show information relating to characterization and optimization of circuits that selectively activate Casp3 in response to Ras activation in accordance with some embodiments. FIG. 9A, Expanded schematic diagram of the full circuit and each of its regulatory interactions (numbered arrows and corresponding boxes). FIG. 9B, Example of reduction index analysis. The reduction index is calculated by comparing the number of surviving transfected cells in experimental vs. Citrine-only conditions, normalized to their respective untransfected populations, as shown in the equation. Dashed lines indicate individual Gaussian distributions in the two-component fit, and their sum. FIG. 9C, Response of RasTEVP to physiological ligand epidermal growth factor, EGF. Left, diagram for activation of the membrane-localized IFP reporter (same as iTEV used in the pulse circuit (FIG. 3E) but with an additional 12 amino-acid N-terminal signal peptide from Lyn for membrane localization) by RasTEVP cleavage upon EGF stimulation. Right, co-transfection of iTEV reporter and RasTEVP or constitutively dimerized membrane-localized TEVP ('neg ctrl TEVP'). Left two bars show RasTEVP activation in response to EGF. Right two bars show negative control TEVP's relatively lower response to EGF stimulation. These transfections included 25 ng of RasTEVP and 5 ng each for the negative control TEVP components. EGF was used at 25 ng/mL. FIG. 9D, Cytoplasmic TEVP-activatable Casp3 causes limited reduction of cell number in the presence of membrane-localized TEVP reconstituted through leucine zippers (compare to FIG. 4B). FIG. 9E, Reduction index is unaffected by $SOS_{CA}$ status in the presence of constitutive Casp3 activation with no Ras-dependent regulation (Casp3 not depicted). For the left bars, TEVP is constitutively active through the membrane-tethered leucine zippers. The right bars uses a G12V mutation in Ras that renders it constitutively active. FIG. 9F, The effects of RasTEVP and Casp3 doses on reduction index. Each bar represents the reduction indices from indicated concentrations of RasTEVP and Casp3 plasmids in control or $SOS_{CA}$ cells. FIG. 9G, Dose of TVMVP tunes the circuit's selectivity for $SOS_{CA}$ cells (the first and fourth pairs of bars also shown in FIG. 4C). 90 ng of RasTEVP and Casp3 were transfected in each case.

FIGS. 10A-10D show information relating to characterization and optimization of example circuits that selectively activate Casp3 in response to Ras activation in accordance with some embodiments. FIG. 10A, Analysis of contributions of individual regulatory edges in FIG. 9A to overall selectivity. Left, removing TVMVP→Casp3 (Arm 3) increases reduction index for both control and $SOS_{CA}$ cells; middle, removing RasTEVP→TVMVP (Arm 4) decreases reduction in $SOS_{CA}$ cells; right, removing TVMVP→RasTEVP (Arm 5) has no significant effect. Despite the qualitatively consistent selectivity, there is quantitative day-to-day variability. FIG. 10B, IRES variants with reported strengths of 30% and 70% of wild-type strength can be used to optimize TVMVP expression level in a single transcript. The IRES variant reported to express at ~70% level of wild type balances survival of control cells and reduction of $SOS_{CA}$ cells. 200 ng for each single-transcript variant. FIG. 10C, Optimizing transfection dose for full single-transcript circuit with 70% IRES. Each pair of bars represents 4 replicate co-cultures (gray dots) of control and $SOS_{CA}$ cells transfected with the indicated amount of the single-transcript circuit. FIG. 10D, Annexin V staining of control, $SOS_{CA}$ and EGFRvIII+ cells. Transfection of a negative control, full circuit and the positive control circuit from FIG. 4D into each cell line at 50 ng each. The fraction of apoptotic cells in all conditions was smaller than what would be indicated by reduction index, as expected due to heterogeneity in the timing of initiation of apoptosis and the loss of Annexin-V+ cells due to cell death. The two effects together caused any given time window to capture only a fraction of the cumulative number of Annexin-V+ cells over the whole time-course.

FIG. 13A, Design for protease-activatable proteases. TVMVP is expressed as a single-chain split variant with dimerizing leucine zippers. As indicated the caged TVMVP has an active N-terminal half (nTVMVP) and inactive C-terminal half (cTVMVP). A leucine-zipper tagged active cTVMVP is co-expressed. An active TEVP can cleave the caging inactive cTVMVP away, allowing active nTVMVP to dimerize with active cTVMVP, effectively activating TVMVP. FIG. 13B, The same design can be applied to TEVP activated by TVMVP. B, A new tripartite split HCVP where the active HCVP lobe is split in half. The N-terminal half is co-expressed with the activating co-peptide. Dimerization of the two halves with leucine zippers reconstitutes activity. FIG. 13C, Activatable HCVP by TEVP. FIG. 13D, Comparison between the same single-caged design applied to TEVP and a double-caged design in which both halves of the TEVP are caged by inactive domains.

FIGS. 14A-14C depict information relating to a non-limiting example of an intein zymogen design to activate proteases. FIG. 14A, Intein zymogens along with 'caging' exteins of inactive protease halves decreases basal splicing. FIG. 14B, Leucine zippers along with the extein inactive protease cage and intein zymogen (ZEI-cage) enhance protease activation. FIG. 14C, ZEI-cage is modular and can activate orthogonal intein pairs, NrdJ1, GP41-1, and Npu, as shown with NrdJ1 TEVP, GP41-1 HCVP, and Npu TVMVP.

DETAILED DESCRIPTION

Some embodiments of the systems, methods and compositions described herein relate to a compound protease. In some embodiments, the compound protease comprises a protease domain with a cut site for another protease, wherein the compound protease is deactivated by cleavage of cut site for the other protease. In some embodiments, the compound protease is activated or deactivated by another protease, thereby forming a protein circuit. The protein circuits may be programmable with different variations on the proteases and their targets to, for example, perform logic gate functions, or be part of bandpass or adaptive pulse circuits. Applications include use in kill switches, synthetic circuits, therapeutics, gene drive payloads, cell fate control, extracellular protein circuits such as those that control clotting, and subcellular functions.

Described herein are methods, compositions, and systems for engineering viral proteases to regulate one another and/or target proteins. It is herein shown that the methods enable engineering of circuits that perform regulatory cascades, binary logic computations, analog band-pass signal processing, generation of dynamic behaviors such as pulsing, coupling to endogenous cellular states such as oncogene activation, and/or the ability to control cellular behaviors such as apoptosis. The flexibility and scalability of the system enables it to be reconfigured to implement a broad range of additional functions in some embodiments. The circuits can also be encoded and delivered to cells in multiple formats, including DNA, RNA, and at the protein level itself, enabling versatile applications with or without genomic integration or mutagenesis.

Figure 1A:
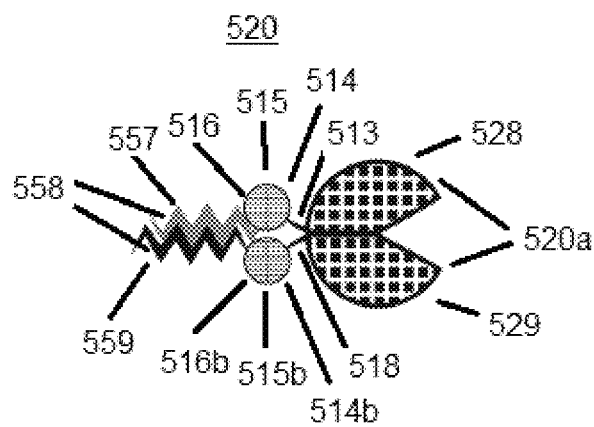
FIGS. 1A-1C depict nonlimiting examples of compound proteases as described herein.
Figure 1B:
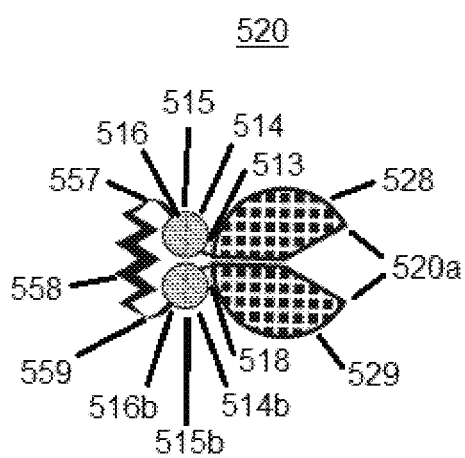
Figure 1C:
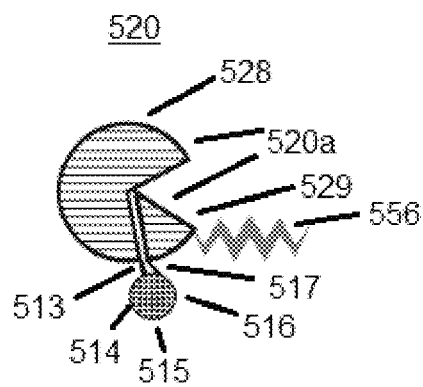

Some non-limiting examples of compound proteases are shown in FIGS. 1A-1C In some embodiments, the compound protease 520 comprises a) a protease domain 520a comprising: a first part 528 of the protease domain 520a, and a second part 529 of the protease domain 520a, wherein when the first part 528 and the second part 529 of the protease domain 520a are associated together, they form an active protease domain 520a, and wherein the first part 528 and the second part 529 of the protease domain 520a do not self-associate on their own to form the active protease domain 520a; b) a cut site 515, wherein the cut site 515 comprises: a first part 514 of the cut site 515, wherein the first part 514 of the cut site 515 is linked to the first part 528 of the protease domain 520a; and a second part 516 of the cut site 515, wherein the second part 516 of the cut site 515 is linked to the second part 529 of the protease domain 520a, wherein when the first and second parts 514, 516 of the cut site 515 are associated together they form an active cut site 515 for an enzyme, and wherein when the active cut site 515 is cut by the enzyme, the first and second parts 514, 516 of the cut site 515 dissociate from one another; and c) an association domain 558, the association domain 558 comprising: a first part 557 of the association domain 558 that is conjugated to the second part 516 of the cut site 515; a second part 559 of the association domain 558 that is linked to the second part 529 of the protease domain 520a, wherein the association domain 558 is configured to stabilize the active protease domain 520a.

As described herein, a "compound protease" refers to a protease with at least two parts of a protease domain. The parts may be linked together by one or more cut sites such as a cut site specific for another protease. The parts of the protease domain may but need not be separate subunits of the protease, or may include separate portions of a peptide or peptides that makes up the protease.

As described to herein, a "protease domain" includes one or more peptides that when associated together have protease activity. For example, the protease activity may be the ability to cleave another peptide.

As described herein, a "cut site" is a peptide sequence specific for one or more proteases that when recognized or bound by the one or more proteases are cleaved by the one or more proteases. The peptide sequence of the cut site may be specific for one protease or a type of proteases, or may be general to multiple proteases or types of proteases.

As used herein, "linked" or "connected" may mean directly or indirectly linked or connected. A non-limiting example of a direct link or connection includes a covalent bond such as a peptide, amino, amide, or phosphodiester bond. Another non-limiting example of a direct link or connection includes a noncovalent bond such as a hydrogen bond, a hydrophobic bond, or a hydrophilic bond. A non-limiting example of an indirect link or connection between two molecules is a covalent or noncovalent bond between each of the two molecules but where the bond is to a third molecule (such as an association domain) that binds to each of the two molecules.

As used herein, "stabilize" may refer to the ability of a peptide or molecule to maintain the same or another molecule or peptide in a particular state such as an active conformation. "Stabilize" may also refer to the ability of a peptide or molecule to prevent or decrease the amount of degradation that the same or another molecule or peptide faces.

As used herein, "destabilize" may refer to the ability of a peptide or molecule to prevent or stop the same or another molecule or peptide from maintaining a particular state. "Destabilize" may also refer to the ability of a peptide or molecule to allow or increase the amount of degradation that the same or another molecule or peptide faces, such as by increasing the affinity of the same or other molecule or peptide to a digestive protein.

Some embodiments include the use of degrons. Examples of degrons include a portion of a protein that affect the regulation of protein degradation rates. Some degrons are ubiquitin-dependent or ubiquitin-independent.

Some embodiments of the compound protease include a protease domain. Examples of protease domains are shown in FIGS. 1A and 1B. The protease domain 520A in each of FIGS. 1A and 1B includes a first part 528 and a second part 529. Examples of a first and second part of a protease domain include separate halves or pieces of a dimer that work together to cleave a peptide, or separate portions of a protease that do not dimerize or that are not halves. For example, one part of a protease domain may be a fourth of the protease while another part of the protease domain may be three fourths of the protease domain, or there may be more than two parts. Each of the parts 528, 529 of each of the protease domains 520a in FIGS. 1A and 1B are separate halves of the protease domain 520a and are connected to a cut site 515, 515b by a linking peptide 513, 518. Another example of a protease domain 520a is shown in FIG. 1C, which includes a first part 528 and a second part 529, wherein the first part 528 is larger than the second part 529. In the example in FIG. 1C, the first and second parts 528, 529 of the protease domain 520a are each connected to different parts 514, 516 of a single cut site 515 by linking peptides 513, 517.

In some embodiments, the protease domain comprises a first part 528 of the protease domain 520a, and a second part 529 of the protease domain 520a. In some embodiments, the first part 528 and the second part 529 of the protease domain 520a associate together. In some embodiments, when the first part 528 and the second part 529 of the protease domain 520a are associated together, they form an active protease domain 520a. In some embodiments, the first part 528 and the second part 529 of the protease domain 520a do not self-associate on their own to form the active protease domain 520a. For example, the protease domain 520a may include a first part 528 of the protease domain 520a, and a second part 529 of the protease domain 520a, wherein when the first part 528 and the second part 529 of the protease domain 520a are associated together, they form an active protease domain 520a, and wherein the first part 528 and the second part 529 of the protease domain 520a do not self-associate on their own to form the active protease domain 520a.

Some embodiments of the compound protease include a cut site. A cut site may be made of two parts that associate together to form the cut site. The cut site may be specific to an individual protease, or may be specific to multiple proteases. Examples of cut sites are shown in FIGS. 1A-1C. In the examples shown in each of FIGS. 1A and 1B, two cut sites 515, 515b are shown. One of the cut sites in each of FIGS. 1A and 1B 515 includes a first part 514 of the cut site 515 and a second part 516 of the cut site 515, the first part 514 connecting to the first part 528 of the protease domain 520, and the second part 516 of the cut site 515 connecting directly to a part 557 of an association domain 558 and linking indirectly through the association domain 558 to the second part 529 of the protease domain 520a. The second site 515b in each of FIGS. 1A and 1B also includes a first part 514b of the cut site 515b and a second part 516b of the cut site 515b, the first part 514b connecting directly to the second part 529 of the protease domain 520a, and the second part 516b of the cut site 515b connecting directly to a part 559 of the association domain 558 and linking indirectly through the association domain 558 to the first part 528 of the protease domain 520. In the example shown in FIG. 1C, the protease 520 includes a single cut 515 having two parts 514, 516, each part connecting directly to a part 528, 529 of the protease domain 520a through a linking peptide 513, 517.

In some embodiments, the cut site comprises a first part 514 of the cut site 515. In some embodiments, the first part 514 of the cut site 515 is linked to the first part 528 of the protease domain 520a. In some embodiments, the cut site comprises a second part 516 of the cut site 515. In some embodiments, the second part 516 of the cut site 515 is linked to the second part 529 of the protease domain 520a. In some embodiments, the first and second parts 514, 516 of the cut site 515 associate together. In some embodiments, when the first and second parts 514, 516 of the cut site 515 are associated together they form an active cut site 515 for an enzyme. In some embodiments, when the active cut site 515 is cut by the enzyme, the first and second parts 514, 516 of the cut site 515 dissociate from one another. In some embodiments, when the first and second parts 514, 516 of the cut site 515 are dissociated from one another, the protease domain 520a is inactive or deactivated. For example, the cut site may include a first part 514 of the cut site 515, wherein the first part 514 of the cut site 515 is linked to the first part 528 of the protease domain 520a; and a second part 516 of the cut site 515, wherein the second part 516 of the cut site 515 is linked to the second part 529 of the protease domain 520a, wherein when the first and second parts 514, 516 of the cut site 515 are associated together they form an active cut site 515 for an enzyme, and wherein when the active cut site 515 is cut by the enzyme, the first and second parts 514, 516 of the cut site 515 dissociate from one another.

Some embodiments of the compound protease include an association domain. An example of an association domain is shown in FIG. 1A. The association domain 558 in FIG. 1A includes two parts 557, 559 each binding together noncovalently to ultimately link the first and second parts 528, 529 of the protease domain 520a together. Another example of an association domain is shown in FIG. 1B. The association domain 558 in FIG. 1B includes a single peptide strand with two parts 557, 559 that each connect to a cut site 515, 515b and ultimately link the first and second parts 528, 529 of the protease domain 520a together. In some embodiments, the association domain comprises a first part 557 of the association domain 558. In some embodiments, the first part 557 of the association domain 558 is conjugated to the second part 516 of the cut site 515. In some embodiments, the association domain comprises a second part 559 of the association domain 558. In some embodiments, the second part 559 of the association domain 558 is linked to the second part 529 of the protease domain 520a. In some embodiments, the association domain 558 is configured to stabilize the active protease domain 520a. For example, the association domain may include a first part 557 of the association domain 558 that is conjugated to the second part 516 of the cut site 515; a second part 559 of the association domain 558 that is linked to the second part 529 of the protease domain 520a, wherein the association domain 558 is configured to stabilize the active protease domain 520a.

Examples of association domains include a leucine zipper motif or a complementary leucine zipper motif, a scaffold protein or a fragment thereof, a scaffold-binding motif, an antibody, an epitope, tetratricopeptide repeat, a tetracopeptide repeat-binding motif, a G-protein-coupled receptor, a β-arrestin, and/or a G protein. In some embodiments, the association domain includes any protein(s) or component(s) of protein(s) that bind together. Thus, the association domain is contemplated to cover any protein:protein interaction according to some embodiments. In some embodiments, the association domain includes a ligand-binding protein or domain and/or the ligand.

In some embodiments of the compound protease, the first and second parts of the association domain of the compound protease comprise separate peptide strands that hybridize together, for example, as shown in FIG. 1A. In some embodiments of the compound protease, the first and second parts 557, 559 of the association domain 558 of the compound protease 520 are a single peptide strand, for example, as shown in FIG. 1B.

Some embodiments do not include an association domain linking the first and second parts 528, 529 of a protease domain 520a together. For example, in the example shown in FIG. 1C, the first and second parts 528, 529 of the protease domain 520a are instead linked together through the cut site. The example in FIG. 1C shows the use of optional linking peptides 513, 517 which some embodiments do not include. The example in FIG. 1C does include a part 556 of an association domain for a different purpose—that of helping to recruit another protease or compound protease to the cut site 515 of the protease 520 in FIG. 1C. For example, the other protease or compound protease may be recruited to the cut site 515 of the protease 520 in FIG. 1C when the other protease or compound protease includes a complementary part of the association domain to the part 556 of the association domain included on the protease domain 520a of the protease 520 shown in FIG. 1C.

In some embodiments, the compound protease comprises or consists of a tobacco etch virus NIa (TEV) protease, tobacco vein mottling virus (TVMV) NIa protease, sugarcane mosaic virus NIa protease, sunflower mild mosaic virus NIa protease, turnip mosaic virus NIa protease, plum pox virus NIa protease, soybean mosaic virus protease, hepatitis c virus (HCV) ns3 protease, hepatitis a virus 3c protease, dengue virus NS3 protease, zika virus NS3 protease, yellow fever virus NS3 protease, or human herpes virus 1 protease. In some embodiments, the compound protease comprises or consists of a human site-specific protease such as thrombin and/or enteropeptidase.

Some embodiments comprise or consist of a nucleic acid encoding the compound protease. Examples of nucleic acids include DNA and RNA.

Embodiments

Proteases

Some embodiments of the compounds, methods or systems described herein relate to a protease such as a compound protease. In some embodiments, the protease includes any protease as described herein. For example, the protease may include a protease as described under any of the subheadings, "Proteases," "Systems," and/or "Methods."

In some embodiments, the compound protease includes a protease domain, one or more cut sites, and/or one or more association domains and/or parts of association domains. In some embodiments, the protease includes a compound protease such as is shown in any of FIGS. 1A-1C. For example, the protease may include a) a protease domain 520a including: a first part 528 of the protease domain 520a, and a second part 529 of the protease domain 520a, wherein when the first part 528 and the second part 529 of the protease domain 520a are associated together, they form an active protease domain 520a, and wherein the first part 528 and the second part 529 of the protease domain 520a do not self-associate on their own at physiological conditions to form the active protease domain 520a; b) a cut site 515, wherein the cut site 515 includes: a first part 514 of the cut site 515, wherein the first part 514 of the cut site 515 is linked to the first part 528 of the protease domain 520a; and a second part 516 of the cut site 515, wherein the second part 516 of the cut site 515 is linked to the second part 529 of the protease domain 520a, wherein when the first and second parts 514, 516 of the cut site 515 are associated together they form an active cut site 515 for an enzyme, and wherein when the active cut site 515 is cut by the enzyme, the first and second parts 514, 516 of the cut site 515 dissociate from one another; and c) an association domain 558, the association domain 558 including: a first part 557 of the association domain 558 that is conjugated to the second part 516 of the cut site 515; a second part 559 of the association domain 558 that is linked to the second part 529 of the protease domain 520a, wherein the association domain 558 is configured to stabilize the active protease domain 520a.

In some embodiments, the ability or lack thereof of the first part 528 and the second part 529 of the protease domain 520a to self-associate on their own to form the active protease domain 520a is concentration dependent such that at physiological conditions they do not self-associate.

In some embodiments, the protease domain comprises, is comprised of, or is composed of a peptide or co-peptide, or multiple peptides or co-peptides.

In some embodiments, the compound protease includes one or more cut sites. In some embodiments, one or more of the cut sites are specific for a different protease or different proteases than the compound protease. For example, the compound protease would not be able to cleave itself according to some embodiments. Thus, in some embodiments, the compound protease is not naturally occurring, and/or the compound protease does not include a natural cut site (such as for the protease itself). For example, the compound protease may not include a natural cut site for itself between a main protease domain and a co-peptide of the compound protease.

Some embodiments of the protease include a compound protease such as the compound protease 520 shown in FIG. 1C, the compound protease 520 including: a) a protease domain 520a including: a first part 528 of the protease domain 520a, and a second part 529 of the protease domain 520a, wherein when the first part 528 and the second part 529 of the protease domain 520a are associated together, they form an active protease domain 520a, and wherein the first part 528 and the second part 529 of the protease domain 520a do not self-associate on their own to form the active protease domain 520a; b) a cut site 515, wherein the cut site 515 includes: a first part 514 of the cut site 515, wherein the first part 514 of the cut site 515 is linked to the first part 528 of the protease domain 520a; and a second part 516 of the cut site 515, wherein the second part 516 of the cut site 515 is linked to the second part 529 of the protease domain 520a, wherein when the first and second parts 514, 516 of the cut site 515 are associated together they form an active cut site 515 for an enzyme, and wherein when the active cut site 515 is cut by the enzyme, the first and second parts 514, 516 of the cut site 515 dissociate from one another; c) a first peptide 513 connecting the first part 528 of the protease domain 520a to the first part 514 of the cut site 515; and d) a second peptide 517 connecting the second part 529 of the protease domain 520a to the second part 516 of the cut site 515, wherein the first and second linkers 513, 517 are configured to stabilize the active protease domain 520a. In some embodiments, the first peptide 513 connecting the first part 528 of the protease domain 520a to the first part 514 of the cut site 515 includes a linker. In some embodiments, the second peptide 517 connecting the second part 529 of the protease domain 520a to the second part 516 of the cut site 515 includes a linker.

Some embodiments of the protease include a compound protease such as the compound protease 520 shown in FIGS. 1A-1C, the compound protease 520 including: a) a protease domain 520a including: a first part 528 of the protease domain 520a, and a second part 529 of the protease domain 520a, wherein when the first 528 part and the second part 529 of the protease domain 520a are associated together, they form an active protease, and wherein the first part 528 and the second part 529 of the protease domain 520a do not self-associate on their own to form the active protease; and b) a cut site 515, wherein the cut site 515 includes: a first part 514 of the cut site 515, wherein the first part 514 of the cut site 515 is linked to the first part 528 of the protease domain 520a; and a second part 516 of the cut site 515, wherein the second part 516 of the cut site 515 is linked or indirectly connected to the second part 529 of the protease domain 520a, wherein when the first and second parts 514, 516 of the cut site 515 are associated together they form an active cut site 515 for an enzyme, and wherein when the active cut site 515 is cut by the enzyme, the first and second parts 514, 516 of the cut site dissociate from one another.

In some embodiments of the compound protease, such as is shown in FIG. 1C, the first part 514 of the cut site 515 is covalently linked to the first part 528 of the protease domain 520a by a first peptide linkage 513, and/or wherein the second part 516 of the cut site 515 is covalently linked to the second part 529 of the protease domain 520a by a second peptide linkage 517.

Some embodiments of the proteases described herein include one or more linkers or linker peptides. The linkers or linker peptides may connect or link (directly or indirectly, and/or covalently or noncovalently) various parts of the protease such as a cut site or a part of the cut site to a protease domain or a part of a protease domain. However, this disclosure is not limited to only linkers or linker peptides connecting the protease parts. Examples of a linker is a peptide that includes 1-10, 10-25, 25-50, 50-100, or 100-1000 amino acids. For example, the compound protease may include a first peptide linkage 513 that includes a linker peptide including 1-10, 10-25, 25-50, 50-100, or 100-1000 amino acids, and/or a second peptide linkage 517 includes a linker peptide including 1-10, 10-25, 25-50, 50-100, or 100-1000 amino acids.

In some embodiments of the compound protease, wherein the second part 529 of the protease domain 520a includes a part 556 of an association domain connected to the second part 529 of the protease domain 520a, wherein the part 556 of the association domain connected to the second part 529 of the protease domain 520a is configured to recruit the enzyme to the active cut site 515 by binding a second part of the association domain on the enzyme.

In some embodiments of the compound protease, such as is shown in FIGS. 1A and 1B, the compound protease includes a second cut site 515b, wherein the second cut site 515b includes: a first part 514b of the second cut site 515b, wherein the first part 514b of the second cut site 515b is linked to the second part 529 of the protease domain 520a; and a second part 516b of the second cut site 515b, wherein the second part 516b of the second cut site 515b is linked or indirectly connected to the first part 528 of the protease domain 520a; wherein when the first and second parts 514b, 516b of the second cut site 515b are associated together they form an active second cut site 515b for the enzyme, and wherein when the active second cut site 515b is cut by the enzyme, the first and second parts 514b, 516b of the second cut site dissociate from one another.

In some embodiments of the compound protease, such as is shown in FIG. 1A, the compound protease includes an association domain 558 that includes: a first part 557 of the association domain 558, conjugated to the second part 516 of the first cut site 515; a second part 559 of the association domain 558, conjugated to the second part 516b of the second cut site 515b, wherein the association domain 558 is configure to stabilize the active protease domain. In some embodiments of the compound protease, the first part 514 of the cut site 515 is covalently linked to the first part 528 of the protease domain 520a by a first peptide linkage 513, and/or wherein the first part 514b of the second cut site 515b is covalently linked to the second part 529 of the protease domain 520a by a second peptide linkage 518. In some embodiments, the first peptide linkage 513 includes a linker peptide including 1-10, 10-25, 25-50, 50-100, or 100-1000 amino acids. In some embodiments, the second peptide linkage 518 includes a linker peptide including 1-10, 10-25, 25-50, 50-100, or 100-1000 amino acids. In some embodiments of the compound protease, the second part 516 of the cut site 515 is indirectly connected to the second part 529 of the protease domain 520a through the association domain 558, wherein the first and second parts 557, 559 of the association domain are covalently or non-covalently linked together.

Some embodiments of the compound protease, such as the example shown in FIG. 1B, include an association domain 558 of the compound protease 520 including a first part 557 and a second part 559, wherein the first part 557 of the association domain 558 links to the second part 516 of the first cut site 515, and wherein the second part 559 of the association domain 558 links to the second part 516b of the second cut site 515b. In some embodiments, the first part 514 of the cut site 515 is covalently linked to the first part 528 of the protease domain 520a by a first peptide linkage 513, and/or wherein the first part 514b of the second cut site 515b is covalently linked to the second part 529 of the protease domain 520a by a second peptide linkage 518. In some embodiments, the first peptide linkage 513 includes a linker peptide including 1-10, 10-25, 25-50, 50-100, or 100-1000 amino acids. In some embodiments, the second peptide linkage 518 includes a linker peptide including 1-10, 10-25, 25-50, 50-100, or 100-1000 amino acids. In some embodiments, the second part 516 of the cut site 515 is indirectly connected to the second part 529 of the protease domain 520a through the association domain 558. In some embodiments, the association domain connecting to the second part 516 of the cut site 515 and to the to the second part 516b of the second cut site 515b is configured to recruit the enzyme to the active cut site 515 and/or to the active second cut site 515b by binding a second part of the association domain on the enzyme.

In some embodiments of the compound protease, the compound protease includes a degron. In some embodiments, the compound protease includes multiple degrons. In some embodiments, at lease one degron of the compound protease destabilizes the compound protease when present on the compound protease by enhancing degradation of the compound protease. In some embodiments, at least one of the degrons of the compound protease is or comprises a conditional N-end degron. In some such embodiments, the at least one degron or the condition N-end degron does not inactivate or destabilize the compound protease until the degron or a component thereof is cleaved by another protease to reveal the degron and allow it to stabilize the compound protease. In some embodiments, one or more degrons of the compound protease comprise a conditional N-end degron such as an N-end degron that is conditional on cleavage of a cut site specific for an enzyme, a second protease, or the compound protease, on the compound protease.

In some embodiments, the protease or compound protease is a viral protease, or is a modified form of a viral protease. In some embodiments, the protease or compound protease is a mammalian or human protease, or is a modified form of a mammalian or human protease.

Some embodiments of the compound proteases or of a target protein for a protease include a localization tag. For example, the protease 120 shown in the example in FIG. 4A (panel 3) includes a membrane targeting signal (mts). Such localization enable sub-cellular computation or signal transduction in some embodiments. In some cases, the protease (or split protease) includes the localization sequence at one or more termini of protease.

Figure 12A:
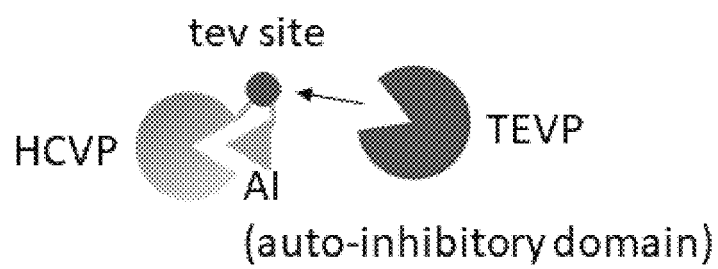
FIGS. 12A-12D depict designs and resulting data of example compound proteases in accordance with some embodiments described herein.
Figure 12A:
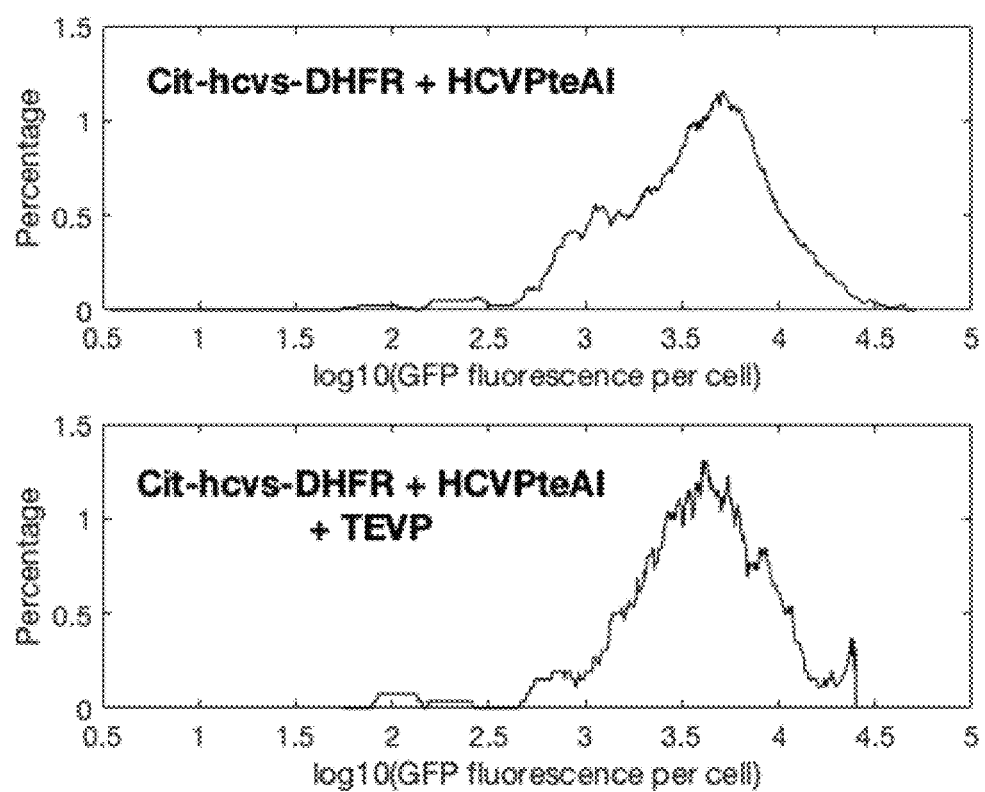
Figure 12B:
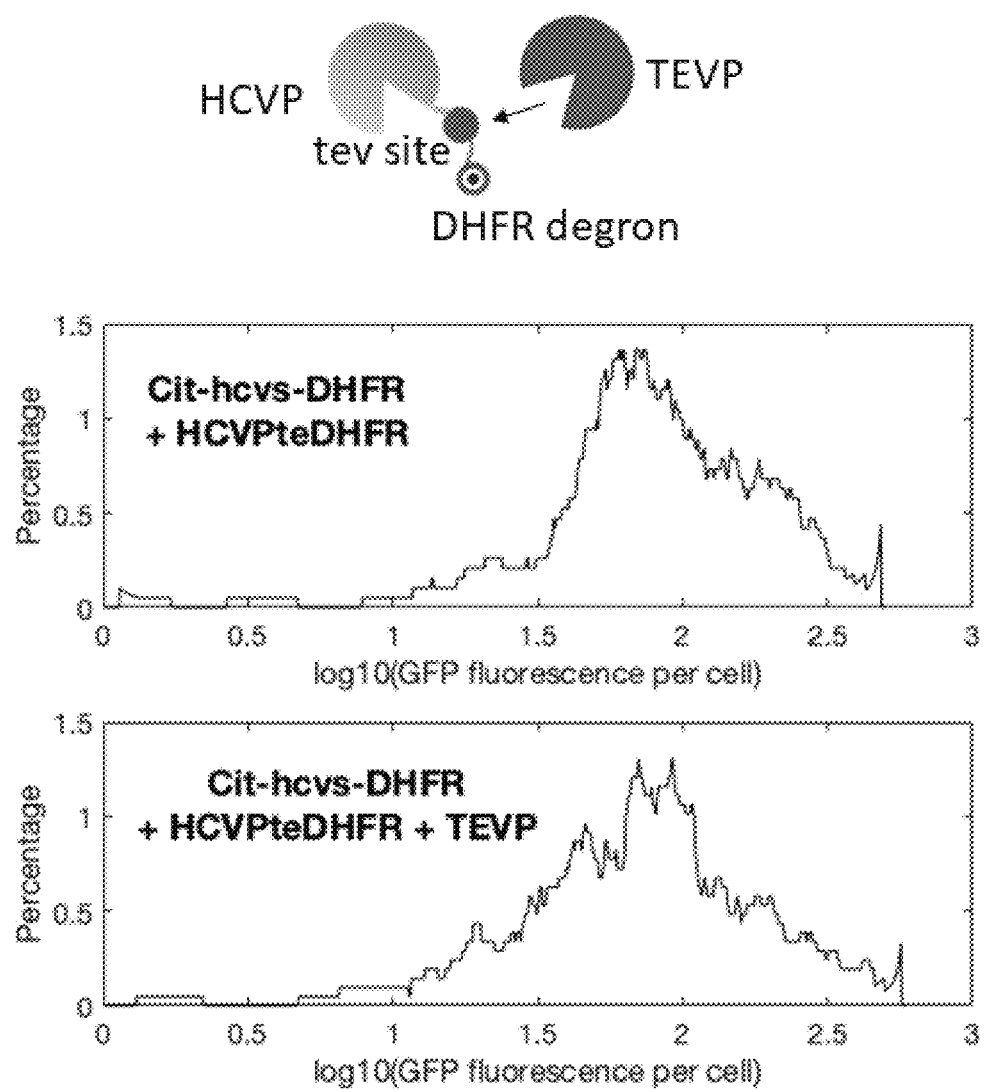
Figure 12C:
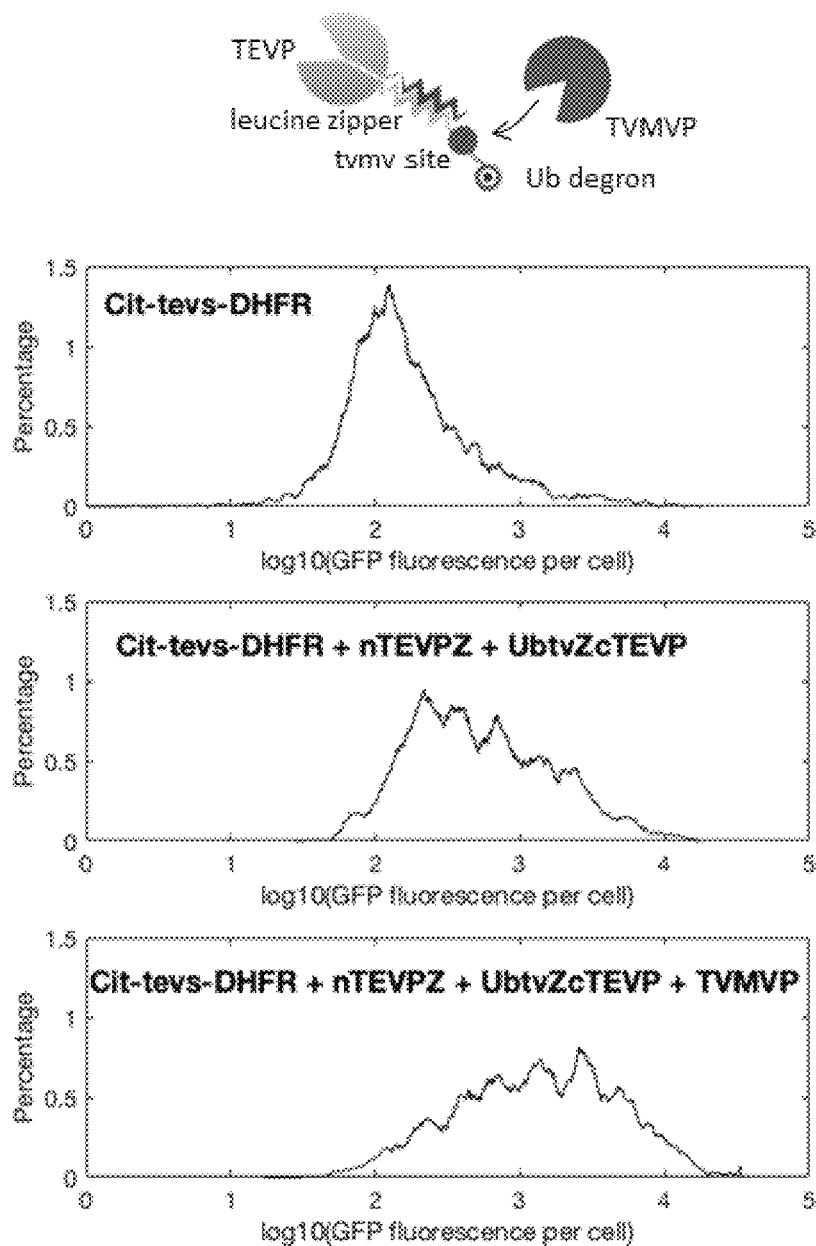

Some embodiments relate to a protease such as a compound protease that interacts with another enzyme or protease by being positively regulated by that other enzyme or protease. As shown in FIG. 12C, the inventors observed some positive regulatory effect in a design where one protease clips a degron off of another protease. Thus, some embodiments of the compound protease include a degron linked to a protease domain or other component of the compound protease by a cut site of the compound protease. The degron may act to destabilize the compound protease as long as the degron is present on the compound protease. In some such embodiments, cleavage of the cut site removes the degron to stabilize the compound protease. In some embodiments, the compound protease is configured to be activated and/or destabilized by another compound protease, protease, or enzyme. In some embodiments, the compound protease is configured to be deactivated and/or destabilized by another compound protease, protease, or enzyme.

Some embodiments relate to positive regulation for cellular protein-level regulation circuits. Positive regulation of one protein activity by another is beneficial for some protein-level circuits. Here is described some designs and experimental results establishing the ability to achieve positive protein-protein regulation in a modular fashion. Two classes of designs are focused on here, but other embodiments are envisioned: (1) Reversible activation by swappable association domains; (2) Irreversible activation by intein-mediated protein splicing.

Figure 12D:
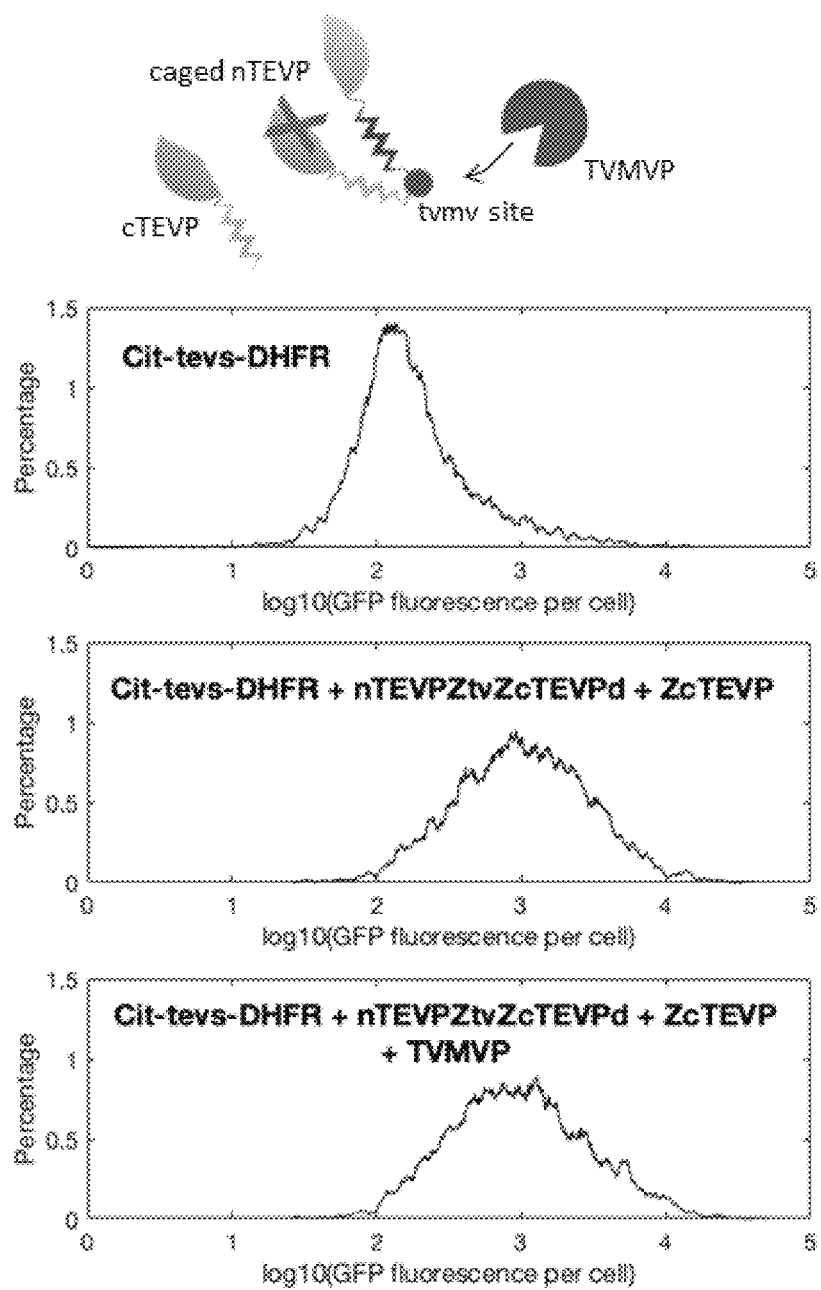

In some embodiments, the compound protease is cleavage-activatable by another protease. For example, the compound protease may be tagged with an auto-inhibitory domain that can be removed with another protease (FIG. 12A). In some embodiments, the compound protease is tagged with a degron (such as a DHFR degron) that can be removed with another protease (FIG. 12B). In some embodiments, the compound protease comprises a split protease tagged with a degron (for example, four tandem repeats of ubiquitin) on the end of a leucine zipper, and the degron is removable by another protease (FIG. 12C). In some embodiments, the compound protease includes an N-terminal half that is caged with a complementary leucine zipper and/or a catalytically inactive C-terminal half, and the caging domains are removable with another protease (FIG. 12D).

Some embodiments relate to a compound protease, the compound protease comprising: a) a protease domain comprising: a first part of the protease domain, and a second part of the protease domain, wherein when the first part and the second part of the protease domain are associated together, they form an active protease domain; and/or b) a cut site, wherein the cut site comprises: a first part of the cut site, and a second part of the cut site, wherein when the first and second parts of the cut site are associated together they form an active cut site for an enzyme, and wherein when the active cut site is cut by the enzyme, the first and second parts of the cut site dissociate from one another; wherein the compound protease is configured to be activated or deactivated by cleavage of the active cut site by the enzyme.

Some embodiments relate to a cleavage-activatable compound protease, comprising: a) a protease domain comprising: a first part of the protease domain, and a second part of the protease domain, wherein when the first part and the second part of the protease domain are associated together, they form an active protease domain; and/or b) a cut site, wherein the cut site comprises: a first part of the cut site, and a second part of the cut site, wherein when the first and second parts of the cut site are associated together they form an active cut site for an enzyme, and wherein when the active cut site is cut by the enzyme, the first and second parts of the cut site dissociate from one another; wherein the compound protease is configured to be activated by cleavage of the active cut site by the enzyme. In some embodiments, the cleavage-activatable compound protease comprises an association domain, and the association domain prevents the first part of the protease domain from associating with the second part of the protease until the cut site is cut by the enzyme. In some embodiments, the cleavage-activatable compound protease comprises an association domain, wherein the association domain cages the first part of the protease domain and prevents the first part of the protease domain from associating with the second part of the protease until the cut site is cut by the enzyme. In some embodiments, the cleavage-activatable compound protease further comprises a three-way split protease.

1. Reversible activation by swappable association domains

Single Caged Design:

In this design, a target protease is 'caged' in an inactive form that can be uncaged by an activating protease to turn on its protease activity. More specifically, the target protease is caged by splitting it, and including an inactivating mutation in one half (FIG. 1A). Inclusion of a cleavage site for the activating protease, allows the inactive half to be released, and permits association of the active half with a separately expressed active half to reconstitute an active protease in accordance with some embodiments.

Figure 13A:
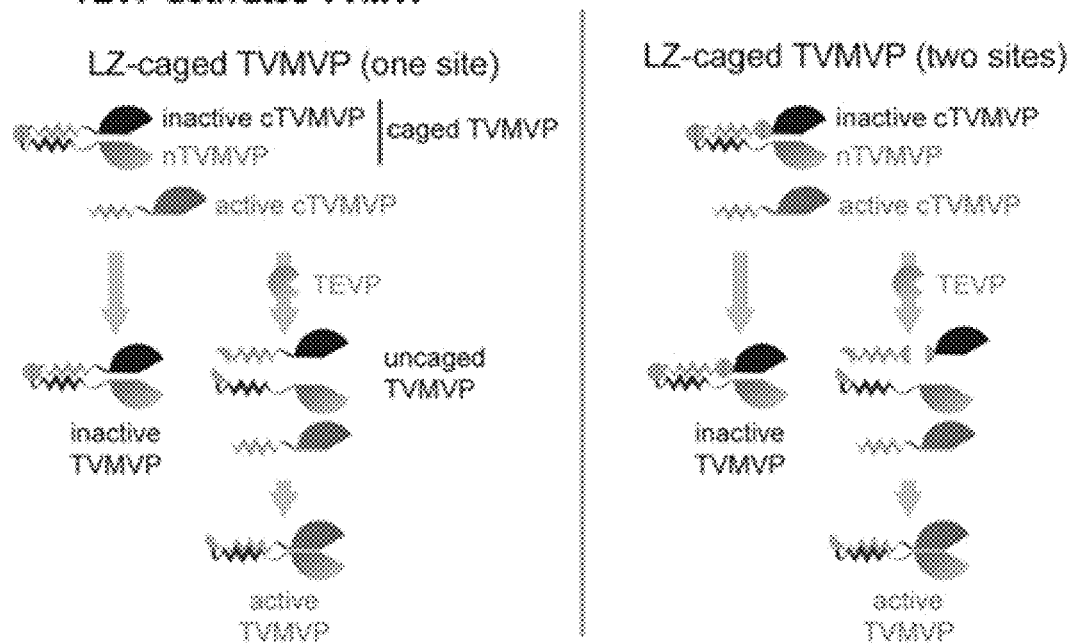
FIGS. 13A-13D depict information relating to the design of non-limiting example composable activatable protein components.
Figure 13A:
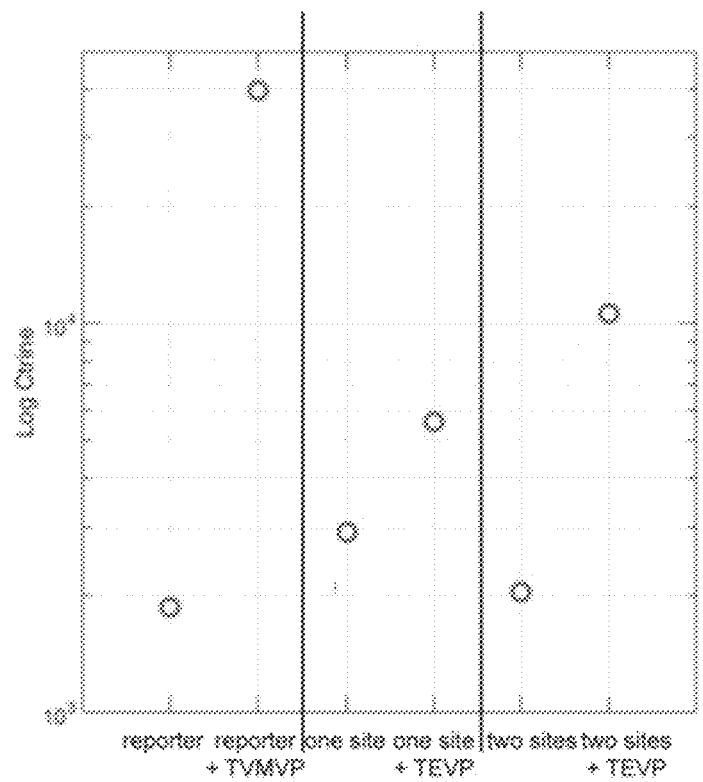

Experimental Validation:

For an initial test, TVMVP was used as a starting protease. In a simplified design, a single-chain 'caged' TVMVP was expressed. The 'caged' TVMVP comprises an active N-terminal lobe and an inactive C-terminal lobe. Residues involved in catalytic cleavage located in the C-half of the protease domain were mutated. Heterodimerizing leucine zippers were included to maintain caging dimerization of the inactive form. One TEVP cleavage site was inserted between the heterodimerizing leucine zippers and the inactive domain in order to allow 'decaging' of the inactive half from the active half of the protease (FIG. 13A, left cartoon). This design was compared to a 'caged' TVMVP with two TEVP cleavage sites: the first one between the heterodimerizing leucine zippers and the second one between the inactive C-terminal lobe and its corresponding leucine zipper (FIG. 13A, right cartoon). The active C-terminal lobe of TVMVP was expressed with the corresponding heterodimerizing leucine zipper. Co-expression of the 'caged' TVMVP with the active C-terminal half of TVMVP showed that this design was capable of maintaining its inactive state in the presence of the active cTVMVP. Cleavage by TEVP activated TVMVP with a single TEVP cleavage site (one site, middle column of plot in FIG. 13A). The design with two TEVP cleavage sites ('two sites' in FIG. 13A) performed better in terms of having an expanded dynamic range.

Figure 13B:
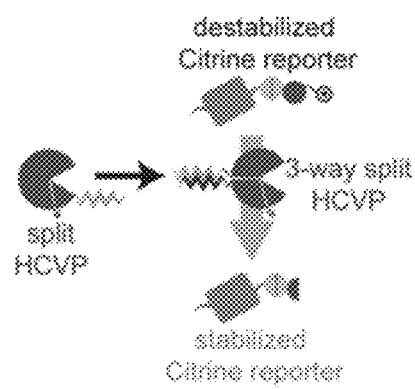
Figure 13B:
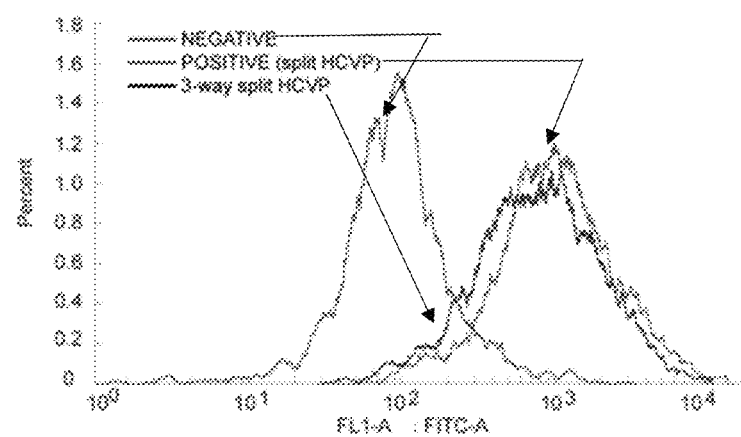
Figure 13C:
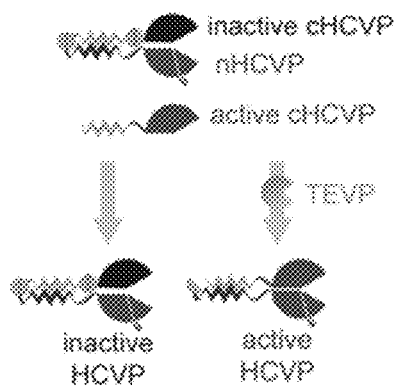
Figure 13C:
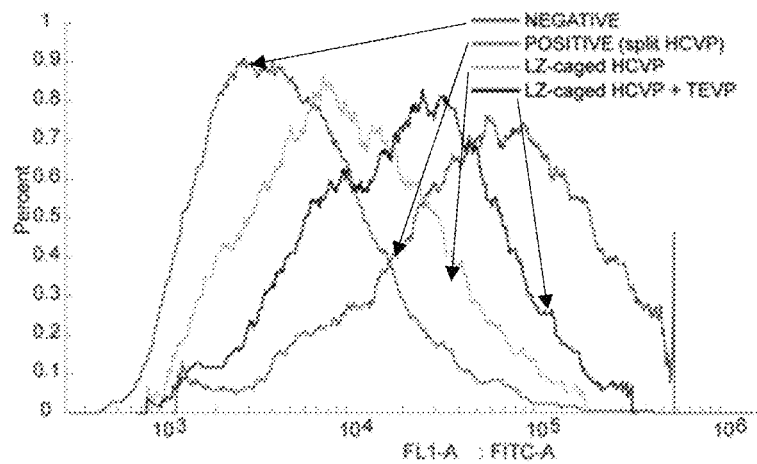
Figure 13D:
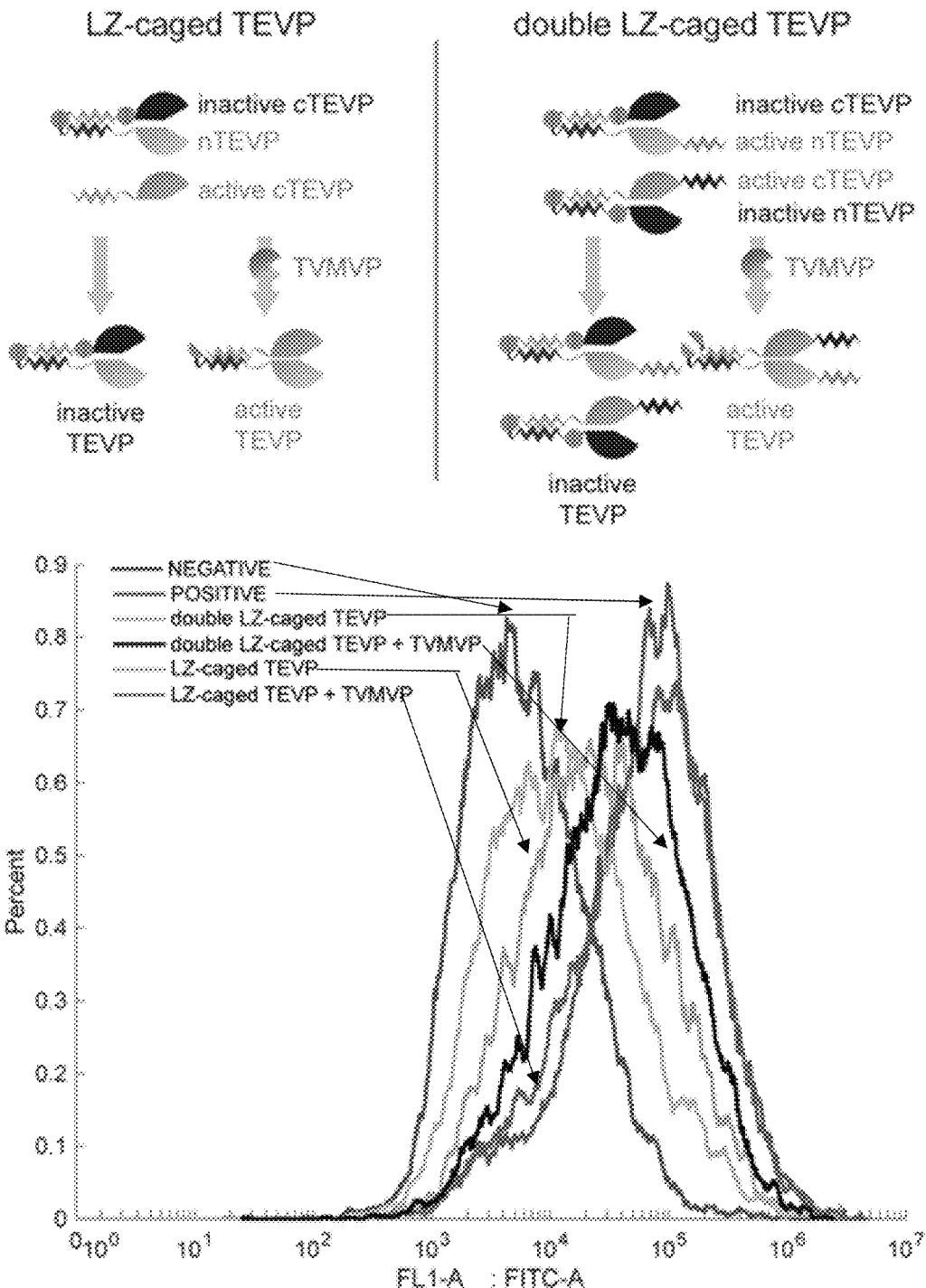

Double Caged Design:

The single caged design was also applied to a TEV protease (FIG. 13D, left) and enabled regulation by TVMV protease. In order to reduce the baseline level of activity in both the 'off' and 'on' states, a double-caged design was also developed (FIG. 13D, right). In this design, two forms of the split target protease are expressed, each of which contains an inactivating mutation in opposite domains, as shown. Each target protease contained cleavage sites for the activating protease. As a result, cleavage can enable swapping of these domains to produce a fully active reconstituted target protease, as can be shown.

Generality:

Similar designs can be applied to additional proteases. This was demonstrated using a Hepatitis C Virus (HCV) protease (FIGS. 13B, 13C). First, a 3-way split HCV protease was designed. The HCVP contained a core HCVP and activity-enhancing co-peptide (small pie slice, FIG. 13B). A TEVP cleavage site was successfully inserted between the core and the activity-enhancing peptide to successfully reduce HCVP activity (see description under the heading, "Further embodiments"). On top of this split, a second split site was added within the core HCVP domain. The N-terminal lobe was then expressed as a single chain with its co-peptide. Reconstitution of HCVP with heterodimerizing leucine zippers had the same level of activity as the wildtype HCVP (FIG. 13B). The simple uncaging design showed activation of HCV protease activity by TEV protease (FIG. 13C).

2. Irreversible Activation by Intein-Based Activatable Proteases

Background:

Inteins, intervening proteins, are autoprocessing domains which are able to carry out protein splicing (Gramespacher et al, JACS, 2017). Inteins excise themselves from a polypeptide precursor and ligate the two exteins, external proteins, through a new peptide bond. Split inteins, unlike the contiguous inteins, are translated in two distinct polypeptide sequences of an N-intein and C-intein, each with its own extein. Upon association, the split inteins will perform protein splicing in trans. Split intein zymogens were demonstrated in which each split intein pair is caged and activated upon proteolysis (Gramespacher et al, JACS, 2017).

Figure 14A:
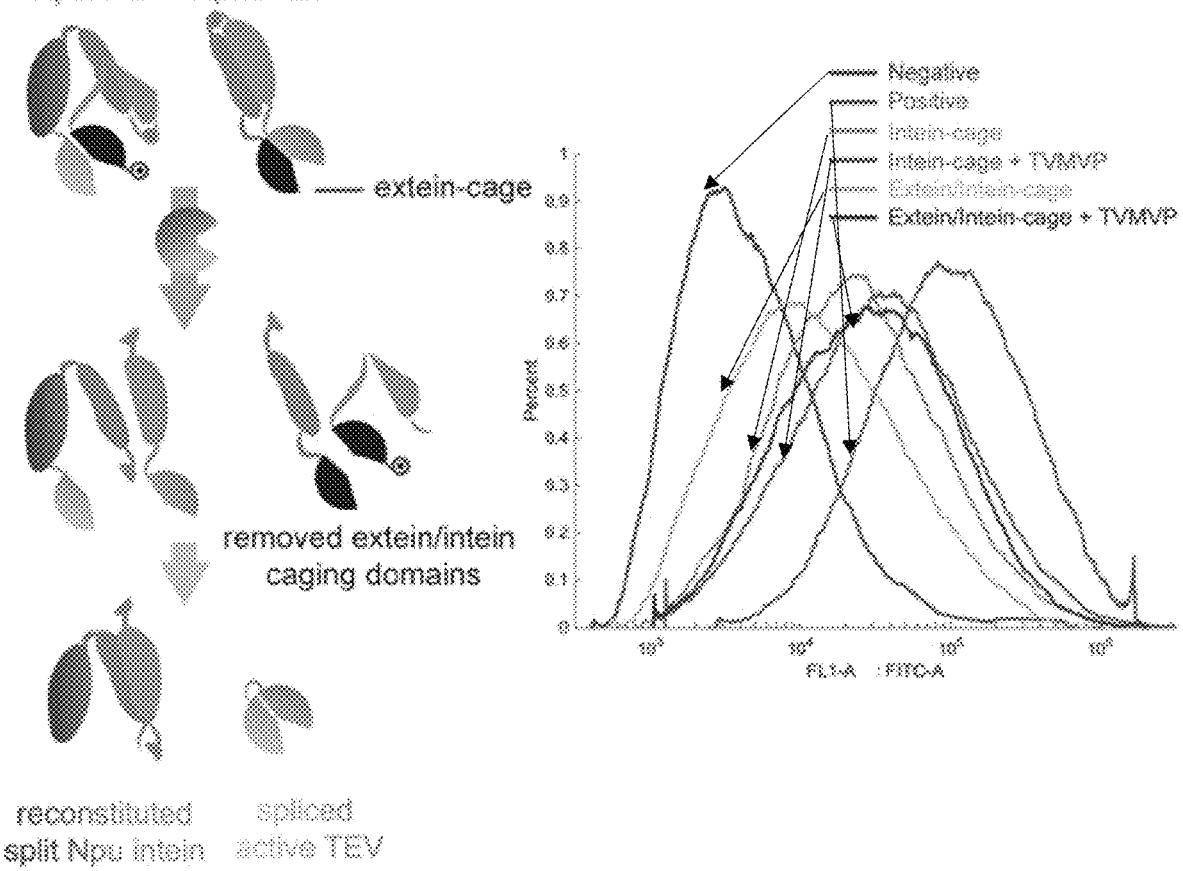
Figure 14B:
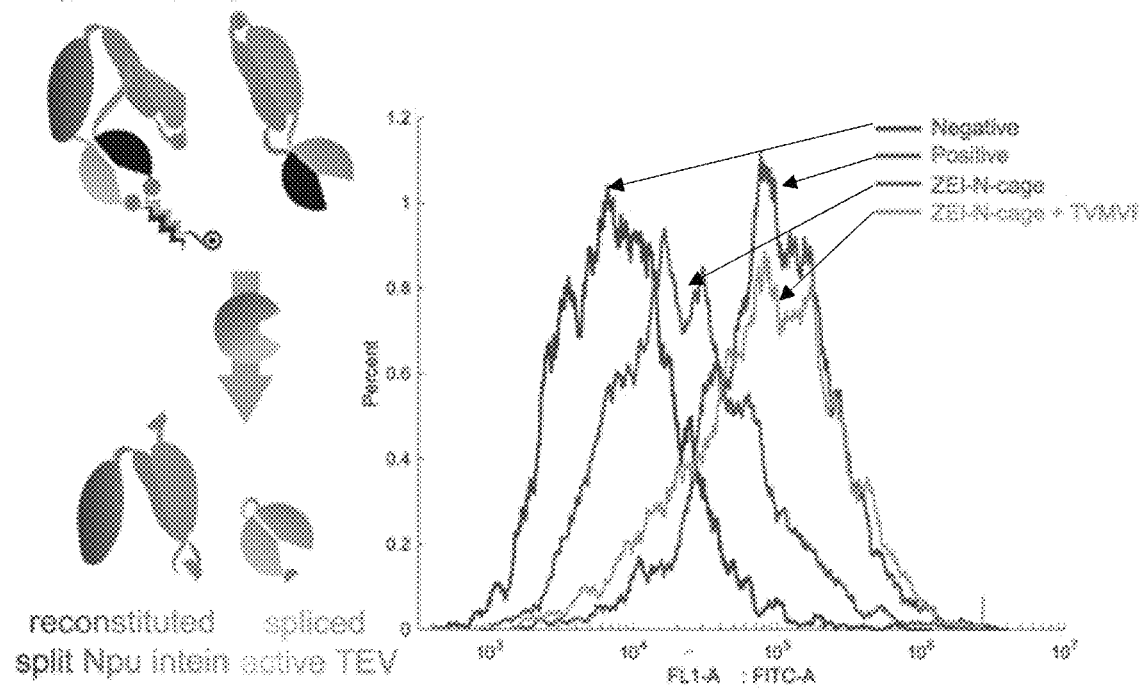

Design and Validation:

A split intein-based activatable protease was designed, in which two halves of a split protease are each fused to complementary caged inteins, such that cleavage of the caged inteins can permit protein splicing to reconstitute the split extein as a functional protease (FIG. 14A). The inventors used TEVP as a target protease and TVMVP as an activating protease. This design showed limited activation of TEVP (FIG. 14A). The inventors therefore caged the extein halves by using the corresponding inactive protease half (FIG. 14A, protease domains). This designed successfully reduced baseline activation (FIG. 14A). The inventors next introduced a heterodimerizing leucine zipper pair to each half of the protease to sterically constrain the ability of the split inteins to associate with each other. The inventors found that addition of the leucine zippers to our overall design enhanced spliced TEVP activity, showing a broad dynamic range for regulation (FIG. 14B). The inventors further demonstrated this overall design can be transferred from one orthogonal intein pair to another (NrdJ1, GP41-1, and Npu, FIG. 14C), and these intein pairs can be used to control different output proteases (TEVP, HCVP, and TVMVP, respectively).

Systems

Some embodiments relate to a system such as a synthetic protein circuit. The system or synthetic protein circuit may include any of the proteases described herein such as one or more of the compound proteases shown in FIGS. 1A-1C. In some embodiments, the system or synthetic protein circuit includes a first protease, second protease, third protease, fourth protease, fifth protease, sixth protease, seventh protease, eighth protease, ninth protease and/or tenth protease. Any of said proteases may comprise or be composed of a compound protease as described herein. In some embodiments of the system or synthetic protein circuit, the first protease 110 and the second protease 120 each include an HCV protease, a TEV protease, or a TVMV protease. Some embodiments include positive protease-protease regulation (FIG. 12C). For example, some embodiments relate to a synthetic protein circuit that includes a mode of positive protease-protease regulation, such as one that is mediated through degron removal.

Some embodiments relate to a synthetic protein circuit such as a protein circuit or a part thereof shown in FIGS. 1D-1J. In some embodiments, the synthetic protein circuit includes: a first protease 110; and a second protease 120 including a cut site 115 specific for the first protease 110, wherein the second protease 120 is inactivated by cleavage of the cut site 115 specific for the first protease 110.

Figure 1E:
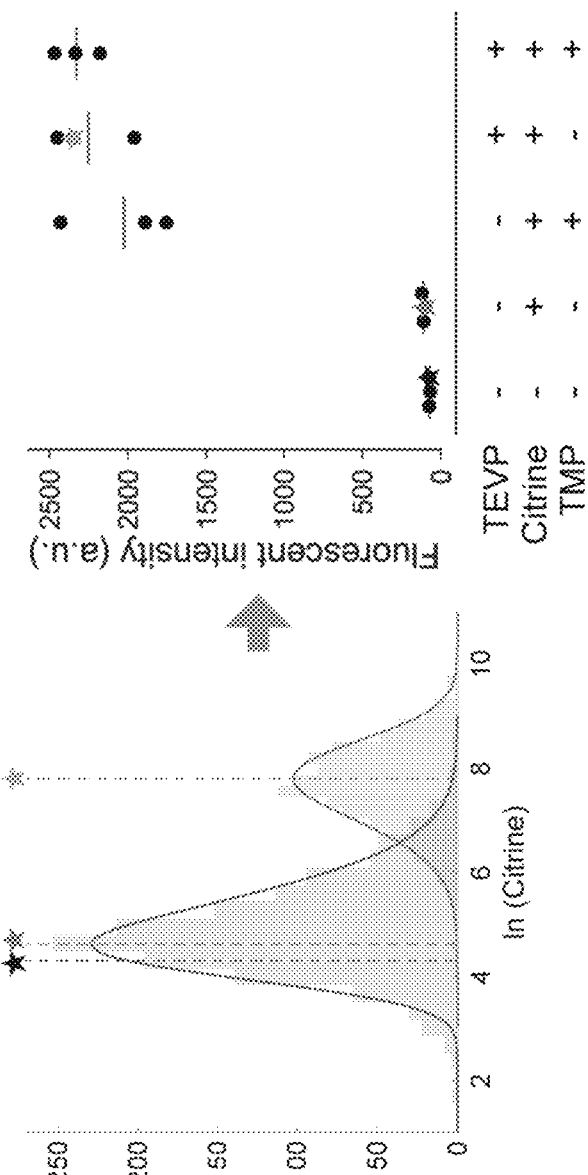
Figure 1E:
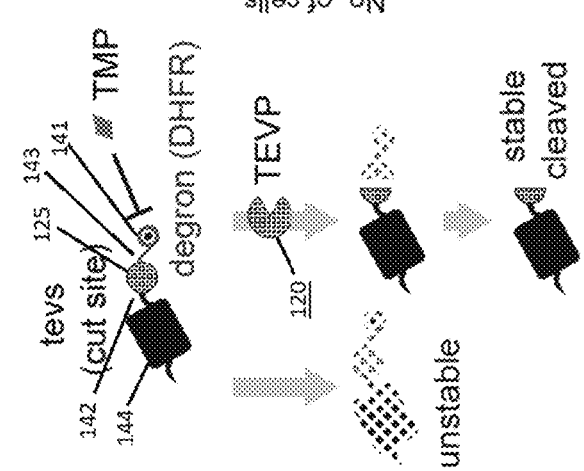
Figure 1H:
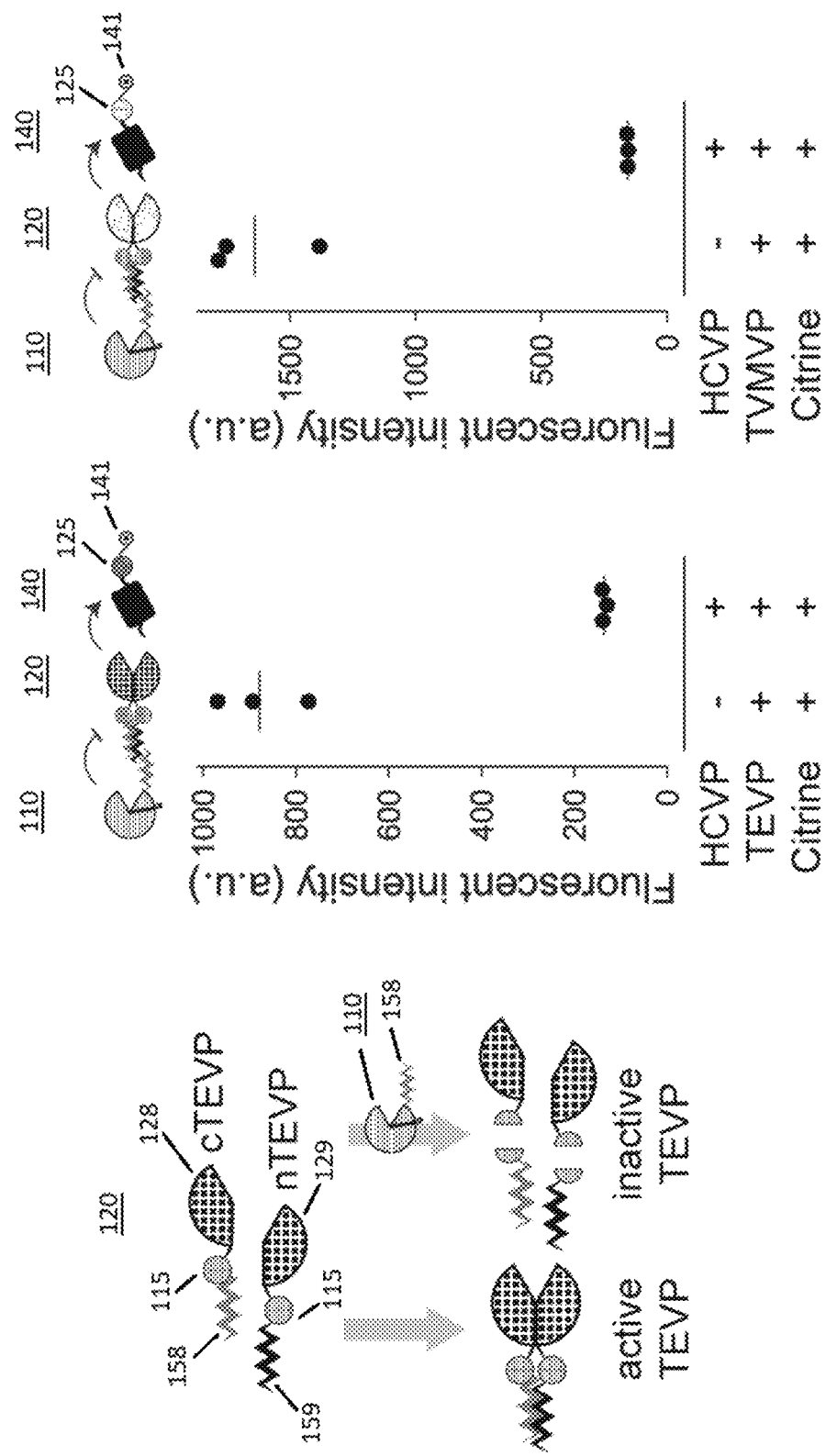

Some embodiments of the synthetic protein circuit include a target protein 140, such as the target protein shown in FIG. 1H, including: a degron 141 of the target protein 140 that destabilizes the target protein 140 when present on the target protein 140 by enhancing degradation of the target protein 140, and a cut site 125 specific for the second protease 120, wherein the target protein 140 is configured to be stabilized or destabilized by cleavage of the cut site 125 specific for the second protease 210.

In some embodiments of the synthetic protein circuit, the second protease 120 includes a first cleavage domain 128 and a second part 129 of the cleavage domain, the first part 128 connecting to the cut site 115 specific for the first protease 110, and the second part 129 connecting to another cut site 115 specific for the first protease 110, the second protease's 120 two cut sites 115 specific for the first protease 110 each connecting to an association domain 158 of the second protease 120 such as a leucine zipper. In some embodiments, the second protease's 120 two cut sites 115 specific for the first protease 110 each connect to a separate association domain 158, 159 of the second protease 120, wherein the second protease 120 is active when the separate association domains 158, 159 bind together, and wherein the second protease 120 is configured to be deactivated by cleavage of either of its two cut sites 115 specific for the first protease 110. In some embodiments, one of the second protease's 120 association domains 158, 159 includes a complementary association domain 159 such as leucine zipper that is complementary or antiparallel to the other association domain 158 of the second protease 120. In some embodiments, such as in the example shown in FIG. 1I, the second protease's 120 two cut sites 115 specific for the first protease 110 each connect to a single association domain 159 of the second protease 120, and wherein the second protease 120 is configured to be deactivated by cleavage of either of its two cut sites 115 specific for the first protease 110.

In some embodiments of the synthetic protein circuit, the first protease 110 includes an association domain 158 of the first protease 110 that binds to a complementary association domain 159 of the second protease 120, thereby allowing or enhancing the first protease's 110 ability to cleave a cut site 115 specific to the first protease 110 on the second protease 120.

Some embodiments of the synthetic protein circuit include a third, fourth, fifth, sixth, seventh, eighth, ninth and/or tenth protease 130, each protease 110, 120, 130 including a cut site specific to at least one of the proteases 110, 120, 130, and wherein each protease 110, 120, 130 is configured to be destabilized or deactivated by cleavage of its cut site.

Some embodiments of the synthetic protein circuit include a protease activatable target protein. In some embodiments, such as in the examples shown in FIGS. 1E and 1H, the target protein's 140 cut site 125 specific to the second protease 120 includes a first part 125a of the cut site 125 of the target protein 140 and a second part 125b of the cut site 125 of the target protein 140, the first part 125a of the cut site 125 of the target protein 140 connecting to a domain or motif 144 of the target protein, and the second part 125b of the cut site 125 of the target protein 140 connecting to the degron 141 of the target protein 140, and wherein the target protein 140 is stabilized by cleavage of its cut site 125 specific for the second protease 120.

In some embodiments of the synthetic protein circuit, such as is shown in FIG. 1F, the degron 141 of the target protein 140 includes a masking peptide 146 that connects to the degron 141 of the target protein 140 and blocks cleavage of the target protein's 140 cut site 125 specific for the second protease 120, wherein the masking peptide 146 of the degron 141 of the target protein 140 includes the target protein's 140 cut site 125 specific for the second protease 120, and wherein the target protein 140 is configured to be destabilized by cleavage of its cut site 125 specific for the second protease 120, wherein cleavage of the target protein's 140 cut site 125 specific for the second protease 125 uncovers the target protein's 140 degron 141.

In some embodiments of the synthetic protein circuit, the target protein 140 consists of or comprises a protease, a reporter protein, a fluorescent protein, a scaffold, an actuator protein, a transcriptional regulator, or a signaling protein.

In some embodiments of the system, the synthetic protein circuit includes a logic gate such as a logic gate shown in FIGS. 2A-2I. In some embodiments, the system includes a synthetic protein circuit, including: a first protease 110, optionally including an association domain 158 of the first protease 110; a second protease 120, optionally including a complementary association domain 159 of the second protease 120; and a target protein 140 including a degron 141 of the target protein 140 that destabilizes the target protein 140 when present on the target protein 140 by enhancing degradation of the target protein 140; wherein the target protein 140 is configured to interact with the first protease 110, the second protease 120, a third protease 130 and/or a fourth protease 240 to form an OR, AND, NOR, NAND, IMPLY, NIMPLY, XOR or XNOR logic gate.

In some embodiments, the synthetic protein circuit includes an OR logic gate. In some embodiments, the target protein 140 further includes a cut site 115 specific for the first protease 110 and a cut site 125 specific for the second protease 120 between the degron 141 of the target protein 140 and a part 144 of the target protein 140, and wherein the target protein 140 is stabilized by cleavage of either of its cut sites 115, 125.

In some embodiments, the synthetic protein circuit includes an AND logic gate. In some embodiments, the target protein 140 further includes a cut site 115 of the target protein 140 specific for the first protease 110 between the degron 141 of the target protein 140 and a part 144 of the target protein 140, and a cut site 125 specific for the second protease 120 connected to another degron 142 of the target protein 140 and an optional association domain 158 of the target protein 140, and wherein the target protein 140 is stabilized by cleavage of both of its cut sites 115, 125.

In some embodiments, the synthetic protein circuit includes a NOR logic gate. In some embodiments, the synthetic protein circuit includes a third protease 130 including: a cut site 115 specific for the first protease 110, a cut site 125 specific for the second protease 120, and an optional association domain 158 of the third protease 130, wherein the third protease 130 is configured to be deactivated by cleavage of either of its cut sites 115, 125; and wherein the target protein 140 includes a cut site 135 specific for the third protease 130 between the degron 141 of the target protein 140 and a part 144 of the target protein 140, wherein the target protein 140 is stabilized by cleavage of its cut site 135 specific for the third protease 130. In some embodiments, the third protease 130 further includes a first domain 138 of the third protease 130 and a second domain 139 of the third protease 130; wherein the first domain 138 of the third protease 130 includes the third protease's 130 cut sites 115, 125 specific for the first and second proteases 110, 120 and the optional association domain 158 of the third protease 130; wherein the second domain 139 the third protease 130 includes another cut site 115 specific for the first protease 110, another cut site 125 specific for the second protease 120, and an optional complementary association domain 159 the third protease 130; and wherein the third protease 130 is configured to be deactivated by cleavage of any of its cut sites 115, 115, 125, 125.

In some embodiments, the synthetic protein circuit includes a NAND logic gate. In some embodiments, the synthetic protein circuit includes a third protease 130 including a cut site 115 specific for the first protease 110, and configured to be deactivated by cleavage of its cut site 115; and a fourth protease 230 including a cut site 125 specific for the second protease 120, and configured to be deactivated by cleavage of its cut site 125; wherein the target protein 140 includes a cut site 135 specific for the third and fourth proteases 130, 230 between the degron 141 of the target protein 140 and a part 144 of the target protein 140, wherein the target protein 140 is stabilized by cleavage of its cut site 135. In some embodiments, the third protease 130 further includes a first domain 138 of the third protease 130, a second domain 139 of the third protease 130, and an optional complementary association domain 159 of the third protease 130; wherein the first domain 138 of the third protease 130 includes the cut site 115 specific for the first protease 110; wherein the second domain 139 of the third protease 130 includes another cut site 115 specific for the first protease 110; wherein the complementary association domain 159 the third protease 130 optionally includes two parts 159a, 159b of the third protease 130, each part 159a, 159b the third protease 130 connected to one of the third protease's 130 cut sites 115, 115; and wherein the third protease 130 is configured to be deactivated by cleavage of either of its cut sites 115, 115.

In some embodiments of the synthetic protein circuit, the fourth protease 230 protease further includes a first domain 238 of the fourth protease 230, a second domain 239 of the fourth protease 230, and an optional association domain 158 of the fourth protease 230; wherein the first domain 238 of the fourth protease 230 includes the cut site 125 specific for the second protease 120; wherein the second domain 239 of the fourth protease 230 includes another cut site 125 specific for the second protease 120; wherein the association domain 158 of the fourth protease 230 optionally includes two parts 158a, 158b, each part 158a, 158b connected to one of the fourth protease's 230 cut sites 125, 125; and wherein the fourth protease 230 is configured to be deactivated by cleavage of either of its cut sites 125, 125.

In some embodiments, the synthetic protein circuit comprises an IMPLY logic gate. In some embodiments, the synthetic protein circuit includes a third protease 130 including a cut site 125 specific for the second protease 120, and configured to be deactivated by cleavage of its cut site 125; wherein the target protein 140 further includes a cut site 115 specific for the first protease 110 and a cut site 135 specific for the third protease 130 between the degron 141 of the target protein 140 and a part 144 of the target protein 140, and wherein the target protein 140 is stabilized by cleavage of either cut sites 115, 135. In some embodiments, the third protease 130 further includes a first domain 138, a second domain 139, and an optional association domain 158; wherein the first domain 138 of the third protease 130 includes the third protease's cut site 125 specific for the second protease 120; wherein the second domain 139 of the third protease 130 includes another cut site 125 specific for the second protease 120; wherein the association domain 158 of the third protease 130 optionally includes two parts 158a, 158b of the third protease 130, each part 158a, 158b of the third protease 130 connected to one of the third protease's 130 cut sites 125, 125; and wherein the third protease 130 is configured to be deactivated by cleavage of either of its cut sites 125, 125.

In some embodiments, the synthetic protein circuit comprises a NIMPLY logic gate. In some embodiments, the synthetic protein circuit includes a third protease 130 including a cut site 115 specific for the first protease 110, and configured to be deactivated by cleavage of its cut site 115; wherein the target protein 140 further includes a cut site 135 specific for the third protease 130 between the degron 141 and a part 144 of the target protein, and a cut site 125 specific for the second protease 120 connected to another degron 142 of the target protein 140 and an optional association domain 158 of the target protein 140, and wherein the target protein 140 is stabilized by cleavage of both of its cut sites 125, 135. In some embodiments, the third protease 130 further includes a first domain 138 of the third protease 130, a second domain 139 of the third protease 130, and an optional complementary association domain 159 of the third protease 130; wherein the first domain 138 of the third protease 130 includes the cut site 115 specific for the first protease 110; wherein the second domain 139 of the third protease 130 includes another cut site 115 specific for the first protease 110; wherein the complementary association domain 159 of the third protease 130 optionally includes two parts 159a, 159b of the third protease 130, each part 159a, 159b of the third protease 130 connected to one of the third protease's 130 cut sites 115, 115; and wherein the third protease 130 is configured to be deactivated by cleavage of either of its cut sites 115, 115.

In some embodiments, the synthetic protein circuit comprises an XOR logic gate. In some embodiments, the synthetic protein circuit includes a second target 240 protein including a degron 241 of the second target 240 protein that destabilizes the second target protein 240 when present on the second target protein 240; wherein the target protein 140 further includes a cut site 115 specific for the first protease 110 between its degron 141 and a part 144 of the target protein 140, an other degron 142 of the target protein 140, and a cut site 125 specific for the second protease 120 connected to the other degron 142 of the target protein 140, wherein the target protein 140 is destabilized by its first degron 141 unless its cut site 115 specific for the first protease 110 is cleaved by the first protease 110, and wherein the target protein 140 is destabilized by cleavage of its cut site 125 specific for the second protease 120; and wherein the second target protein 240 further includes a cut site 125 specific for the second protease 120 between its degron 241 and the part 244 of the second target protein 240, an other degron 242 of the second target protein 240, and a cut site 115 specific for the first protease 110 connected to the other degron 242 of the second target protein 240, wherein the second target protein 240 is destabilized by its first degron 241 unless its cut site 125 specific for the second protease 120 is cleaved by the second protease 120, and wherein the second target protein 240 is destabilized by cleavage of its cut site 115 specific for the first protease 110. In some embodiments, the second target protein 240 further includes a complementary association domain 159 of the second target protein 240 connected at or near the other degron 242 of the second target protein 240 or the second target protein's 240 cut site 115 specific for the first protease 110. In some embodiments, the target protein's 140 other degron 142 includes a masking peptide 146 of the other degron 142 of the target protein 140 connected to the target protein's 140 other degron 142, wherein the masking peptide 146 of the other degron 142 of the target protein 140 prevents the target protein's 140 other degron 142 from destabilizing the target protein 140 when the masking peptide 146 of the other degron 142 of the target protein 140 is present on the target protein 140, wherein the masking peptide 146 of the other degron 142 of the target protein 140 is configured to be cleaved from the target protein 140 when the target protein's 140 cut site 125 specific for the second protease 120 is cleaved by the second protease 120, wherein the target protein 140 is configured to be destabilized by cleavage of its cut site 125 specific for the second protease 120, wherein cleavage of the target protein's 140 cut site 125 specific for the second protease 120 uncovers the target protein's 140 other degron 142 thereby destabilizing the target protein 140. In some embodiments, the second target protein's 240 other degron 242 includes a masking peptide 246 of the other degron 142 of the second target protein 240 connected to the second target protein's 240 other degron 242, wherein the masking peptide 246 of the other degron 142 of the second target protein 240 prevents the second target protein's 240 other degron 242 from destabilizing the second target protein 140 when the masking peptide 246 of the other degron 142 of the second target protein 240 is present on the second target protein 240, wherein the masking peptide 246 of the other degron 142 of the second target protein 240 is configured to be cleaved from the second target protein 240 when the second target protein's 240 cut site 115 specific for the first protease 110 is cleaved by the first protease 110, wherein the second target protein 240 is configured to be destabilized by cleavage of its cut site 115 specific for the first protease 110, wherein cleavage of the second target protein's 240 cut site 115 specific for the first protease 110 uncovers the second target protein's 240 other degron 242 thereby destabilizing the second target protein 240.

In some embodiments, the synthetic protein circuit comprises an XNOR logic gate. In some embodiments, the synthetic protein circuit includes a third protease 130 including a cut site 115 specific for the first protease 110, a cut site 125 specific for the second protease 120, and one or more optional association domains 158, 159 of the third protease 130, wherein the third protease 130 is configured to be deactivated by cleavage of either of its cut sites 115, 125; wherein the target protein 140 further includes a second degron 142 of the target protein, a cut site 115 specific for the first protease 110, a cut site 125 specific for the second protease 120, and two cut sites 135, 135 specific for the third protease 130, and wherein the target protein 140 is stabilized by cleavage of: its cut site 115 specific for the first protease 110 and its cut site 125 specific for the second protease 120, or both of its cut sites 135, 135 specific for the third protease 130. Other combinations may also be included such as follows: 115 and the left 135, or 125 and the right 135.

In some embodiments of the synthetic protein circuit, the third protease 130 further includes a first domain 138 of the third protease 130 and a second domain 139 of the third protease 130; wherein the first domain 138 of the third protease 130 includes the cut sites 115, 125 specific for the first and second proteases 110, 120 and the optional association domain 158 of the third protease 130; wherein the second domain 139 of the third protease 130 includes another cut site 115 specific for the first protease 110, another cut site 125 specific for the second protease 120, and an optional complementary association domain 159 of the third protease 130; and wherein the third protease 130 is configured to be deactivated by cleavage of any of its cut sites 115, 115, 125, 125. In some embodiments, the target protein's 140 cut site 115 specific for the first protease 110 and one of the target protein's 140 two cut sites 135, 135 specific for the third protease 130 separate the target protein's 140 first degron 141 from a part 144 of the target protein 140; and wherein the target protein's 140 cut site 125 specific for the second protease 120 the other of the two cut sites 135 specific for the third protease 130, and the association domain 159 of the target protein 140 separate the target protein's 140 second degron 142 from the part 144 of the target protein 140.

In some embodiments of the synthetic protein circuit, the system or synthetic protein circuit comprises a bandpass circuit or filter, or an adaptive pulse circuit such as is shown, exemplified, or described in FIGS. 3A-3H. In some embodiments of the bandpass circuit or filter, a second protease 120 is tuned by a third protease 130. In other embodiments, a first protease is tuned by a second, third, or fourth protease. In accordance with some embodiments, any protease may tune another protease. Some embodiments include a system such as a synthetic protein circuit, including: a first protease 110; a second protease 120; and target proteins 140 each including: a first degron 141 of the target protein 140 that destabilizes the target protein 140 when present on the target protein 140 by enhancing degradation of the target protein 140, a cut site 115 specific for the first protease 110 between the degron 141 of the target protein 140 and a part 144 of the target protein 140, wherein the target protein 140 is configured to be stabilized by cleavage of its cut site 115 specific for the first protease 110, and a cut site 125 specific for the second protease 120 connected to another degron 142 of the target protein 140, wherein the target protein 140 is configured to be destabilized by cleavage of the cut site 125 specific for the second protease 120 regardless of whether the first degron 141 of the target protein 140 is present on the target protein 140. In some embodiments, the other degron 142 of each target protein 140 includes a conditional N-end degron.

Some embodiments include a third protease 130 including a cut site 125 specific for the second protease 120, wherein the third protease 130 is configured to be deactivated by cleavage of its cut site 125 specific for the second protease 120; and wherein the second protease 120 includes a cut site 135 specific for the third protease 130, wherein the second protease 120 is configured to be deactivated by cleavage of its cut site 135 specific for the third protease 130.

In some embodiments of the synthetic protein circuit, the second protease 120 further includes a first domain 128 of the second protease 120, a second domain 129 of the second protease 120, a first complementary association domain 159, and an optional second complementary association domain 159c of the second protease 120 connected to the first or second domain 128, 129 of the second protease 120; wherein the first domain 128 of the second protease 120 includes the cut site 135 specific for the third protease 130; wherein the second domain 129 of the second protease 120 includes another cut site 135 specific for the third protease 130; wherein the first complementary association domain 159 of the second protease 120 optionally includes two parts 159a, 159b of the complementary association domain 159 of the second protease 120, each part 159a, 159b of the complementary association domain 159 of the second protease 120 connecting to one of the second protease's 120 cut sites 135 specific for the third protease 130; and wherein the second protease 120 is configured to be deactivated by cleavage of either of its cut sites 135, 135.

In some embodiments of the synthetic protein circuit, the third protease 130 further includes an optional association domain 159 of the third protease 130, and wherein cleavage of the third protease's 130 cut site 125 by the second protease 120 removes at least part of a cleavage domain 139 of the third protease 130, thereby deactivating the third protease 130.

In some embodiments of the synthetic protein circuit, the stability of the target proteins 140 includes an analog behavior that is dependent on a concentration of the first protease 110, wherein a higher concentration of the first protease 110 has a greater stabilizing effect on the target proteins 140 than a lower concentration of the first protease 110. In some embodiments, the stability of the target proteins 140 includes an analog behavior that is dependent on a concentration of the second protease 120, wherein a higher concentration of the second protease 120 has a greater destabilizing effect on the target proteins 140 than a lower concentration of the second protease 120. In some embodiments, the concentration of the second protease 120 is decreased by a higher concentration of the third protease 130 as compared to a lower concentration of the third protease 130, or by a higher amount of a nucleic acid encoding the third protease 130 as compared to a lower amount of a nucleic acid encoding the third protease 130. In some embodiments, the analog behavior of the target protein 140 that is dependent on a concentration of the second protease 120 is more sharp and/or includes a greater threshold for destabilizing the target protein 140 at a higher concentration of the third protease 130 as compared to a lower concentration of the third protease 130, or at a higher amount of a nucleic acid encoding the third protease 130 as compared to a lower amount of a nucleic acid encoding the third protease 130.

In some embodiments of the synthetic protein circuit, the first protease 110 further includes a first domain 118 of the first protease 110 and a second domain 119 of the first protease 110; wherein the first domain 118 of the first protease 110 connects to a first conditional dimerization domain 368 of the first protease 110; wherein the second domain 119 of the first protease 110 connects to a second conditional dimerization domain 369 of the first protease 110; wherein the first and second conditional dimerization domains 368, 369 of the first protease 110 are configured to dimerize with each other upon binding a dimerizing agent 367. In some embodiments, the conditional dimerization domains 368, 369 of the first protease 110 each include one of an FK506 binding protein (FKBP), GyrB, GAI, Snap-tag, eDHFR, BCL-xL, CalcineurinA (CNA), CyP-Fas, FRB domain of mTOR, GID1, HaloTag, TIR1, auxin inducible degron, and/or Fab (AZ1). In some embodiments, the dimerizing agent 367 includes FK1012, FK506, FKCsA, Rapamycin, Coumermycin, Gibberellin, HaXS, TMP-HTag, auxin, or ABT-737. In some embodiments, at least one of the conditional dimerization domains 368, 369 and/or the dimerizing agent 367 include a leucine zipper motif or a complementary leucine zipper motif, a scaffold protein or a fragment thereof, a scaffold-binding motif, an antibody, an epitope, tetratricopeptide repeat, a tetracopeptide repeat-binding motif, a G-protein-coupled receptor, a β-arrestin, and/or a G protein.

Some embodiments relate to a system such as a synthetic protein circuit, including: a first protease 110; a second protease 120; and a target protein 140 including: one or more cut sites specific for a first, second, and/or third protease, and a degron of the target protein 140 configured to stabilize or destabilize the target protein 140 based on its configuration with one or more of the target protein's 140 cut sites specific for the first, second, and/or third proteases. In some embodiments, the first protease 110 further includes a first domain 118 of the first protease 110 and a second domain 119 of the first protease 110; wherein the first domain 118 of the first protease 110 connects to a first conditional dimerization domain 368 of the first protease 110; wherein the second domain 119 of the first protease 110 connects to a second conditional dimerization domain 369 of the first protease 110; wherein the first and second conditional dimerization domains 368, 369 of the first protease 110 are configured to dimerize with each other upon binding a dimerizing agent 367.

In some embodiments of the system or synthetic protein circuit, the analog behavior of the target protein 140 includes a bandpass behavior.

Some embodiments relate to a nucleic acid encoding all or a portion of the system or synthetic protein circuit described herein. In some embodiments, the nucleic acid includes DNA. In some embodiments, the DNA includes a vector configured for transient expression in a cell. In some embodiments, the DNA includes an expression construct configured to integrate into a host cell's DNA. In some embodiments, the nucleic acid includes RNA such as an mRNA.

Methods

Some embodiments relate to a method, including: providing a reaction solution with a protease or compound protease as described herein, and an enzyme such as a protease or compound protease or an enzyme described herein; and subjecting the reaction solution to a condition that allows the enzyme to cleave the cut site 515 of the compound protease 520. In some embodiments, providing the reaction solution comprises providing a reaction solution in vitro. Some embodiments include providing the reaction solution to a cell or to cells.

Some embodiments relate to a method of activating a signaling pathway in a cell, including providing to the cell a synthetic protein circuit or a nucleic acid encoding the synthetic protein circuit, the synthetic protein circuit including: a protease 410 including a first part 418 of the protease 410 and a second part 419 of the protease 410, the first part 418 of the protease 410 connecting to a signaling protein 471, and the second part 419 of the protease 410 connecting to a binding protein 472 that binds to an activated form of the signaling protein 471, wherein the first part 418 and the second part 419 are configured to form an active protease 410 when the binding protein 472 binds to the activated form of the signaling protein 471; and an effector protein 480 including a cut site 415 specific for the protease 410, wherein the effector protein 480 configured to be activated by cleavage of its cut site 415 specific for the protease 410. An example of utilizing such a method is shown in FIGS. 4A-4E. In some embodiments, the synthetic protein circuit further includes a second protease 120 that inactivates the first protease 410 and/or the effector protein 480. In some embodiments, the signaling pathway includes a cell death pathway. In some embodiments, the signaling protein 471 includes a signal transduction protein such as Ras or a fragment thereof. In some embodiments, the binding protein 472 includes Raf or a fragment thereof such as a Ras-binding domain (RBD). In some embodiments, the effector protein 480 includes a protease, a cell death protein such as a caspase, an immunomodulatory, or a specific antigen. In some embodiments, the method includes the use of a mutual inhibition motif such as a bandpass filter or adaptive pulse circuit as described herein.

Further Embodiments

As provided herein, synthetic protein-level circuits allows for engineering of powerful new cellular behaviors. Rational protein circuit design is facilitated by a composable protein-protein regulation system, in which individual protein components can regulate one another to create a variety of different circuit architectures. Here, it is shown that engineered viral proteases can function as composable protein components, which can together implement a broad variety of circuit-level functions in mammalian cells. In some versions of this system, termed CHOMP (Circuits of Hacked Orthogonal Modular Proteases), input proteases dock with and cleave target proteases to inhibit their function. These components can be connected to generate regulatory cascades, binary logic gates, and dynamic analog signal-processing functions. To demonstrate the utility of this system, a circuit was rationally designed that induces cell death in response to upstream activators of the Ras oncogene. Because CHOMP circuits can perform complex functions yet be encoded as single transcripts and delivered without genomic integration, they offer a scalable platform to facilitate protein circuit engineering for biotechnological applications. According to some embodiments, these engineered proteases enable programmable protein-level circuits that implement diverse functions in mammalian cells.

Synthetic biology allows for rational design of circuits that confer new functions in living cells. Many natural cellular functions are implemented by protein-level circuits, in which proteins specifically modify each other's activity, localization, or stability. For example, caspase-mediated programmed cell death is regulated by a circuit of proteases that activate one another through cleavage. Synthetic protein circuits could provide advantages over gene regulation circuits, including faster operation, direct coupling to endogenous pathways, single transcript delivery, and function without genomic integration (FIG. 1D).

A challenge is designing 'composable' protein components whose inputs and outputs are of the same type, so that they can form a wide variety of protein circuits, much as a few electronic components can be wired to produce a variety of electronic circuits (FIG. 1D). While natural protein domains have been combined to generate proteins with hybrid functions or to re-wire cellular pathways for research and biomedical applications, the lack of composability has limited the ability to design protein-level function in living cells.

Viral proteases are useful for such systems. Many of them exhibit strong specificity for short cognate target sites, which can be recognized and cleaved in various protein contexts. Natural viral diversity provides multiple proteases with distinct specificities. Viral proteases can be used with degrons to control protein stability. They can also activate transcription factors, synthetic intein zymogens, and other proteases in a purified protein system.

Figure 5A:
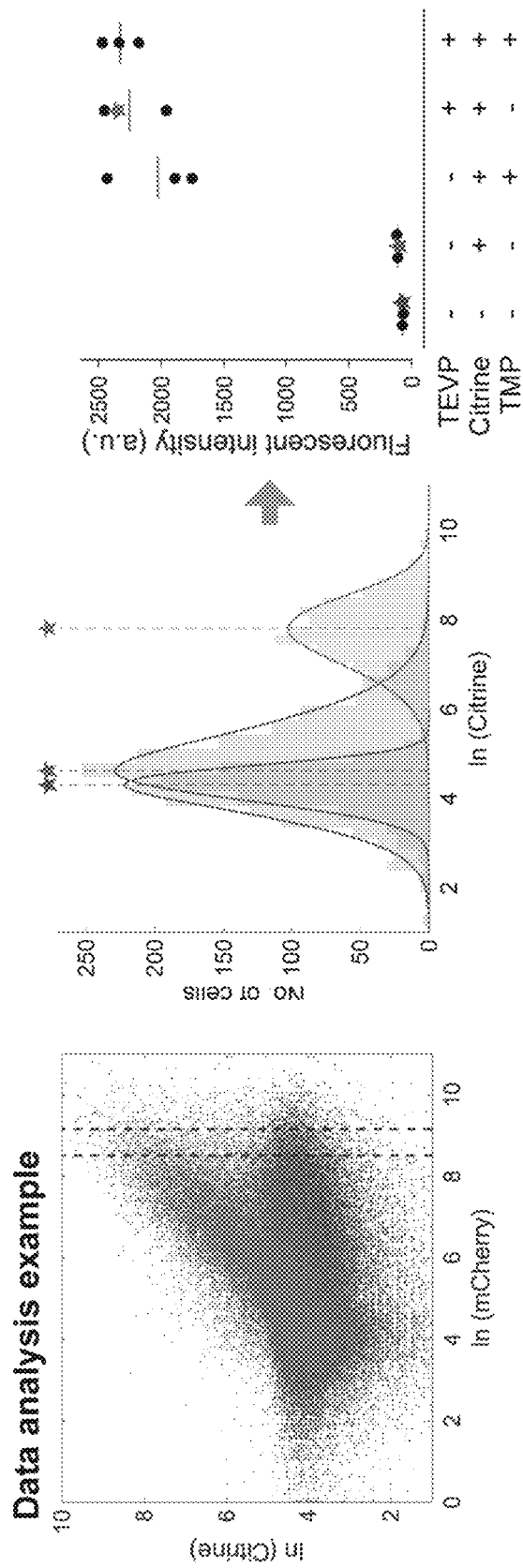
FIGS. 5A-5J depict information and data relating to the characterization and optimization of CHOMP components of some embodiments.
Figure 5B:
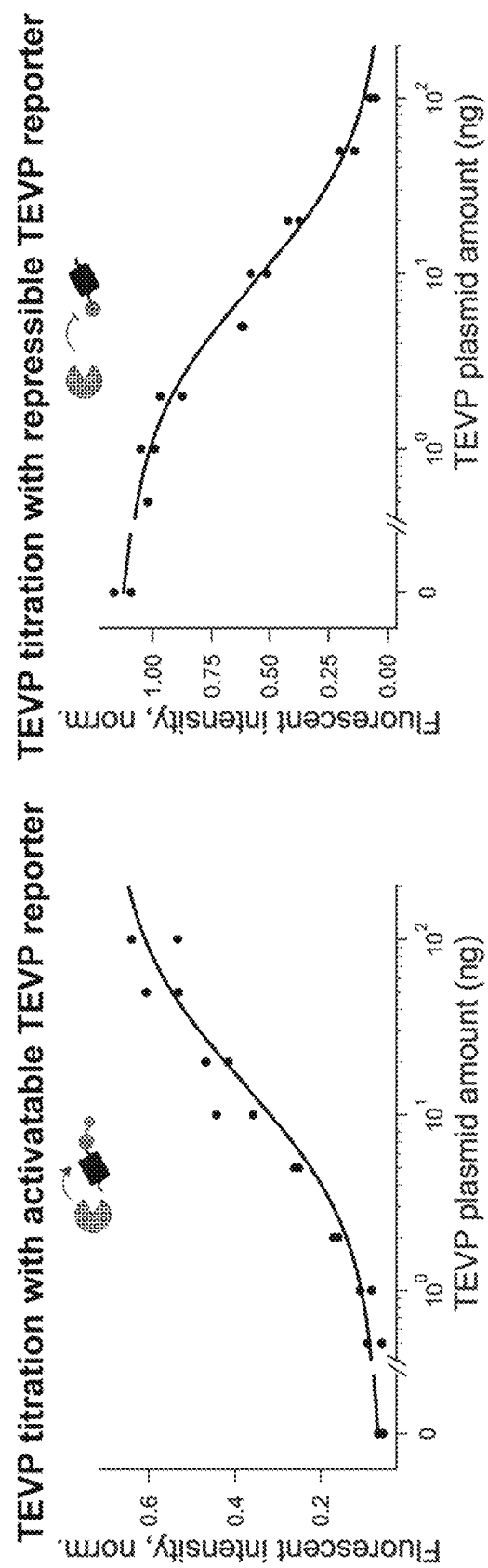
Figure 5C:
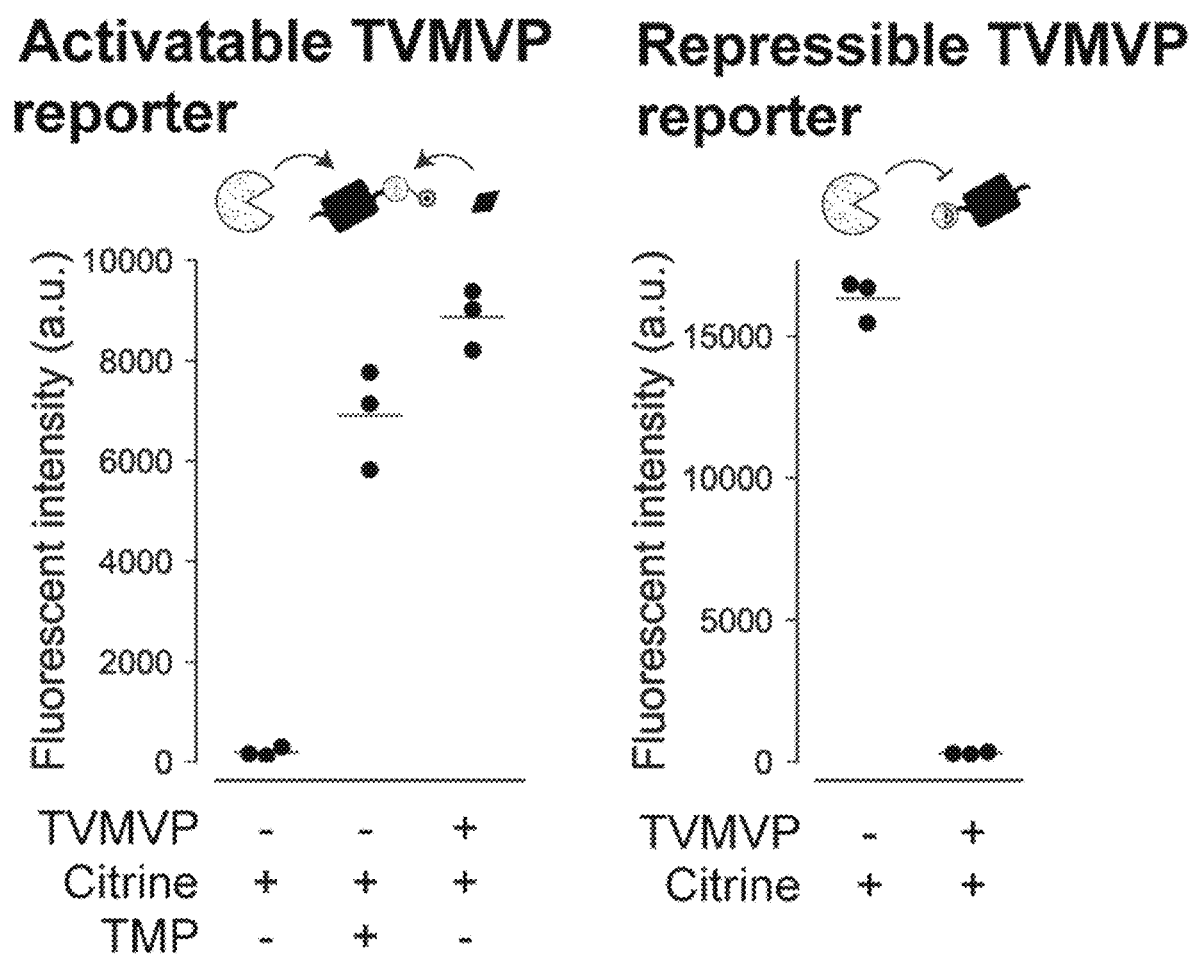

One protease used herein was the tobacco etch virus protease (TEVP). To quantify TEVP activity, a reporter (target protein) was designed in which a cognate cleavage site (tevs) is inserted between a Citrine fluorescent protein and a dihydrofolate reductase (DHFR) degron, which can be inhibited by trimethoprim (TMP) as a positive control (FIG. 1E). Human embryonic kidney (HEK293) cells were transfected with plasmids expressing different combinations of TEVP, the reporter, and an mCherry co-transfection marker, and cells were analyzed by flow cytometry. The mCherry signal was used to select highly transfected cells, which showed the largest separation of basal reporter fluorescence from cellular autofluorescence to maximize the observable dynamic range of the reporter (FIG. 1E and FIG. 5A). Treating cells with TEVP strongly increased reporter abundance to levels similar to those obtained by TMP inhibition of the degron (FIG. 1E, FIG. 5B, left). A complementary repressible reporter (target protein) was also designed in which TEVP cleavage exposes a destabilizing N-terminal tyrosine residue (FIG. 1F, FIG. 5B, right). These designs generalized in a straightforward way to the related tobacco vein mottling virus protease (TVMVP) and with some modifications to the unrelated hepatitis C virus protease (HCVP) (FIG. 5C, 1G). Furthermore, measuring activation of each reporter in response to each protease revealed limited cross-activation (FIG. 1G). Thus, according to some embodiments, at least three viral proteases can be used to orthogonally increase or decrease cognate reporters.

Figure 5D:
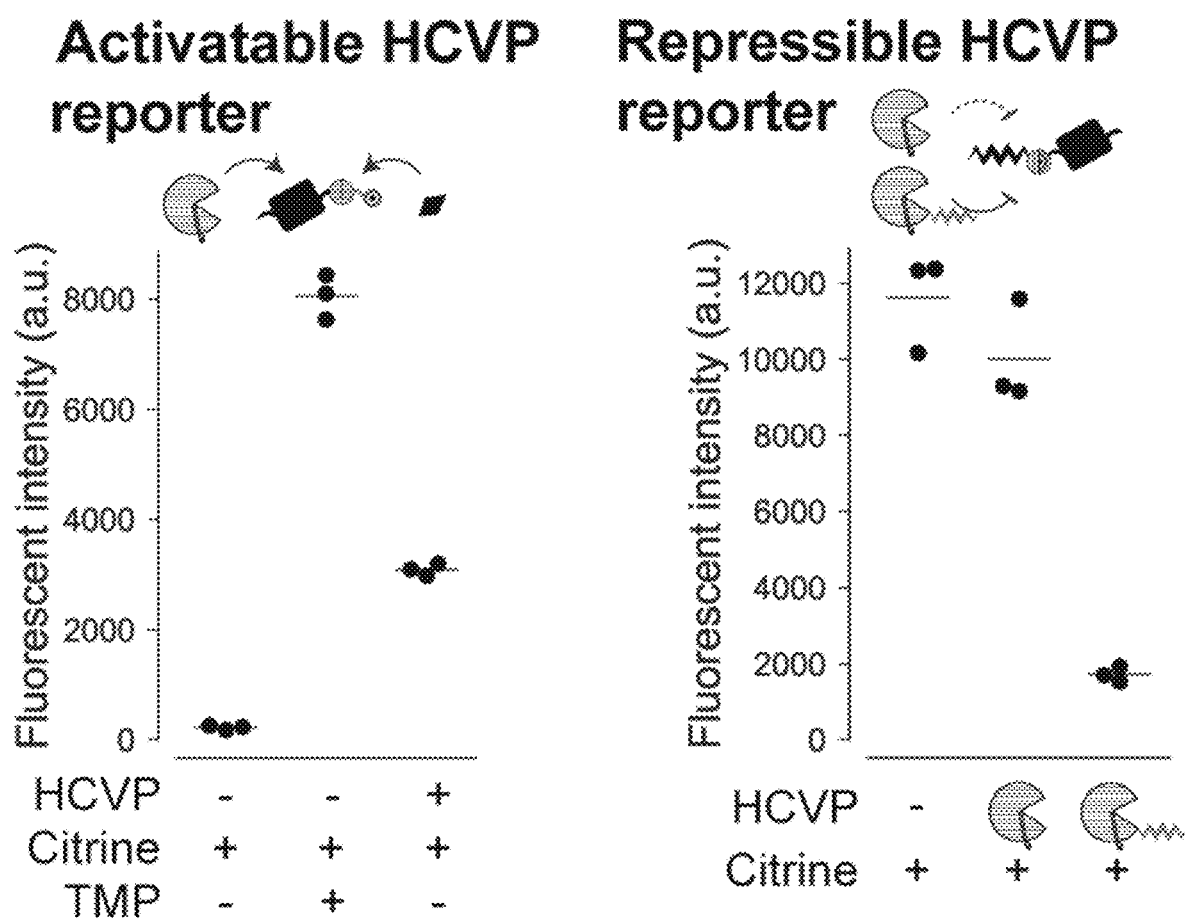
Figures 5E, 5F:
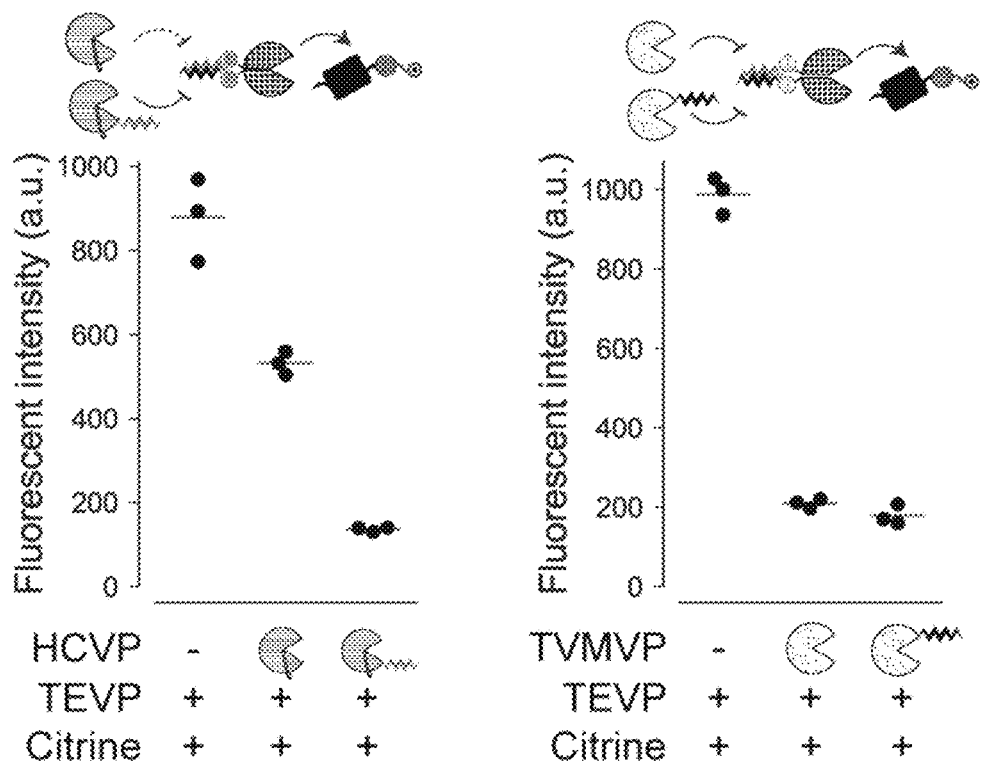

Protease-protease regulation was achieved to enable design of complex circuits. The degron strategy used for the reporters failed to produce strong regulation, possibly because proteases may cleave degrons within the same protease molecule with relaxed specificity. Instead, a scheme was designed that regulates protease activity, rather than abundance. Antiparallel hetero-dimerizing leucine zipper domains were incorporated to each half of a split TEVP to reconstitute its activity (FIG. 1H, left). The inventors also inserted HCVP cleavage sites between the leucine zippers and TEVP, to allow HCVP to inhibit TEVP. Finally, the inventors fused a leucine zipper (complementary to one of the zippers on split TEVP) to HCVP, thus enhancing its ability to dock with, and inhibit its TEVP target (FIG. 5E, left). This design successfully produced repression of TEVP by HCVP (FIG. 1H, left).

Figure 1I:
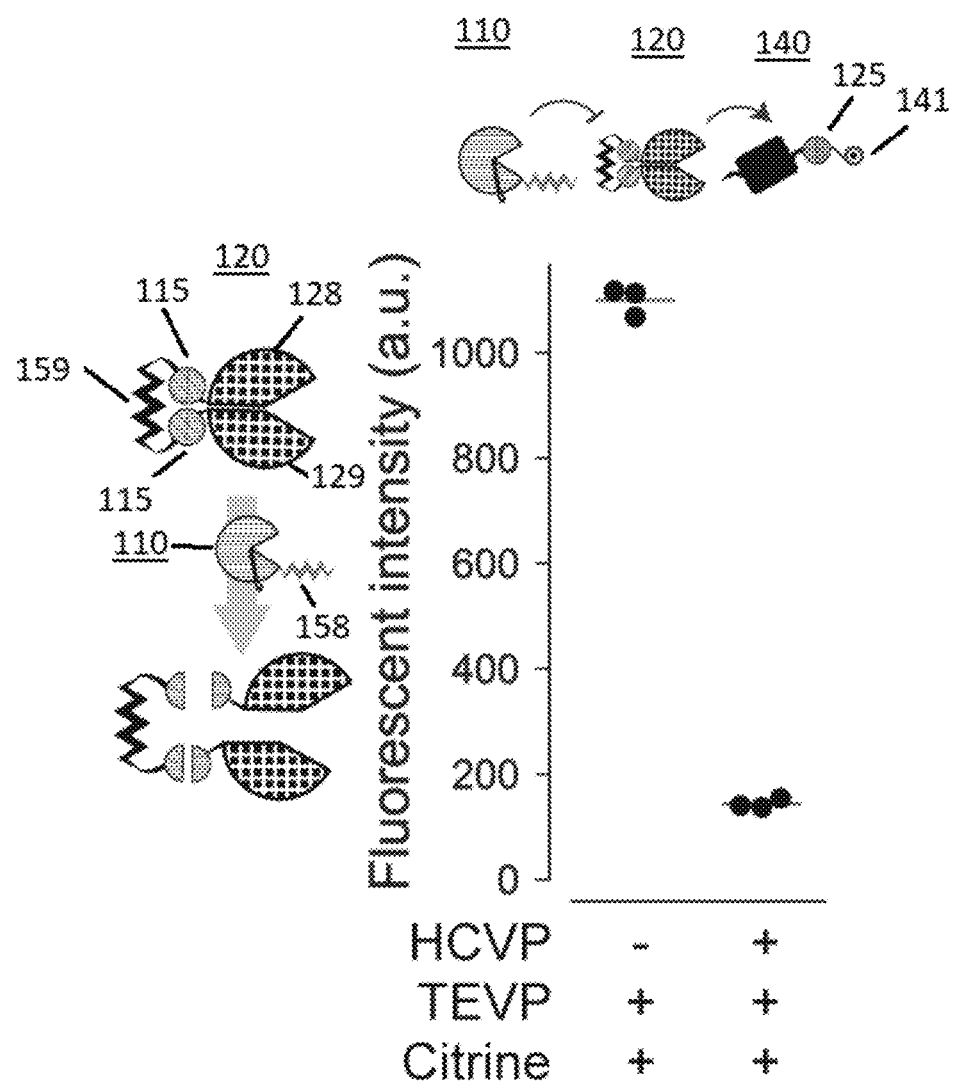
Figure 1J:
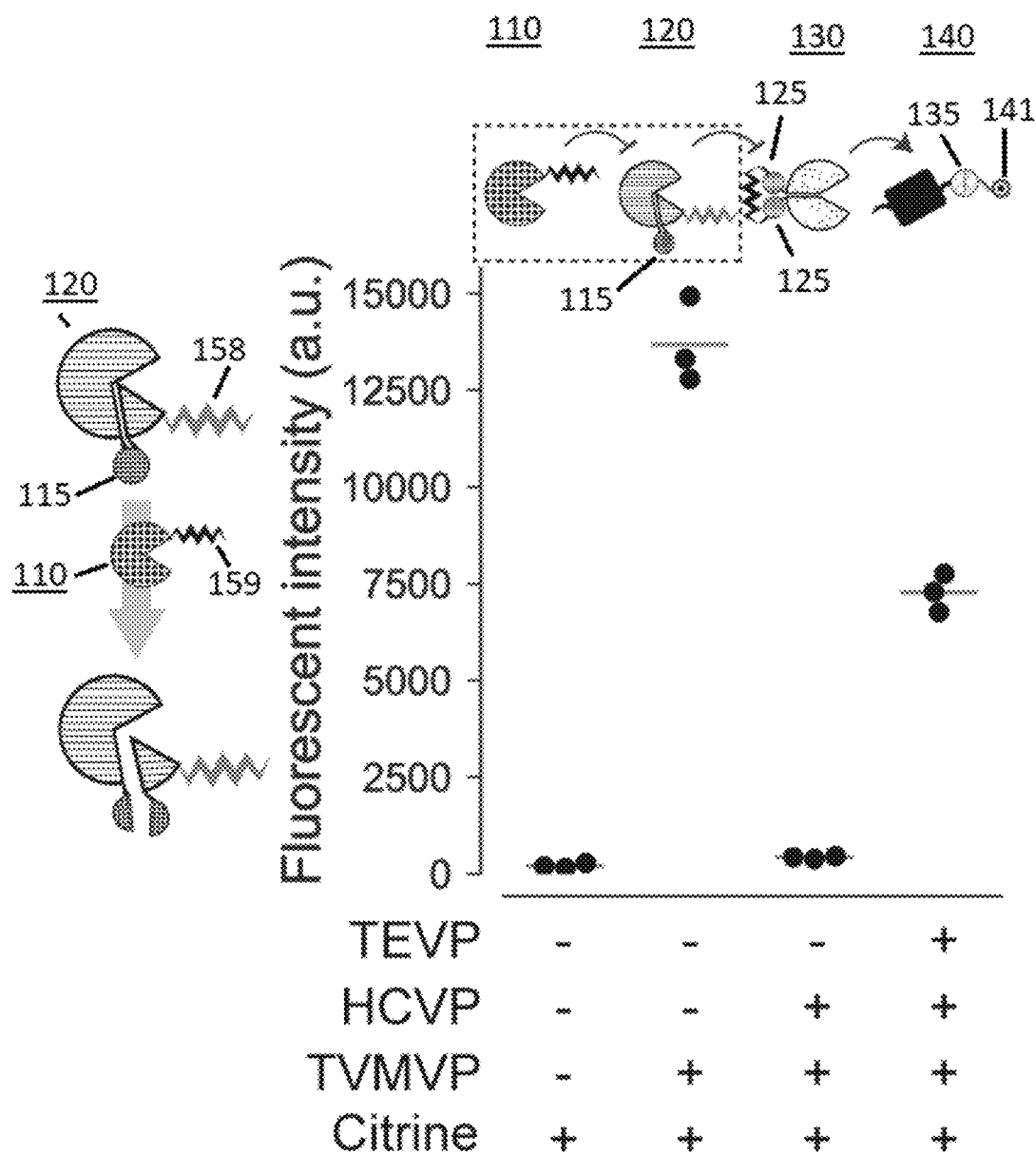
Figure 5G:
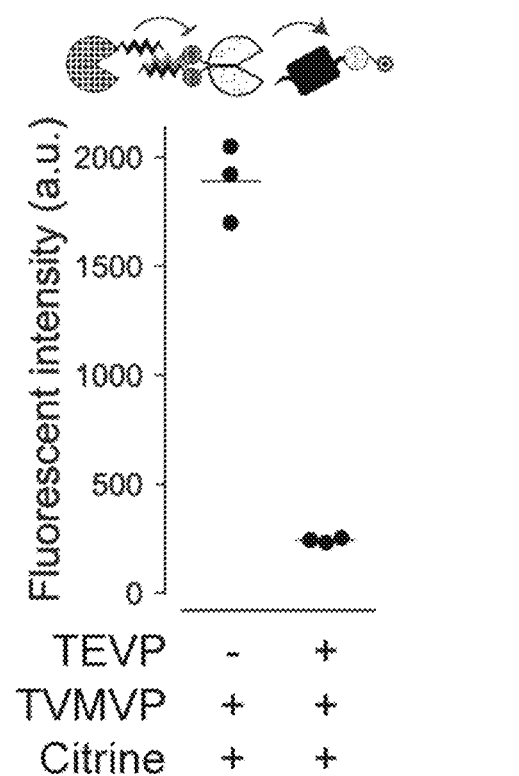
Figure 5H:
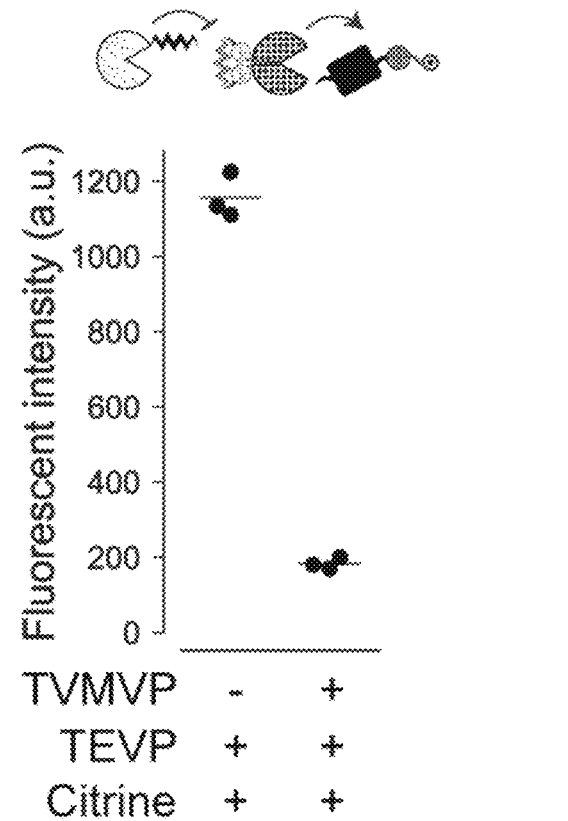
Figure 5I:
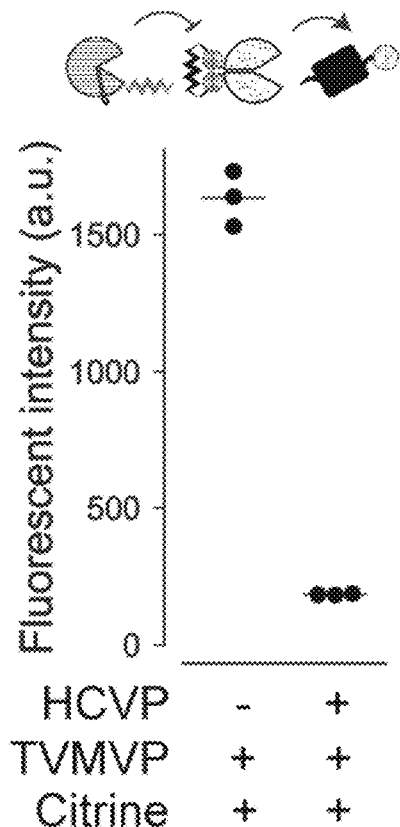
Figure 5I:
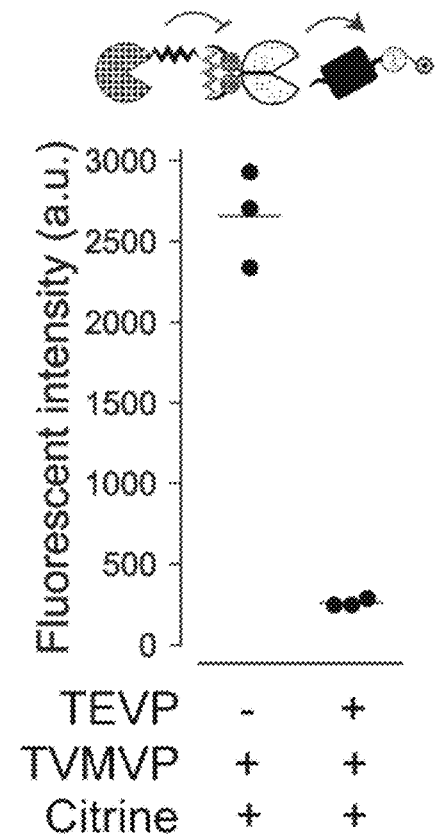
Figure 5J:
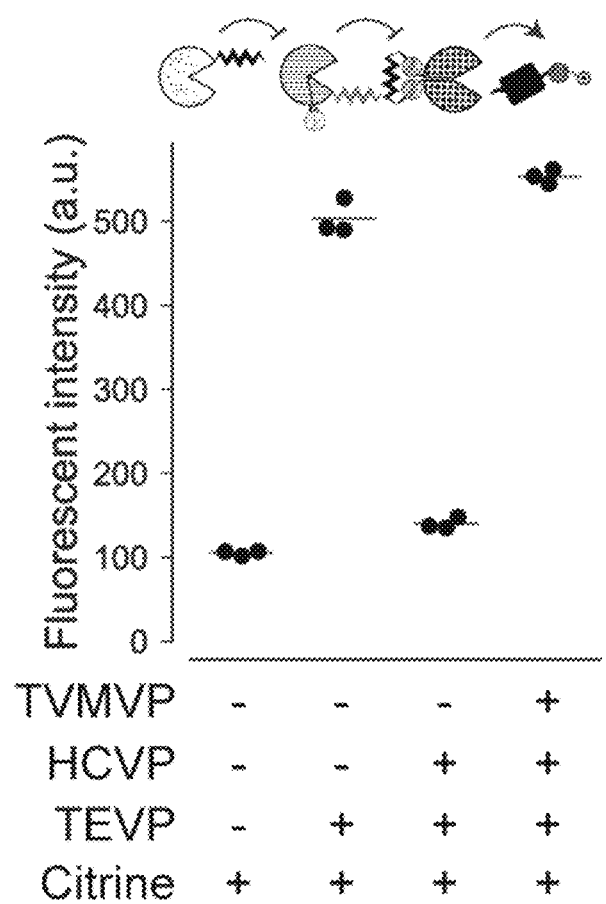

To generalize this design, a similar TEVP variant repressed by TVMVP was engineered (FIG. 5E, right). Based on its sequence similarity to TEVP (FIG. 5F), TVMVP variants repressed by either HCVP (FIG. 1H, right) or TEVP (FIG. 5G) were also engineered. To make these designs more compact, the inventors linked the two halves of each regulated protease with a single leucine zipper flanked by cleavage sites for the input protease, creating single-chain repressible proteases (FIG. 1I and FIGS. 5H, 5I). Similar approaches enabled engineering protease regulation of the unrelated protease HCVP using a different split strategy described herein. In these constructs, cleavage by either TEVP or TVMVP strongly reduced HCVP activity, enabling signal propagation through three-stage protease cascades (FIG. 1J and FIG. 5J). Together, this strategy established a composable protease regulation system.

Figure 2A:
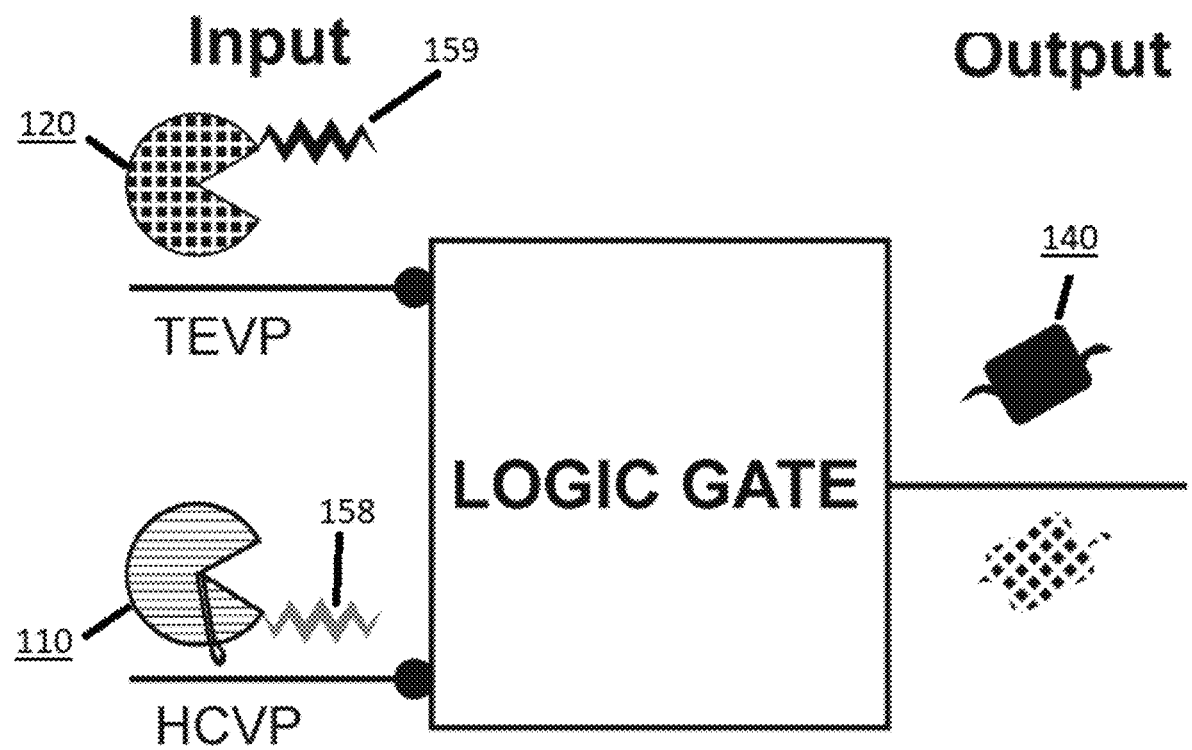
Figure 2B:
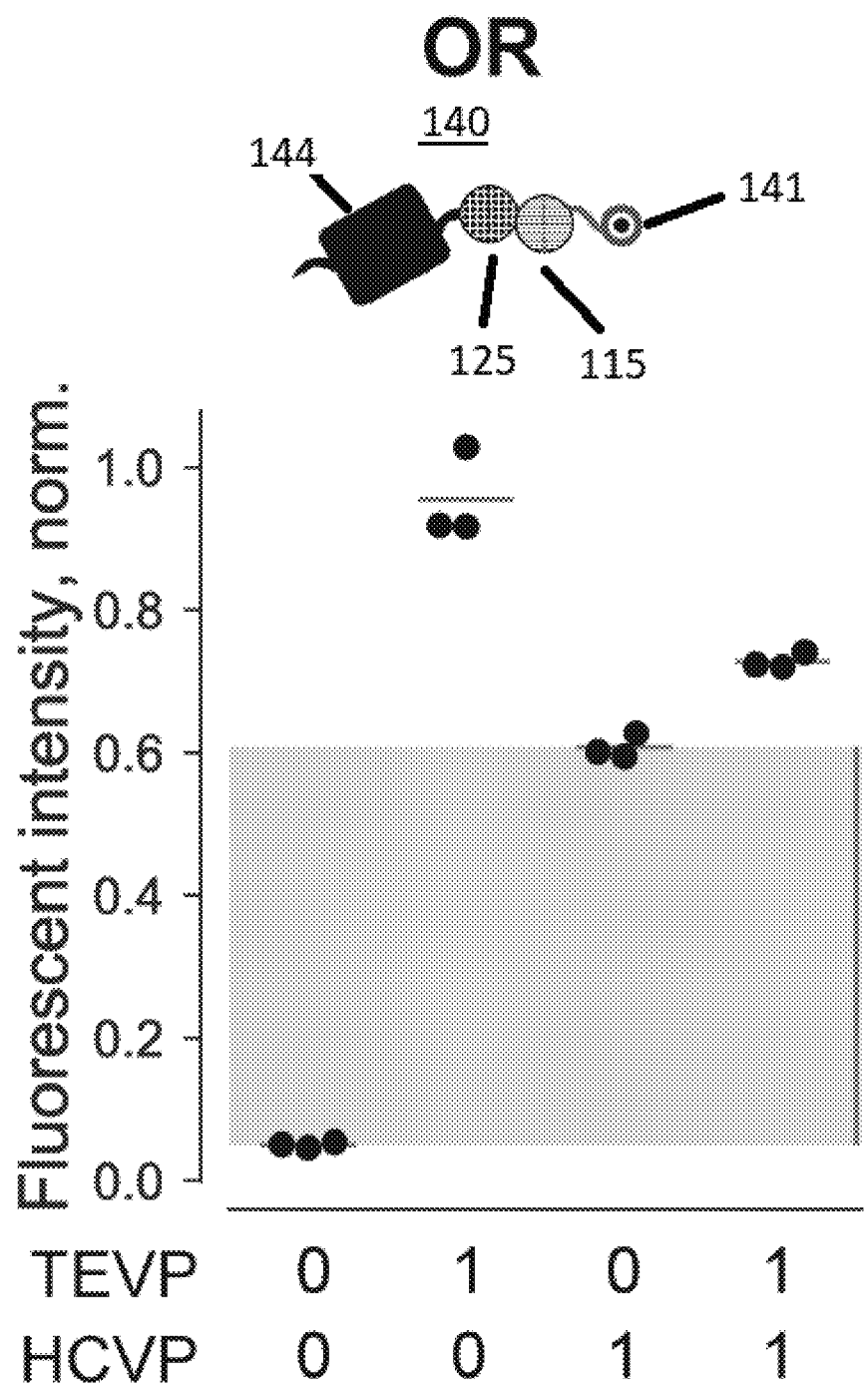
Figure 2D:
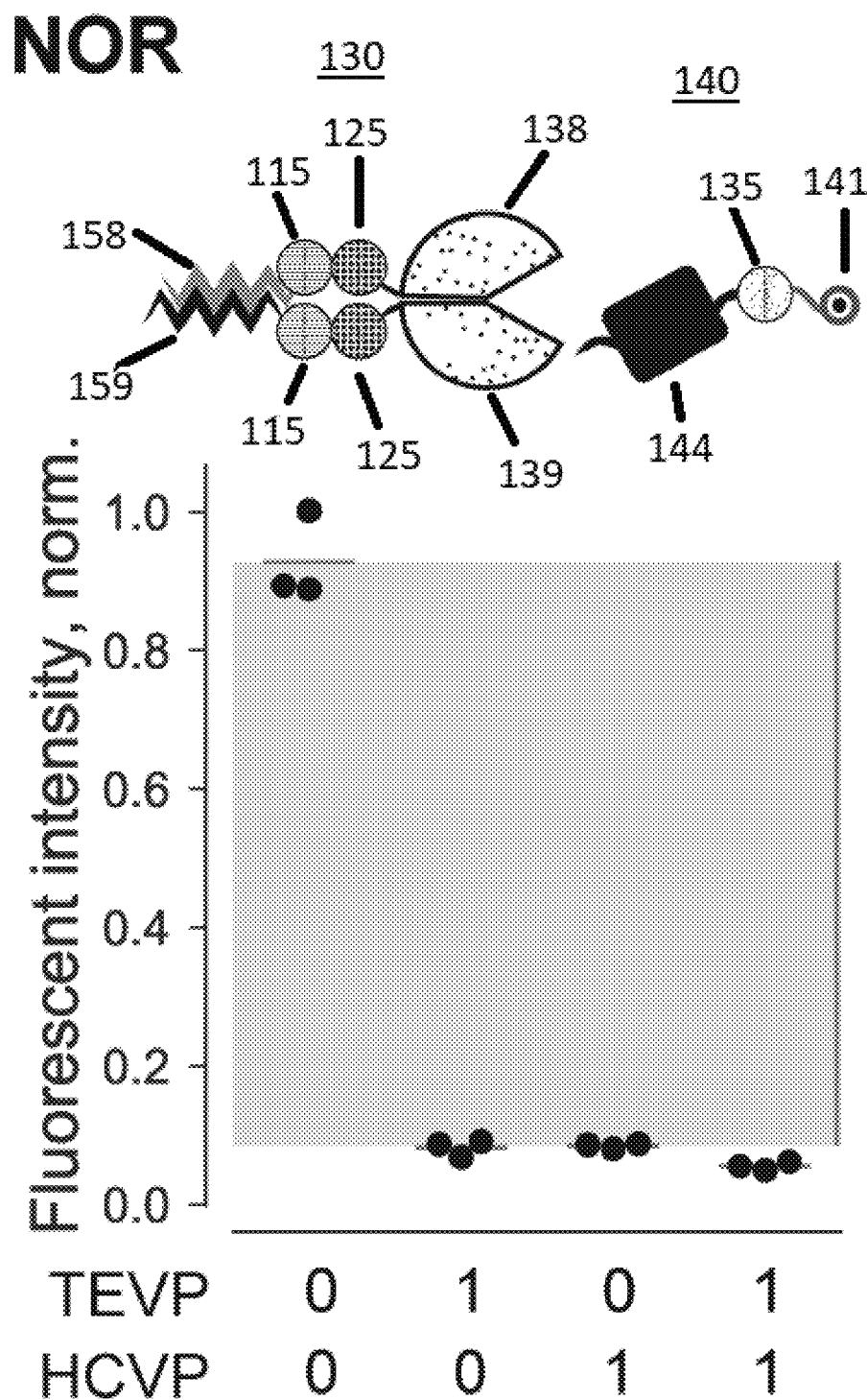
Figure 2E:
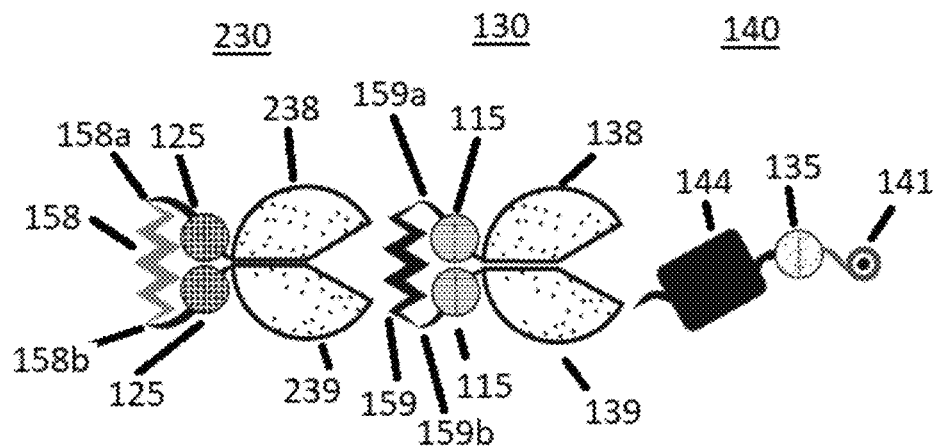
Figure 2E:
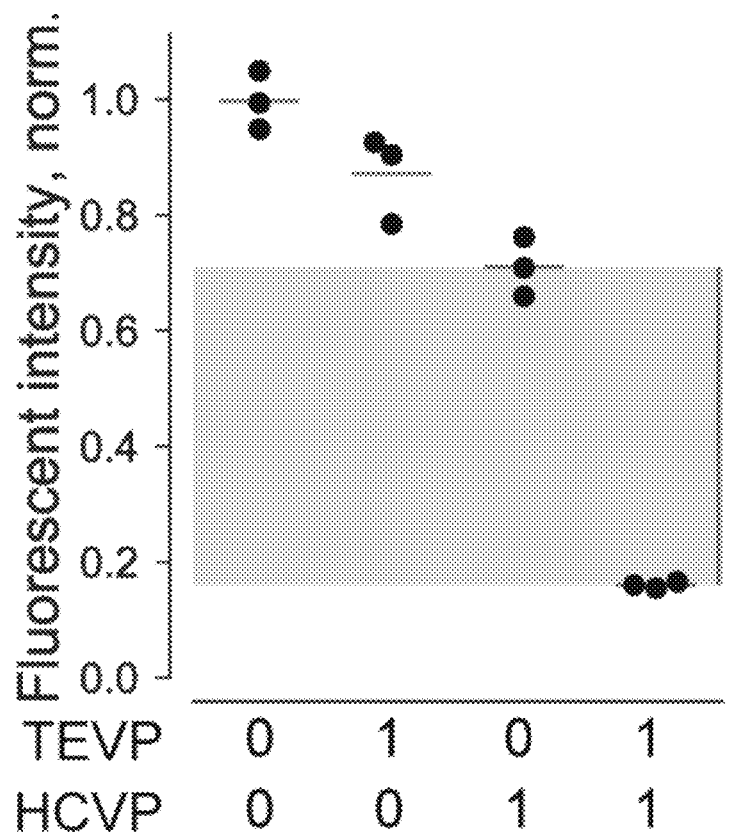
Figure 2F:
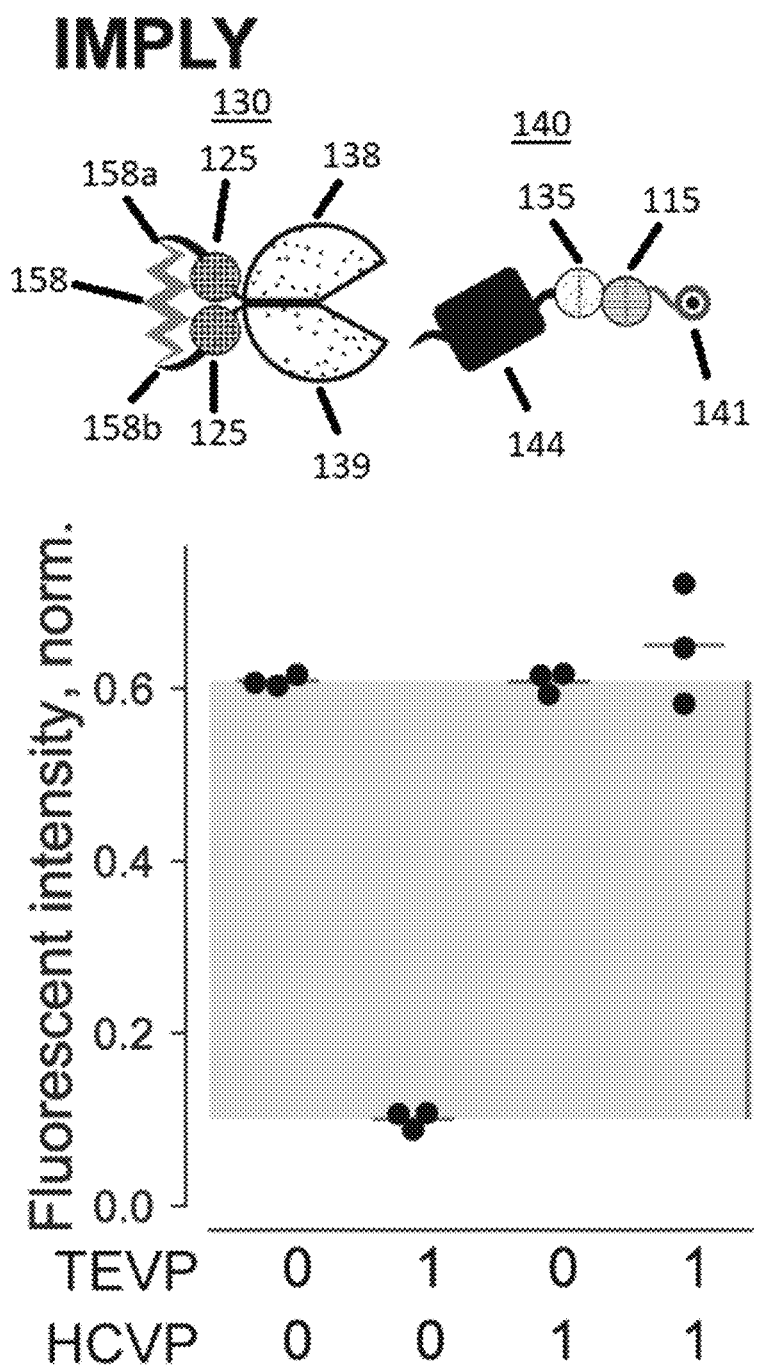
Figure 2G:
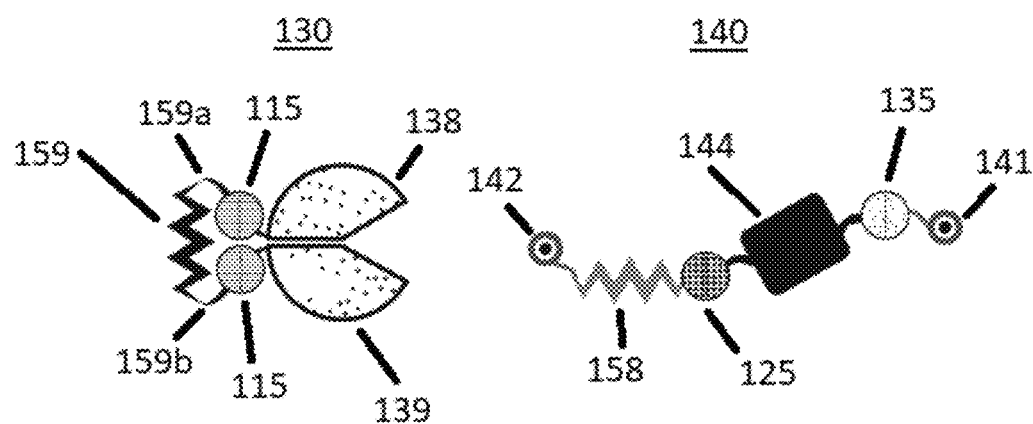
Figure 2G:
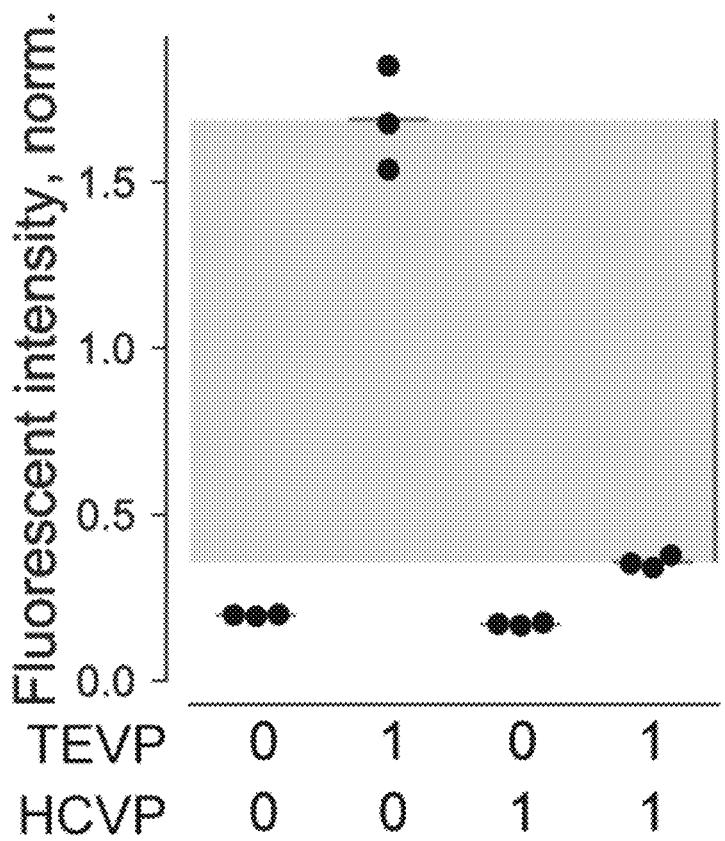
Figure 2H:
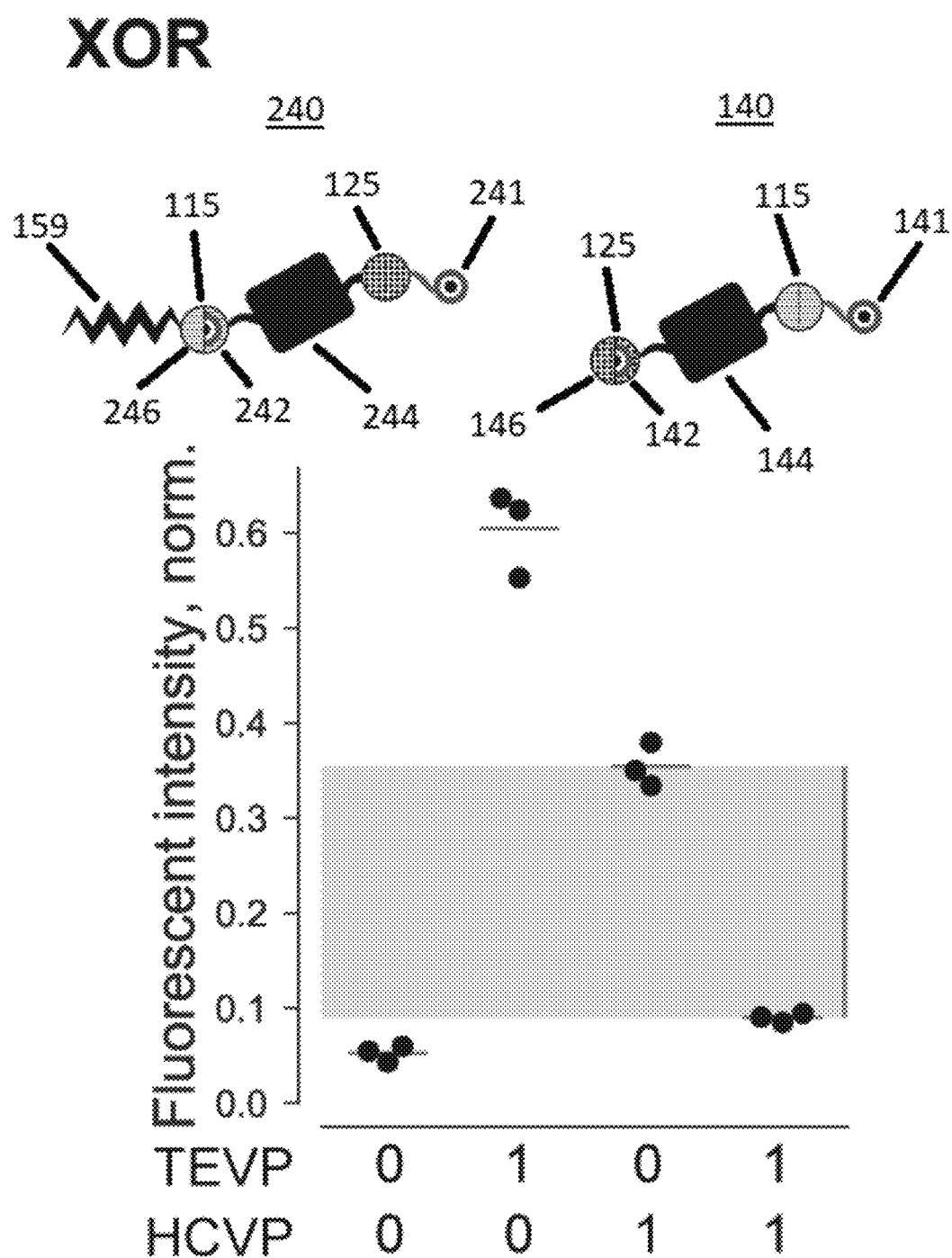
Figure 2I:
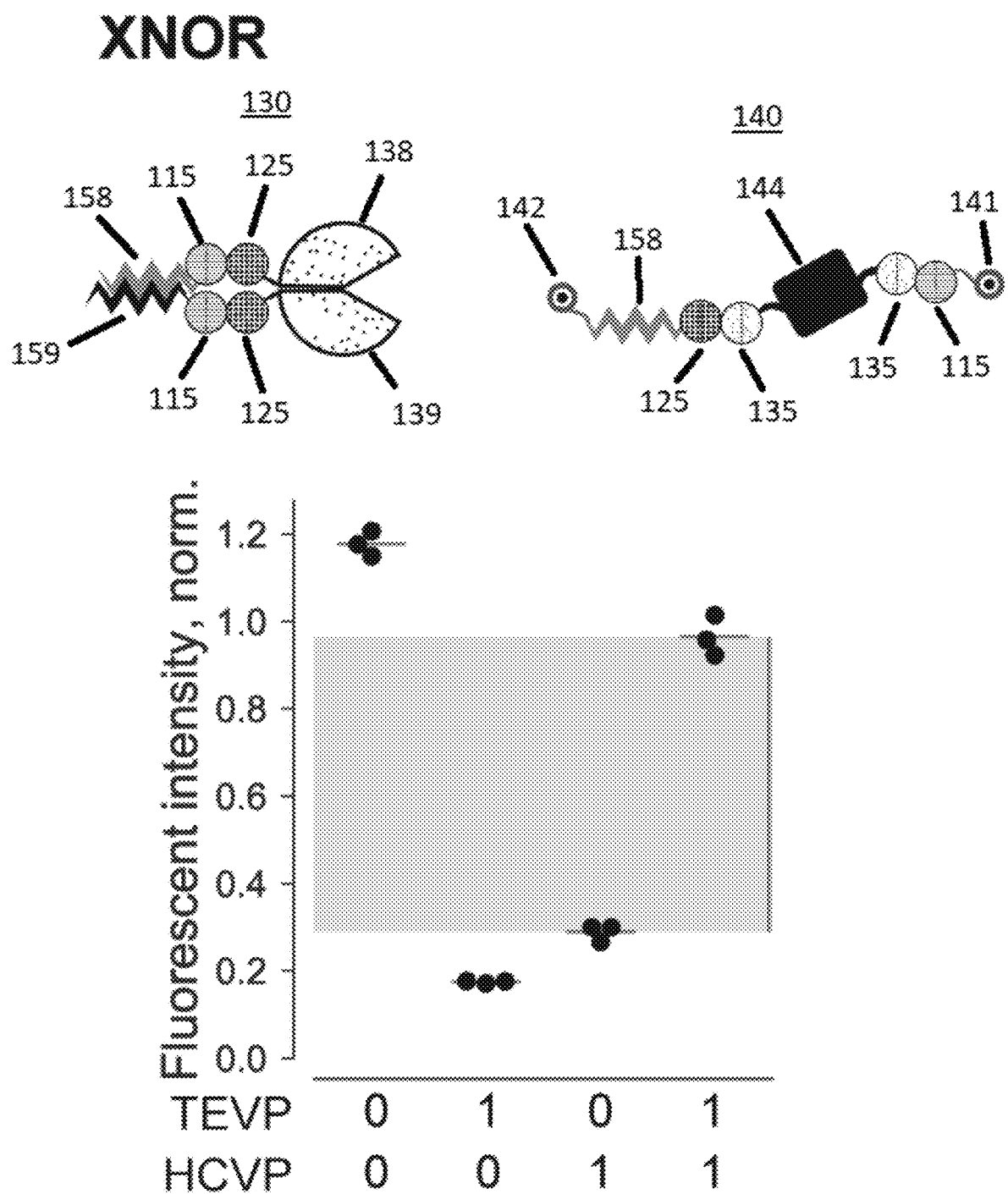
Figure 6A:
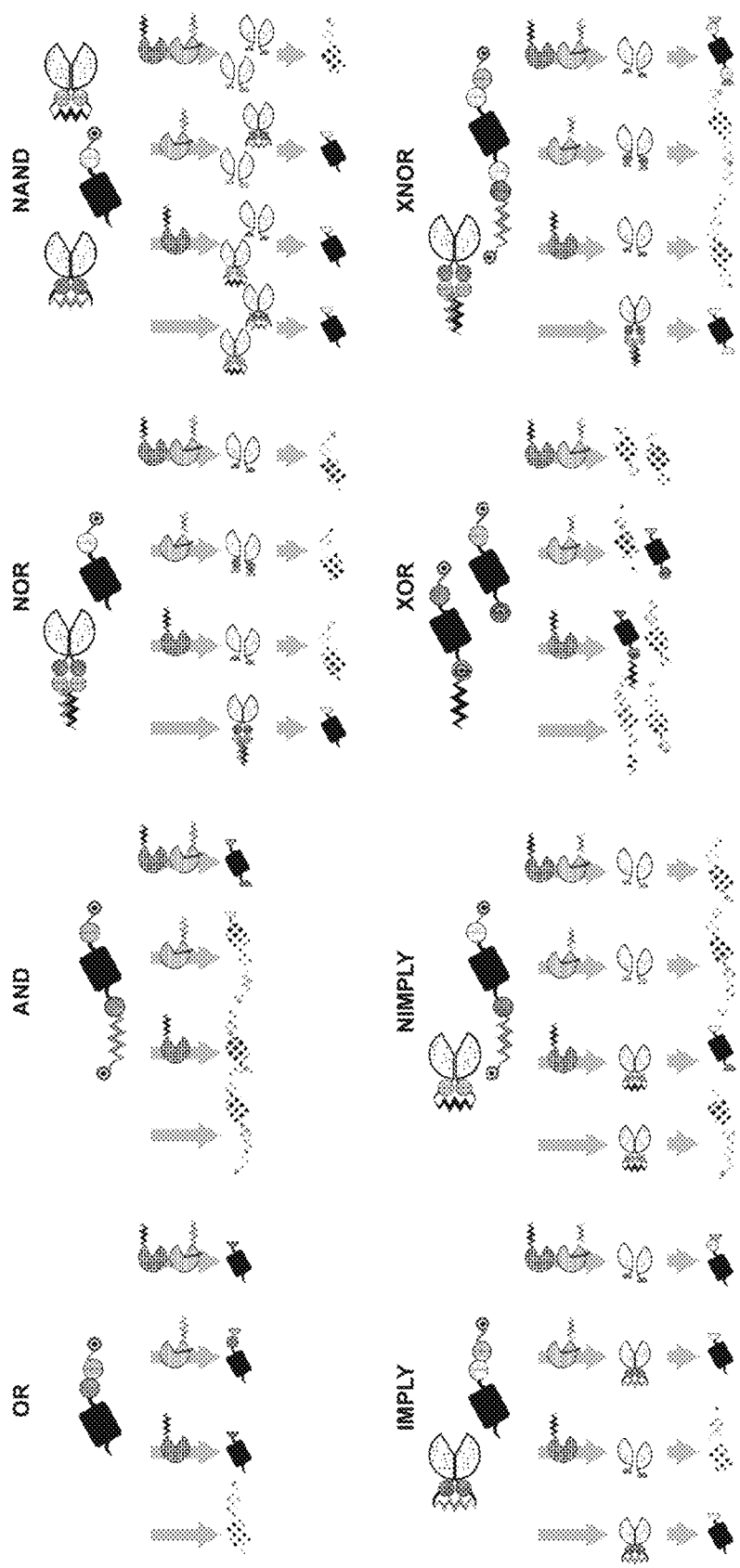
Figure 6B:
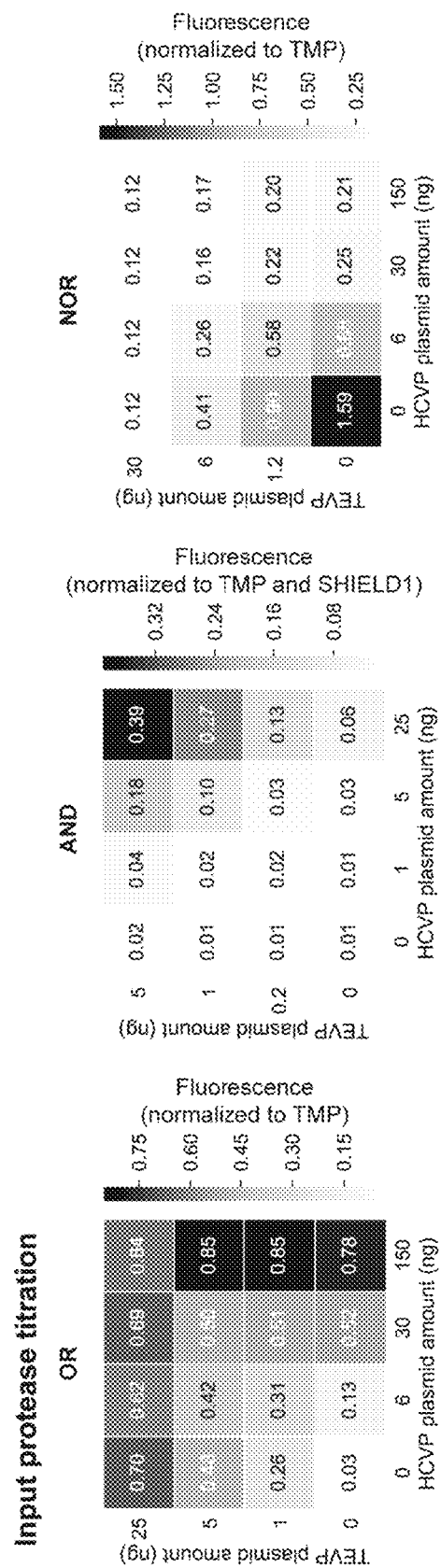
Figure 7A:
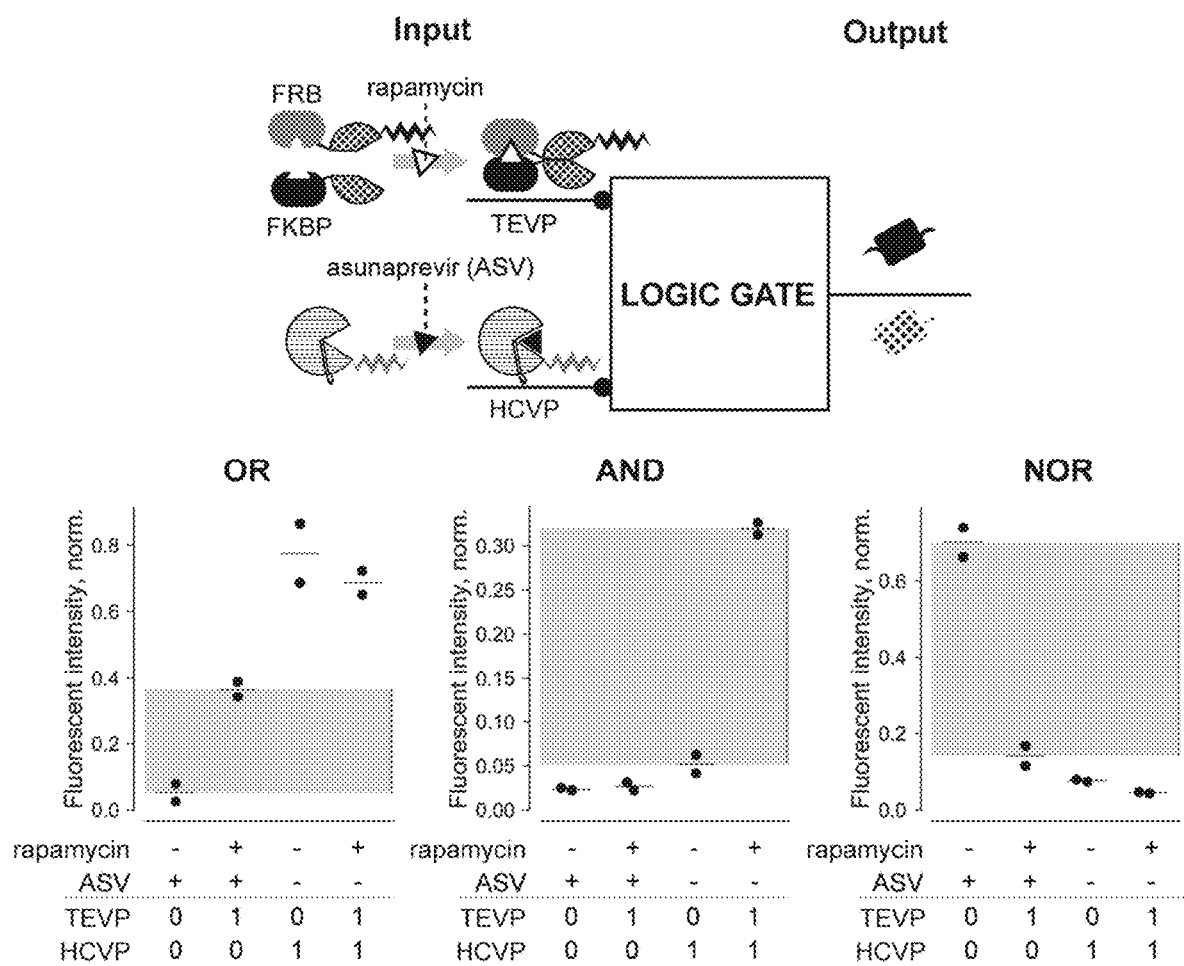
FIGS. 7A and 7B show information relating to expanding the inputs and complexity of logic gates in accordance with some embodiments.

Using this system, core circuit functions were designed, starting with Boolean logic. The inventors identified three design principles that together would be sufficient to enable all 8 two-input gates: First, incorporation of a consecutive pair of distinct cleavage sites between a degron and a target protein can implement OR logic, since cleavage of either site is sufficient to stabilize the protein (FIGS. 2A, 2B and 6A). Second, to implement AND logic, the inventors flanked the target protein with FKBP and DHFR degrons on the N- and C-termini, respectively, each removable with a distinct cleavage site. On the N-terminus, a leucine zipper facilitated input protease docking. In this design, removal of both degrons stabilized the protein (FIGS. 2A, 2C and 6A). Third, to implement negation, the inventors either used the N-end degron strategy (FIG. 1F) or propagated signals through an intermediate protease repression step (FIG. 1H). Co-transfection of each basic gate (OR, AND, and NOR as a specific case of negation) with varying concentrations of its inputs revealed the expected logic functions (FIGS. 2A, 6B). Further, varying the concentration of the reporter plasmid enabled tuning of output levels without disrupting the logical computation, facilitating matching of input and output levels in more complex circuits (FIG. 6C). Finally, by utilizing the HCVP inhibitor asunaprevir (ASV) and a rapamycin-induced TEVP, the inventors found that these gates could also be controlled by small molecule inputs (FIG. 7A). These results thus show that three core gates exhibit robust and tunable operation across multiple input methods.

Figure 7B:
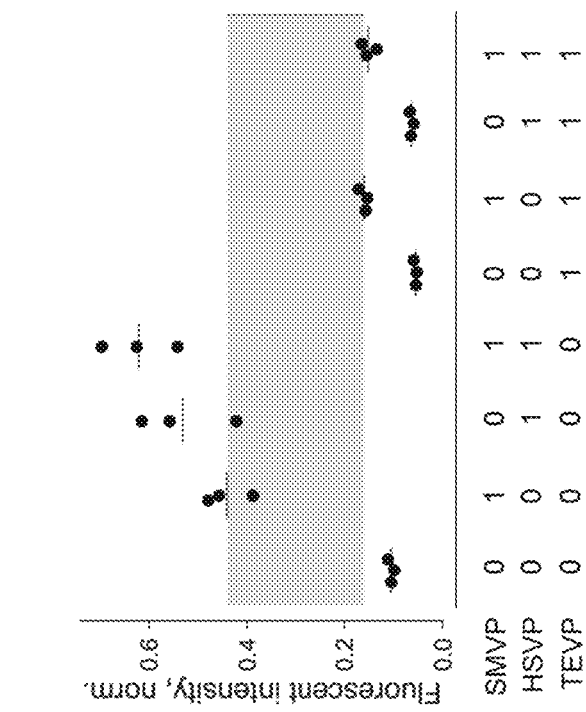
Figure 7B:
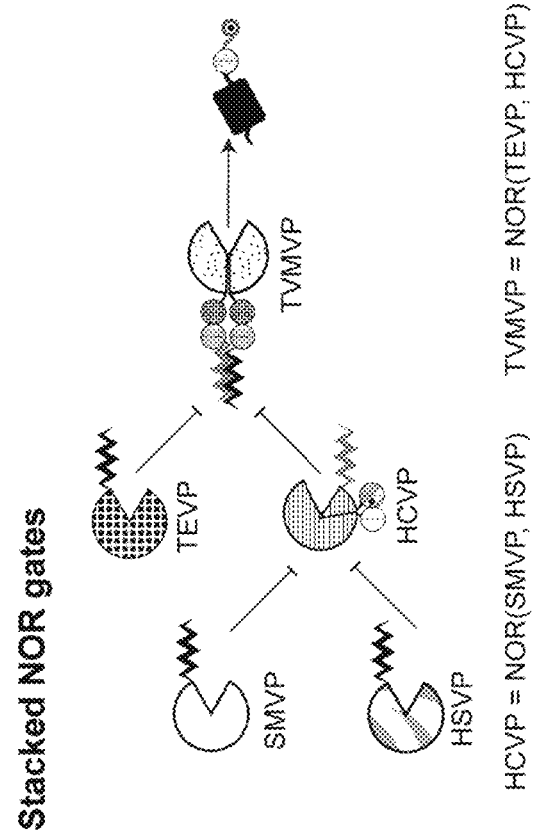

Next, these combined principles to were used to design and validate the other two-input gates (FIGS. 2A and 6A). Furthermore, to test whether output from one gate could be directly used as input to a subsequent gate, the inventors constructed a more complex nested NOR function using additional orthogonal proteases from soybean mosaic virus (SMVP) and herpes simplex virus (HSVP) (FIG. 7B). The output from this system was consistent with that expected from the logical function NOR(TEVP, NOR(SMVP, HSVP)) (FIG. 7B).

Beyond Boolean logic, analog signal filtering can allow for many cellular functions, such as the ability to selectively respond to specific input concentration ranges. The incoherent feed-forward loop (IFFL) motif, in which an input both activates and inhibits the same target, provides a simple implementation for this function. Inspired by the IFFL, the inventors combined an activating arm, in which TEVP removes a C-terminal degron, with a repressing arm, in which TVMVP reveals a destabilizing N-end tyrosine (FIG.

3A). To tune the position and sharpness of the bandpass, the inventors also introduced a positive feedback loop based on reciprocal inhibition between HCVP and TVMVP on the repression arm, such that the amount of HCVP expression sets a threshold for TVMVP activity (FIG. 3A).

Figure 3B:
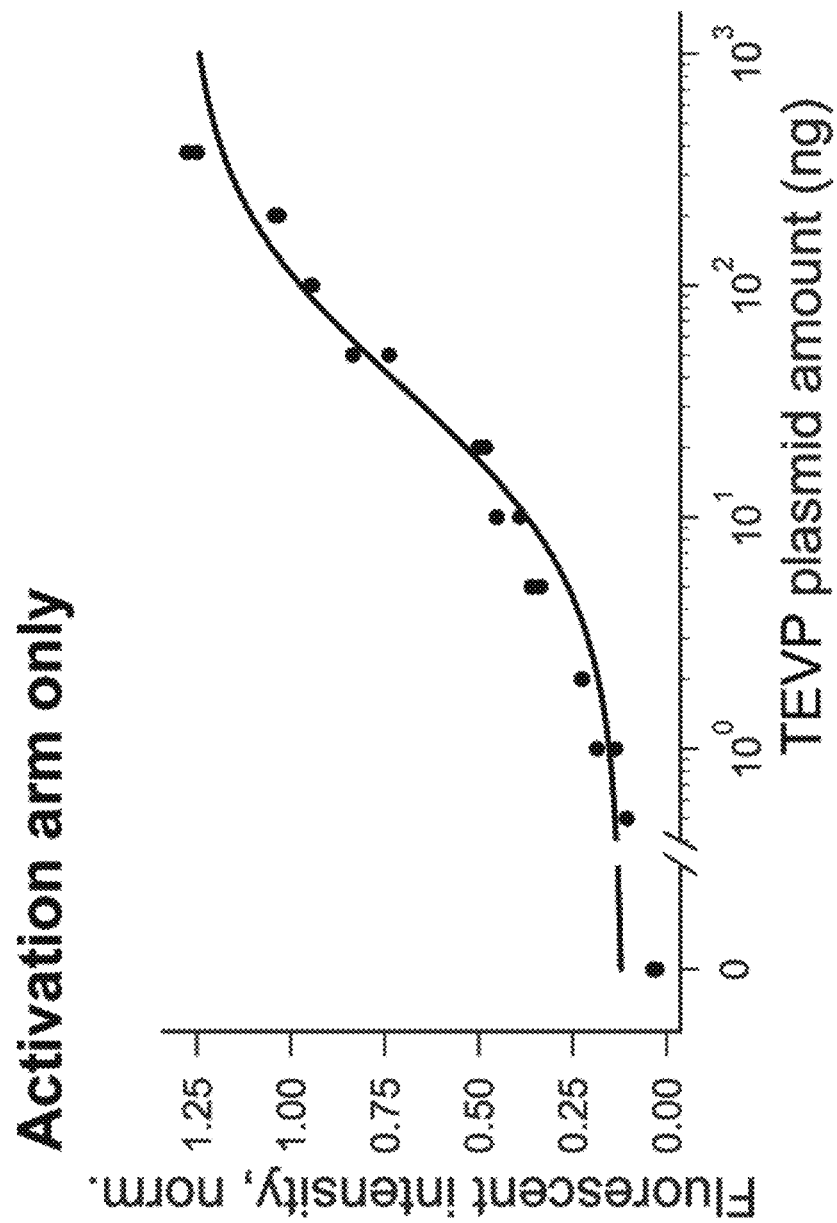
Figure 3C:
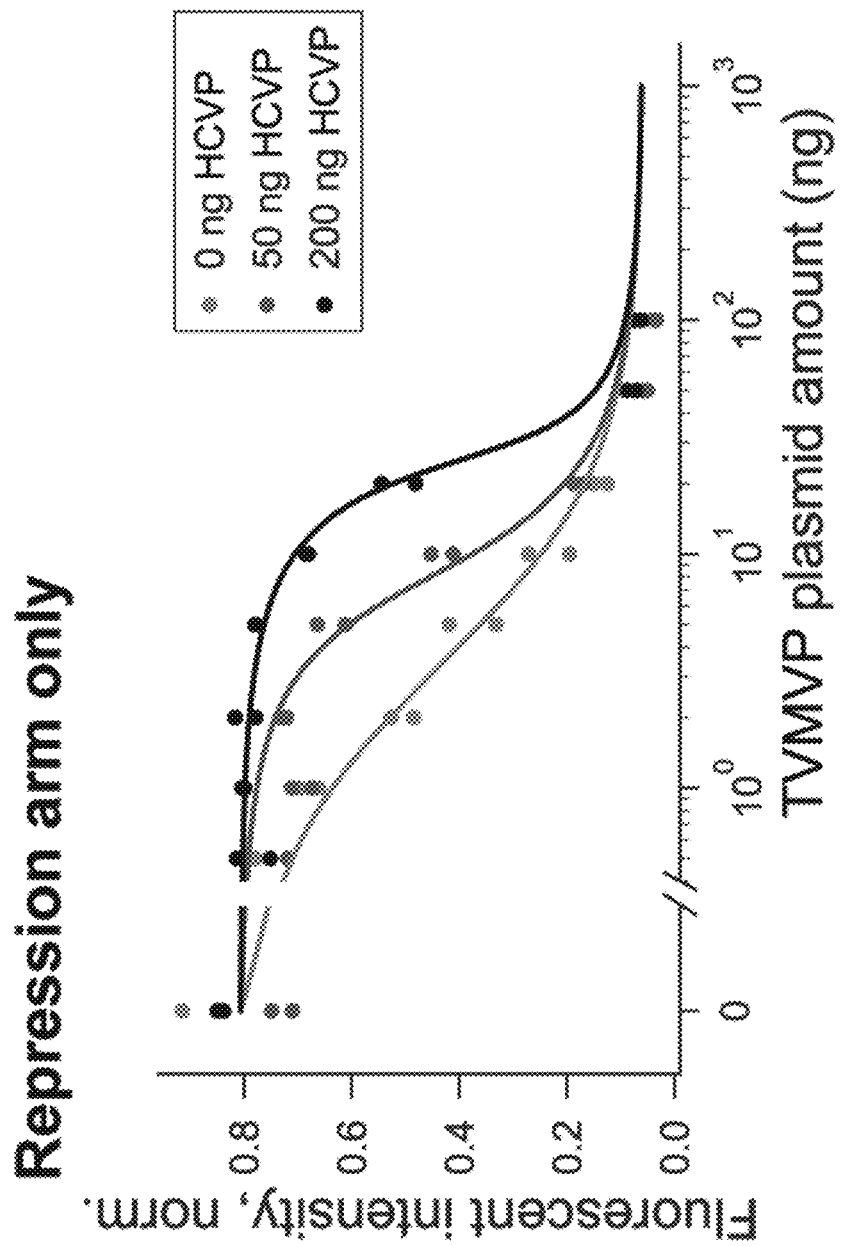
Figure 3D:
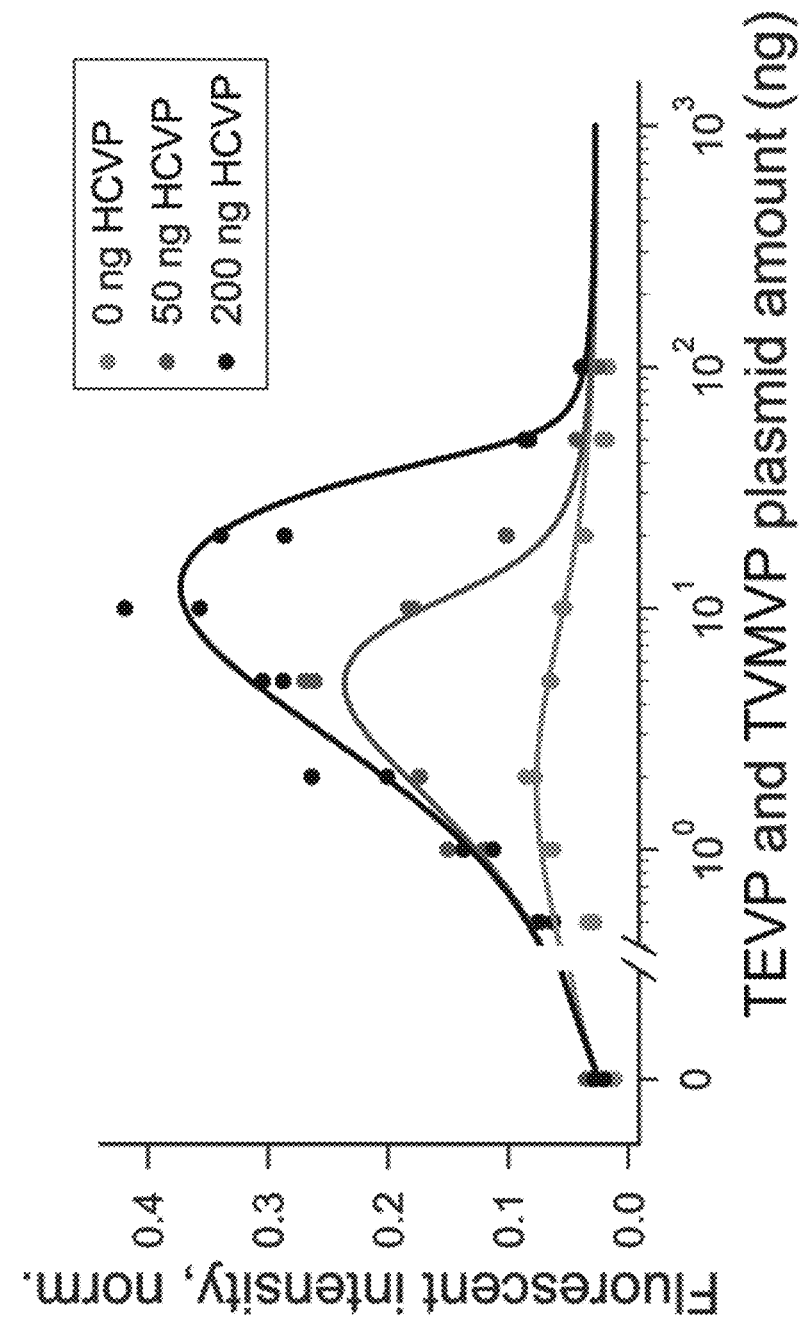
Figure 8A:
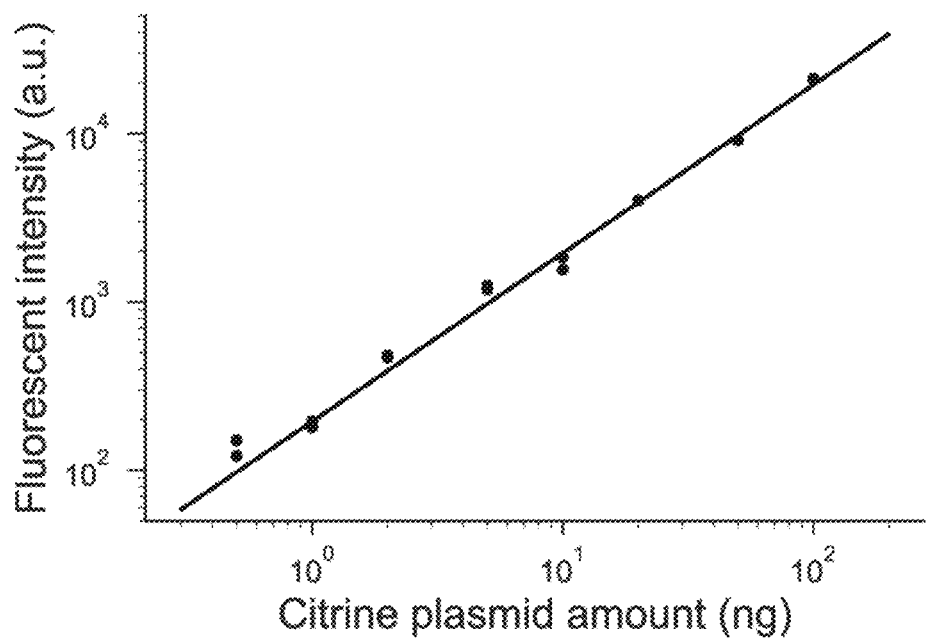
FIGS. 8A-8D show information relating to characterization of bandpass and pulse-generation circuits in accordance with some embodiments.
Figure 8B:
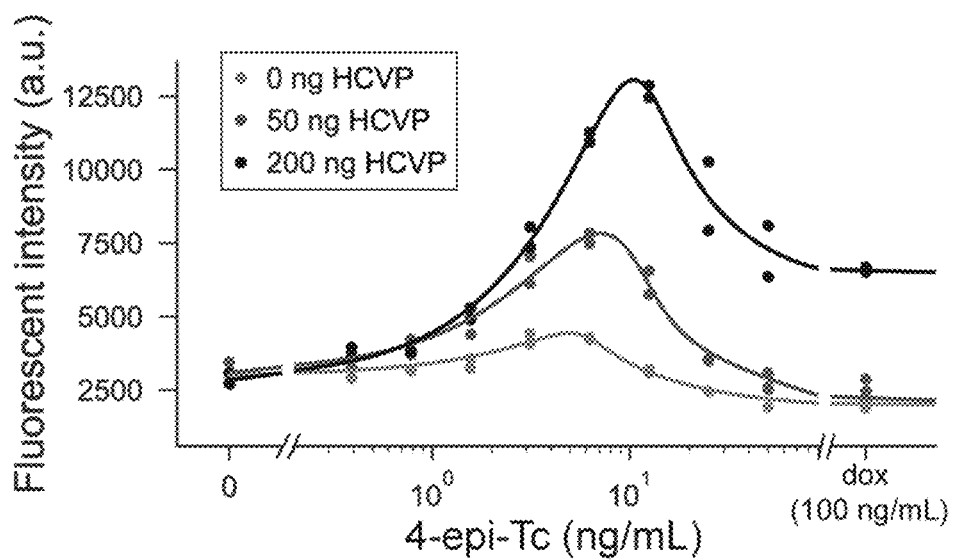

To characterize this bandpass circuit, the abundance of TEVP and TVMVP were considered as input, and varied it through the concentration of transfected DNA, which correlated linearly with protein abundance (FIG. 8A). The individual activating and repressing arms of the circuit generated increasing and decreasing responses, respectively, to increasing amounts of TEVP and TVMVP (FIG. 3B, 3C). Addition of HCVP increased both the threshold and the sharpness of the response to TVMVP titration (FIG. 3C). Combining the two arms into a single circuit generated the anticipated bandpass behavior, when the inventors co-varied TEVP and TVMVP expression through either different amounts of plasmid (FIG. 3D) or 4-epitetracycline (4-epi Tc) induction (FIG. 8B). Finally, varying the abundance of HCVP tuned the position and amplitude of the bandpass response (FIG. 3D and FIG. 8B). These results demonstrate rational engineering of tunable analog bandpass filters.

Figure 8C:
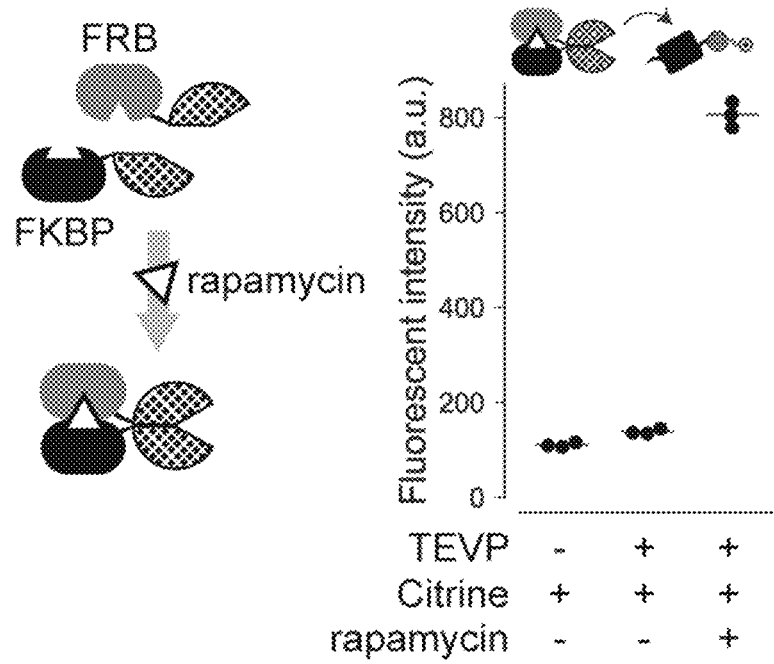
Figure 8D:
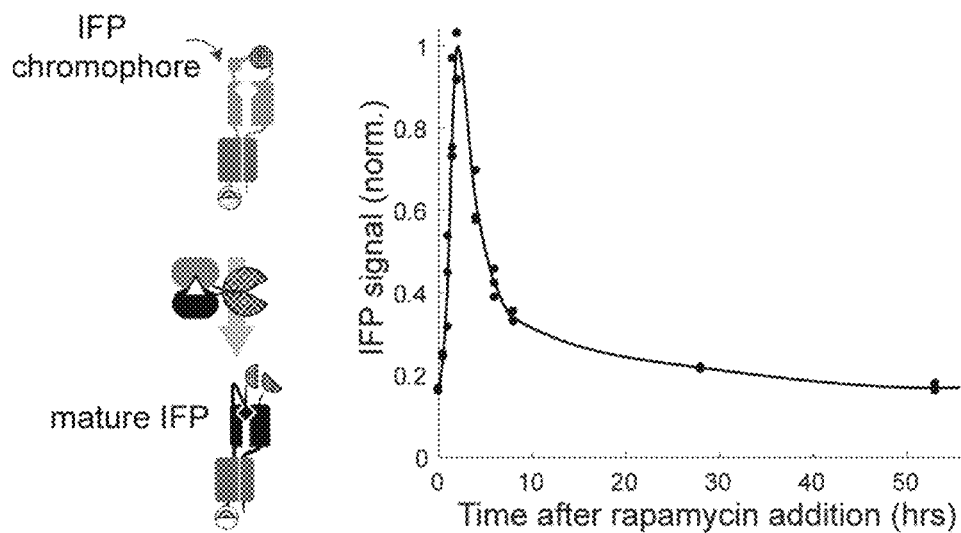

Temporal signal processing, such as adaptation to a change in input, plays a role in some biological systems. To engineer adaptation with CHOMP, the inventors designed an IFFL, containing the 3-step cascade (FIG. 1J) to introduce a delay in the repressing arm relative to that of the activating arm (FIG. 3E). To enable sudden induction, the inventors adopted the rapamycin-induced TEVP used for the logic gates (FIGS. 7A, 8C). To facilitate dynamic readout of circuit output in individual cells the inventors used a far-red fluorescent protein (IFP) that is synthesized in a non-fluorescent state, but can be post-translationally switched on by TEVP (FIG. 8D, left). The inventors also added a conditional N-end degron to enable repression by TVMVP (FIG. 3E).

Figure 3F:
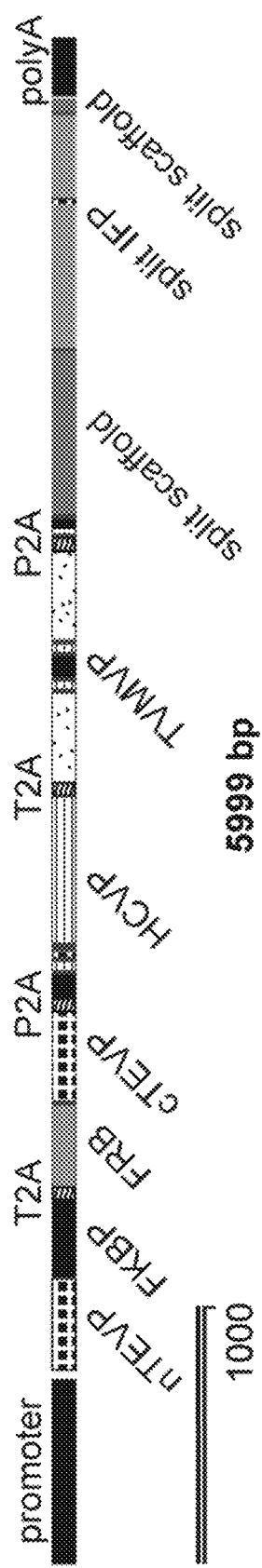
Figure 3G:
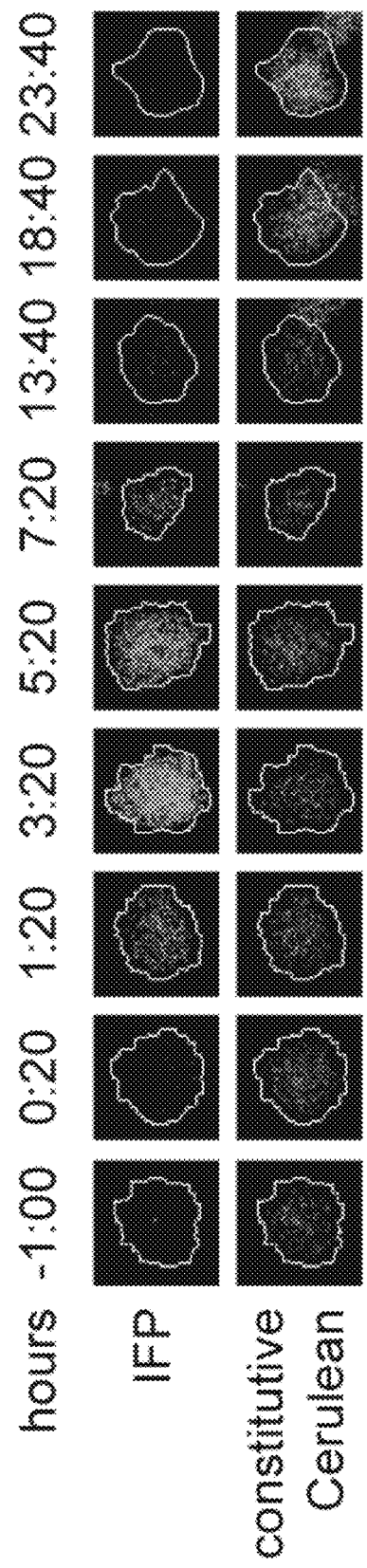
Figure 3H:
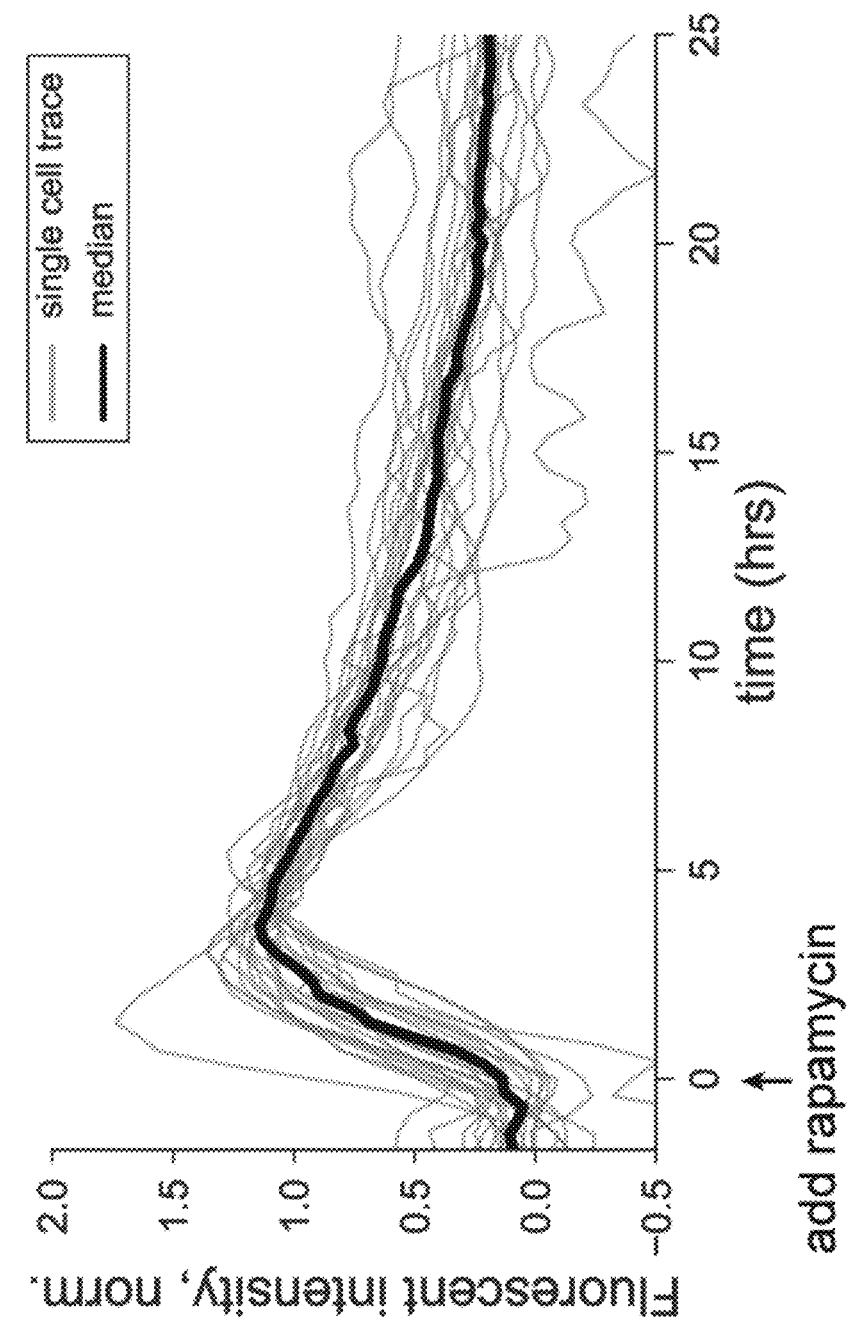

The inventors encoded the entire pulse-generation circuit as a single open reading frame, with interleaved 2A "self-cleaving" peptides to separate distinct protein components (FIG. 3F). This gene was then stably incorporated in the genome. The inventors used flow cytometry to analyze the response of the reporter in a single clone over time after rapamycin addition. Cells exhibited the expected adaptive dynamics, with a rise in fluorescence on a timescale of hours and a subsequent decay to baseline over ~1 day (FIG. 8D, right). To obtain a direct view of dynamics in individual cells, the inventors also analyzed the same cell line by time-lapse fluorescence microscopy (FIG. 3G). Analysis of individual cells revealed similar adaptive dynamics, responding maximally at 269±68 (mean±s.d.) min after rapamycin addition, decaying to 50% of their peak values over the subsequent 491±170 min, and eventually reaching fluorescence similar to that before induction (FIG. 3H). These results demonstrate the design of single-gene multi-component circuits that generate dynamic signal responses.

Figure 4A:
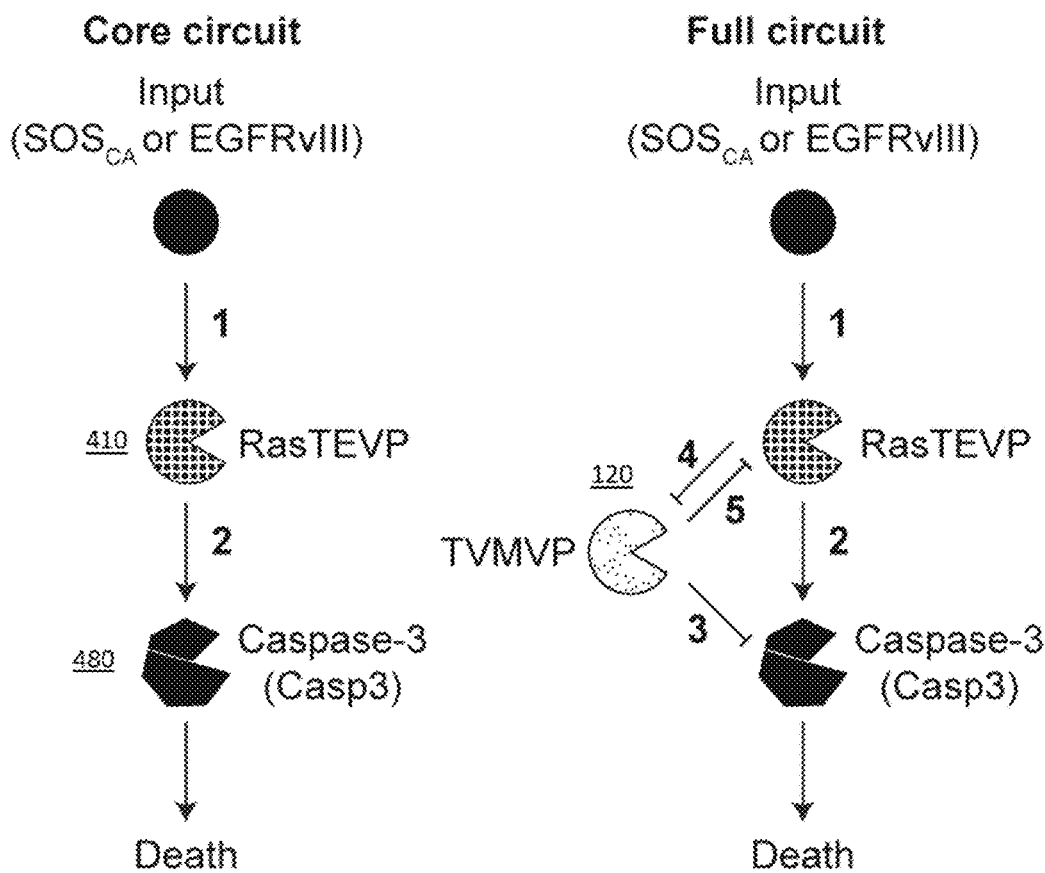
Figure 4A:
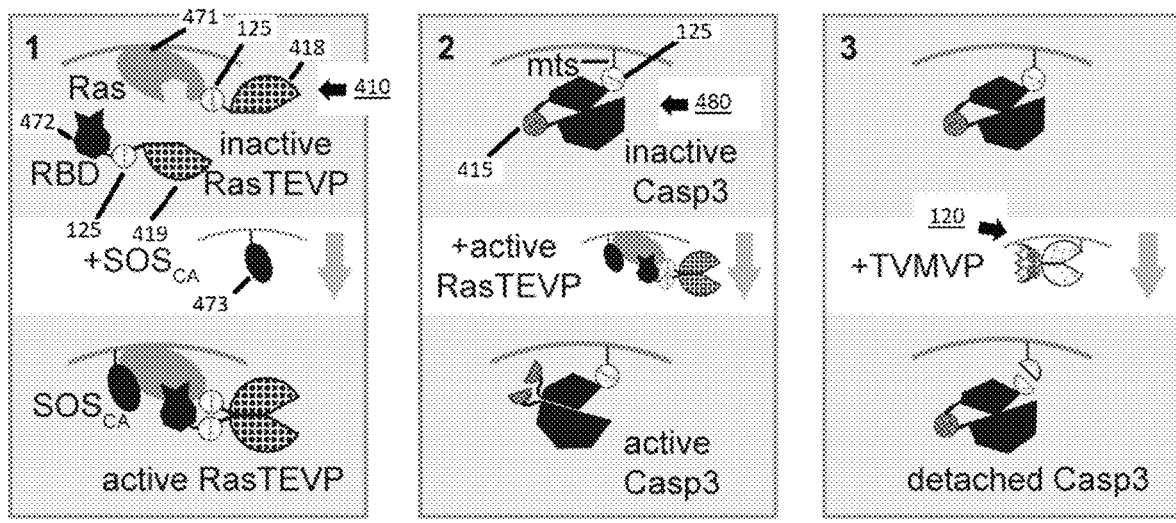

By coupling directly to endogenous cellular outputs and inputs, protein-level circuits could act as programmable therapeutic devices. As a proof of principle for such a strategy, the inventors designed a circuit to selectively kill cells with elevated activation of Ras, a protein whose activity is increased in many cancers. More specifically, the inventors designed a core circuit that responds to upstream activators of Ras, such as SOS and EGFR, by activating an engineered TEV protease, which in turn activates Caspase-3 (Casp3) to induce cell death (FIG. 4A, core circuit). The inventors then improved this circuit by incorporating additional proteases and interactions (FIG. 4A, full circuit).

Figure 4B:
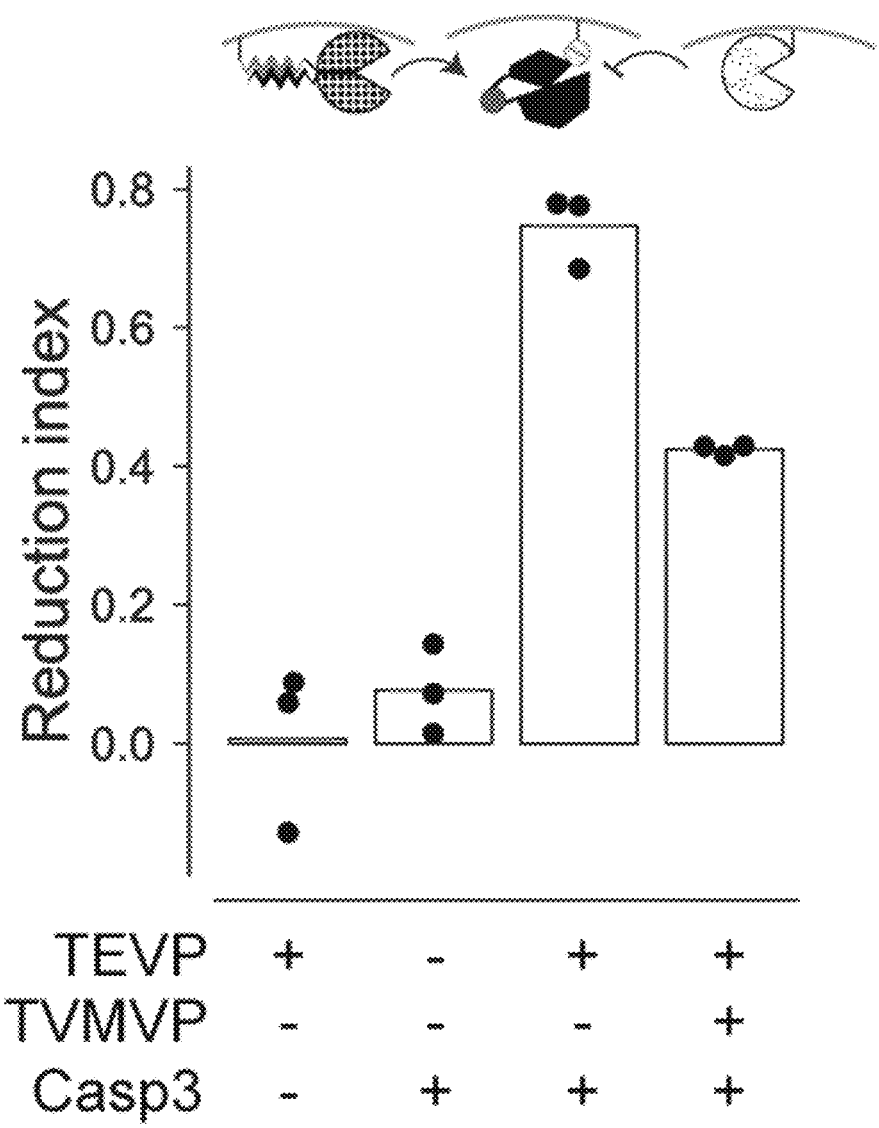
Figure 9B:
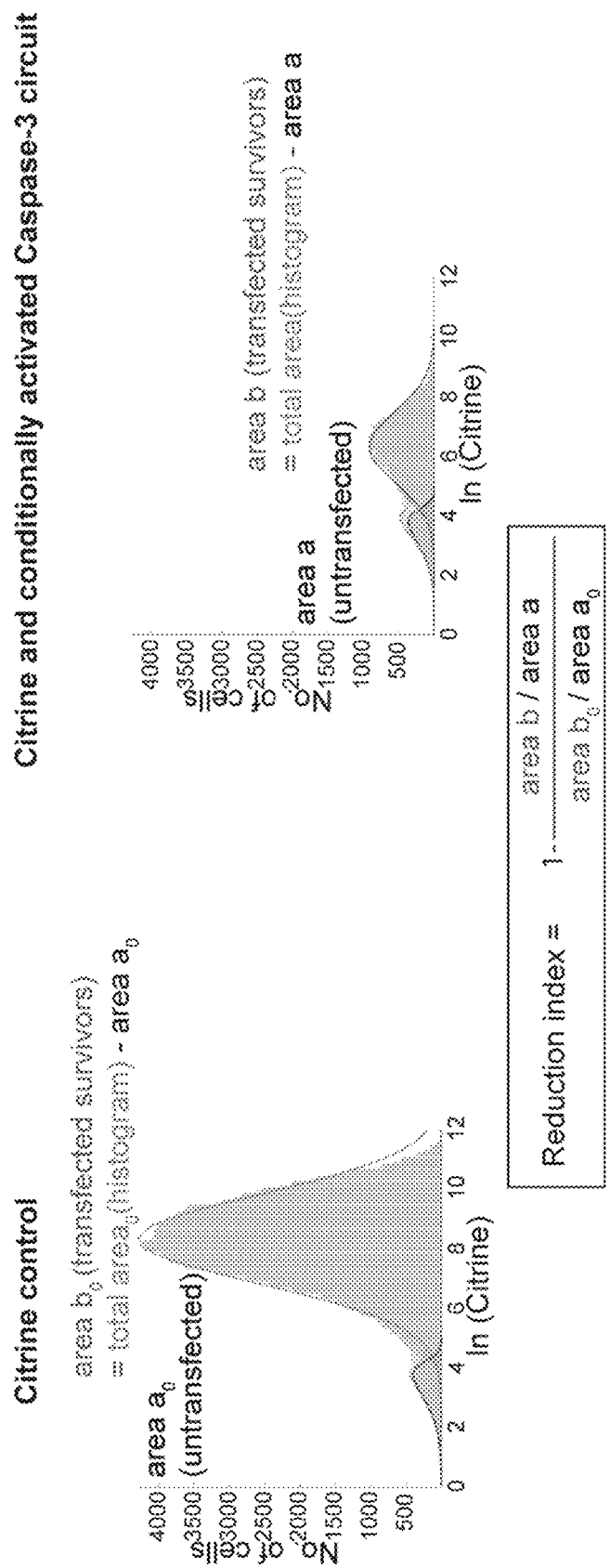

To enable efficient protease-dependent induction of cell death at the plasma membrane, where Ras activation occurs, the inventors membrane localized a TEVP-activated Casp3 variant by incorporating the 20 amino acid membrane-targeting sequence) ('mts') from the C-terminus of human H-Ras (FIG. 4A, box 2). Using flow cytometry, the inventors quantified the effect of this Casp3 variant on cell numbers in terms of a 'reduction index' whose value measures the relative reduction in cell number compared to a control condition (FIG. 9B). The membrane-targeted Casp3 decreased cell numbers when co-transfected with a similarly membrane-localized TEVP variant (FIG. 4B), with higher efficiency than the original cytoplasmic Casp3 variant (FIG. 9D). Further, to allow bidirectional regulation by TEVP and TVMVP, the inventors also incorporated a TVMVP cleavage site adjacent to the mts tag (FIG. 4A, Box 3), enabling membrane-localized TVMVP to remove Casp3 from the membrane and thereby attenuate its activation by TEVP (FIG. 4B).

Figure 4C:
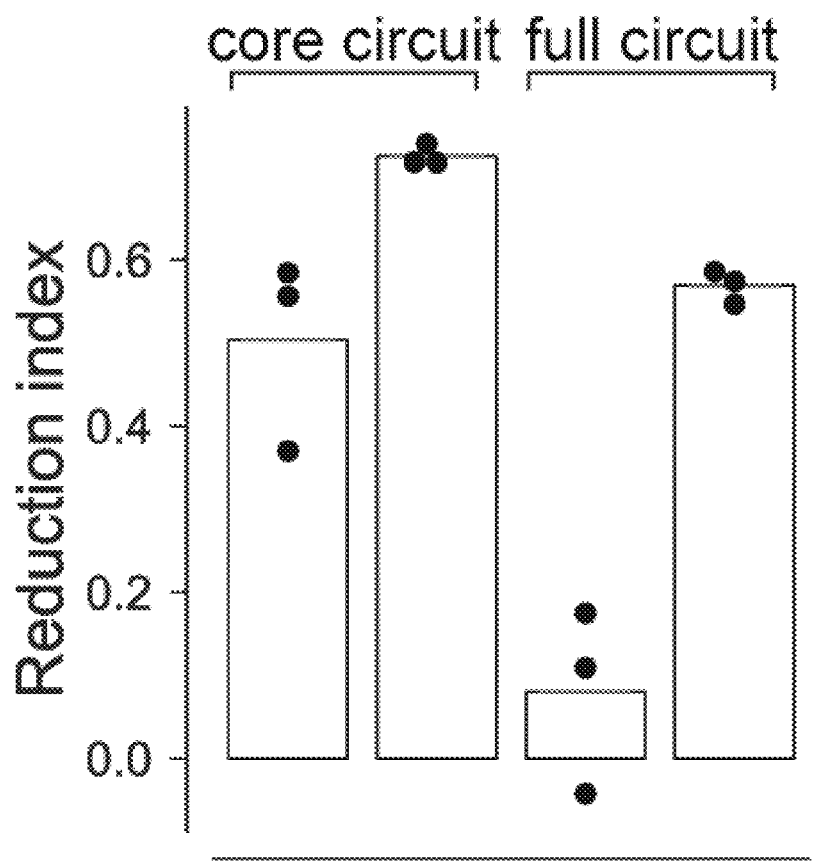
Figure 9C:
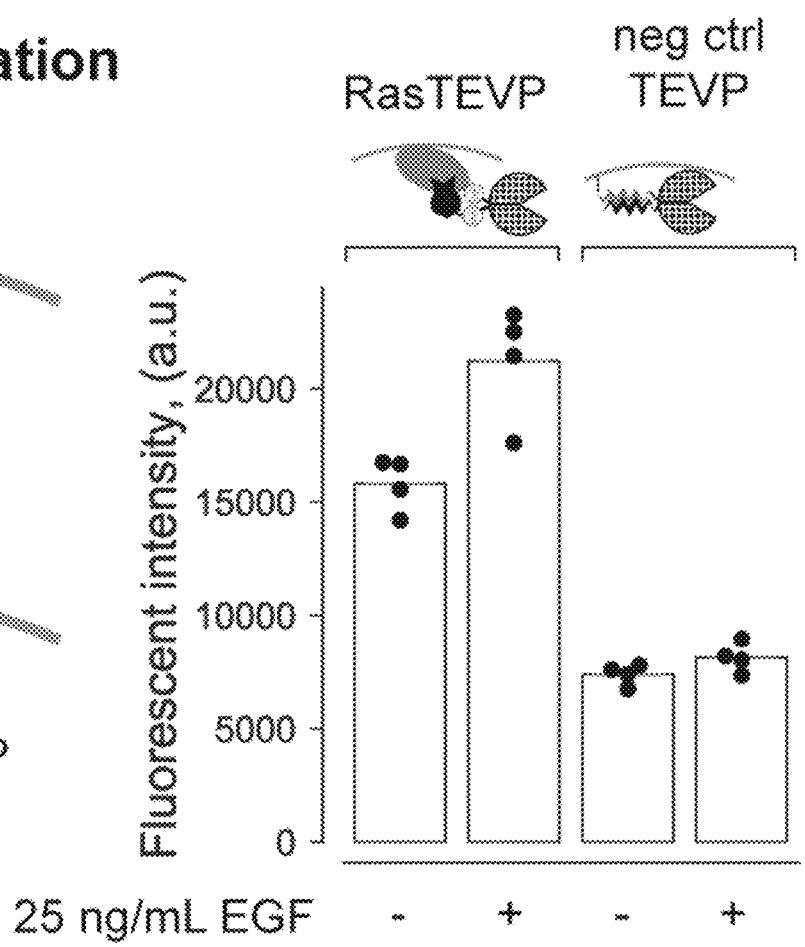
Figure 9F:
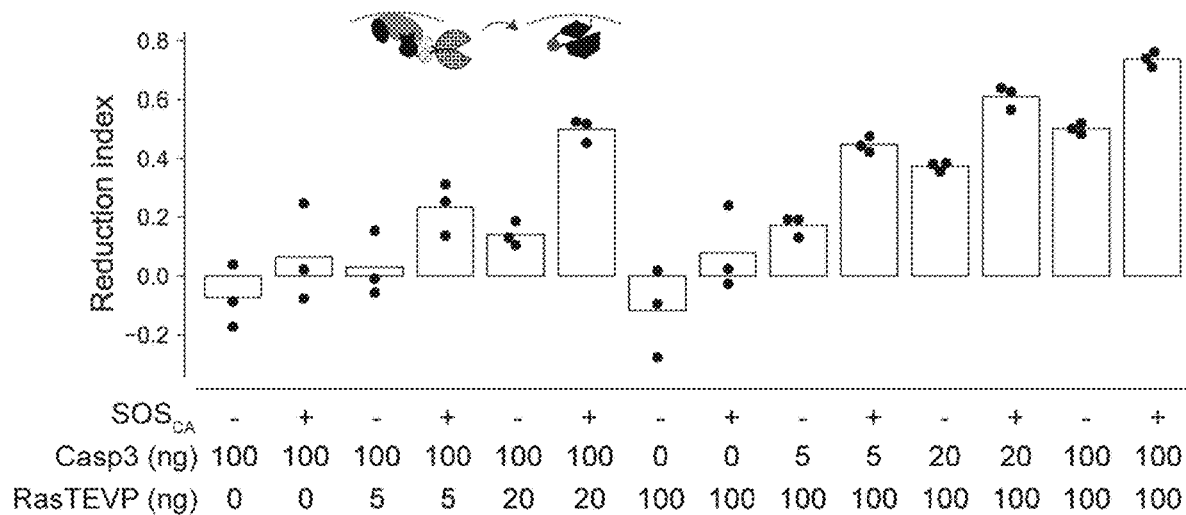

Next, to couple Ras-activating inputs to TEVP, the inventors fused the N-terminal half of TEVP to Ras and its C-terminal half to the Ras-binding domain (RBD) of Raf, which binds to the active form of Ras. In this design, upstream activators of Ras should reconstitute RasTEVP (FIG. 4A, core circuit and Box 1, FIG. 9C) and thereby activate Casp3. To validate this design, the inventors constructed a HEK293 cell line stably expressing a constitutively active Son of Sevenless ($SOS_{CA}$) variant with a membrane-localization myristoylation signal and no inhibitory C-terminal region. Transfection of the core circuit reduced cell numbers both in this $SOS_{CA}$ cell line and its parental control line lacking ectopic $SOS_{CA}$, but preferentially affected the $SOS_{CA}$ cells (FIG. 4C, core circuit, and FIG. 9F). This selectivity required the regulated Ras-RBD interaction (FIG. 9E). However, while this core circuit provided some selectivity, it also exhibited a relatively high background rate of Casp3 activation in the control cells.

Figure 9G:
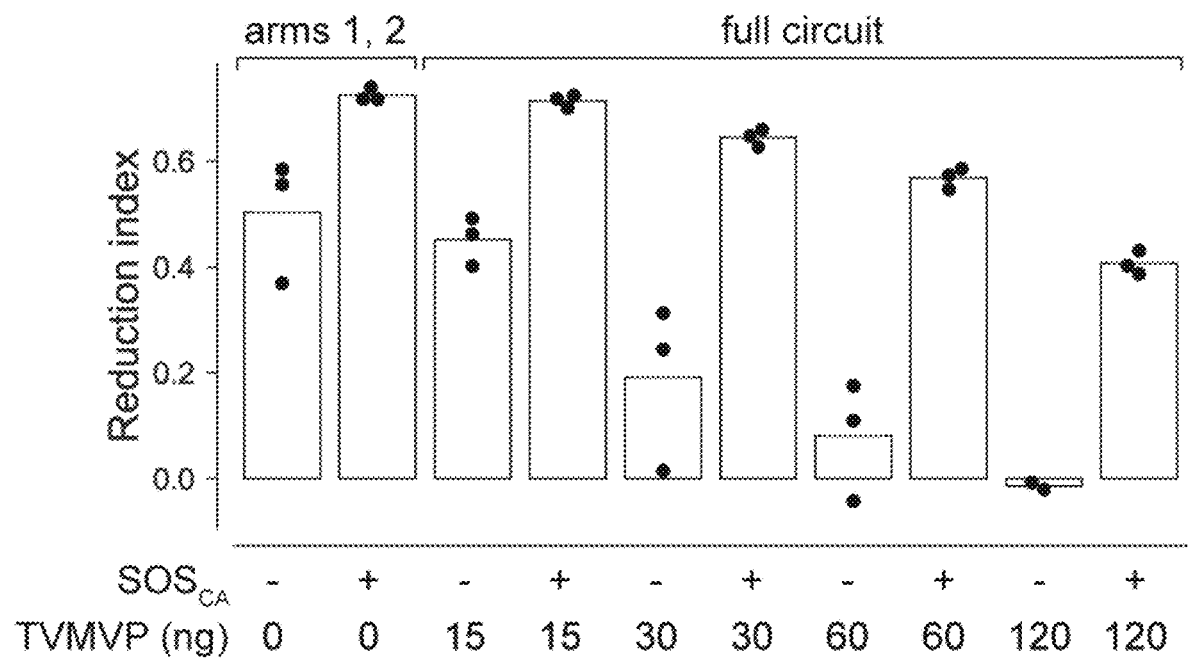
Figure 10A:
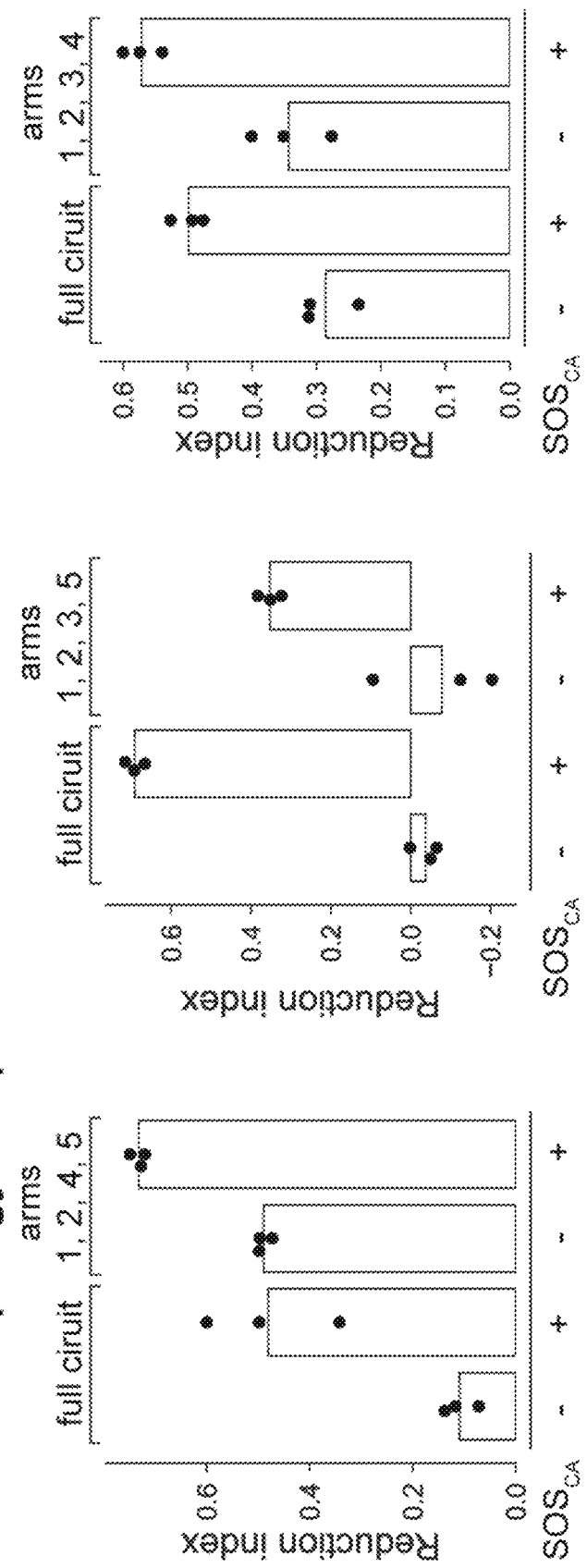

To improve the circuit's selectivity, the inventors incorporated a TVMVP-TEVP reciprocal inhibition motif (FIG. 9A, boxes 4 and 5) similar to the one used in the bandpass circuit, as well as feed-forward repression of Casp3 activation by TVMVP (FIG. 4A, Box 3). In this "full circuit" design, TVMVP should suppress activation of Casp3 in control cells, both directly and indirectly through TEVP. By contrast, in $SOS_{CA}$ cells, elevated activation of TEVP should override the inhibitory effects of TVMVP. The full circuit indeed improved selectivity (FIGS. 4C, 9G, 10A). More specifically, expressing TVMVP in amounts comparable to, but lower than those of TEVP nearly abolished off-target effects in control cells, while retaining most of the on-target reduction in cell number (FIGS. 4C, 9G).

Figure 4E:
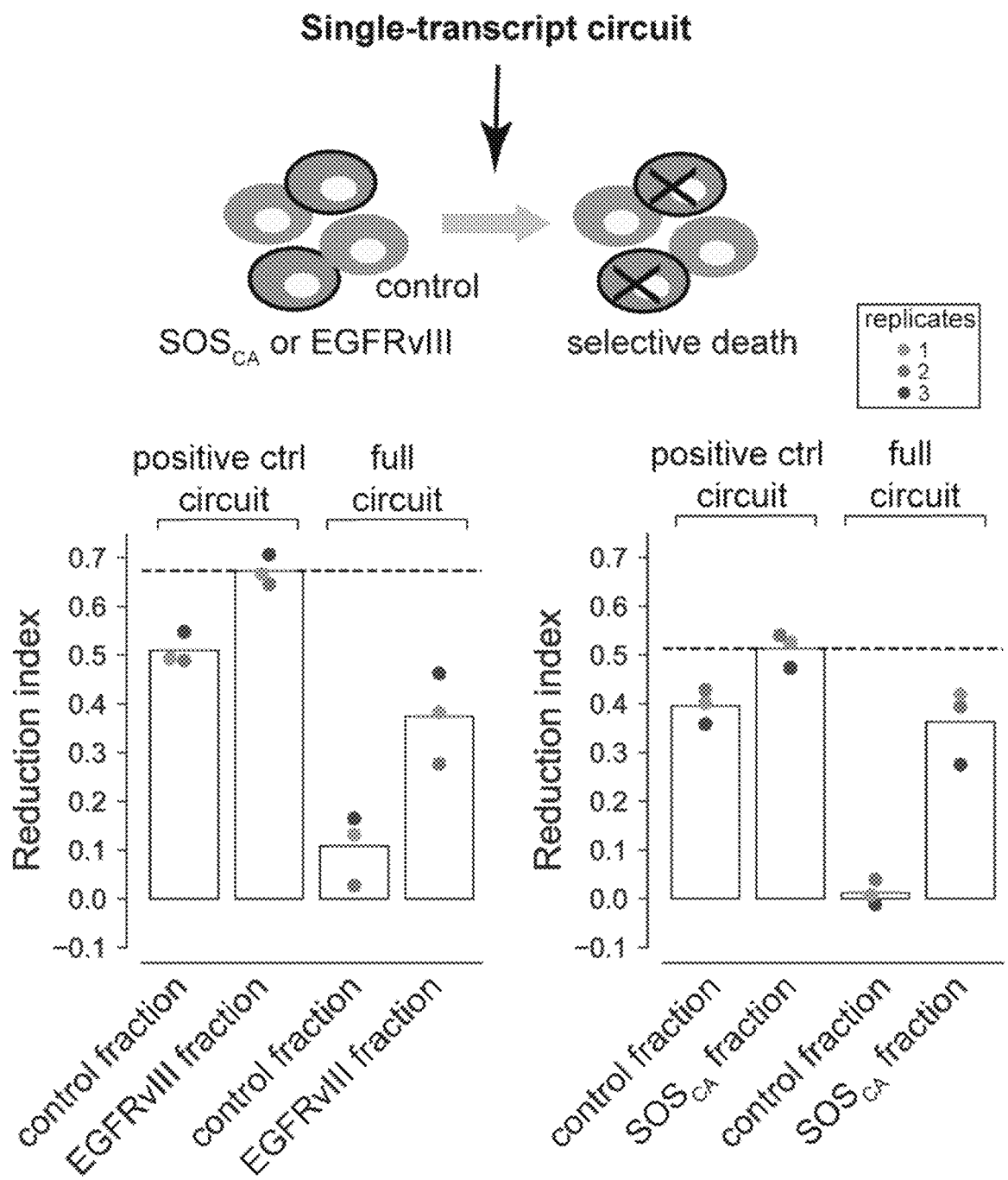
Figure 10D:
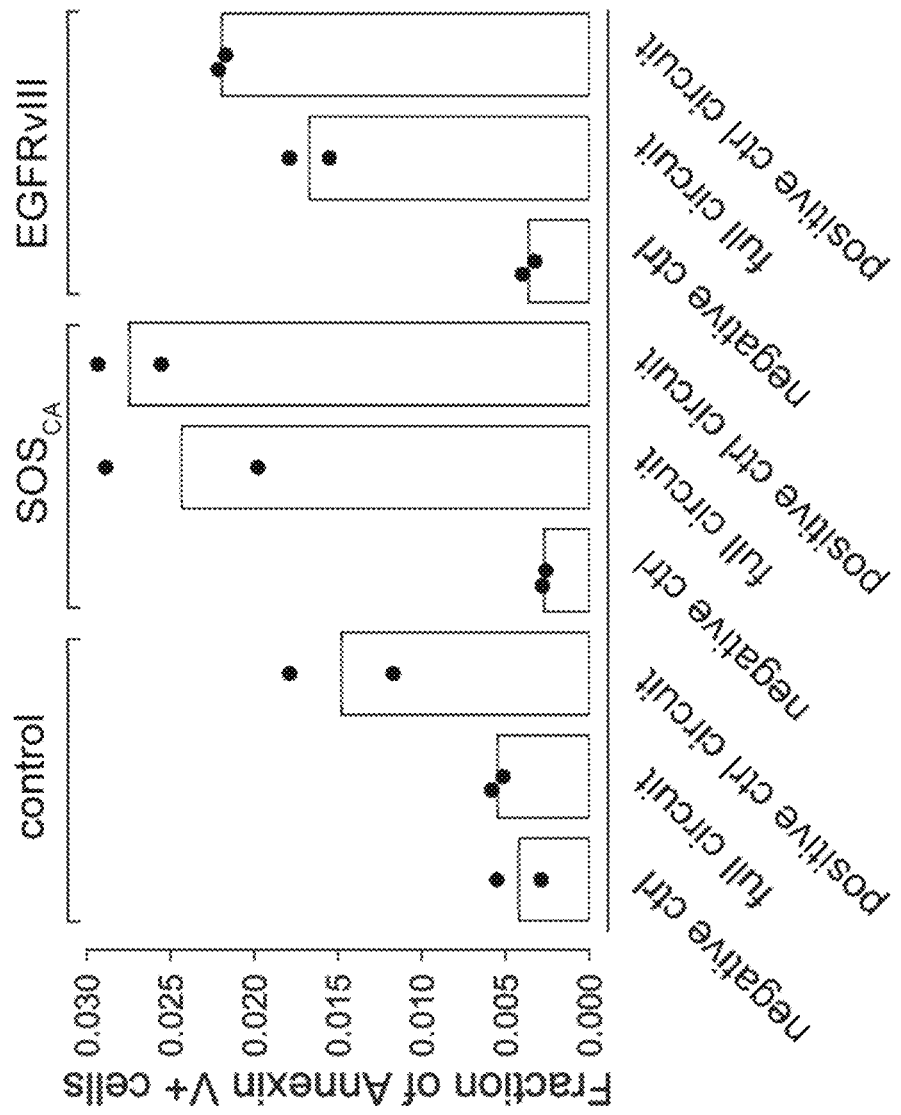

Further, the inventors encoded the full 4-protein circuit on a single transcript, optimizing the relative abundance of components with internal ribosome entry site (IRES) variants (FIGS. 4D, 10B), and transfected it into a mixed population of $SOS_{CA}$ and control cells. At its optimal concentration (FIG. 10C), the single-transcript circuit reduced the number of $SOS_{CA}$ cells by ~40%, approaching the ~50% upper limit achieved by a positive control circuit that constitutively activates Casp3 (FIG. 4D, and FIG. 4E, right). (The upper limit is constrained by gene delivery and expression efficiency.) Importantly, it exhibited minimal effects on the control population (FIG. 4E, right). $SOS_{CA}$-dependent killing could also be observed using Annexin-V staining as an independent readout of apoptosis (FIG. 10D). Finally, to test the generality of the circuit, the inventors considered EGFRvIII, an oncogenic EGFR mutant found in glioblastoma and other cancer types. The single-transcript full circuit also selectively killed EGFRvIII cells (FIG. 4E, left, and FIG. 10D). Together, these results show that a CHOMP circuit can be engineered to detect and kill in response to upstream activators of Ras through rational iterative design optimization. Thus, according to some embodiments, the methods described herein may be used in a biomedically relevant environment.

The results demonstrate how a set of composable protein regulators and circuit design principles enable a remarkably broad range of protein-based circuits and functions. The use of a small number of composable components shifts the design problem, in part, from the level of the individual protein to the level of the protein circuit. In some embodiments where the operation of CHOMP components does not depend on how they are expressed, they can be optimized through transient transfections, accelerating the overall design-build-test cycle.

Some embodiments include protease-activating proteases, which in some cases simplify circuit designs and facilitate signal amplification. Some embodiments include multiple CHOMP inputs and outputs, and/or use direct sensing of the activities of Ras and/or other oncogenes, and/or use combinatorial sensing of multiple inputs.

Figure 11:
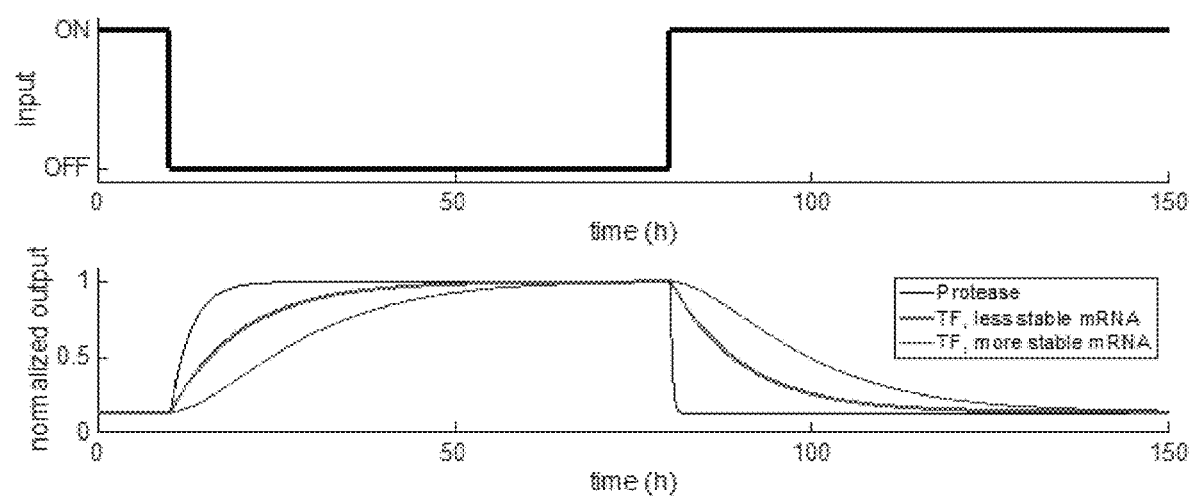
FIG. 11 show information relating to simulated protease-protease and TF-TF regulation dynamics in accordance with some embodiments. This plot compares the dynamic response of some embodiments of protease-protease regulation and transcriptional regulation to step changes in an input protease/TF.

Proteases can respond rapidly to an increase in input protease activity (FIG. 11). CHOMP circuits can also operate in parallel at specific subcellular sites within a cell. In some embodiments where CHOMP circuits have a relatively compact genetic design and do not use regulatory interactions with DNA, they are introduced into differentiated and/or post-mitotic cells with gene therapy vectors and/or viruses, and/or improve the specificity of oncolytic virotherapy. Synthetically, hybrid circuits combining transcriptional or translational regulation with engineered proteases offers the programmability of base-pairing interactions together with protein level operation. For example, existing cancer-detection circuits may conditionally express CHOMP components to increase specificity and couple to protein-mediated inputs and outputs. In some embodiments, integrating these capabilities is used to, for example, produce smart therapeutics or sentinels based on CHOMP circuits.

Where applicable, the experiments described in this section were performed in accordance with the materials and methods described in Example 1.

Characterization and Optimization of HCVP and its Reporter.

For HCV protease (HCVP), the inventors adopted a construct in which the protease and its co-peptide are fused to create a more active single chain protease. This HCVP initially showed more modest regulation than the other proteases, especially for the repressible reporter (FIG. 5D). The inventors reasoned that increasing the protease affinity to its target could improve its regulatory range. Indeed, incorporating a pair of hetero-dimerizing leucine zippers in the protease and its target improved regulation (FIG. 5D, right).

Characterization and Optimization of Circuits that Selectively Reduce Ras-Activating Cells To exclude the possibility that $SOS_{CA}$ cells are generally more sensitive to Casp3 activation, the inventors first analyzed constitutively dimerized split TEVP variants, one using leucine zippers, and the other adopting a RasG12V mutant that binds constitutively to RBD (FIG. 9E). When co-transfected with the TEVP-activatable Casp3, these control constructs displayed no selectivity for $SOS_{CA}$ cells (FIG. 9E), indicating that the regulated Ras-RBD interaction is necessary for the selectivity observed in the main text (FIG. 4C).

To assess the contribution of each additional regulatory interaction in the full circuit, the inventors systematically removed them one at a time, and compared their effects on control and $SOS_{CA}$ cells to the full circuit. Removal of Casp3 inhibition by TVMVP re-introduced substantial reduction in control cells (FIG. 10A, left), and removal of TVMVP inhibition by RasTEVP increased survival in $SOS_{CA}$ cells (FIG. 10A, middle). By contrast, removal of RasTEVP inhibition by TVMVP had no effect on survival in either control or $SOS_{CA}$ cells (FIG. 10A, right). These results indicate that Arms 3,4 (FIGS. 9A, 10A) are major contributors to full circuit performance.

For single-transcript delivery of the full circuit, the inventors interposed a wild type internal ribosome entry site (IRES) between Casp3 and RasTEVP coding sequences, followed by one of several IRES variant sequences (61) and then the TVMVP (FIG. 10B). Inspired by TVMVP titration results (FIG. 9G), the inventors chose variants with ~30% and ~70% of wild-type strength for the second IRES (55), and found that the circuit functioned optimally with the ~70% IRES (FIG. 10B).

Response of RasTEVP to EGF Stimulation

To assess the response of RasTEVP to a physiological ligand that normally activates the Ras pathway, the inventors stimulated cells expressing either RasTEVP or constitutively dimerized and membrane-localized TEVP (negative control TEVP) with epidermal growth factor (EGF). When co-transfected with a membrane-localized iTEV reporter, the control construct TEVP-mts exhibited minimal response to EGF stimulation, whereas RasTEVP displayed a modest response to EGF (FIG. 9C).

Comparison of Protease-Protease and Transcriptional Regulatory Dynamics

In the experiments described in this subsection, the inventors use a minimal model to address the question of how a simple transcription factor regulatory step differs in dynamics from a simple protease regulatory step. To make a controlled comparison between the two kinds of regulation, the inventors assume that shared biochemical parameters, such as protein degradation rates, are similar in the two systems. The main conclusion is that protease regulation can occur more rapidly than transcriptional regulation but with timescales that depend on the direction of regulation. By contrast, transcriptional regulation is expected to be slower but show similar timescales in both directions of regulation. While the inventors have considered typical biochemical parameter values here, the inventors note that additional features of any specific system, including feedback structure, could impact their dynamic behavior. Additionally, the quantitative values of the resulting timescales in general depend on the specific choice of biochemical parameter values.

Protease-Protease Regulation.

The inventors modeled repression of one protease by another through direct cleavage, based on the scheme in FIG. 1E. The inventors assume the concentration of the input protease, denoted $P_c$, is maintained at a constant level, with its activity controlled by a small molecule input, as in the scheme of FIG. 3E. The output protease, denoted P, is produced at a constant rate A, and undergoes first-order degradation with rate $\gamma_p$. The input protease cleaves the output protease at a single cleavage site, converting it to a cleaved form, whose concentration is denoted $P_c$, with a cleavage rate constant k. The cleaved protease irreversibly dissociates at rate $k_d$, and undergoes first-order degradation with rate $\gamma_p$ for a total rate of elimination of $\gamma_p+k_d$. A single cleavage is assumed for simplicity, but the same conclusions hold true for two independent cleavage sites, cleavage of either of which is sufficient to inactivate the output protease.

The reactions in the protease-protease model are as follows, where denotes 'nothing':

Synthesis of the output protease:

Degradation of the output protease

Catalytic cleavage of the output protease:

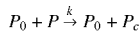

Dissociation of the cleaved protease

Degradation of the cleaved protease:

Assuming protease cleavage functions in a linear regime far from saturation, consistent with published $K_m$ values and our bandpass modeling, the reaction can be expressed as a set of ordinary differential equations (ODEs):

$$\frac{dP}{dt} = A - kP_0P - \gamma_p P$$

$$\frac{dP_c}{dt} = kP_0P - P_c(k_d + \gamma_p)$$

Because the absolute value of the production rate A does not affect the dynamics of the system, the inventors arbitrarily set its value to 1 Mh$^{-1}$. For the dissociation rate, the inventors assumed $k_d$=5 h$^{-1}$ based on indirect measurements (71). For the protein degradation rate, the inventors assumed a biologically realistic value of $\gamma_p$=0.1 h$^{-1}$.

Based on our bandpass fits (FIGS. 3B-3D), cleavage by a protease, when the input protease activity is high, occurs at a rate comparable to the rate of degron-mediated degradation (~5 h$^{-1}$). The inventors also assumed that the OFF input protease is 20-fold less active than the ON state based on the dynamic range observed in FIGS. 1D-1J. (Note that the value of this regulatory range does not affect our conclusions about the timescales of regulation.) Finally, the inventors assumed the small-molecule-induced ON-OFF switch reaches steady-state much faster than the other reactions, so that the cleavage term can be approximated by a step function, taking one of two possible values:

kP=0.25 h$^{-1}$ (input OFF) or 5 h$^{-1}$ (input ON)

To simulate output dynamics in response to changes in the input, the inventors first set the input protease to ON, and the output protease to its steady state value of $P+P_c$. At t=10 h, the inventors switched the input to OFF and simulated the equations for 70 h (10-80 h). Finally, the inventors switched the input back to ON and simulated another 70 h (80 h-150 h). FIG. 11 plots the resulting dynamics of the output protease, normalized to its maximum value. Note the asymmetric response time, which is faster for input OFF→ON switch than ON→OFF $$\left(t_{\frac{1}{2}} = 0.32h^{-1} \text{ vs. } 2.3\,h^{-1}\right).$$

Transcriptional Regulation.

As a comparison to protease regulation, the inventors modeled a logically equivalent transcriptional repression step. The input transcription factor was maintained at a constant concentration of $T_G$, with its activity assumed to be controlled by a small molecule, as with the protease. The input transcription factor regulates the output mRNA, $T_m$, whose production follows a standard rate law:

$$\frac{K}{K+T_0}A_m \cdot T_m$$

undergoes first-order degradation with rate $\gamma_m$. The output protein $T_p$ is translated from the mRNA at rate $A_p$, and degraded with rate $\gamma_p$. The reactions are as follows:

mRNA synthesis:

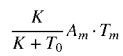

mRNA degradation:

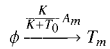

protein synthesis:

protein degradation:

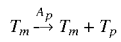

These reactions can be converted to ODEs for each of the components:

Without loss of generality the inventors set the production rate $A_m=1$ Mh$^{-1}$ and $A_p=1$ h$^{-1}$. The inventors used the same protein degradation rate as in the protease regulation case above: $\gamma_p=0.1$ h$^{-1}$. For mRNA degradation, the inventors simulate two values at opposite extremes of the biological range for mammalian mRNA (72): $\gamma_m=0.1$ h$^{-1}$ (more stable), and 5 h$^{-1}$ (less stable). As above, the inventors also assumed that the small-molecule-controlled input ON-OFF switch is much faster than the other reactions. To match the protease conditions, the inventors assumed $T_0$ also undergoes a 20-fold regulation, from $T_0=0.5$K OFF) to 10K (input ON), although the inventors note that the exact dynamic range of $T_0$ or the exact choice of the Hill function does not affect output dynamics.

We simulated this simple model of transcriptional regulation with fast and slow mRNA degradation rates, following the same ON→OFF→ON input temporal profile used in the protease regulation case. To focus on the timescale of regulation, the inventors normalized each curve to its maximal value. For transcriptional regulation, $$t_{\frac{1}{2}} = 7.2\ h^{-1}$$

and 17 h$^{-1}$ for fast and slow mRNA decay, respectively, regardless whether the input undergoes ON→OFF or OFF→ON switch. When input switches from ON to OFF, protease and transcriptional regulation occurs on comparable timescales, although their difference is more apparent in the slower mRNA degradation case. When input switches from OFF to ON, however, protease regulation generates a much faster response time compared to transcriptional regulation and the ON to OFF switch in the protease regulation case (FIG. 11). Intuitively, the dynamics of each process is limited by the slowest rate at which a species decays, which is the relatively slow protein degradation rate for transcriptional control (or both protein and mRNA degradation rates when mRNA is more stable); in contrast, the output protease decays at a much faster rate because, in addition to regular protein degradation, it is also cleaved by input protease, and the rate is even higher when the input is switched to its active state.

REFERENCES

1. J. Bonnet, P. Yin, M. E. Ortiz, P. Subsoontorn, D. Endy, Amplifying genetic logic gates. *Science.* 340, 599-603 (2013).
2. B. H. Weinberg et al., Large-scale design of robust genetic circuits with multiple inputs and outputs for mammalian cells. *Nat. Biotechnol.* 35, 453-462 (2017).
3. S. Ausländer, D. Auslander, M. Müller, M. Wieland, M. Fussenegger, Programmable single-cell mammalian biocomputers. *Nature.* 487, 123-127 (2012).
4. K. Rinaudo et al., A universal RNAi-based logic evaluator that operates in mammalian cells. *Nat. Biotechnol.* 25, 795-801 (2007).
5. L. Wroblewska et al., Mammalian synthetic circuits with RNA binding proteins for RNA-only delivery. *Nat. Biotechnol.* 33, 839-841 (2015).
6. A. S. Khalil et al., A synthetic biology framework for programming eukaryotic transcription functions. *Cell.* 150, 647-658 (2012).
7. N. Roquet, A. P. Soleimany, A. C. Ferris, S. Aaronson, T. K. Lu, Synthetic recombinase-based state machines in living cells. *Science.* 353, aad8559 (2016).
8. A. A. K. Nielsen et al., Genetic circuit design automation. *Science.* 352, aac7341 (2016).
9. B. Angelici, E. Mailand, B. Haefliger, Y. Benenson, Synthetic Biology Platform for Sensing and Integrating Endogenous Transcriptional Inputs in Mammalian Cells. *Cell Rep.* 16, 2525-2537 (2016).
10. J. J. Lohmueller, T. Z. Armel, P. A. Silver, A tunable zinc finger-based framework for Boolean logic computation in mammalian cells. *Nucleic Acids Res.* 40, 5180-5187 (2012).
11. I. Budihardjo, H. Oliver, M. Lutter, X. Luo, X. Wang, Biochemical pathways of caspase activation during apoptosis. *Annu. Rev. Cell Dev. Biol.* 15, 269-290 (1999).
12. M. A. Marchisio, J. Stelling, Computational design of synthetic gene circuits with composable parts. *Bioinformatics.* 24, 1903-1910 (2008).
13. B. J. Yeh, R. J. Rutigliano, A. Deb, D. Bar-Sagi, W. A. Lim, Rewiring cellular morphology pathways with synthetic guanine nucleotide exchange factors. *Nature.* 447, 596-600 (2007).
14. J. E. Dueber, B. J. Yeh, K. Chak, W. A. Lim, Reprogramming control of an allosteric signaling switch through modular recombination. *Science.* 301, 1904-1908 (2003).
15. S.-H. Park, A. Zarrinpar, W. A. Lim, Rewiring MAP kinase pathways using alternative scaffold assembly mechanisms. *Science.* 299, 1061-1064 (2003).
16. P. L. Howard, M. C. Chia, S. Del Rizzo, F.-F. Liu, T. Pawson, Redirecting tyrosine kinase signaling to an apoptotic caspase pathway through chimeric adaptor proteins. *Proc. Natl. Acad. Sci. U.S.A.* 100, 11267-11272 (2003).
17. D. M. Barrett, N. Singh, D. L. Porter, S. A. Grupp, C. H. June, Chimeric antigen receptor therapy for cancer. *Annu. Rev. Med.* 65, 333-347 (2014).
18. L. Morsut et al., Engineering Customized Cell Sensing and Response Behaviors Using Synthetic Notch Receptors. *Cell.* 164, 780-791 (2016).
19. K. T. Roybal et al., Precision Tumor Recognition by T Cells With Combinatorial Antigen-Sensing Circuits. *Cell.* 164, 770-779 (2016).
20. V. Stein, M. Nabi, K. Alexandrov, Ultrasensitive Scaffold-Dependent Protease Sensors with Large Dynamic Range. *ACS Synth. Biol.* 6, 1337-1342 (2017).
21. V. Stein, K. Alexandrov, Protease-based synthetic sensing and signal amplification. *Proc. Natl. Acad. Sci. U.S.A.* 111, 15934-15939 (2014).
22. J. C. Carrington, W. G. Dougherty, A viral cleavage site cassette: identification of amino acid sequences required for tobacco etch virus polyprotein processing. *Proc. Natl. Acad. Sci. U.S.A.* 85, 3391-3395 (1988).
23. J. Tözsér et al., Comparison of the substrate specificity of two potyvirus proteases. *FEBS J.* 272, 514-523 (2005).
24. R. Bartenschlager, The NS3/4A proteinase of the hepatitis C virus: unravelling structure and function of an unusual enzyme and a prime target for antiviral therapy. *J. Viral Hepat.* 6, 165-181 (1999).
25. M. J. Adams, J. F. Antoniw, F. Beaudoin, Overview and analysis of the polyprotein cleavage sites in the family Potyviridae. *Mol. Plant Pathol.* 6, 471-487 (2005).
26. C. Taxis, G. Stier, R. Spadaccini, M. Knop, Efficient protein depletion by genetically controlled deprotection of a dormant N-degron. *Mol. Syst. Biol.* 5, 267 (2009).
27. M. T. Butko et al., Fluorescent and photo-oxidizing TimeSTAMP tags track protein fates in light and electron microscopy. *Nat. Neurosci.* 15, 1742-1751 (2012).

28. H. K. Chung et al., Tunable and reversible drug control of protein production via a self-excising degron. *Nat. Chem. Biol.* 11, 713-720 (2015).
29. J. Fernandez-Rodriguez, C. A. Voigt, Post-translational control of genetic circuits using Potyvirus proteases. *Nucleic Acids Res.* 44, 6493-6502 (2016).
30. N. H. Kipniss et al., Engineering cell sensing and responses using a GPCR-coupled CRISPR-Cas system. *Nat. Commun.* 8, 2212 (2017).
31. G. Barnea et al., The genetic design of signaling cascades to record receptor activation. *Proc. Natl. Acad. Sci. U.S.A.* 105, 64-69 (2008).
32. N. M. Daringer, R. M. Dudek, K. A. Schwarz, J. N. Leonard, Modular extracellular sensor architecture for engineering mammalian cell-based devices. *ACS Synth. Biol.* 3, 892-902 (2014).
33. J. A. Gramespacher, A. J. Stevens, D. P. Nguyen, J. W. Chin, T. W. Muir, Intein Zymogens: Conditional Assembly and Splicing of Split Inteins via Targeted Proteolysis. *J. Am. Chem. Soc.* 139, 8074-8077 (2017).
34. D. S. Waugh, An overview of enzymatic reagents for the removal of affinity tags. *Protein Expr. Purif.* 80, 283-293 (2011).
35. M. Iwamoto, T. Bjorklund, C. Lundberg, D. Kirik, T. J. Wandless, A general chemical method to regulate protein stability in the mammalian central nervous system. *Chem. Biol.* 17, 981-988 (2010).
36. A. Varshaysky, The N-end rule: functions, mysteries, uses. *Proc. Natl. Acad. Sci. U.S.A.* 93, 12142-12149 (1996).
37. S. Nallamsetty et al., Efficient site-specific processing of fusion proteins by tobacco vein mottling virus protease in vivo and in vitro. *Protein Expr. Purif.* 38, 108-115 (2004).
38. S. S. Taremi, B. Beyer, M. Maher, N. Yao, Construction, expression, and characterization of a novel fully activated recombinant single-chain hepatitis C virus protease. *Proteins* (1998) (available at http://onlinelibrary.wiley.com/doi/10.1002/pro.0.5560071011/full).
39. I. Ghosh, A. D. Hamilton, L. Regan, Antiparallel Leucine Zipper-Directed Protein Reassembly: Application to the Green Fluorescent Protein. *J. Am. Chem. Soc.* 122, 5658-5659 (2000).
40. M. C. Wehr et al., Monitoring regulated protein-protein interactions using split TEV. *Nat. Methods.* 3, 985-993 (2006).
41. L. A. Banaszynski, L.-C. Chen, L. A. Maynard-Smith, A. G. L. Ooi, T. J. Wandless, A rapid, reversible, and tunable method to regulate protein function in living cells using synthetic small molecules. *Cell.* 126, 995-1004 (2006).
42. F. Rossi, C. A. Charlton, H. M. Blau, Monitoring protein-protein interactions in intact eukaryotic cells by beta-galactosidase complementation. *Proc. Natl. Acad. Sci. U.S.A.* 94, 8405-8410 (1997).
43. S. A. Ghabrial, H. A. Smith, T. D. Parks, W. G. Dougherty, Molecular genetic analyses of the soybean mosaic virus NIa proteinase. *J. Gen. Virol.* 71 (Pt 9), 1921-1927 (1990).
44. S. P. Weinheimer et al., Autoproteolysis of herpes simplex virus type 1 protease releases an active catalytic domain found in intermediate capsid particles. *J. Virol.* 67, 5813-5822 (1993).
45. Y. Hart, U. Alon, The utility of paradoxical components in biological circuits. *Mol. Cell.* 49, 213-221 (2013).
46. A. Porcher, N. Dostatni, The bicoid morphogen system. *Curr. Biol.* 20, R249-54 (2010).
47. S. Basu, Y. Gerchman, C. H. Collins, F. H. Arnold, R. Weiss, A synthetic multicellular system for programmed pattern formation. *Nature.* 434, 1130-1134 (2005).
48. D. Greber, M. Fussenegger, An engineered mammalian band-pass network. *Nucleic Acids Res.* 38, e174 (2010).
49. W. Ma, A. Trusina, H. El-Samad, W. A. Lim, C. Tang, Defining network topologies that can achieve biochemical adaptation. *Cell.* 138, 760-773 (2009).
50. S. Basu, R. Mehreja, S. Thiberge, M.-T. Chen, R. Weiss, Spatiotemporal control of gene expression with pulse-generating networks. *Proc. Natl. Acad. Sci. U.S.A* 101, 6355-6360 (2004).
51. T.-L. To et al., Rationally designed fluorogenic protease reporter visualizes spatiotemporal dynamics of apoptosis in vivo. *Proc. Natl. Acad. Sci. U.S.A.* 112, 3338-3343 (2015).
52. A. L. Szymczak et al., Correction of multi-gene deficiency in vivo using a single "self-cleaving" 2A peptide-based retroviral vector. *Nat. Biotechnol.* 22, 589 (2004).
53. A. D. Cox, S. W. Fesik, A. C. Kimmelman, J. Luo, C. J. Der, Drugging the undruggable RAS: Mission possible? *Nat. Rev. Drug Discov.* 13, 828-851 (2014).
54. J. Downward, Targeting RAS signalling pathways in cancer therapy. *Nat. Rev. Cancer.* 3, 11-22 (2003).
55. D. C. Gray, S. Mahrus, J. A. Wells, Activation of specific apoptotic caspases with an engineered small-molecule-activated protease. *Cell.* 142, 637-646 (2010).
56. J. F. Hancock, K. Cadwallader, H. Paterson, C. J. Marshall, A CAAX or a CAAL motif and a second signal are sufficient for plasma membrane targeting of ras proteins. *EMBO J.* 10, 4033-4039 (1991).
57. A. F. Oliveira, R. Yasuda, An improved Ras sensor for highly sensitive and quantitative FRET-FLIM imaging. *PLoS One.* 8, e52874 (2013).
58. R. Yasuda et al., Supersensitive Ras activation in dendrites and spines revealed by two-photon fluorescence lifetime imaging. *Nature Neuroscience*; New York. 9, 283-291 (2006).
59. A. Aronheim et al., Membrane targeting of the nucleotide exchange factor Sos is sufficient for activating the Ras signaling pathway. *Cell.* 78, 949-961 (1994).
60. E. Y. C. Koh et al., An internal ribosome entry site (IRES) mutant library for tuning expression level of multiple genes in mammalian cells. *PLoS One.* 8, e82100 (2013).
61. C. J. Wikstrand, C. J. Reist, G. E. Archer, M. R. Zalutsky, D. D. Bigner, The class III variant of the epidermal growth factor receptor (EGFRvIII): characterization and utilization as an immunotherapeutic target. *J. Neurovirol.* 4, 148-158 (1998).
62. T. S. Gardner, C. R. Cantor, J. J. Collins, Construction of a genetic toggle switch in *Escherichia coli*. *Nature.* 403, 339-342 (2000).
63. M. B. Elowitz, S. Leibler, A synthetic oscillatory network of transcriptional regulators. *Nature.* 403, 335-338 (2000).
64. J. Stricker et al., A fast, robust and tunable synthetic gene oscillator. *Nature.* 456, 516-519 (2008).
65. S. J. Russell, K.-W. Peng, J. C. Bell, Oncolytic virotherapy. *Nat. Biotechnol.* 30, 658-670 (2012).
66. L. Nissim, R. H. Bar-Ziv, A tunable dual-promoter integrator for targeting of cancer cells. *Mol. Syst. Biol.* 6, 444 (2010).
67. Z. Xie, L. Wroblewska, L. Prochazka, R. Weiss, Y. Benenson, Multi-input RNAi-based logic circuit for identification of specific cancer cells. *Science.* 333, 1307-1311 (2011).

68. R. Kojima, D. Aubel, M. Fussenegger, Toward a world of theranostic medication: Programming biological sentinel systems for therapeutic intervention. *Adv. Drug Deliv. Rev.* 105, 66-76 (2016).
69. F. Lienert, J. J. Lohmueller, A. Garg, P. A. Silver, Synthetic biology in mammalian cells: next generation research tools and therapeutics. *Nat. Rev. Mol. Cell Biol.* 15, 95-107 (2014).
70. L. Bintu et al., Dynamics of epigenetic regulation at the single-cell level. *Science.* 351, 720-724 (2016).
71. M. W. Kim et al., Time-gated detection of protein-protein interactions with transcriptional readout. *Elife.* 6 (2017), doi:10.7554/eLife.30233.
72. B. Schwanhäusser et al., Global quantification of mammalian gene expression control. *Nature.* 473, 337-342 (2011).
73. C. Herrmann, G. A. Martin, A. Wittinghofer, Quantitative analysis of the complex between p21ras and the Ras-binding domain of the human Raf-1 protein kinase. *J. Biol. Chem.* 270, 2901-2905 (1995).

Additional Embodiments

Programmable Protein Circuits in Living Cells

Synthetic biology approaches provide ways to program living cells to perform desired behaviors or functions. Synthetic biology could enable a diverse array of applications in biomedicine and biotechnology. Most efforts so far have been based on genetic components that regulate each other's transcription or translation. Synthetic circuits based on proteins could provide distinct capabilities, improving both circuit delivery and function within the cell. The design and implementation of protein-level circuits has been hindered by the lack of a general purpose system in which proteins can be composed to regulate one another in a flexible, programmable manner.

Here we describe methods for engineering viral proteases to regulate one another and target proteins. We show that these methods enable engineering of circuits that perform regulatory cascades, binary logic computations, analog band-pass signal processing, generation of dynamic behaviors such as pulsing, coupling to endogenous cellular states such as oncogene activation, and the ability to control cellular behaviors such as apoptosis. The flexibility and scalability of this system enables it to be reconfigured to implement a broad range of additional functions. These circuits can also be encoded and delivered to cells in multiple formats, including DNA, RNA, and at the protein level itself, enabling versatile applications without genomic integration or mutagenesis.

Applications could include the following:

Kill switches: The ability to kill engineered cells in response to a signal is a key requirement for emerging cell based therapies. Existing methods may produce toxicity or cell death when not desired, i.e. in the absence of the kill switch input. This invention includes the construction of kill switches in which such effects can be suppressed through a protease-based reciprocal inhibition motif or through feed-forward loop structures.

Virally delivered synthetic circuits: The invention includes the ability to deliver complex programmed protein-level functions into cells using a variety of non-integrating vectors. This capability avoids potential mutagenesis that occurs with gene regulation based systems.

Oncolytic viral therapies: By encoding these protein level circuits on oncolytic viruses, one could deliver functions that specifically kill or inactivate tumor cells conditionally depending on their state.

Gene drive payloads: Gene drive technology is a rapidly growing area of biotechnology that enables the efficient super-Mendelian propagation of genetic systems within mating populations of organisms. Gene drive applications will depend on the ability to package sophisticated functions in compact genetic systems. The system described here can enable gene drives payloads that perform such functions. For example, for insect vector control, a protein-circuit that would specifically kill mosquitoes infected by human pathogens such as Dengue virus.

Cell type specific control of cell fate. Regenerative medicine requires precise manipulation of cell fate. These protein level circuits can be transiently introduced into cells to control the activation of fate regulating genes and thereby induce specific cell fates. This activity can be coupled to modules within the circuit that detect the state of the cell and make cell fate control conditional on cell state. This avoids the problem of activating the same genes in a heterogeneous cell population, and also avoids permanent genetic modification.

Extracellular protein level feedback circuits that control blood clotting. The system described here enables the design of protein circuits that could function outside cells to detect blood clots or other pathological conditions and trigger clot removing functions.

Subcellular functions. The system described here enables the design of protein circuits that function in specific subcellular compartments or sites. These circuits could operate to modulate the behavior of specific synapses or organelles such as mitochondria.

The above are a few examples of the many possible applications of this system.

The ability to design synthetic circuits that can process signals and actuate cellular responses in a programmable manner could facilitate regenerative medicine, cell-based therapies, and other applications. Approaches based on transcriptional or translational regulation have made remarkable advances towards this goal [refs]. However, gene regulatory circuits can require potentially mutagenic genome integration procedures, are limited in operational speed and stability, and interact only indirectly with key protein-level cellular activities. Synthetic protein-level circuits based on a modular and composable set of protein components could in principle circumvent these limitations. Here, we show that viral proteases can be engineered to regulate one another in a composable fashion, and then used to implement a broad variety of circuits including regulatory cascades, binary logic, analog signal processing, dynamic responses, and the sensing and conditional actuation of endogenous cellular pathways. The system, termed CHOMP (Circuits of Hacked Orthogonal Modular Proteases), combines protease-specific cleavage sites, cleavage-dependent degrons, split protein complementation, and modular dimerization domains. Multi-protein CHOMP circuits can be encoded compactly as single transcripts and operate without genomic integration, avoiding the need for permanent genetic modification and accelerating the design-build-test cycle. They thus offer a flexible new platform for programming diverse protein-level functionality in mammalian cells.

Many natural cellular functions are implemented by protein-level circuits, in which proteins specifically modify each other's activity, localization, or stability. For example, programmed cell death utilizes a circuit based on proteases (caspases) that activate one another through cleavage. The inherent modularity of some protein domains enables their potential use as flexible components for synthetic circuit design. Varshaysky (1995) proposed a mechanism for a protein-level logic gate in which modular degrons regulate the stability of a protein in response to a combination of protein-level inputs. Modular protein interaction domains have been used to re-wire endogenous protein circuits, and couple their activities to non-natural inputs (I) [other refs]. Nevertheless, a general purpose system for protein-level circuit design has remained elusive due to the lack of a set of composable protein components.

Viral proteases provide an ideal basis for protein circuit design (ref). They exhibit strong specificity for short cognate target sites, which can be recognized and cleaved in a variety of protein contexts (ref). Different proteases cleave with distinct site specificities, potentially enabling orthogonal regulation. Viral proteases can also be used in conjunction with degrons to control the stability of other proteins in a modular fashion (Voigt, others). Despite these natural advantages, it has remained unclear whether viral proteases can be engineered to regulate one another to create more complex protein-level circuits (FIG. 1L).

CHOMP Building Blocks

We started with tobacco etch virus (TEV) protease, which is well-characterized and has been used in diverse biotechnology applications. To read out its activity, we constructed a reporter system in which a Citrine fluorescent protein is fused to a DHFR degron that targets the protein for degradation (2) (FIG. 1E). A TEV cleavage site (tevs) introduced between the degron and Citrine allows TEV protease to remove the degron, stabilizing the fluorescent protein. The DHFR degron can also be stabilized by the drug trimethoprim (TMP), serving as a positive control. We transiently transfected HEK293 cells with plasmids expressing the protease, the reporter, and a constitutively expressed mCherry co-transfection marker, and analyzed cells by flow cytometry, gating on high levels of mCherry fluorescence (see Methods, FIG. 1E, and FIG. 5A). TEV protease strongly increased fluorescence of the reporter to levels comparable to those achieved by TMP (FIG. 1E). We also built a complementary reporter inhibited by TEV protease. In this design, TEV cleavage reveals a destabilizing N-terminal tyrosine residue [Varshaysky, others] (FIG. 1F). TEV protease indeed reduced reporter fluorescence (FIG. 1F). Thus, TEV protease can be used to increase or decrease the levels of another protein by removing or revealing degrons.

Figure 5K:
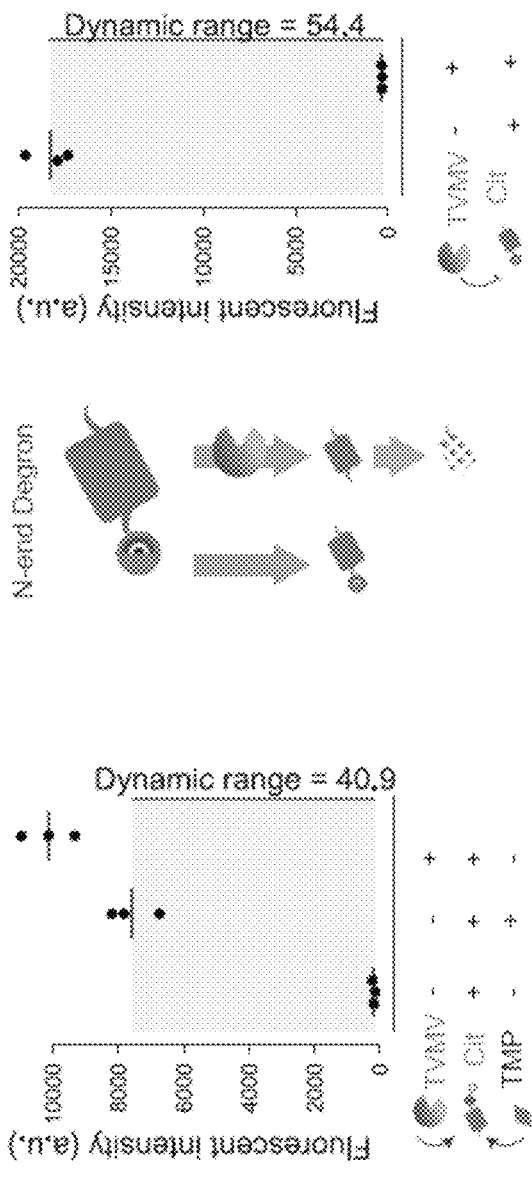
Figure 5K:
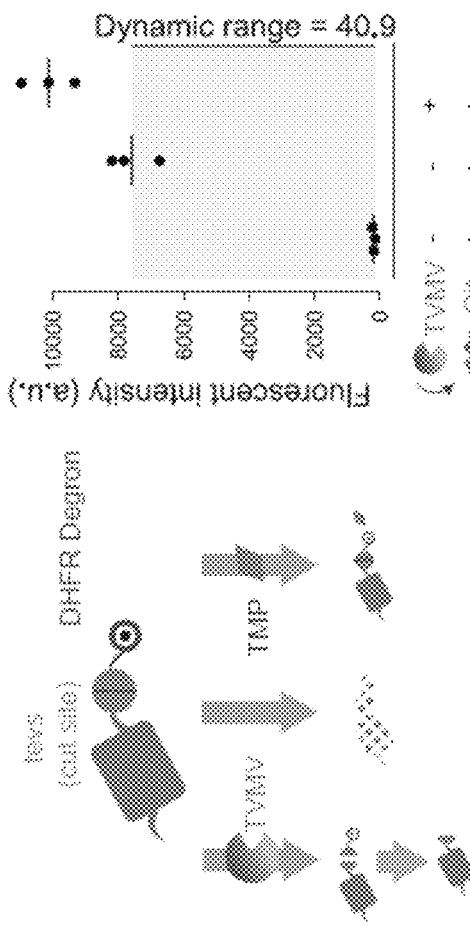

To enable the construction of multi-component circuits, we generalized the reporter designs to proteases from tobacco vein mottling virus (TVMV) (3) and Hepatitis C virus (HCV) (4) (FIGS. 5K, 5L). For HCV, we adopted a construct in which the HCV protease and its co-peptide are fused to create a more active single chain protease (5). This HCV protease initially showed more modest regulation than the other proteases, especially for the repressible reporter (FIG. 5L). We reasoned that increasing the protease affinity to its target could improve its regulatory range. Incorporating a pair of hetero-dimerizing leucine zippers (6) in the protease and its target indeed improved regulation by HCV protease (FIG. 5L). To test the orthogonality of the overall set of proteases, we analyzed regulation of each activatable reporter by each protease (FIG. 1G). Together, these results established a set of positive and negative reporters for three orthogonal proteases, and introduced a mechanism for increasing protease target recognition.

Figure 5M:
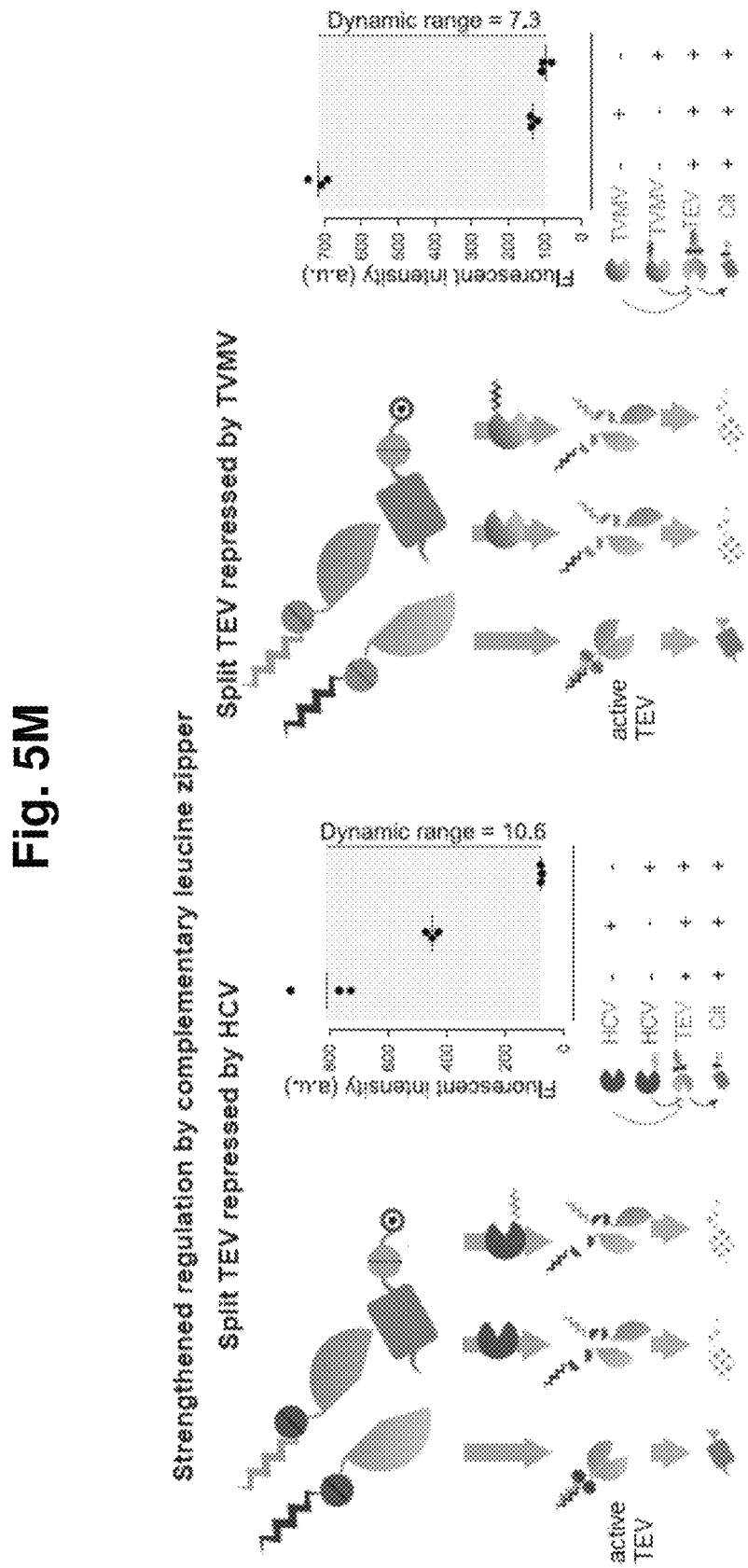

Protease-protease regulation is essential for enabling the design of complex circuits. We first incorporated the conditional degrons used in the reporters within the proteases themselves. However, this strategy failed to produce strong protease-dependent control of target protease activity. Therefore, we took advantage of the previously described ability of dimerizing domains to reconstitute the activity of a split TEV protease variant (7) (FIG. 1H). Attaching antiparallel hetero-dimerizing leucine zipper domains (6) to each half of the split TEV protease reconstituted its activity, as expected (FIG. 1H). To allow HCV protease to inhibit the activity of reconstituted TEV protease, we inserted HCV cleavage sites between the leucine zippers and TEV protease. Finally, inspired by the design of the repressible HCV reporter, we fused a complementary leucine zipper to the HCV protease, enhancing its ability to dock to, and regulate its TEV protease target (FIG. 5M [left]). This design successfully allowed inhibition of TEV protease by HCV protease (FIG. 1J).

Figure 5N:
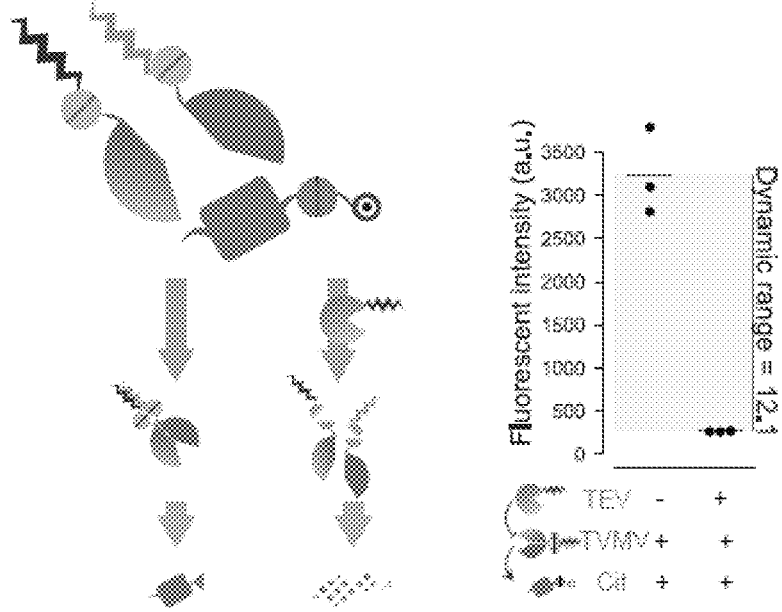

This design appeared to be general in terms of both input and output. Replacement of HCV cleavage sites with TVMV cleavage sites generated a TEV protease that could be inhibited by TVMV protease (FIG. 5M, right). Using a homology-guided approach to identify a corresponding split site in the TVMV protease, we were able to similarly regulate TVMV protease by both HCV and TEV proteases (FIG. 1H and FIG. 5N). In a final design step, to make the components as compact as possible, we engineered a single chain implementation of this design. In this variant, we inserted a single leucine zipper flanked by cleavage sites for the input protease between the two protease halves (FIG. 1I). This construct was also able to transduce inputs from other proteases (FIG. 1I, 5O, 5P, 5R). Although HCV protease lacks a known split site, we were able to effectively split HCV protease by introducing the cleavage site between the major protease domain and the fused co-peptide and leucine zipper. In this construct, cleavage by an input protease strongly reduced HCV's ability to repress its target protease, enabling the design and construction of three-step protease cascades (FIG. 1J and FIG. 1Q)

To explore the capabilities of protease circuits, we next set out to test basic circuits for Boolean logic, analog filtering, and dynamic pulse generation. First, we first asked whether the engineered proteases could be used to create binary logic gates, which are essential modules in complex circuits. More specifically, we designed protease circuits that compute each of the eight non-trivial, two-input binary logical functions. Remarkably, three design principles were sufficient to enable construction of all 8 logic gates: First, the incorporation of a consecutive pair of distinct cleavage sites between a degron and the reporter can implement OR logic, since cleavage of either or both sites is sufficient to eliminate a degron and thereby stabilize the protein (FIG. 2, OR). Second, flanking the reporter with degrons (FKBP [wandless] on the N-terminus, and DHFR on the C-terminus), each removable with a distinct cleavage site, implements AND logic, as both degrons must be removed to stabilize the protein (FIGS. 2A and 2B, OR). Third, as shown in FIGS. 1F and 1H, negation can be implemented either using a cleavage site to reveal an N-end degron, or using an intermediate protease repressed by the input protease.

Using these principles, we designed and built each of the 8 possible binary logic gates (FIGS. 2A-2I and FIG. 6A). To characterize their performance in cells, we co-transfected each gate either with or without each of the two input proteases, HCV and TEV. Although they varied in their quantitative performance, all of the gates showed the expected qualitative behavior. For high-expressing cells, the best-performing logic gates showed dynamic ranges (ratio of high to low output states) of 10-20-fold (OR, NOR, IMPLY). Other gates showed intermediate dynamic ranges of ~7-fold (AND, NAND, NIMPLY). The non-monotonic XOR and XNOR showed more modest dynamic ranges of 5.2 and 3.6, respectively.

Figure 6D:
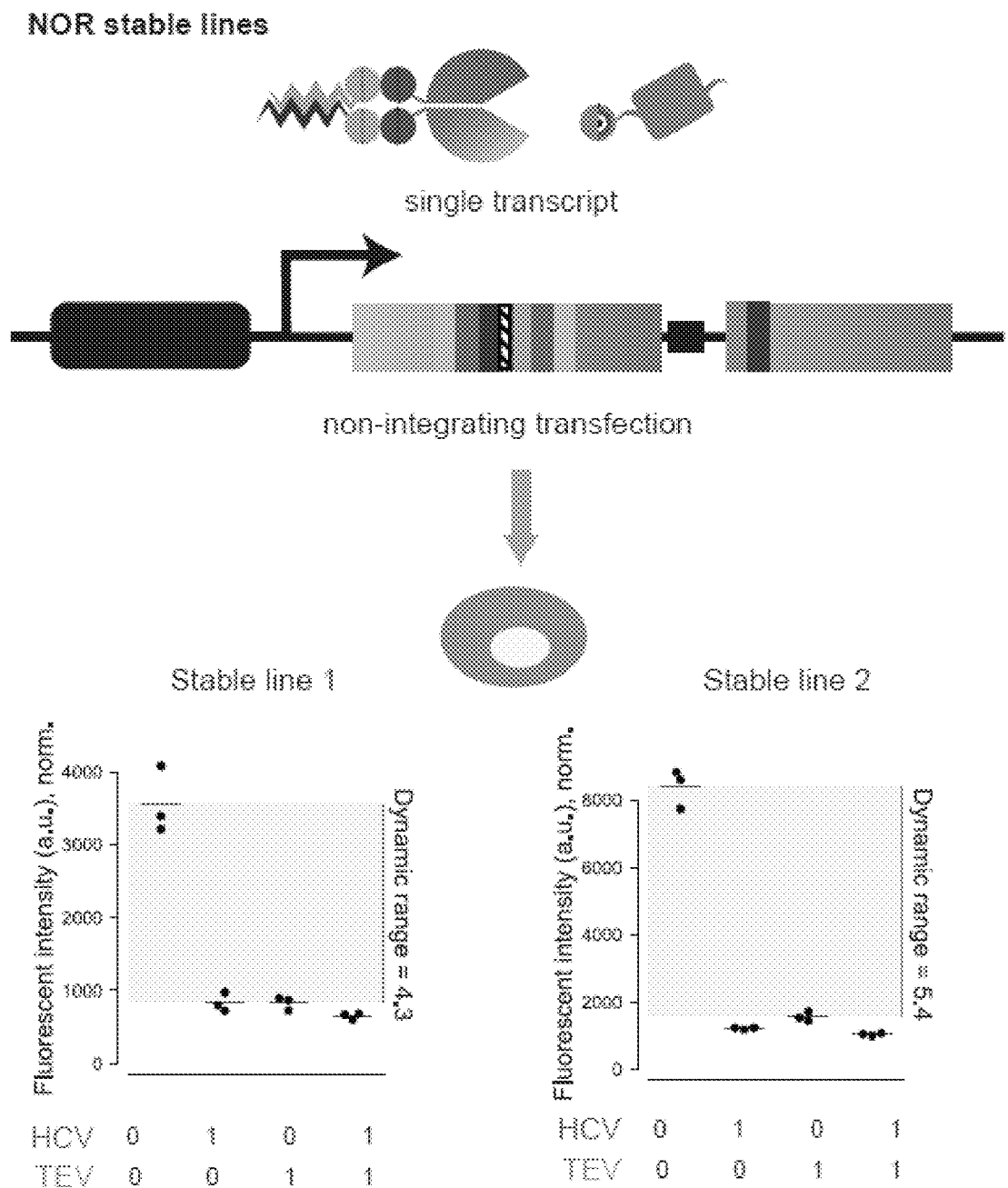
FIG. 6D depicts non-limiting examples of compound proteases, target proteins, and synthetic protein circuits in accordance with some embodiments.

The post-translational operation of the circuits could enable them to function not only when transiently transfected into cells, but also when stably incorporated in the genome. We used the piggyBac transposon system to stably integrate the NOR gate, and verified that it behaves as expected in response to combinations of transiently transfected input protease genes (FIG. 6D). Together, these results indicate that a small number of design principles are sufficient to implement all binary logic operations at the protein level, and suggest that the same circuit can function both as a stable integrant or as a transient transfection.

Beyond Boolean logic, many cellular behaviors require analog signal filtering and, more specifically, the ability to selectively respond to specific input concentration ranges [paradoxical, morphogen]. The incoherent feed-forward loop (IFFL) motif, in which an input both activates and inhibits the same target, can perform bandpass filtering, but have not been implemented at the protein level [ref]. To construct an IFFL we combined an activating arm, in which TEV protease removes a C-terminal degron, with a repressing arm, in which TVMV protease reveals a destabilizing N-end tyrosine (FIG. 3A). In order to enable tuning, we also introduced a double negative feedback loop between HCV and TVMV proteases on the repression arm such that the level of HCV expression sets a threshold for TVMV activity (FIG. 3A). To characterize these circuits we varied the amount of transfected DNA expressing the input TEV and TVMV proteases. This DNA concentration correlates with protein expression level (FIG. 8A).

The activating and repressing arms of the IFFL, taken individually, generated increasing and decreasing responses, respectively, to increasing levels of TEV and TVMV protease (FIG. 3B, 3C). Addition of HCV increased both the threshold and the sharpness of the response to TVMV protease concentration (FIG. 3C). Combining the two arms into a single circuit generated the expected non-monotonic input-output response (FIG. 3D and FIG. 8B). Finally, as predicted from a simple model of the circuit (FIG. 3D, Methods), varying the HCV expression level tuned the width of the bandpass response (FIG. 3D and Extended Data FIG. 8B). Together, these results demonstrate the ability to rationally engineer tunable analog bandpass filters.

Figure 3I:
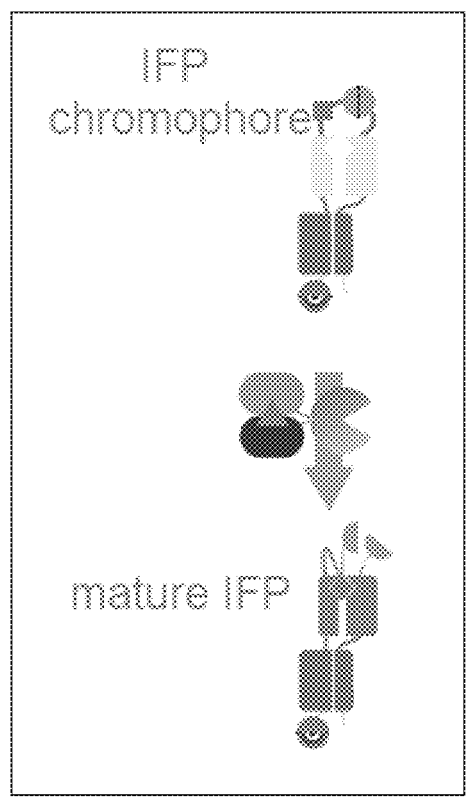
FIG. 3I depicts a non-limiting example of a synthetic protein circuit in accordance with some embodiments.

Temporal signal processing and, more specifically, adaptation to a change in input, play critical roles in diverse biological systems [refs]. To engineer adaptation, we designed a second IFFL circuit that uses the 3-step cascade (FIG. 1J) to introduce a delay in the repressing arm relative to the activating arm (FIG. 3E and FIG. 3I). To analyze responses to rapid changes in inputs, we next constructed a split TEV protease, in which addition of rapamycin reconstitutes TEV function through attached heterodimerization domains (FIG. 8E) [ref]. Finally, to enable rapid read-out of cellular behavior we adopted a previously reported protease-triggered far red fluorescent protein, which is synthesized in a non-fluorescent state but can be switched on by TEV protease [ref]. We encoded the entire circuit and reporter on a single polypeptide (FIG. 3F) and stably incorporated it in the genome (Methods).

Using flow cytometry, we analyzed the response of the reporter over time after rapamycin addition. We observed the predicted adaptive dynamics, with a rapid rise in fluorescence on a timescale of hours and a subsequent decay to baseline over a timescale of ~1 day (FIGS. 3G and 3H). To obtain a more direct view of the dynamics at the level of individual cells, we analyzed the same cell line using quantitative time-lapse fluorescence microscopy (FIG. 3G, filmstrip, Movie S1). Consistent with flow cytometry, individual cells responded maximally at t=210±XXX min after rapamycin addition, and then showed a monotonic decrease in activity to near background levels (FIG. 3H, trace). Together, these results demonstrate the ability to program dynamic signal responses.

Having established that CHOMP can enable programming of binary, analog, and dynamic protein-level behaviors, we next asked whether one could rationally design CHOMP circuits that process endogenous inputs and control endogenous outputs. As a design target, we focused on Ras, which plays a strong role in diverse cancers and is difficult to target with conventional therapeutic strategies [refs]. More specifically, we sought to use CHOMP to conditionally reduce cell survival depending on Ras activation.

Figure 4F:
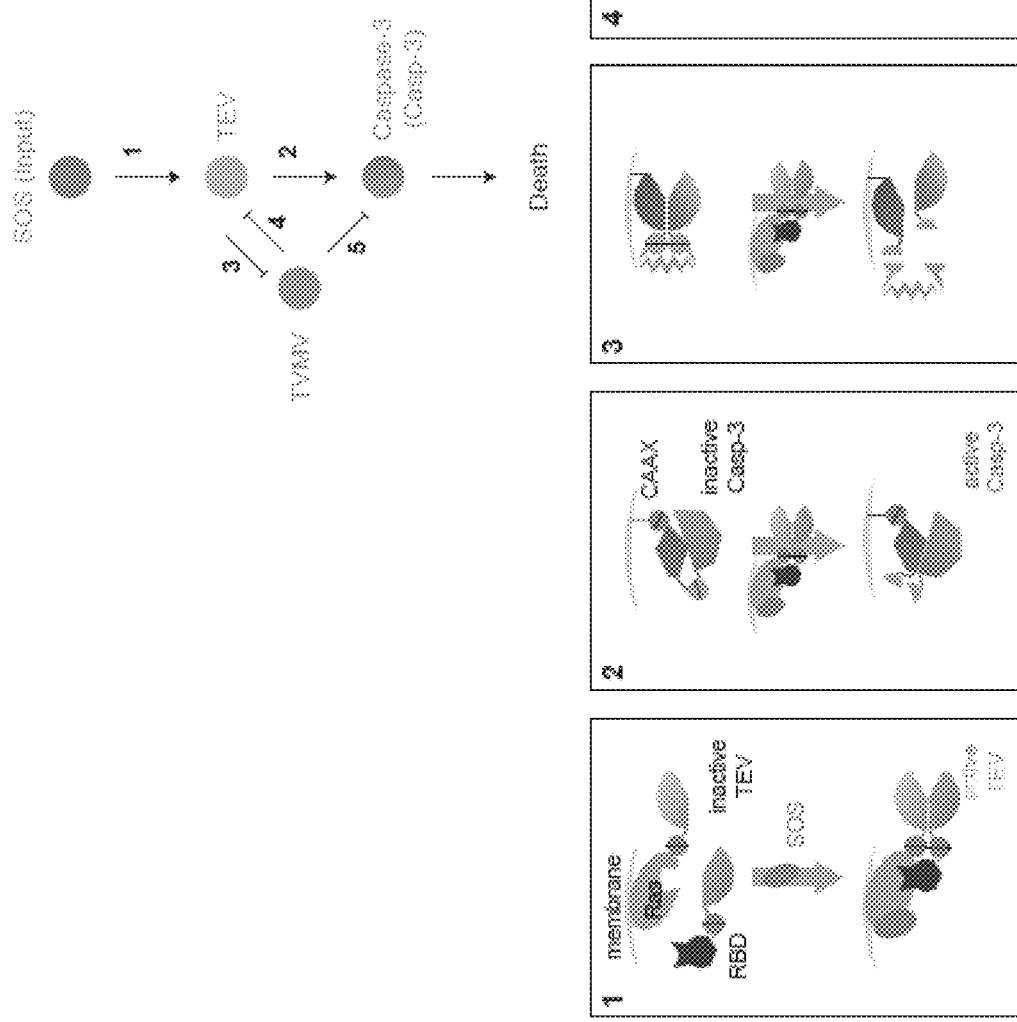
FIG. 4F-4I depict non-limiting examples of synthetic protein circuits in accordance with some embodiments.
Figure 4G:
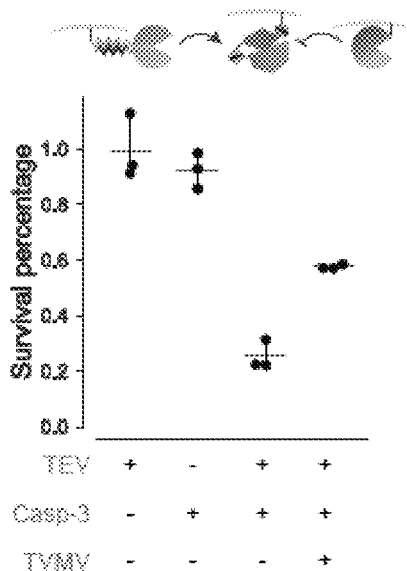
Figure 4H:
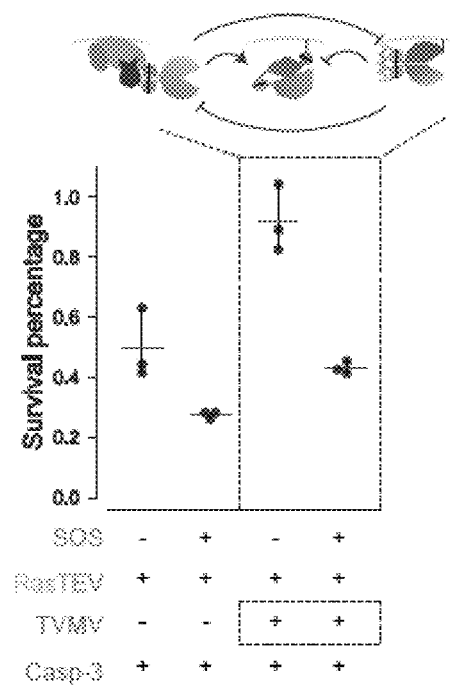
Figure 10E:
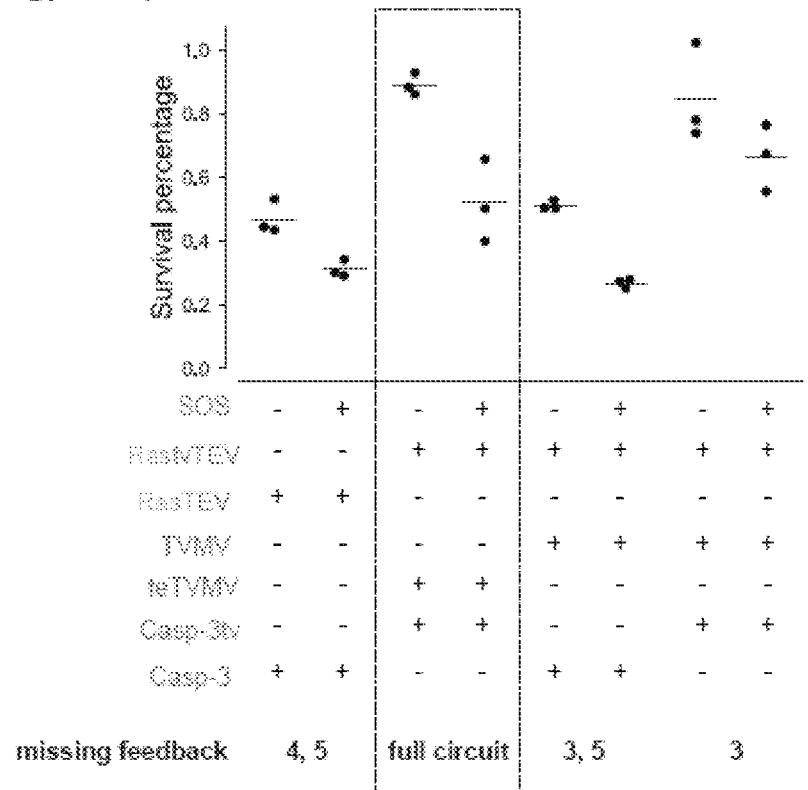
FIG. 10E is a plot showing topology comparison data in accordance with some embodiments.
Figure 10E:
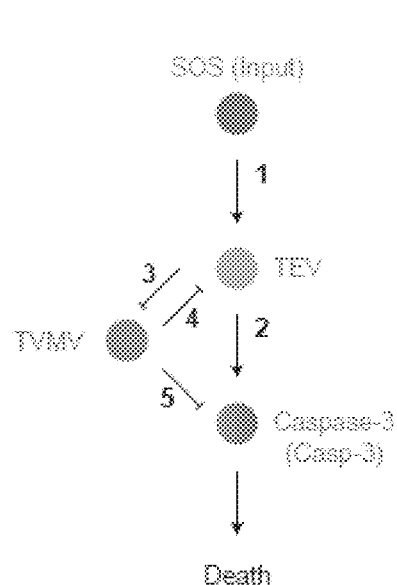
Figure 10E:
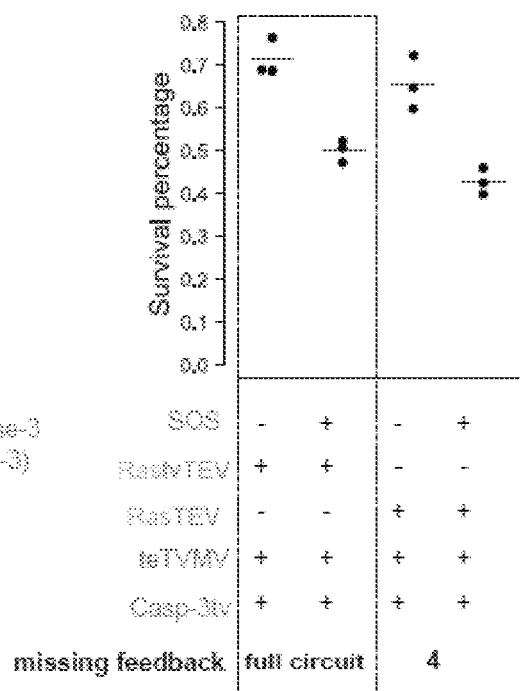
Figure 10F:
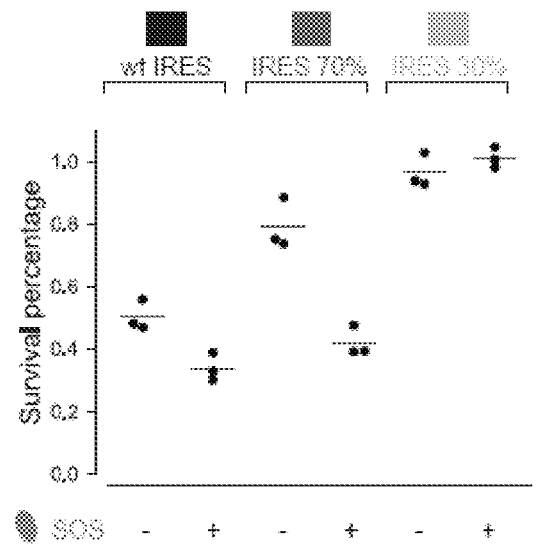
FIGS. 10F and 10G are plots showing titration data in accordance with some embodiments.
Figure 10G:
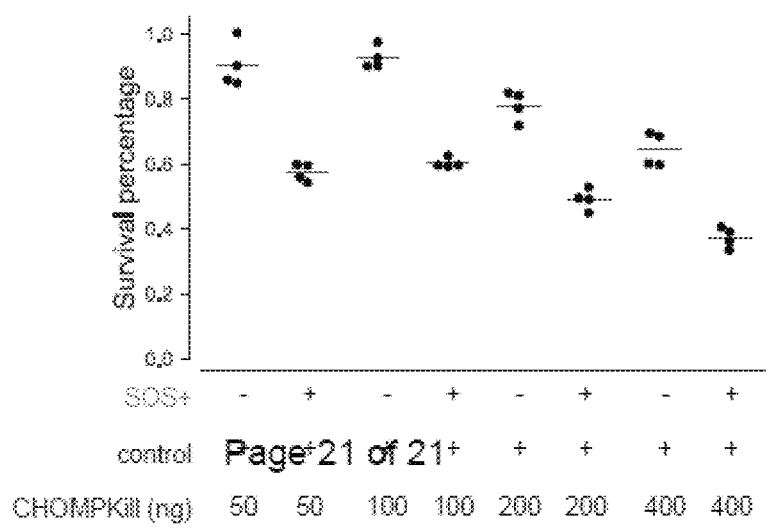

To couple proteases to the activation of cell death, we took advantage of a previously described cytoplasmic TEV-activated Caspase. Because Ras functions at the membrane, we first designed a membrane localized TEV-activated Caspase 3 and a corresponding membrane-localized TEVp by fusing the C-terminal CAAX membrane localization peptide from Ras to both TEV protease and Caspase 3 (FIG. 4F). This membrane-targeted Caspase 3 efficiently reduced cell numbers in a TEVp-dependent manner (FIG. 4G), outperforming the cytoplasmic variant (FIG. 10G). In order to add negative regulation to Caspase 3, we further included a TVMVp cleavage site between Caspase 3 and the membrane localization tag. With this modification, membrane-localized TVMV protease expression could release Caspase from the membrane and thus suppress its activation by TEV protease, providing dual modes of Caspase 3 regulation (FIG. 4G). Next, to couple Caspase 3 to an upstream input that activates Ras, we took advantage of a Raf domain (RBD) that specifically binds to the active form of Ras [ref]. We fused the N-terminal half of TEV protease to Ras and its C-terminal half to RBD so that Ras activation could reconstitute TEV protease activity and thereby activate Caspase 3 (core circuit, FIG. 4F). To validate this design, we stably expressed a constitutively active SOS [ref] that activates Ras in HEK293 cells and compared circuit behavior in this cell to the parental control line lacking ectopic SOS expression [ref]. Although the core circuit preferentially reduced cell survival in SOS+ cells, we also observed substantial reduction in cell number in control cells (FIG. 4H, with 0 ng TVMV).

To better discriminate between parental and SOS+ cells, we further added TVMV protease, configuring it to inhibit both TEV protease and Caspase 3, while also incorporating reciprocal inhibition of TVMV protease by TEV protease (FIG. 4F, full circuit). This addition was designed to suppress basal activation of the Caspase 3 and sharpen the overall response to SOS. More specifically, at low levels of Ras activation (in control cells), TEV protease should reconstitute at low levels, leading to correspondingly low levels of Caspase 3 activity, which are further suppressed by TVMV protease, both through its direct effect on Caspase 3 and through its indirect effect on TEV protease. By contrast, at elevated levels of Ras activation (in SOS cells), TEV protease can be more efficiently reconstituted, activating Caspase 3, while also inhibiting TVMV protease and thereby blocking its inhibitory effects.

To characterize this circuit, we co-transfected varying amounts of the TVMV protease together with the core circuit in SOS+ and control cells. In these experiments, TVMV protease improved discrimination of the SOS state of cells in a dose-dependent fashion (FIG. 9I), with optimal discrimination occurring at TVMV plasmid concentrations of ~33%-66% of the TEV plasmid concentration. Systematic removal of individual regulatory interactions revealed that TEV protease regulation of TVMV protease and TVMV protease regulation of Caspase were major contributors to improved selectivity (FIG. 10E). Together, these results demonstrate the design and implementation of a CHOMP circuit that can transduce endogenous inputs to physiological responses in a rational and tunable fashion.

Figure 4I:
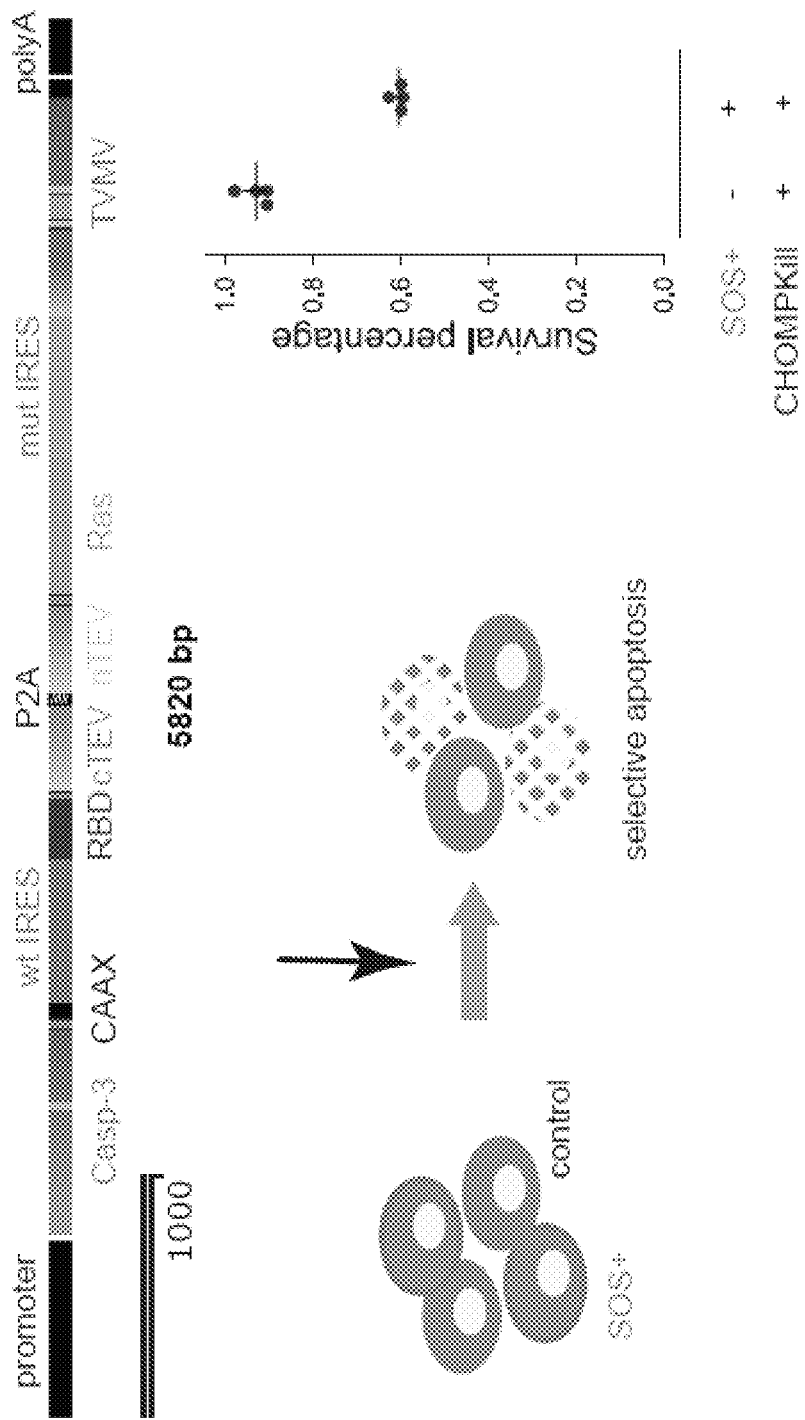

A unique feature of the CHOMP framework is the ability to encode a complete circuit on a single transcript, facilitating its delivery for potential applications. In order to achieve single-transcript delivery, while preserving the ability to control the relative expression levels of different components, we took advantage of IRES sequences of varying strengths [ref]. We encoded the full circuit as a single transcript with a wild-type IRES interposed between Caspase and TEV protease coding sequences, followed by one of several different variant IRES sequence and then the TVMV protease (FIG. 10F). We found that the circuit functioned optimally when the second IRES strength was ~70% of wild-type [ref]. We next transfected different concentrations of this optimal single-transcript circuit into a mixed population of SOS and control cells. Despite the substantial variability inherent to transient transfection, this single construct was able to preferentially reduce the SOS population (FIG. 4I and FIG. 10G). Delivered at optimal concentration, the circuit had little effect on the parental cells, but reduced the SOS+ population by approximately 40% (FIG. 4I), showing how rational design of a relatively simple three-protease circuit can couple cellular responses to endogenous responses.

Discussion

Here we have engineered viral proteases to function as a set of composable, post-translational regulatory components orthogonal to endogenous cellular pathways. These proteases can be designed to regulate one another to create protein-level "CHOMP" circuits that implement binary logic gates (FIGS. 2A-2I), analog signal processing functions (FIGS. 3A-3I), and dynamic responses (FIGS. 3A-3I). By interfacing proteases with endogenous cellular components, we demonstrated, as a proof of principle, that a CHOMP circuit can selectively reduce the survival of cells overexpressing SOS, a key step towards the long-standing challenge of targeting cells with elevated Ras activation (FIGS. 4F-4I). [ref].

The CHOMP framework has several appealing features for general purpose cellular computation. The circuits can be encoded in a compact manner, as a single transcript, without requiring transcriptional regulation of individual components. In the context of genomic integration, this aspect avoids issues with transcriptional interference between circuit components. Furthermore, CHOMP circuits can operate without genomic integration, eliminating possible mutagenic consequences altogether and enabling an accelerated design-build-test cycle in which a circuit can be constructed as one or more DNA molecules and immediately tested in living cells. Our results also demonstrate unique functional capabilities of CHOMP circuits. By circumventing transcriptional regulation, they respond faster than synthetic transcriptional circuits in a "single-shot" response mode (FIGS. 3A-3I), although protein replenishment by translation can be rate-limiting for some dynamic operations. They can also directly respond to, and regulate, endogenous pathway activities (FIGS. 4F-4I).

Additional features would further enhance the power and flexibility of CHOMP. Protease-activating-proteases would simplify some circuit designs and facilitate signal amplification. Protein design strategies to control the intrinsic nonlinearity (effective cooperativity) of input-output responses could enable the construction of interesting dynamical properties such as multistability [ref], oscillation [refs: E2000, Laurent], or excitability [refs]. Finally, all circuits shown here were created with only 3 proteases, but additional orthogonal proteases would allow larger and more complex circuits [viral_protease_review].

We anticipate that the existing CHOMP framework will enable new capabilities for synthetic biology applications. First, CHOMP circuits can operate at the subcellular level, performing local computation at specific sites within the cell. For example, by localizing components to synaptic sites within the same neuron, one could engineer circuits that modulate individual synaptic strengths in response to synaptic activities. Second, CHOMP circuits have a relatively compact genetic design and do not require regulatory interactions at the DNA level. These properties could facilitate their introduction into differentiated and even post-mitotic tissues and cells using gene therapy vectors or other viruses. In particular, they could improve the specificity of oncolytic virus technology [ref]. Third, while we have focused on proteases here, CHOMP circuits are also compatible with other types of synthetic circuits. Hybrid circuits combining transcriptional or translational regulation with engineered proteases could offer the programmability of base-pairing interactions with the computational advantages of CHOMP. For example, existing cancer-detection circuits [refs] could conditionally express CHOMP components to increase specificity and couple to protein-level inputs and outputs. In the future, one can envision CHOMP circuits acting as smart therapeutics [reviews] or sentinels [ref:collins], delivered by non-integrating viruses into cells, where they could be triggered by complex combinations of cellular protein activities to enable sophisticated cellular control.

Further Disclosure Relating to Some Figures.

FIGS. 1E-1L|Design Principles for CHOMP Components.

FIG. 1L, I have a dream. FIG. 1E, A protease-activatable reporter. Left, the reporter consists of a Citrine, a degron, and a TEV cleavage site in between. Citrine level is increased by TEV-mediated degron removal or TMP-mediated degron stabilization. Middle, distribution of Citrine signal from the gated area in the scatter plot in FIG. 5A. Solid curves indicate skew gaussian fits, and vertical dashed lines indicate peak positions of the gaussians. The x coordinates of these dashed lines are reported as "fluorescent intensity". Right, triplicate results quantified using the aforementioned procedure. FIG. 1F, A protease-repressible reporter. Citrine level is reduced by cleavage-mediated exposure of an N-end degron. FIG. 1G, Three orthogonal proteases. Fluorescent intensity in each square is normalized to the TMP-stabilized value of its corresponding reporter. FIG. 1H, A protease-repressible protease. TEV protease is split and then reconstituted through dimerizing leucine zippers. A leucine-zipper-tagged HCV protease docks to and cleaves the sites inserted between TEV protease and leucine zippers, thus repressing TEV. Also FIG. 1H, The repressible design works for TVMV protease as well. FIG. 1I, A modified single-chain TEV protease still allows for docking of and repressive cleavage by HCV protease. FIG. 1J, A three-protease repression cascade. Repressible HCV protease uses a different design, where TEV cleavage separates core HCV protease from its docking leucine zipper and activity-enhancing co-peptide. For FIGS. 1E-1L, 2A-2I, 5A, 5K-5R, 6A, and 6D, The red lines indicate mean and the grey areas separate the expected ON and OFF states.

FIGS. 2A-2I|Logic Gates.

TEV and HCV proteases serve as inputs, and Citrine as output. The designs and performances for all eight non-trivial two-input logic gates are listed. Fluorescent intensity in each panel is normalized to the corresponding reporter stabilized with TMP (degron only at C terminus) or Shield+TMP (degrons at both termini).

FIGS. 3A-3I|Bandpass Filtering and Pulse Generation Using Incoherent Feed-Forward Loops.

FIG. 3A, Diagram of a bandpass circuit. TEV and TVMV protease expressions are controlled through the amount of transfected DNA or doxycycline-inducible enhancer. HCV protease is expressed at various constant levels to tune the threshold of the repression arm. FIG. 3B, Input-output curve of the activation arm. FIG. 3C, Input-output curve of the repression arm, in the presence of constant TEV and different HCV levels. HCV protease increases the threshold and sharpens the curve. Curves in FIG. 3B and FIG. 3C are fitted to mechanistically generated equations (see Methods). FIG. 3D, Bandpass behavior of the complete circuit. Increasing HCV protease shifts peak position and increases peak amplitude. Curves are predictions combining the fits from both individual arms. Data in FIGS. 3B-3D are normalized to TMP-stabilized reporter. FIGS. 3E and 3I, Diagram of pulsing circuit. Rapamycin-induced dimerization of FKBP and FRB domains reconstitutes TEV protease. Cleavage of the reporter TEV site frees the tethered-away chromophore and allows for IFP to mature. FIG. 3F, All pulse circuit components encoded on a single transcript. FIG. 3G, Film-strips showing a single cell stably expressing the pulse circuit, as well as Cerulean as a segmentation marker. After rapamycin induction, IFP signal (red) increases, followed by a slower decay, while Cerulean signal (blue) remains stable. FIG. 3H, Time traces of all observed single cells that pass our analysis threshold (see Methods for details on normalization and smoothing). Black line indicates medians at each time point. Rapamycin is added at 0 minute.

FIGS. 4F-4I|Selective Reduction of Ras-Activating Cells.

FIG. 4F, Layout of a circuit that selectively activates Caspase 3 in response to high Sos activity. The molecular mechanisms of each regulatory edge are listed on the right. FIG. 4G, An engineered Caspase 3 is activatable by TEV protease (diagram in FIG. 4F-2) and repressed by TVMV protease (diagram in 4F-5). We inferred the survival percentage of cells that get the indicated components (see Methods). FIG. 4H, The core circuit (4F-1, 4F-2) preferentially reduces survival in the presence of ectopic Sos, and adding TVMV-linked edges (4F-3, 4F-4, 4F-5) improves selectivity. FIG. 4I, The entire circuit encoded on a single transcript selectively reduces survival of Sos cells co-cultured with control cells. Triplicate results from independent wells are displayed, and the bars indicate mean.

FIGS. 5A, 5K-5R|Characterization and Optimization of CHOMP Components.

Figure 5O:
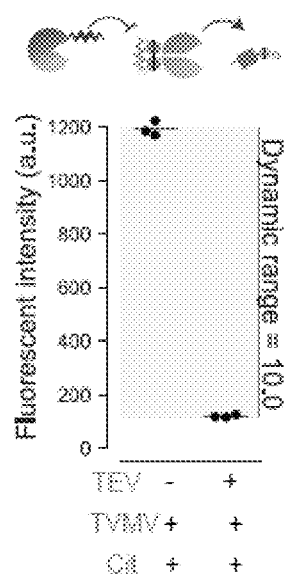
Figure 5R:
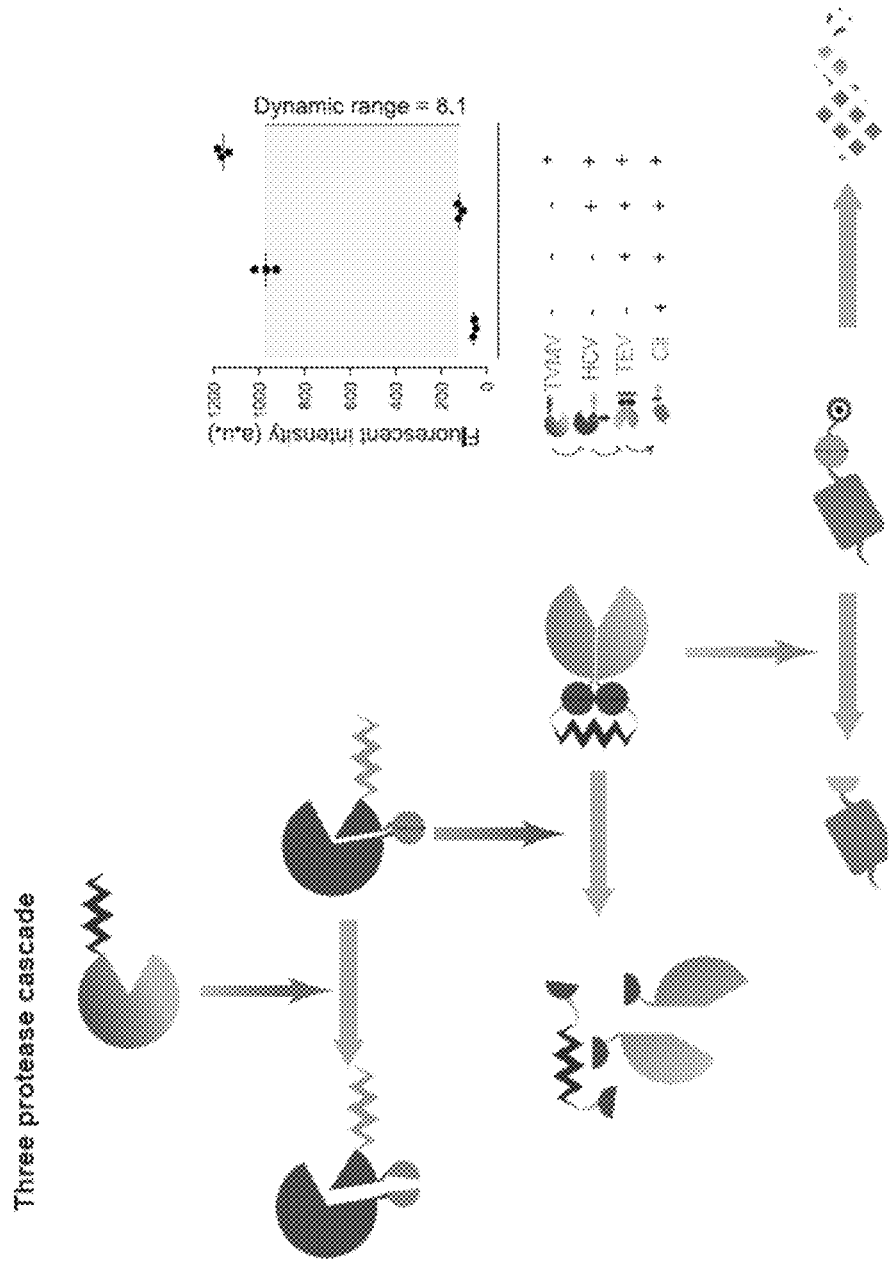

FIG. 5A, Two representative scatter plots of flow cytometry data with (red) and without (blue) TEV. Citrine signal is represented on the y axis and co-transfection marker Cherry on x. The dashed lines delineate gating on high Cherry level that's analyzed in FIG. 1E. FIGS. 5K, 5L, Reporters activatable (left) and repressible (right) by TVMV (FIG. 5K) and HCV (FIG. 5L) proteases. The designs are the same as TEV reporters except for the specific cleavage sites. Repressible HCV reporter contains an extra leucine zipper, and exhibits stronger repression when HCV protease is tagged with the complementary leucine zipper. FIG. 5M, Split TEV proteases repressible by HCV (left) and TVMV (right) proteases. Tagging the regulating proteases with a leucine zipper generally enhances repression. FIG. 5N, Split TVMV protease repressible by TEV protease. FIGS. 5O and 5R, Single-chain TEV protease repressible by TVMV protease. FIG. 5P, Single-chain TVMV protease repressible by HCV (left) and TEV (right) proteases. FIG. 5Q, Three-protease cascade still functions with an alternative layout.

FIGS. 6A, 6D|Logic Gates.

FIG. 6A, Diagrams of the molecular mechanisms for all gates. FIG. 6D, Performance of stably integrated NOR gate in two monoclonal cell lines.

Figure 8E:
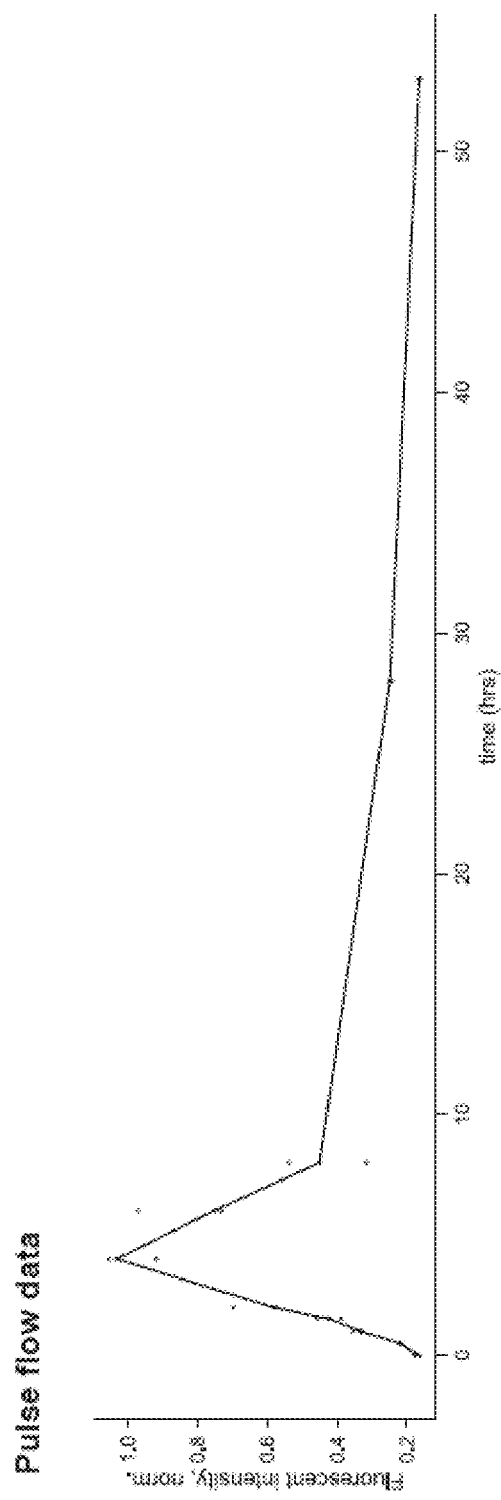
FIG. 8E is a plot showing pulse flow data in accordance with some embodiments.

FIGS. 8A, 8B and 8E|Characterization Related to Incoherent Feed-Forward Loops.

FIG. 8A, Linear correlation between the amount of transfected DNA and Citrine expression from CMV promoter. FIG. 8b, Bandpass behavior in response to TEV and TVMV proteases expressed with different levels of dox inducers. FIG. 8E, Pulsing behavior measured using flow cytometry (same stable cell line as in FIG. 3H). Each point represents the fluorescent signal in an individual well with indicated rapamycin exposure time. The value is extracted from the peak position of skew-Gaussian-fitted histogram in far-red channel (same method as the post-gating fit in the middle panel of FIG. 1E).

Figure 9H:
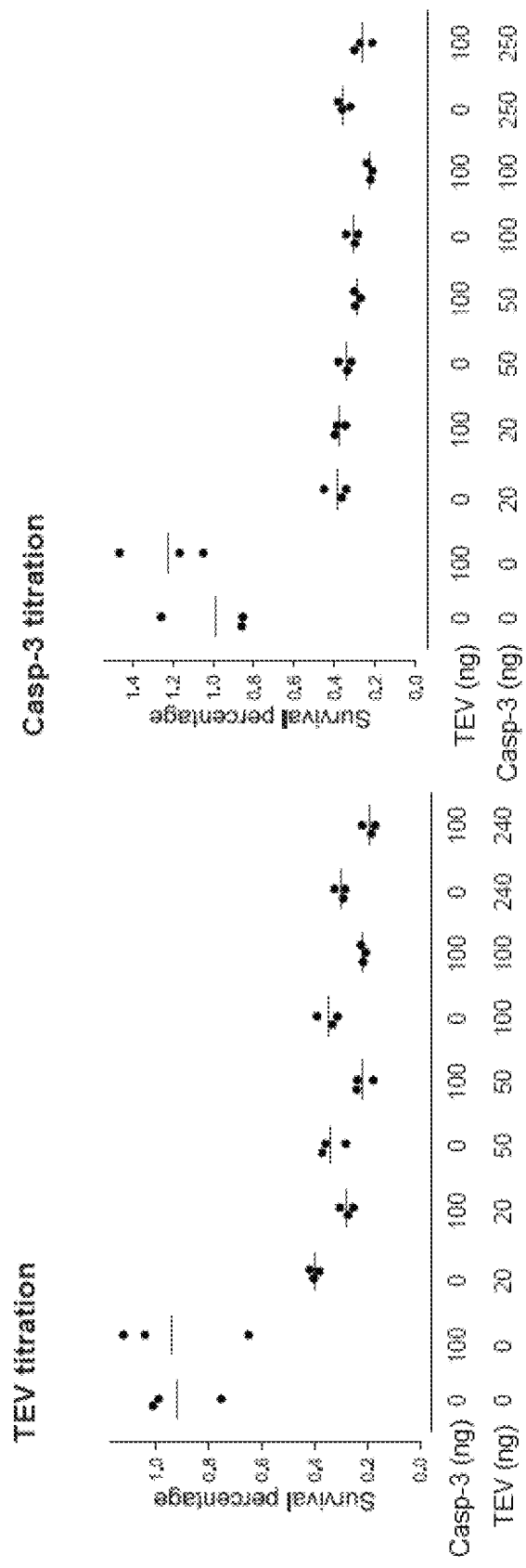
FIGS. 9H and 9I are plots showing titration data in accordance with some embodiments.
Figure 9I:
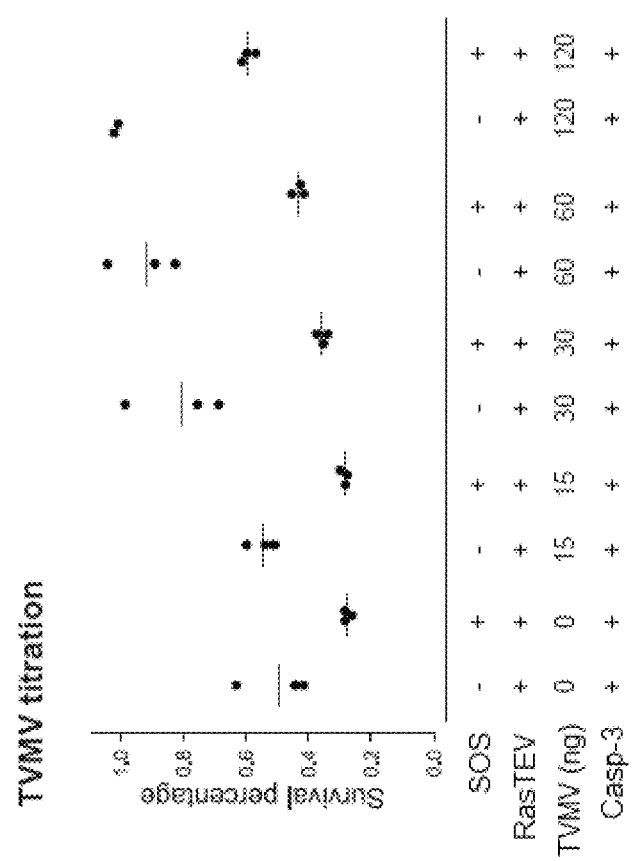

FIGS. 9D, 9H, 9I, and 10E-10G|Characterization and Optimization of Circuits that Selectively Reduce Ras-Activating Cells.

a, Example. FIG. 9D, Cytoplasmic TEV-activatable Caspase 3 causes limited reduction of cell survival in the presence of membrane-localized split TEV protease reconstituted through leucine zippers (compare to FIG. 4G). FIG. 9H, The effects of TEV and Caspase doses on survival reduction. FIG. 9I, Dose of TVMV protease tunes the circuit's selectivity for Sos cells (first and fourth pairs of data points also shown in FIG. 4H). FIG. 10E, Testing the contribution of individual regulatory edges to selectivity. Left, removing TEV→TVMV edge increases overall survival; middle, removing TVMV→Casp3 edge reduces overall survival; right, removing TVMV→TEV edge has no significant effect. FIG. 10F, Using IRES mutants to tune TVMV expression level in a single transcript. The mutant reported to express at ~70% level of wild type exhibits a balance between survival of control cells and reduction of Sos cells. FIG. 10G, Selective survival reduction in response to different doses of the optimal single-transcript circuit (with 70% IRES), delivered into co-cultured control and Sos cells (second pair of data points also shown in FIG. 4I).

REFERENCES

1. B. J. Yeh, R. J. Rutigliano, A. Deb, D. Bar-Sagi, W. A. Lim, Rewiring cellular morphology pathways with synthetic guanine nucleotide exchange factors. *Nature.* 447, 596-600 (2007).
2. M. Iwamoto, T. Bjorklund, C. Lundberg, D. Kirik, T. J. Wandless, A general chemical method to regulate protein stability in the mammalian central nervous system. *Chem. Biol.* 17, 981-988 (2010).
3. S. Nallamsetty et al., Efficient site-specific processing of fusion proteins by tobacco vein mottling virus protease in vivo and in vitro. *Protein Expr. Purif.* 38, 108-115 (2004).

4. R. Bartenschlager, The NS3/4A proteinase of the hepatitis C virus: unravelling structure and function of an unusual enzyme and a prime target for antiviral therapy. *J. Viral Hepat.* 6, 165-181 (1999).
5. S. S. Taremi, B. Beyer, M. Maher, N. Yao, Construction, expression, and characterization of a novel fully activated recombinant single-chain hepatitis C virus protease. *Proteins* (1998) (available at http://onlinelibrary.wiley.com/doi/10.1002/pro.0.5560071011/full).
6. I. Ghosh, A. D. Hamilton, L. Regan, Antiparallel Leucine Zipper-Directed Protein Reassembly: Application to the Green Fluorescent Protein. *J. Am. Chem. Soc.* 122, 5658-5659 (2000).
7. M. C. Wehr et al., Monitoring regulated protein-protein interactions using split TEV. *Nat. Methods.* 3, 985-993 (2006).

EXAMPLES

Example 1—Materials and Methods for Additional Embodiments Relating to Programmable Protein Circuits in Living Cells Where applicable, the materials and methods described in this section were used in any experiments described herein, unless otherwise indicated herein. Some embodiments of the methods, compositions, and systems described herein include materials and/or methods described in this example.

Plasmid Construction

Constructs were generated using standard procedures. The backbones were linearized using restriction digestion or PCR, and inserts were generated using PCR or gBlock synthesis (IDT). A list of plasmids used is included in Table 1, and plasmids and maps are deposited with Addgene.

TABLE 1

| | Miscellaneous |
|---|---|
| 0a | PGK-H2BChe |
| 0b | CMV-TO-H2BCit |
| 0c | CMV-TO-Cer-HO1-FlpIn |
| 0d | CMV-TO-MSos-2A-H2BChe-FlpIn |
| 0e | PB-CMV-TO-EGFRvIII-IRES-nlsChe |
| | reporter |
| 1a | PB-PGK-Cit-tevs-DHFR |
| 1b | PB-PGK-teD-Cit |
| 1c | PB-PGK-Cit-tvmvs-DHFR |
| 1d | PB-PGK-tvD-Cit |
| 1e | PB-PGK-Cit-hcvs-DHFR |
| 1f | PB-PGK-ZhcD-Cit |
| 1g | PB-PGK-Cit-tehc-DHFR |
| 1h | PB-PGK-FKBP-Zte-Cit-hc-DHFR |
| 1i | PB-PGK-Cit-tvhc-DHFR |
| 1j | PB-PGK-FKBP-Zte-Cit-tv-DHFR |
| 1k | PB-PGK-teD-Cit-hcvs-DHFR |
| 1l | PB-PGK-ZhcD-Cit-tevs-DHFR |
| 1m | PB-PGK-FKBP-Ztetv-Cit-tvhc-DHFR |
| 1n | PB-PGK-tvD-Cit-tevs-DHFR |
| 1o | pcDNA3.1-tvD-Cit-tevs-DHFR |
| 1p | PB-CMV-TO-Casp3te |
| 1q | PB-CMV-TO-Casp3te-tv-cx |
| 1r | PB-CMV-TO-Casp3te-cx |
| 1s | PB-CMV-Cit-tehc-DHFR |
| 1t | PB-CMV-FKBP-Zte-Cit-hc-DHFR |
| 1u | PB-CMV-Cit-tvmvs-DHFR |
| 1v | PB-CMV-TO-lyn-tvDiTEV |
| | TEV protease |
| 2a | CMV-TO-TEVP |
| 2b | CMV-TO-nTEVPhcZ-2A-ZhccTEVP |
| 2c | CMV-TO-nTEVPtvhcZ-2A-ZhctvcTEVP |

TABLE 1-continued

| 2d | CMV-TO-TEVPZ |
|---|---|
| 2e | CMV-TO-nTEVPhcZhccTEVP |
| 2f | CMV-TO-nTEVPtvZtvcTEVP |
| 2g | CMV-TO-nTEVPtvR-2A-KtvcTEVP |
| 2h | CMV-TO-nTEVPZ-tv-cx |
| 2i | CMV-TO-ZcTEVP |
| 2j | CMV-TO-nTEVP-tv-ras |
| 2k | CMV-TO-Rbd-tv-cTEVP |
| 2l | CMV-TO-nTEVP-rasG12V |
| 2m | CMV-TO-nTEVP-ras |
| 2n | CMV-TO-Rbd-cTEVP |
| 2o | CMV-TO-rapTEVPZ |
| 2p | CMV-TO-RasTEVP |
| | TVMV protease |
| 3a | CMV-TO-TVMVP |
| 3b | CMV-TO-TVMVPZ |
| 3c | CMV-TO-nTVMVPhcZ-2A-ZhccTVMVP |
| 3d | CMV-TO-nTVMVPteZ-2A-ZtecTVMVP |
| 3e | CMV-TO-nTVMVPhcZhccTVMVP |
| 3f | CMV-TO-nTVMVPteZtecTVMVP |
| 3g | CMV-TO-nTVMVPtehcZ-2A-ZhctecTVMVP |
| 3h | CMV-TO-nTVMVPhcZhccTVMVPZ |
| 3i | CMV-TO-nTVMVPhcZhccTVMVPcx |
| 3j | CMV-TO-nTVMVPteZtecTVMVPcx |
| | HCV protease |
| 4a | CMV-TO-scHCVP |
| 4b | CMV-TO-ZscHCVP |
| 4c | CMV-TO-ZNS4AteHCVP |
| 4d | CMV-TO-ZNS4AtvHCVP |
| 4e | pcDNA3.1-ZNS4AtvHCVP |
| 4f | CMV-TO-ZNS4AhssbHCVP |
| | Combination |
| 5a | CMV-TO-ZscHCVP-TEVPZ |
| 5b | PB-CMV-TO-rapTEV-teHCV-hcTVMV-tvDiTEV-Neo |
| 5c | PB-CMV-TO-Casp-rastvTEV-teTVMV0 |
| 5d | PB-CMV-TO-Casp-rastvTEV-teTVMV1 |
| 5e | PB-CMV-TO-Casp-rastvTEV-teTVMV2 |
| 5f | PB-CMV-TO-Casp-rastvTEVca-teTVMVd1 |
| | Other proteases |
| 6a | CMV-TO-SMVPZ |
| 6b | CMV-TO-HSVPZ |

Tissue Culture

The Flp-In™ T-REx™ 293 Cell Line (Human Embryonic Kidney cells that contain a single stably integrated FRT site at a transcriptionally active genomic locus, and stably expressing the tetracycline repressor protein) was purchased from Thermo Fisher Scientific (R78007). Cells were cultured in a humidity controlled chamber at 37° C. with 5% $CO_2$ in media containing DMEM supplemented with 10% FBS, 1 mM sodium pyruvate, 1 unit/ml penicillin, 1 µg/ml streptomycin, 2 mM L-glutamine and 1×MEM non-essential amino acids. 100 ng/mL doxycycline was added whenever expression is needed from a CMV-TO promoter. All stably integrated transgenes were inducible with doxycycline, which was only added one day before characterization. Trimethoprim (TMP) was delivered at 1 µM. Rapamycin was delivered at 5 nM. Epidermal growth factor (EGF) was delivered at 25 ng/mL. SHIELD1 was delivered at 1 µM. ASV was delivered at 3 µM. For bulk measurement of pulsing dynamics, cells were cultured in the presence of 40 µM biliverdin, and rapamycin was added at different time points before preparation for flow cytometry. For stimulation with EGF, cells were cultured to near 100% confluency before transfection, and, one day after transfection, exposed to 40 µM biliverdin, 25 ng/mL EGF, and 100 ng/mL doxycycline for 6 hours prior to flow cytometry analysis.

Transient Transfection 293 cells were seeded at a density of $0.05 \times 10^6$ cells per well of a 24-well plate and cultured under standard conditions overnight. The following day, the cells were transfected with plasmid constructs using Lipofectamine 2000 (Thermo Fisher) as per manufacturer's protocol.

Flow Cytometry

Two days after transfection, cells were prepared for flow cytometry by trypsinizing with 30 µL of 0.05% trypsin for 1 min at room temperature. Protease activity was neutralized by resuspending the cells in buffer containing 70 µL of HBSS with 2.5 mg/ml Bovine Serum Albumin (BSA). For cells stimulated with EGF, cells were resuspended in buffer containing 70 µL of HBSS with 2.5 mg/mL BSA and 1 mM EDTA. Cells were then filtered through a 40 µm cell strainer and analyzed by flow cytometry (MACSQuant VYB, Miltenyi or CytoFLEX, Beckman Coulter). The inventors used the EasyFlow Matlab-based software package developed in-house by Yaron Antebi to process flow cytometry data.

Annexin V Staining

Staining was performed using a standard kit (ThermoFisher A13201). One day after transfection, cell culture medium was removed from each well, and replaced with 7.5 µL FITC-conjugated annexin V within 150 µL binding buffer. After incubation in dark at 37° C. for 15 min, the staining medium was removed, and the cells trypsinized for flow cytometry analysis.

Fluorescent Signal Quantification from Flow Cytometric Measurements

To maximize the observable reporter dynamic range, the inventors selected and compared cells with the highest expression of the co-transfection marker, which showed the largest separation of basal reporter fluorescence from cellular autofluorescence. For each sample in a comparison group (experiments performed in the same batch and data shown on the same plot), the inventors calculated the 98 and 99.5 percentiles of fluorescence of the co-transfection marker (mCherry in most cases). The inventors identified the sample with the lowest 98 percentile value, and used its 98 and 99.5 percentiles as lower and upper limits to gate on all samples. For all cells within the gate in each sample, the inventors fit the distribution of the logarithm of their signal fluorescence (Citrine in most cases) with skew Gaussian distributions, i.e. $N*\text{normcdf}(x,m,k)*\text{normpdf}(x,m,s)$ in Matlab using non-linear least-square fitting, and reported the mode (peak position, representing the reporter level that's most likely to be observed) of the resulting fit (FIG. 5A). Here, the normcdf$(x,\mu,\sigma)$ and normpdf$(x,\mu,\sigma)$ functions are cumulative probability density and probability density functions for a Gaussian distribution respectively, and the parameter n is a normalization factor, $m=\mu$ is the mean of the Gaussian function, $s=\sigma$ is the inverse standard deviation of the Gaussian, and k parameterizes skewness. No gating was performed on monoclonal cells with the genomically integrated pulsing circuit, because, unlike transient transfection, here expression variation is already limited.

Calculating Reduction Index from Flow Cytometric Measurements

To calculate the reduction of cell numbers, the inventors compared the effects of various treatments on cell numbers, comparing each measurement to a negative control transfected with only a fluorescent marker, and using the size of the untransfected cell population for internal normalization. To do this, the inventors proceeded in several steps: First, the inventors fit the distribution of the logarithm of autofluorescence collected in the Citrine channel from mock transfected cells with the MATLAB function $N_0*\text{normcdf}(x,m_0,k_0)*\text{normpdf}(x,m_0,s_0)$ using non-linear least-square fitting. Here, the parameters $n_0$, $m_0$, $s_0$, and $k_0$ and functions normcdf( ) and normpdf( ) have the same meanings as elsewhere described herein. Reference values for $m_0$, $s_0$, $k_0$, were thus determined from measurement of autofluorescence in untransfected cells and fixed for subsequent two-component model fits. Second, for each transfected well, the inventors fit the distribution of the logarithm of Citrine signal with $N_1*\text{normcdf}(x,m_0,k_0)*\text{normpdf}(x,m_0,s_0) + N_2*\text{normpdf}(x,m_2,s_2)$, where $N_1$, $N_2$, $m_2$, $s_2$ were free parameters and $m_0$, $s_0$, $k_0$ were fixed to values extracted from autofluorescence fit. The area under the curve $N_1*\text{normcdf}(x,m_0,k_0)*\text{normpdf}(x,m_0,s_0)$ ("area $a_0$" and "area a" in FIG. 9B) corresponds to the number of untransfected cells, which serves as an internal reference. Third, the inventors subtracted the number of untransfected cells from the total number of cells to get the number of transfected cells that survived ("area $b_0$" and "area b" in FIG. 9B). For each sample, the number of transfected cells that survived was then normalized to the number of untransfected cells, and the ratio between normalized survival number in that condition ((area a)/(area b) in FIG. 9B) and normalized survival number in the Citrine-only control condition ((area $a_0$)/(area $b_0$) in FIG. 9B) was defined as survival percentage. Finally, the reduction index was defined as 1-survival percentage.

In experiments with $SOS_{CA}$ cells, a small fraction of these cells silenced their transgene expression during cell culture. To make sure that the inventors were only analyzing cells that do express a Ras activator, the inventors gated on mCherry that's co-expressed with $SOS_{CA}$, and excluded the mCherry-population. This co-expressed mCherry marker was also utilized in co-culture experiments, to distinguish $SOS_{CA}$/EGFRvIII cells from control cells, so that the inventors could calculate their reduction index separately.

Mathematical Modeling of the Bandpass Circuit

To analyze the behavior of the bandpass circuit, the inventors constructed a minimal ordinary differential equation model representing the key components and interactions within the circuit. The model incorporated three types of interactions: protein production, first-order degradation, and cleavage by proteases. In the model, protease regulation of substrates is described by differential equations of the following form:

$$\frac{d[\text{Substrate}]}{dt} = A - k_{cat}^{Protease}[\text{Protease}][\text{Substrate}] - k_{dA}[\text{Substrate}] \quad (1)$$

$$\frac{d[\text{Substrate}_{cleaved}]}{dt} = \\ k_{cat}^{Protease}[\text{Protease}][\text{Substrate}] - k_{dB}[\text{Substrate}_{cleaved}] \quad (2)$$

Here, A represents the production rate of a proteolytic substrate, $k_{cat}^{Protease}$ represents the catalytic coefficient, assuming that proteolysis can be described as a Michaelis-Menten reaction far from saturation, and the first-order degradation rates $k_{dA}$ and $k_{dB}$ represent degradation through basal cellular degradation pathways. These rate constants can take higher or lower values depending on whether the substrate protein and its cleaved form are unstable or stable, respectively.

To simplify the analysis without loss of generality, the inventors set A=1 in the equations for fluorescent reporters, effectively using arbitrary normalized units for the fluorescent protein concentrations. [Substrate] in the normalized version thus corresponds to [Substrate]/A in the original version.

We first considered a $\text{Cit}_{DHFR}$ reporter, whose DHFR degron can be removed by TEVP with a coefficient $k_{cat}^{TE}$.

In its initial form, the reporter degrades at rate $k_{d1}$ (Equation 3), while its cleaved product, Cit, degrades at a rate $k_{d2}$ (Equation 4).

$$\frac{dCit_{DHFR}}{dt} = 1 - k_{cat}^{TE}[TEVP][Cit_{DHFR}] - k_{d1}[Cit_{DHFR}] \quad (3)$$

$$\frac{dCit}{dt} = k_{cat}^{TE}[TEVP][Cit_{DHFR}] - k_{d2}[Cit] \quad (4)$$

The steady-state solutions for Eqs. 3, 4 are:

$$Cit_{DHFR} = \frac{1}{k_{cat}^{TE}[TEVP] + k_{d1}} \quad (5)$$

$$Cit = \frac{k_{cat}^{TE}[TEVP]}{k_{d2}(k_{cat}^{TE}[TEVP] + k_{d1})} \quad (6)$$

Experimentally measured reporter fluorescence corresponds to the sum $Cit_{DHFR}$=Cit. The absolute value of the independent variable [TEVP] is not known. However, based on experiments in which protein expression levels correlated linearly with the amount of transfected plasmid (FIG. 8A), the inventors substituted the concentration of transfected plasmid, $p_{TE}$, for [TEVP] in all equations, effectively absorbing the constant of proportionality relating [TEVP] and $p_{TE}$ into the $k_{cat}^{TE}$ values. With these simplifications, measured fluorescence can be written:

$$Cit_{total} = Cit_{DHFR} + Cit = \frac{\frac{k_{cat}^{TE} p_{TE}}{k_{d2}} + 1}{k_{cat}^{TE} p_{TE} + k_{d1}} \quad (7)$$

Using Matlab's curve fitting toolbox, the inventors determined best fit values of the parameters $k_{cat}^{TE}$, $k_{d1}$ and $k_{d2}$ by fitting Eq. 7 to the experimentally measured $p_{TE}$–$Cit_{total}$ curve (FIG. 3B).

To model the repression arm of the bandpass circuit, the inventors must take into account the mutual inhibitory activities of TVMVP and HCVP in the circuit. These protease-protease equations take on the general form outlined in Eqs 1, 2. However, because reporter and protease concentrations are measured in different units (fluorescence and plasmid concentration, respectively), their production rates cannot both be arbitrarily set to 1. Instead, the inventors denoted the protease production rate B, to account for the different units used for these two species. Specifically, for 1 unit of plasmid input to produce 1 unit of protease at steady-state, B must equal the degradation rate of the protease multiplied by the amount of plasmid input ($p_{Protease}$), as shown below in Equations 8 and 9.

$$\frac{d[TVMVP]}{dt} = k_{dTV} p_{TV} - k_{cat}^{HC}[HCVP][TVMVP] - k_{dTV}[TVMVP] \quad (8)$$

$$\frac{d[HCVP]}{dt} = k_{dHC} p_{HC} - k_{cat}^{TV}[TVMVP][HCVP] - k_{dHC}[HCVP] \quad (9)$$

At steady-state, the concentration of TVMV protease can be expressed as a function of the plasmid inputs of TVMVP and HCVP:

$$[TVMVP] = \frac{W + (W^2 + 4k_{cat}^{TV} k_{dTV}^2 k_{dHC} p_{TV})^{\frac{1}{2}}}{2 k_{cat}^{TV} k_{dTV}} \quad (10)$$

where $W \equiv k_{dTV} k_{cat}^{TV} p_{TV} - k_{dHC} k_{dTV} - k_{cat}^{HC} k_{dHC} p_{HC}$. The reporter repressed by TVMVP is denoted Cit when not cleaved (first-order degradation rate $k_{d3}$), and $Cit_{Ndeg}$ when cleaved by TVMVP to expose an N-end degron (first-order degradation rate $k_{d4}$). We then used a procedure similar to Eqs. 3-7 to express reporter expressions in terms of [TVMVP]:

$$Cit = \frac{1}{k_{cat}^{TV}[TVMVP] + k_{d3}} \quad (11^*)$$

$$Cit_{Ndeg} = \frac{k_{cat}^{TV}[TVMVP]}{k_{d4}(k_{cat}^{TV}[TVMVP] + k_{d3})} \quad (12^*)$$

$$Cit_{total} = \frac{\frac{k_{cat}^{TV}[TVMVP]}{k_{d4}} + 1}{k_{cat}^{TV}[TVMVP] + k_{d3}} \quad (13^*)$$

For all equations denoted with "*", [TVMVP] takes the value defined in Eq. 10.

We estimated the values of parameters, $k_{cat}^{HC}$, $k_{cat}^{TV}$, $k_{dHC}$, $k_{dTV}$, $k_{d3}$, $k_{d4}$, by fitting Eq. 13 to experimentally measured $Cit_{total}$, $p_{TV}$, and $p_{Hc}$. (FIG. 3C).

To characterize the cooperativity caused by TVMVP-HCVP mutual inhibition, the inventors fit the repression curves in FIG. 3C with a sigmoidal function:

$$Cit_{total} = \frac{C}{1 + \left(\frac{p_{TV}}{K}\right)^n} \quad (14)$$

The 95% confidence intervals for the Hill coefficient, n, were 0.95±0.13, 2.0±0.4, and 2.4±0.5, for $p_{HC}$ values of 0, 50, and 200 ng, respectively.

Finally, for the reporter that's simultaneously regulated by the activation and repression arms, depending on whether the DHFR degron is removed and whether the N-end degron is exposed, there are four possible species $Cit_{DHFR}$, $Cit_{DHFR \to Ndeg}$, Cit, and $Cit_{Ndeg}$, the first-order degradation rates of which are denoted as $k_{dA}$, $k_{dB}$, $k_{dC}$, and $k_{dD}$, respectively. Similarly, the dynamics of these four species can be expressed as:

$$\frac{dCit_{DHFR}}{dt} = \quad (15^*)$$
$$1 - k_{cat}^{TE}[TEVP][Cit_{DHFR}] - k_{cat}^{TV}[TVMVP][Cit_{DHFR}] - k_{dA}[Cit_{DHFR}]$$

$$\frac{dCit_{DHFR+Ndeg}}{dt} = k_{cat}^{TV}[TVMVP][Cit_{DHFR}] - \quad (16^*)$$
$$k_{cat}^{TE}[TEVP][Cit_{DHFR+Ndeg}] - k_{dB}[Cit_{DHFR+Ndeg}]$$

$$\frac{dCit}{dt} = k_{cat}^{TE}[TEVP][Cit_{DHFR}] - k_{cat}^{TV}[TVMVP][Cit] - k_{dC}[Cit] \quad (17^*)$$

$$\frac{dCit_{Ndeg}}{dt} = \quad (18^*)$$
$$k_{cat}^{TE}[TEVP][Cit_{DHFR+Ndeg}] + k_{cat}^{TV}[TVMVP][Cit] - k_{dD}[Cit_{Ndeg}]$$

We summed the steady-state solutions of all species from these equations to derive the final input-output equation for the bandpass circuit:

$$Cit_{total} = \frac{1 + X + Y + \frac{k_{cat}^{TE} p_{TE} X + k_{cat}^{TV}[TVMVP]Y}{k_{dD}}}{k_{cat}^{TE} p_{TE} + k_{cat}^{TV}[TVMVP] + k_{dA}}, \quad (19^*)$$

Where $$X \equiv \frac{k_{cat}^{TV}[TVMVP]}{k_{cat}^{TE} p_{TE} + k_{dB}} \text{ and } Y \equiv \frac{k_{cat}^{TE} p_{TE}}{k_{cat}^{TV}[TVMVP] + k_{dC}}$$

We used this equation to fit the experimentally observed bandpass behavior (FIG. 3D).

Cell Line Construction

Some of the experiments do require more stable/homogenous transgene expression, for which the inventors used antibiotic selection to generate cell lines with stably integrated transgenes. Two days after transfection in 24-well plates, cells were transferred to 6-well plate and selected with either 50 μg/mL Hygromycin (Hyg) or 400 μg/mL Geneticin (Gen). $SOS_{CA}$ cells: CMV-TO-MSos-2A-H2BChe-FlpIn co-transfected with pOG44, Hyg; pulse cells: PB-CMV-TO-rapTEV-teHCV-hcTVMV-tvDiTEV-Neo co-transfected with a plasmid expressing PiggyBac transposase, Gen; EGFRvIII+ cells: PB-CMV-TO-EGFRvIII-IRES-nlsChe co-transfected with a plasmid expressing PiggyBac transposase, Gen. After PiggyBac-based integration, monoclonal cell populations were established through limiting dilution, and preliminary screening was performed to identify clones with highest transgene expression (based on GFP that serves as the scaffold in iTEV, and mCherry that's co-expressed with EGFRvIII), which were used in subsequent experiments. Among the pulse cell clones with highest GFP expression, the one with the least variance was selected. The inventors then subjected this clone to another round of transgenesis (Hyg, CMV-TO-Cer-HO1-FlpIn co-transfected with pOG44) to provide Cerulean as a segmentation marker and heme oxygenase-1 to increase the intracellular concentration of biliverdin that's necessary for enhancing iTEV signal. The final cell line was used in time-lapse imaging.

Time-Lapse Imaging

For time-lapse imaging of pulse dynamics (FIGS. 3A-3H) monoclonal pulse-generation cells were mixed with parental wild-type HEK293 cells at a 1:10 ratio. Cells were plated on 24-well glass-bottom plates which had been coated with 5 μg/mL with hamster fibronectin for 1 hour at room temperature. Cells were induced with 100 ng/mL doxycycline overnight in normal culturing conditions. The following morning, the media was replaced with imaging media containing FluoroBrite DMEM (Thermo Fisher) supplemented with 10% FBS, 1 mM sodium pyruvate, 1 unit/ml penicillin, 1 μg/ml streptomycin, 2 mM L-glutamine and 1×MEM non-essential amino acids and 100 ng/mL doxycycline.

Time-lapse images were acquired on an inverted Olympus IX81 fluorescence microscope with Zero Drift Control (ZDC), an ASI 2000XY automated stage, iKon-M CCD camera (Andor, Belfast, NIR), and a 60× oil objective (1.42 NA). Fluorophores were excited with an X-Cite XLED1 light source (Lumen Dynamics). Cells were kept in a custom-made environmental chamber enclosing the microscope, with humidified 5% CO2 flow at 37° C. Microscope and image acquisition were controlled by Metamorph software (Molecular Devices).

Imaging started approximately 2 hours after changing the media to fluorescent imaging media. 5 nM rapamycin was added after approximately 2 hours of imaging to induce the pulse. Images were acquired every 20 or 25 min, typically for 20-40 hrs. Cells that were in the field of view before rapamycin induction and remained alive and visible in the field of view without death for at least 20 hours were used for initial data analysis.

For analysis, the inventors only included cells that remained alive throughout the duration of the experiment, remained within the field of view, and had detectable signal/background ratio. IFP fluorescence intensity is dependent on the biliverdin chromophore. Addition of exogenous biliverdin increases IFP fluorescence but also produces IFP-independent background fluorescence. For movies, to minimize background, the inventors omitted biliverdin from the media, relying instead on lower concentrations produced endogenously. Under these conditions, IFP excitation illumination levels caused some phototoxicity, resulting in a subpopulation of ~50% of cells that died within ~7 hours. The remaining cells continued active division until the end of the movie, or until exit from the field of view. These cells exhibited a range of IFP fluorescence levels overlapping background. 30-60% of these cells in which IFP fluorescence exceeded background. About half of this set had morphologies that were amenable to image-based segmentation and therefore were analyzed further. Within this group, the inventors verified that the circuit dynamics were independent of expression level, as measured by peak IFP fluorescence, suggesting that circuit dynamics are not influenced by expression level within this range, according to some embodiments.

Single-Cell Tracking and Image Normalization:

Single-cell tracking and image normalization procedures were performed as described herein. Briefly, cells constitutively express cytoplasmic Cerulean as a segmentation marker. Due to the diffuse and weak Cerulean signal, manual segmentation was frequently required and cell boundaries were identified in part by phase contrast and GFP fluorescence images (GFP is the protein identified as the "split scaffold" in FIG. 3E. It serves a structural role in the context of the IFP reporter, but also fluoresces).

We performed image correction to account and correct for non-uniform illumination as well as background. The inventors assumed a time-independent spatially inhomogeneous illumination profile that is characteristic of the optical path, I(x,y). This was extracted by fitting the low intensity "non-cell" pixels in the images with a two dimensional paraboloid. In addition the inventors considered two sources of background fluorescence: First, the detector produces a basal pixel value even in the absence of light. This value, denoted B, is spatially homogeneous and time-independent. Second, the inventors considered the autofluorescence of the media. This background source changes over time, and exhibits a spatial profile proportional to the illumination profile, A(t)*I(x,y). With these assumptions, the inventors extracted the corrected fluorescence value using the following equation:

$$F_{corrected}(x, y, t) = \frac{F_{raw}(x, y, t) - B}{I(x, y)} - A(t)$$

For generating a movie, mean intensities <5% were set to zero and mean intensities >99.5% were set to maximum pixel values to limit the effect of extreme pixel values due to noise on image brightness and contrast settings.

Quantification of Amplitude and Pulse Decay:

Data Processing:

The amplitude and pulse decay calculations were based on total levels of fluorescence in the IFP fluorescent channel. To systematically quantify the fluorescent signal in the IFP channel, total IFP signal intensity IFP(x,y,t) was normalized by the total constitutive Cerulean signal CFP(x,y,t) and rescaled with a baseline variable (90th percentile of $$\frac{IFP(x, y, t)}{CFP(x, y, t)}$$

at all x positions.) To capture the pulse of IFP signal and avoid distortion of the peak shape, the resulting data was smoothed with a Savitzky-Golay filter using a 3rd order polynomial and a window length of 9. After smoothing, the data were interpolated to equidistant timepoints of 20 minute intervals (FIG. 3H).

Fitting:

Pulsing dynamics were fitted by taking the smoothed and interpolated data and subtracting the minimum value of the normalized signal intensity from each timepoint. Using MATLAB's tfest function, the normalized data were deconvolved with a finite impulse signal and a third-order linear transfer function resulting in the equation:

$$y = a_1 e^{p1x(t)} + a_2 e^{p2x(t)} + a_3 e^{p3x(t)}$$

The resulting fit was used to determine: (1) the location at which the maximal value of IFP occurred and (2) the delay time, $\tau$, after peak signal at which the signal intensity decayed to 50% its maximum value. After determining the peak location and $\tau$, the mean and standard deviation were calculated.

Example 2—Engineering of a Split HCV Protease

Hepatitis C Virus (HCV) protease had not, to the inventors' knowledge, been successfully split. The inventors used a strategy based on the following criteria: (1) each fragment had to be predicted to be a folded subunit, (2) the location of the split between the two fragments had to occur in a loop or unstructured region; and (3) the three residues of the catalytic triad could not be located on the same fragment. The inventors engineered a split Hepatitis C Virus (HCV) protease mutants satisfying these criteria and tested their catalytic activity by rescue of a degron-tagged fluorescent protein relative to a non-rescued fluorescent protein control. Based on initial results, the inventors further tested additional split sites by shifting the position at which we split the two fragments by one residue in both the N and C terminal direction. The following split sites exhibited the best performance: sHCV 120 and sHCV 122. See Wehr et al, Monitoring regulated protein-protein interactions using split TEV. *Nat. Methods* 3, 985 (2006), for some materials and methods relating to this methodology.

Example 3—Alternative Designs for Protease Activated Proteases

Described below are some additional embodiments of compound proteases, and resulting data when the designs were tested.

Design: HCV protease is tagged with an auto-inhibitory domain that can be removed with TEV protease (FIG. 12A). Result: This domain included a mutated HCV cleavage site sequence that binds to, but is no longer cleaved by, HCV protease. Adding TEV protease (lower panel) did not increase HCV protease activity compared to a control lacking TEV protease (upper panel). Plots represent flow cytometry distributions of the Cit-hcvs-DHFR reporter.

Design: HCV protease is tagged with a DHFR degron that can be removed with TEV protease (FIG. 12B). Result: Adding TEV protease did not increase HCV protease activity, as indicated by a Cit-hcvs-DHFR reporter.

Design: Split TEV protease is tagged with a degron (four tandem repeats of ubiquitin, because the typical DHFR degron is even less effective) on the end of one of the leucine zippers, and the degron is removable by TVMV protease (FIG. 12C). Result: The degron did not fully repress TEV protease activity, and adding TVMV protease only led to a small increase of TEV protease activity, as indicated by a Cit-tevs-DHFR reporter. However, this design was at least partially successful because some positive regulatory effect was seen.

Design: The N-terminal half of TEV protease is caged with a complementary leucine zipper and a catalytically inactive C-terminal half, and the caging domains are removable with TVMV protease (FIG. 12D). Result: The caging domains did not fully repress TEV protease activity, and adding TVMV protease did not increase TEV protease activity, as indicated by a Cit-tevs-DHFR reporter.

Example 4—Applications

Some applications of some embodiments of the systems, methods and/or compositions provided herein include the following:

Kill switches: the ability to kill engineered cells in response to a signal is useful for many emerging cell based therapies. Existing methods may produce toxicity or cell death when not desired, i.e. in the absence of the kill switch input. Some embodiments include the construction of kill switches in which such effects can be suppressed through a protease-based reciprocal inhibition motif or through feed-forward loop structures.

Virally delivered synthetic circuits: some embodiments include the ability to deliver complex programmed protein-level functions into cells using a variety of non-integrating vectors. This capability may avoid potential mutagenesis that occurs with gene regulation based systems.

Oncolytic viral therapies: by encoding protein level circuits on oncolytic viruses, one may deliver functions that specifically kill or inactivate tumor cells conditionally depending on the tumor cells' state(s).

Gene drive payloads: gene drive technology may enable efficient super-Mendelian propagation of genetic systems within mating populations of organisms. Gene drive applications of the current embodiments are enabled by the disclosure herein based on the ability to package sophisticated functions in compact genetic systems. Some embodiments of the systems described herein can enable gene drive payloads that perform such functions. For example, for insect vector control, a protein-circuit that specifically kills mosquitoes infected by human pathogens such as Dengue virus.

Cell type specific control of cell fate. Regenerative medicine sometimes requires precise manipulation of cell fate. Protein level circuits can be transiently introduced into cells to control the activation of fate regulating genes and thereby induce specific cell fates. This activity can be coupled to modules within the circuit that detect the state of the cell and make cell fate control conditional on cell state. This may avoid a problem of activating the same genes in a heterogeneous cell population, and also may avoid permanent genetic modification.

Extracellular protein level feedback circuits that control blood clotting. The system described herein enables protein circuits that function outside cells to detect blood clots or pathological conditions and trigger clot removing functions.

Subcellular functions. The disclosure herein enables protein circuits that function in specific subcellular compartments or sites. Circuits can operate to modulate the behavior of specific synapses or organelles such as mitochondria.

T-Cell therapies. The disclosure herein enables protein circuits that function when in the presence or absence of ligand on an adjacent cell. Circuits can operate to control activity of T-cells, which may express a chimeric antigen receptor. The circuit can enable tuning and/or control of the receptor activity, and can also function to integrate multiple internal and external signals into a response.

These are only some examples of the many applications of the systems, methods and compositions provided herein.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All titles, headings and subheadings used herein are meant to add additional disclosure of some embodiments, but are in no way limiting with regard to the subject matter contained anywhere herein.

What is claimed is:

1. A system comprising:
   a first protease;
   a second protease; and
   one or more target proteins each comprising:
   a first degron of the target protein that destabilizes the target protein when present on the target protein by enhancing degradation of the target protein,
   a cut site specific for the first protease between the degron of the target protein and a part of the target protein, wherein the target protein is configured to be stabilized by cleavage of its cut site specific for the first protease,
   another degron of the target protein, and
   a cut site specific for the second protease connected to the other degron of the target protein, wherein the target protein is configured to be destabilized by cleavage of the cut site specific for the second protease regardless of whether the first degron of the target protein is present on the target protein.

2. The system of claim 1, wherein the other degron of each target protein comprises an N-end degron that is conditional on cleavage of the cut site specific for the second protease.

3. The system of claim 1, further comprising a third protease comprising a cut site specific for the second protease, wherein the third protease is configured to be deactivated by cleavage of its cut site specific for the second protease; and wherein the second protease comprises a cut site specific for the third protease, wherein the second protease is configured to be deactivated by cleavage of its cut site specific for the third protease.

4. The system of claim 1,
   wherein the second protease further comprises a first domain of the second protease, a second domain of the second protease, a first complementary association domain, and an optional second complementary association domain of the second protease connected to the first or second domain of the second protease;
   wherein the first domain of the second protease comprises the cut site specific for the third protease;
   wherein the second domain of the second protease comprises another cut site specific for the third protease;
   wherein the first complementary association domain of the second protease optionally comprises two parts of the complementary association domain of the second protease, each part of the complementary association domain of the second protease connecting to one of the second protease's cut sites specific for the third protease; and
   wherein the second protease is configured to be deactivated by cleavage of either of its cut sites.

5. The system of claim 1, wherein the third protease further comprises an optional association domain of the third protease, and wherein cleavage of the third protease's cut site by the second protease removes at least part of a cleavage domain of the third protease, thereby deactivating the third protease.

6. The system of claim 1, wherein the stability of the target proteins comprises an analog behavior that is dependent on a concentration of the first protease, wherein a higher concentration of the first protease has a greater stabilizing effect on the target proteins than a lower concentration of the first protease.

7. The system of claim 1, wherein the stability of the target proteins comprises an analog behavior that is dependent on a concentration of the second protease, wherein a higher concentration of the second protease has a greater destabilizing effect on the target proteins than a lower concentration of the second protease.

8. The system of claim 7, wherein the concentration of the second protease is decreased by a higher concentration of the third protease as compared to a lower concentration of the third protease or by a higher amount of a nucleic acid encoding the third protease as compared to a lower amount of a nucleic acid encoding the third protease.

9. The system of claim 7, wherein the analog behavior of the target protein that is dependent on a concentration of the second protease is more sharp and/or comprises a greater threshold for destabilizing the target protein at a higher concentration of the third protease as compared to a lower concentration of the third protease, or at a higher amount of a nucleic acid encoding the third protease as compared to a lower amount of a nucleic acid encoding the third protease.

10. The system of claim 1,
wherein the first protease further comprises a first domain of the first protease and a second domain of the first protease;
wherein the first domain of the first protease connects to a first conditional dimerization domain of the first protease;
wherein the second domain of the first protease connects to a second conditional dimerization domain of the first protease;
wherein the first and second conditional dimerization domains of the first protease are configured to dimerize with each other upon binding a dimerizing agent.

11. The system of claim 10, wherein the conditional dimerization domains of the first protease each comprise one of an FK506 binding protein (FKBP), GyrB, GAI, Snap-tag, eDHFR, BCL-xL, CalcineurinA (CNA), CyP-Fas, FRB domain of mTOR, GID1, HaloTag, and/or Fab (AZ1).

12. The system of claim 10, wherein the dimerizing agent comprises FK1012, FK506, FKCsA, Rapamycin, Coumermycin, Gibberellin, HaXS, TMP-HTag, or ABT-737.

13. The system of claim 1, wherein the first protease comprises tobacco etch virus protease (TEVP).

14. The system of claim 1, wherein the second protease comprises tobacco vein mottling virus protease (TVMVP).

15. The system of claim 1, wherein one target protein of the one or more target proteins comprises Citrine.

16. The system of claim 1, wherein one target protein of the one or more target proteins comprises, from the N-terminal to the C-terminal of the one target protein, an N-end degron as the other degron comprising a tobacco vein mottling virus protease (TVMVP) cut site specific for the second protease, Citrine, a tobacco etch virus protease (TEVP) cut site as the cut site specific for the first protease, and a non-N-end degron as the first degron.

* * * * *